(12) United States Patent
Georgopoulos

(10) Patent No.: US 6,630,141 B1
(45) Date of Patent: Oct. 7, 2003

(54) ISOLATED ANTIBODY THAT BINDS TO AN IKAROS POLYPEPTIDE

(75) Inventor: Katia Georgopoulos, Lexington, MA (US)

(73) Assignee: The General Hospital Corporation, Boston, MA (US)

( * ) Notice: Subject to any disclaimer, the term of this patent is extended or adjusted under 35 U.S.C. 154(b) by 191 days.

(21) Appl. No.: 09/723,909

(22) Filed: Nov. 28, 2000

Related U.S. Application Data

(63) Continuation of application No. 08/711,417, filed on Sep. 5, 1996, now Pat. No. 6,228,611, which is a continuation-in-part of application No. 08/238,212, filed on May 2, 1994, now abandoned, which is a continuation-in-part of application No. 08/121,438, filed on Sep. 14, 1993, now abandoned, which is a continuation-in-part of application No. 07/946,233, filed on Sep. 14, 1992, now abandoned.

(51) Int. Cl.$^7$ .................... A61K 39/395; C07K 16/00
(52) U.S. Cl. ................. 424/139.1; 424/141.1; 530/387.9; 530/388.1
(58) Field of Search ............. 424/139.1, 141.1; 530/387.9, 388.1

(56) References Cited

U.S. PATENT DOCUMENTS 6,228,611 B1 * 5/2001 Georgopoulos

OTHER PUBLICATIONS

George et al., in *Macromolecular Sequencing and Synthesis: Selected Methods and Applications.* David H. Schlesinger, ed., 1988. Alan R. Liss, Inc: New York, Chapter 12, pp. 127–149.
Denny et al. Gene 106:221–227, (1991).
U.S. patent application Ser. No. 07/946,233, Georgopoulos, filed Sep. 1992.
U.S. patent application Ser. No. 08/121,438, Georgopoulos, filed Sep. 1993.
U.S. patent application Ser. No. 08/238,212, Georgopoulos, filed May 1994.
Adams, B. et al. "Pax–5–encodes the transcription factor BSAP and is expressed in B lymphocytes, the developing CNS, and adult testis"*Genes & Development 6*: 1589–1607 (1992);.
Akbar, A.N. et al, "A possible role for bcl–2 in regulating T–cell memory –a 'balancing act' between cell death and survival" *Immunology Today 14*(11): 526–531 (1993);.
Ardavin, C. et al. "Thymic dendritic cells and T cells develop simultaneously in the thymus from a common precursor population" *Nature 362*; 761–761 (1993).
Asarnaw, D.M. et al. "Limited Diversity of γδ Antigen Receptor Genes of Thy–1$^+$ Dendritic Epidermal Cells" *Cell 55*: 837–847 (Dec. 2, 1988).
Beg, A.A. et al. "The IκB proteins: multifunctional regulators of Rel/NF–κB transcription factors" *Genes & Development 7*: 2064–2070 (1993).
Bigby, M. et al. "Ratio of Langerhan Cells to Thy–1$^+$ Dendritic Epidermal Cells in Murine Epidermis Influences the Intensity of Contact Hypersensitivity" *The Journal of Investigative Dermatology 89*(5): 495–499 (Nov. 1987);.
Boise, L.H. et al. "bcl–x, a bcl–2–Related Gene that Functions as a Dominant Regulator of Apoptotic Cell Death" *Cell 74*: 597–608 (1993).
Bours, V. et al. "The Oncoprotein Bcl–3 Directly Transactivates through κB Motifs via Association with DNA–Binding p50B Homodimers" *Cell 72*: 729–739 (1993);.
Cepko, C.L. et al "Construction and Applications of a Highly Transmissable Murine Retrovirus Shuttle Vector" *Cell 37*: 1053–1062 (1984).
Clevers, H.C. et al. "Transcription factors in early T–cell development" *Immunology Today 14*(2): 591–596 (1993).
Connelly, C.S. et al. "The Role of Transgenic Animals in the Analysis of Various Biological Aspects of Normal and Pathologic States" *Experimental Cell Research 183*: 257–276 (1989).
Delwel, R. et al. Four of the Seven Zinc Fingers of the *Evi–1* Myeloid–Transforming Gene Are Required for Sequence–Specific Binding to GA(C/T)AAGA(T/C)AAGATAA, *Molecular and Cellular Biology 13*(7): 4291–4300 (1993).
Ehlich, A. et al. "Immunoglobulin Heavy and Light Chain Genes Rearrange Independently at Early Stages of B Cell Development" *Cell 72*: 695–704 (1993).
Fife, A. et al. "Gram negative septicaemia diagnosed on peripheral blood smear appearances" *Journal of Clinical Pathology 47*: 82–84 (1994).
Fleming, W.H. et al. "Functional Heterogeneity Is Associated with the Cell Cycle Status of Murine Hematopoietic Stem Cells" *J. Cell Biol. 122*: 897–902 (1993).
Franzoso, G. et al. "The oncoprotein Bcl–3 can facilitate NF–κB–mediated transactivation by removing inhibiting p50 homodimers from select κB sites" *The EMBO Journal*, vol. 12, No. 10 3893–3901 (1993).
Furley, A.J. et al. "Developmentally Regulated Rearrangement and Expression of Genes Encoding the T Cell Receptor–T3 Complex" *Cell*, vol. 46: 75–87 (Jul. 1986).
Garni–Wagner, B.A. et al. "Natural Killer Cells in the Thymus" *The Journal of Immunology 144* (3): 796–803 (1990).
Georgopoulos, K. "Ikaros an Early Lymphoid Restricted Regulatory Protein a Putative Mediator for T Cell Specification" *Biochem. Suppl. 0* (17 Part A): 158, B 631 (1993).
Georgopoulos, K. et al. "Functionally Distinct Isoforms of the CRE–BP DNA–Binding Protein Mediate Activity of a T–Cell–Specific Enhancer" *Molecular and Cellular Biology 12*(2): 747–757 (Feb. 1992).

(List continued on next page.)

Primary Examiner—Christina Chan
Assistant Examiner—Michail A. Belyavskyi
(74) Attorney, Agent, or Firm—Fish & Richardson PC

(57) ABSTRACT

Purified DNA including a sequence encoding an Ikaros protein.

12 Claims, 20 Drawing Sheets

OTHER PUBLICATIONS

Georgopoulos, K. et al. "Ikaros, an Early Lymphoid–Specific Transcription Factor and a Putative Mediator For T Cell Commitment" *Science* 258: 808–812 (Oct. 1992).

Georgopoulos, K. et al. "A T cell–specific enhancer is located in a DNase I–hypersensitive area at the 3' end of the CD3–δ gene" *The EMBO Journal* 7(8): 2401–2407 (Aug. 1988).

Georgopoulos, K. et al. "Tissue–specific nuclear factors mediate expression of the CD3δ gene during T cell development" *The EMBO Journal* 9(1): 109–115 (Jan. 1990).

Godfrey, D.I. and A. Zlotnik "Control points in early T–cell development" *Immunology Today* 14(11): 547–553 (1993).

Gogos, J. A. et al. "Sequence Discrimination by Alternatively Spliced Isoforms of a DNA Binding Zinc Finger Domain" *Science* 257: 1951–1955 (1992).

Hackett, Jr., J. et al. "Origin and Differentiation of Natural Killer Cells" *The Journal of Immunology* 136(8): 3124–3131 (1986).

Hackett, Jr., J. et al. "Transplantable progenitors of natural killer cells are distinct from those of T and B lymphocytes" *Proc. Natl. Acad. Sci USA* 83: 3427–3431 (1986).

Hardy, R.R. et al. "Resolution and Characterization of Pro–B and Pre–Pro–B Cell Stages in Normal Mouse Bone Marrow" *J. Exp. Med.* 173: 1213–1225 (May 1991).

Havran, W.L. and J.P. Allison. "Developmentally ordered appearance of thymocytes expressing different T–cells antigen receptors" *Nature* 335: 443–445 (1988).

Havran, W.L. and J.P. Allision "Origin of Thy–1+ dendritic epidermal cells of adult mice from fetal thymic precursors" *Nature* 334: 68–70 (1990).

Havran, W.L. et al. "Limited diversity of T–cell receptor γ–chain expression of murine Thy–1+dendritic epidermal cells revealed by Vγ3–specific monoclonal antibody" *Proc. Natl. Acad. Sci. USA* 86: 4185–4189 (1989).

Haynes, B. et al. "Ontogeny of T–cell precursors: a model for the initial stages of human T–cell development" *Immunology Today* 10(3): 87–90 (1989).

Hestdal, K. et al. "Characterization and Regulation of RB6–8C5 Antigen Expression on Murine Bone Marrow Cells" *J. Immunol.* 147(1): 22–28 (Jul. 1, 1991).

Ho, I.–C. et al. "Human GATA–3: a lineage–restricted transcription factor that regulates the expression of the T cell receptor β gene" *The EMBO Journal* 10(5): 1187–1192 (1991).

Ho, I.–C. et al. "Sequence–Specific Binding of Human Ets–1 to the T Cell Receptor β Gene Enhancer" *Science* 250: 814–818 (1990).

Hsu, T. et al. "Multiple Zinc Finger Forms Resulting from Developmentally Regulated Alternative Splicing of a Transcription Factor Gene" *Science* 257: 1946–1950 (1992).

Ikuta, K. et al. "A Developmental Switch in Thymic Lymphocyte Maturation Potential Occurs at the Level of Hematopoietic Stem Cells" *Cell* 62: 863–874 (1990).

Ikuta, K. et al. "Lymphocyte Development From Stem Cells" *Annu. Rev. Immunol.* 10: 759–783 (1992).

Jiang, J. and M. Levine "Binding Affinities and Cooperative Interactions with bHLH Activators Delimit Threshold Responses to the Dorsal Gradient Morphogen" *Cell* 72: 741–752 (1993).

Juhlin, L. and W.B. Shelley "New Staining Techniques for the Langerhans Cell" *Acta Dermatovener* 57: 289–296 (1977).

Kang, S.–M. et al. "NF–κB Subunit Regulation in Nontransformed CD4+ T Lymphocytes" *Science* 256: 1452–1456 (1992).

Karasuyama, H. et al. "The Expression of $V_{pre-B}$/γ5 Surrogate Light Chain in Early Bone Marrow Precursor B Cells of Normal and B Cell–Deficient Mutant Mice" *Cell* 77: 133–143 (Apr. 8, 1994).

Lagasse, E. and I.L. Weissman "BCL–2 Transgene Inhibits Neutrophils Cell Death But Not Their Engulfment By Microphages" *J. Biochem.* 0(Suppl. 17D): 168 (Mar. 13–31 1993).

Leiden, J.M. "Transcriptional regulation during T–cell development: The β TCR gene as a molecular model" *Immunology Today* 13(1): 22–30 (Jan. 1992).

Lenardo, M.J. and D. Baltimore "NF–κB: A Pleiotropic Mediator of Inducible and Tissue–Specific Gene Control" *Cell* 58: 227–229 (1989).

Li, E. et al. "Targeted Mutation of the DNA Methyltransferase Gene Results in Embryonic Lethality" *Cell* 69: 915–926 (1992).

Li, Y.–S. et al. "The Regulated Expression of B Lineage Associated Genes During B Cell Differentiation in Bone Marrow and Fetal Liver" *J. Exp. Med.* 178: 951–960 (1993).

Liang, P. et al. "Distribution and cloning of eukaryotic mRNAs by means of differential display: refinements and optimization" *Nucleic Acids Research* 21(14): 3269–3275 (1993).

Mann, R. et al., "Construction of a Retrovirus Packaging Mutant and Its Use to Produce Helper–Free Defective Retrovirus" *Cell* 33: 153–159 (1993).

Martin, D.I.K. et al. "Expression of an erythroid transcription factor in megakaryocytic and mast cell lineages" *Nature* 344: 444–447 (1990).

McDonnell, T.J. and S.J. Korsmeyer "Progression from lymphoid hyperplasia to high–grade malignant lymphoma in mice transgenic for the t(14;18)" *Nature* 349: 254–256 (1991).

McDonnell, T.J. et al. "bcl–2–Immunoglobulin Transgenic Mice Demonstrate Extended B Cell Survival and Follicular Lymphoproliferation" *Cell* 57: 79–88 (1989).

Metcalf, D. "The molecular control of cell division, differentation commitment and maturation in haemopoietic cells" *Nature* 339: 27–30 (1989).

Mombaerts, P. et al. "RAG–1–Deficient Mice Have No Mature B and T Lymphocytes" *Cell* 68: 869–877 (1992).

Mucenski, M.L. et al. "A Functional c–*myb* Gene is Required for Normal Murine Fetal Hepatic Hematopoiesis" *Cell* 65: 677–689 (1991).

Oltvai, Z.N. et al. "Bcl–2 Heterodimerizes In Vivo with a Conserved Homolog, Bax, That Accelerates Programmed Cell Death" *Cell* 74: 609–619 (1993).

Oosterwegel, M. et al. "Cloning of Murine TCF–1, a T Cell–specific Transcription Factor Interacting with Functional Motifs in the $CD3_{-3}$ and T Cell Receptor β Enhancers" *J. Exp. Med.* 173: 1133–1142 (May 1991).

Oosterwegel, M. et al. "Differential expression of the HMG box factors *TCF–1* and *LEF–1* during murine embryogenesis" *Development* 118: 439–448 (1993).

Philpott, K.L. et al. "Lymophoid Development in Mice Congenitally Lacking T Cell Receptor αβ–Expressing Cells" *Science* 256: 1448–1452 (Jun. 5, 1992).

Raulet, D.H. et al. "Control of γδ T–Cell Development" *Immunological Reviews* 120: 185–204 (1991).

Read, D. and J.L. Manley "Alternatively spliced transcripts of the *Drosophila tramtrack* gene encode zinc finger proteins with distinct DNA binding specificities" *The EMBO Journal* 11(3): 1035–1044 (1992).

Rodewald, H.–R. et al. "A Population of Early Fetal Thymocytes Expressing $Fc_{65}RII/III$ Contains Precursors of T Lymphocytes and Natural Killer Cells" *Cell* 69: 139–150 (1992).

Rolink, A. and F. Melchers "Molecular and Cellular Origins of B Lymphocyte Diversity" *Cell* 66: 1061–1064 (1991).

Rudnicki, M.A. et al. "Inactivation of *MyoD* in Mice Leads to Up–Regulation of the Myogenenic HLH Gene *Myf–5* and Results in Apparently Normal Muscle Development" *Cell* 71: 383–390 (1992).

Sawyers, C.L. et al. "Leukemia and the Disruption of Normal Hematopoieis" *Cell* 64: 337–350 (1991).

Sentman, C.L. et al. "bcl–2 Inhibits Muliple Forms of Apoptosis but Not Negative Selection in Thymocytes" *Cell* 67: 879–888 (1991).

Shinkai, Y. et al. "RAG–2–Deficient Mice Lack Mature Lymphocytes Owing to Inability to Initiate V(D)J Rearrangement" *Cell* 68: 855–867 (1992).

Singh, H. et al., "Molecular Cloning of an Enhancer Binding Protein: Isolation by Screening of an Expression Library with a Recognition Site DNA" *Cell* 52: 415–423 (Feb. 12, 1988).

Skeath, J.B. et al. "Gene regulation in two dimensions" the proneural *achaete* and *scute* genes are controlled by combinations of axis–patterning genes through a common intergenic control region *Genes & Development* 6: 2606–2619 (1992).

Spangrude, G.J. "Enrichment of murine haemopoietic stem cells: diverging roads" *Immunology Today* 10(10): 344–350 (1989).

Spangrude, G.J. et al. "Purification and Characterization of Mouse Hematopoeitic Stem Cells" *Science* 241: 58–62 (Jul. 1, 1988).

Spanopoulou, E. et al. "Functional immunoglobulin transgenes guide ordered B–cell differentiation in Rag–1–deficient mice" *Genes & Development* 8: 1030–1042 (1994).

Travis, A. et al. "LEF–1, a gene encoding a lymphoid–specific with protein, an HMG domain, regulates T–cell receptor α enhancer function" *Genes & Development* 5: 880–894 (1991).

Turner, Jr., C.A. et al. "Blimp–1, a Novel Zinc Finger–Containing Protein that Can Drive the Maturation of B Lymphocytes into Immunoglobulin–Secreting Cells" *Cell* 77: 297–306 (Apr. 22, 1994).

van de Wetering, M. et al. "Identification and cloning of TCF–1, a T lymphocyte–specific transcription factor containing a sequence–specific HMG box" *The EMBO Journal* 10(1): 123–132 (1991).

von Boehmer, H. "The Development Biology of T Lymphocytes" *Ann. Rev. Immunol.* 6: 309–326 (1988).

Waterman, M.L. et al. "A thymus–specific member of the HMG protein family regulates the human T cell receptor Cα enhancer" *Genes & Development* 5: 656–669 (1991).

Weintraub, H. "The MyoD Family and Myogenesis: Redundancy, Networks, and Thresholds" *Cell* 75: 1241–1244 (Dec. 31, 1993).

Xu, Y. et al. "LH–2: A LIM/homeodomain gene expressed in developing lymphocytes and neural cells" *Proc. Natl. Acad. Sci. USA* 90: 227–231 (1993).

Yokohama, W.M. "Flow Cytometry Analysis Using the Becton Dickinson FACScan" in *Current Protocols in Immunology*, J.E. Coligan et al. (Eds.) Brooklyn, NY: Greene Publishing Associates, 5.4.1–5.4.14 (1992).

Zervos, A.S. et al. "Mxi1, a Protein that Specifically Interacts with Max to Bind Myc–Max Recognition Sites" *Cell* 72: 223–232 (1993).

* cited by examiner

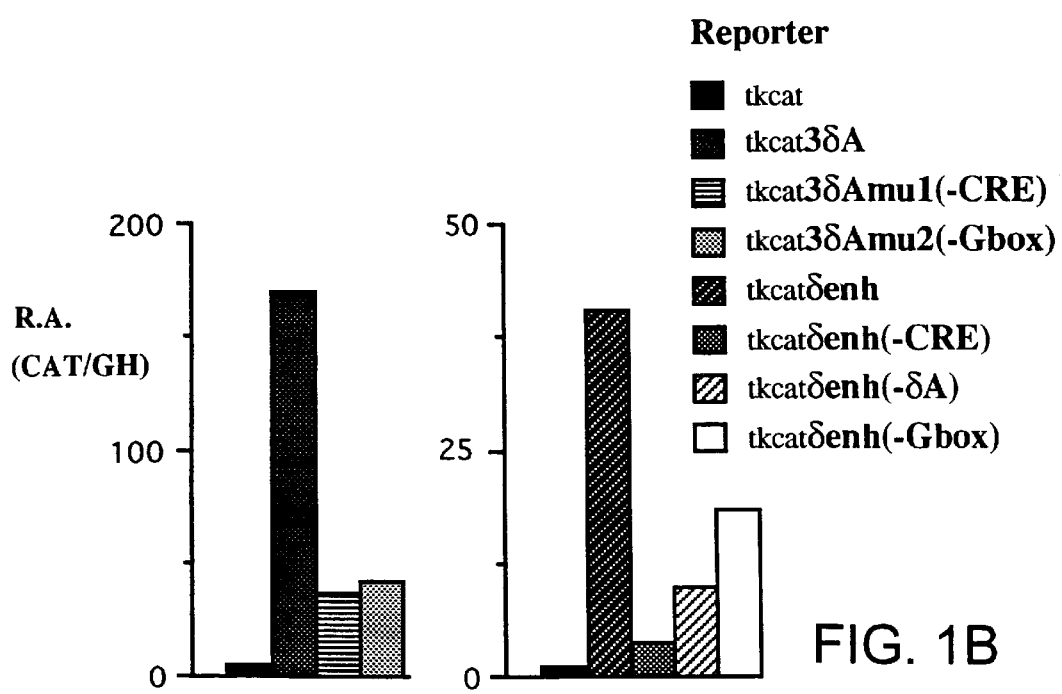
FIG. 1A
FIG. 1B
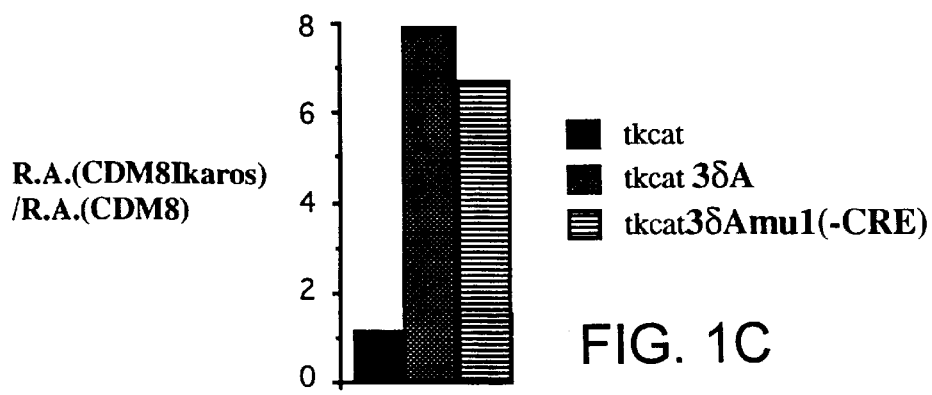
FIG. 1C

```
AATTCGTTCT ACCTTCTCTG AACCCCAGTG GTGTGTCAAG GCCGGACTGG GAGCTTGGGG     60

GAAGAGGAAG AGGAAGAGGA ATCTGCGGCT CATCCAGGGA TCAGGGTCCT TCCCAAGTGG    120

CCACTCAGAG GGGACTCAGA GCAAGTCTAG ATTTGTGTGG CAGAGAGAGA CAGCTCTCGT    180

TTGGCCTTGG GGAGGCACAA GTCTGTTGAT AACCTGAAGA CA                      222
```

```
ATG GAT GTC GAT GAG GGT CAA GAC ATG TCC CAA GTT TCA GGA AAG GAG     270
Met Asp Val Asp Glu Gly Gln Asp Met Ser Gln Val Ser Gly Lys Glu
 1            5                  10                 15

AGC CCC CCA GTC AGT GAC ACT CCA GAT GAA GGG GAT GAG CCC ATG CCT     318
Ser Pro Pro Val Ser Asp Thr Pro Asp Glu Gly Asp Glu Pro Met Pro
              20                  25                 30

GTC CCT GAG GAC CTG TCC ACT ACC TCT GGA GCA CAG CAG AAC TCC AAG     366
Val Pro Glu Asp Leu Ser Thr Thr Ser Gly Ala Gln Gln Asn Ser Lys
         35                  40                  45

AGT GAT CGA GGC ATG GGT GAA CGG CCT TTC CAG TGC AAC CAG TCT GGG     414
Ser Asp Arg Gly Met Gly Glu Arg Pro Phe Gln Cys Asn Gln Ser Gly
    50                  55                  60

GCC TCC TTT ACC CAG AAA GGC AAC CTC CTG CGG CAC ATC AAG CTG CAC     462
Ala Ser Phe Thr Gln Lys Gly Asn Leu Leu Arg His Ile Lys Leu His
65              70                  75                  80

TCG GGT GAG AAG CCC TTC AAA TGC CAT CTT TGC AAC TAT GCC TGC CGC     510
Ser Gly Glu Lys Pro Phe Lys Cys His Leu Cys Asn Tyr Ala Cys Arg
                85                  90                  95

CGG AGG GAC GCC CTC ACC GGC CAC CTG AGG ACG CAC TCC GTT GGT AAG     558
Arg Arg Asp Ala Leu Thr Gly His Leu Arg Thr His Ser Val Gly Lys
            100                 105                 110

CCT CAC AAA TGT GGA TAT TGT GGC CGG AGC TAT AAA CAG CGA AGC TCT     606
Pro His Lys Cys Gly Tyr Cys Gly Arg Ser Tyr Lys Gln Arg Ser Ser
        115                 120                 125

TTA GAG GAG CAT AAA GAG CGA TGC CAC AAC TAC TTG GAA AGC ATG GGC     654
Leu Glu Glu His Lys Glu Arg Cys His Asn Tyr Leu Glu Ser Met Gly
    130                 135                 140

CTT CCG GGC GTG TGC CCA GTC ATT AAG GAA GAA ACT AAC CAC AAC GAG     702
Leu Pro Gly Val Cys Pro Val Ile Lys Glu Glu Thr Asn His Asn Glu
145                 150                 155                 160

ATG GCA GAA GAC CTG TGC AAG ATA GGA GCA GAG AGG TCC CTT GTC CTG     750
Met Ala Glu Asp Leu Cys Lys Ile Gly Ala Glu Arg Ser Leu Val Leu
                165                 170                 175

GAC AGG CTG GCA AGC AAT GTC GCC AAA CGT AAG AGC TCT ATG CCT CAG     798
Asp Arg Leu Ala Ser Asn Val Ala Lys Arg Lys Ser Ser Met Pro Gln
            180                 185                 190
```

FIG. 2A

```
AAA TTT CTT GGA GAC AAG TGC CTG TCA GAC ATG CCC TAT GAC AGT GCC    846
Lys Phe Leu Gly Asp Lys Cys Leu Ser Asp Met Pro Tyr Asp Ser Ala
        195             200             205

AAC TAT GAG AAG GAG GAT ATG ATG ACA TCC CAC GTG ATG GAC CAG GCC    894
Asn Tyr Glu Lys Glu Asp Met Met Thr Ser His Val Met Asp Gln Ala
        210             215             220

ATC AAC AAT GCC ATC AAC TAC CTG GGG GCT GAG TCC CTG CGC CCA TTG    942
Ile Asn Asn Ala Ile Asn Tyr Leu Gly Ala Glu Ser Leu Arg Pro Leu
225             230             235             240

GTG CAG ACA CCC CCC GGT AGC TCC GAG GTG GTG CCA GTC ATC AGC TCC    990
Val Gln Thr Pro Pro Gly Ser Ser Glu Val Val Pro Val Ile Ser Ser
            245             250             255

ATG TAC CAG CTG CAC AAG CCC CCC TCA GAT GGC CCC CCA CGG TCC AAC   1038
Met Tyr Gln Leu His Lys Pro Pro Ser Asp Gly Pro Pro Arg Ser Asn
        260             265             270

CAT TCA GCA CAG GAC GCC GTG GAT AAC TTG CTG CTG CTG TCC AAG GCC   1086
His Ser Ala Gln Asp Ala Val Asp Asn Leu Leu Leu Leu Ser Lys Ala
        275             280             285

AAG TCT GTG TCA TCG GAG CGA GAG GCC TCC CCG AGC AAC AGC TGC CAA   1134
Lys Ser Val Ser Ser Glu Arg Glu Ala Ser Pro Ser Asn Ser Cys Gln
290             295             300

GAC TCC ACA GAT ACA GAG AGC AAC GCG GAG GAA CAG CGC AGC GGC CTT   1182
Asp Ser Thr Asp Thr Glu Ser Asn Ala Glu Glu Gln Arg Ser Gly Leu
305             310             315             320

ATC TAC CTA ACC AAC CAC ATC AAC CCG CAT GCA CGC AAT GGG CTG GCT   1230
Ile Tyr Leu Thr Asn His Ile Asn Pro His Ala Arg Asn Gly Leu Ala
            325             330             335

CTC AAG GAG GAG CAG CGC GCC TAC GAG GTG CTG AGG GCG GCC TCA GAG   1278
Leu Lys Glu Glu Gln Arg Ala Tyr Glu Val Leu Arg Ala Ala Ser Glu
        340             345             350

AAC TCG CAG GAT GCC TTC CGT GTG GTC AGC ACG AGT GGC GAG CAG CTG   1326
Asn Ser Gln Asp Ala Phe Arg Val Val Ser Thr Ser Gly Glu Gln Leu
        355             360             365

AAG GTG TAC AAG TGC GAA CAC TGC CGC GTG CTC TTC CTG GAT CAC GTC   1374
Lys Val Tyr Lys Cys Glu His Cys Arg Val Leu Phe Leu Asp His Val
        370             375             380

ATG TAT ACC ATT CAC ATG GGC TGC CAT GGC TGC CAT GGC TTT CGG GAT   1422
Met Tyr Thr Ile His Met Gly Cys His Gly Cys His Gly Phe Arg Asp
385             390             395             400

CCC TTT GAG TGT AAC ATG TGT GGT TAT CAC AGC CAG GAC AGG TAC GAG   1470
Pro Phe Glu Cys Asn Met Cys Gly Tyr His Ser Gln Asp Arg Tyr Glu
                405             410             415
```

FIG. 2B

```
TTC TCA TCC CAT ATC ACG CGG GGG GAG CAT CGT TAC CAC CTG AGC        1515
Phe Ser Ser His Ile Thr Arg Gly Glu His Arg Tyr His Leu Ser
             420             425                 430

TAAACCCAGC CAGGCCCCAC TGAAGCACAA AGATAGCTGG TTATGCCTCC TTCCCGGCAG  1575

CTGGACCCAC AGCGGACAAT GTGGGAGTGG ATTTGCAGGC AGCATTTGTT CTTTTATGTT  1635

GGTTGTTTGG CGTTTCATTT GCGTTGGAAG ATAAGTTTTT AATGTTAGTG ACAGGATTGC  1695

ATTGCATCAG CAACATTCAC AACATCCATC CTTCTAGCCA GTTTTGTTCA CTGGTAGCTG  1755

AGGTTTCCCG GATATGTGGC TTCCTAACAC TCT                               1788
```

(SEQ.ID.NO:2)

FIG. 2C

```
AAT GTT AAA GTA GAG ACT CAG AGT GAT GAA GAG AAT GGG CGT GCC TGT      48
Asn Val Lys Val Glu Thr Gln Ser Asp Glu Glu Asn Gly Arg Ala Cys
 1               5                  10                  15

GAA ATG AAT GGG GAA GAA TGT GCG GAG GAT TTA CGA ATG CTT GAT GCC      96
Glu Met Asn Gly Glu Glu Cys Ala Glu Asp Leu Arg Met Leu Asp Ala
                20                  25                  30

TCG GGA GAG AAA ATG AAT GGC TCC CAC AGG GAC CAA GGC AGC TCG GCT     144
Ser Gly Glu Lys Met Asn Gly Ser His Arg Asp Gln Gly Ser Ser Ala
            35                  40                  45

TTG TCG GGA GTT GGA GGC ATT CGA CTT CCT AAC GGA AAA CTA AAG TGT     192
Leu Ser Gly Val Gly Gly Ile Arg Leu Pro Asn Gly Lys Leu Lys Cys
        50                  55                  60

GAT ATC TGT GGG ATC ATT TGC ATC GGG CCC AAT GTG CTC ATG GTT CAC     240
Asp Ile Cys Gly Ile Ile Cys Ile Gly Pro Asn Val Leu Met Val His
65                  70                  75                  80

AAA AGA AGC CAC ACT GGA GAA CGG CCC TTC CAG TGC AAT CAG TGC GGG     288
Lys Arg Ser His Thr Gly Glu Arg Pro Phe Gln Cys Asn Gln Cys Gly
                85                  90                  95

GCC TCA TTC ACC CAG AAG GGC AAC CTG CTC CGG CAC ATC AAG CTG CAT     336
Ala Ser Phe Thr Gln Lys Gly Asn Leu Leu Arg His Ile Lys Leu His
            100                 105                 110

TCC GGG GAG AAG CCC TTC AAA TGC CAC CTC TGC AAC TAC GCC TGC CGC     384
Ser Gly Glu Lys Pro Phe Lys Cys His Leu Cys Asn Tyr Ala Cys Arg
        115                 120                 125

CGG AGG GAC GCC CTC ACT GGC CAC CTG AGG ACG CAC TCC GTT GGT AAA     432
Arg Arg Asp Ala Leu Thr Gly His Leu Arg Thr His Ser Val Gly Lys
    130                 135                 140

CCT CAC AAA TGT GGA TAT TGT GGC CGA AGC TAT AAA CAG CGA ACG TCT     480
Pro His Lys Cys Gly Tyr Cys Gly Arg Ser Tyr Lys Gln Arg Thr Ser
145                 150                 155                 160

TTA GAG GAA CAT AAA GAG CGC TGC CAC AAC TAC TTG GAA AGC ATG GGC     528
Leu Glu Glu His Lys Glu Arg Cys His Asn Tyr Leu Glu Ser Met Gly
                165                 170                 175

CTT CCG GGC ACA CTG TAC CCA GTC ATT AAA GAA GAA ACT AAG CAC AGT     576
Leu Pro Gly Thr Leu Tyr Pro Val Ile Lys Glu Glu Thr Lys His Ser
            180                 185                 190

GAA ATG GCA GAA GAC CTG TGC AAG ATA GGA TCA GAG AGA TCT CTC GTG     624
Glu Met Ala Glu Asp Leu Cys Lys Ile Gly Ser Glu Arg Ser Leu Val
        195                 200                 205

CTG GAC AGA CTA GCA AGT AAT GTC GCC AAA CGT AAG AGC TCT ATG CCT     672
Leu Asp Arg Leu Ala Ser Asn Val Ala Lys Arg Lys Ser Ser Met Pro
    210                 215                 220

CAG AAA TTT CTT GGG GAC AAG GGC CTG TCC GAC ACG CCC TAC GAC AGT     720
Gln Lys Phe Leu Gly Asp Lys Gly Leu Ser Asp Thr Pro Tyr Asp Ser
225                 230                 235                 240
```

FIG. 3A

```
GCC ACG TAC GAG AAG GAG AAC GAA ATG ATG AAG TCC CAC GTG ATG GAC        768
Ala Thr Tyr Glu Lys Glu Asn Glu Met Met Lys Ser His Val Met Asp
                245                 250                 255

CAA GCC ATC AAC AAC GCC ATC AAC TAC CTG GGG GCC GAG TCC CTG CGC        816
Gln Ala Ile Asn Asn Ala Ile Asn Tyr Leu Gly Ala Glu Ser Leu Arg
                260                 265                 270

CCG CTG GTG CAG ACG CCC CCG GGC GGT TCC GAG GTG GTC CCG GTC ATC        864
Pro Leu Val Gln Thr Pro Pro Gly Gly Ser Glu Val Val Pro Val Ile
            275                 280                 285

AGC CCG ATG TAC CAG CTG CAC AGG CGC TCG GAG GGC ACC CCG CGC TCC        912
Ser Pro Met Tyr Gln Leu His Arg Arg Ser Glu Gly Thr Pro Arg Ser
        290                 295                 300

AAC CAC TCG GCC CAG GAC AGC GCC GTG GAG TAC CTG CTG CTG CTC TCC        960
Asn His Ser Ala Gln Asp Ser Ala Val Glu Tyr Leu Leu Leu Leu Ser
305                 310                 315                 320

AAG GCC AAG TTG GTG CCC TCG GAG CGC GAG GCG TCC CCG AGC AAC AGC       1008
Lys Ala Lys Leu Val Pro Ser Glu Arg Glu Ala Ser Pro Ser Asn Ser
                325                 330                 335

TGC CAA GAC TCC ACG GAC ACC GAG AGC AAC AAC GAG GAG CAG CGC AGC       1056
Cys Gln Asp Ser Thr Asp Thr Glu Ser Asn Asn Glu Glu Gln Arg Ser
                340                 345                 350

GGT CTT ATC TAC CTG ACC AAC CAC ATC GCC CGA CGC GCG CAA CGC GTG       1104
Gly Leu Ile Tyr Leu Thr Asn His Ile Ala Arg Arg Ala Gln Arg Val
            355                 360                 365

TCG CTC AAG GAG GAG CAC CGC GCC TAC GAC CTG CTG CGC GCC GCC TCC       1152
Ser Leu Lys Glu Glu His Arg Ala Tyr Asp Leu Leu Arg Ala Ala Ser
        370                 375                 380

GAG AAC TCG CAG GAC GCG CTC CGC GTG GTC AGC ACC AGC GGG GAG CAG       1200
Glu Asn Ser Gln Asp Ala Leu Arg Val Val Ser Thr Ser Gly Glu Gln
385                 390                 395                 400

ATG AAG GTG TAC AAG TGC GAA CAC TGC CGG GTG CTC TTC CTG GAT CAC       1248
Met Lys Val Tyr Lys Cys Glu His Cys Arg Val Leu Phe Leu Asp His
                405                 410                 415

GTC ATG TAC ACC ATC CAC ATG GGC TGC CAC GGC TTC CGT GAT CCT TTT       1296
Val Met Tyr Thr Ile His Met Gly Cys His Gly Phe Arg Asp Pro Phe
                420                 425                 430

GAG TGC AAC ATG TGC GGC TAC CAC AGC CAG GAC CGG TAC GAG TTC TCG       1344
Glu Cys Asn Met Cys Gly Tyr His Ser Gln Asp Arg Tyr Glu Phe Ser
                435                 440                 445

TCG CAC ATA ACG CGA GGG GAG CAC CGC TTC CAC ATG AGC TAA              1386
Ser His Ile Thr Arg Gly Glu His Arg Phe His Met Ser
450                 455                 460
```

FIG. 3B (SEQ.ID.NO: 3)

↓Ex1/2
MDVDEGQDMS QVSGKESPPV SDTPDEGDEP MPVPEDLSTT SGAQQNSKSD RGMASNVKVE
                                                              ↓Ex3
TQSDEENGRA CEMNGEECAE DLRMLDASGE KMNGSHRDQG SSALSGVGGI RLPNGKLKCD
         F1                            ↓Ex4             F2
ICGIVCIGPN VLMVHKRSHT GERPFQCNQC GASFTQKGNL LRHIKLHSGE KPFKCHLCNY
                ↓Ex5         F4                                    Ex6
ACRRRDALTG HLRTHSVGKP HKCGYCGRSY KORSSLEEHK ERCHNYLESM GLPGMYPVIK
       F3                                          ↓Ex7
EETNHNEMAE DLCKIGAERS LVLDRLASNV AKRKSSMPQK FLGDKCLSDM PYDSANYEKE

DMMTSHVMDQ AINNAINYLG AESLRPLVQT PPGSSEVVPV ISSMYQLHKP PSDGPPRSNH

SAQDAVDNLL LLSKAKSVSS EREASPSNSC QDSTDTESNA EEQRSGLIYL TNHINPHARN

GLALKEEQRA YEVLRAASEN SQDAFRVVST SGEQLKVYKC EHCRVLFLDH VMYTIHMGCH
                                                  F5

GCHGFRDPFE CNMCGYHSOD RYEFSSHITR GEHRYHLS (SEQ ID NO: 5)   FIG. 4
                              F6

Oligo1/2 IK-1/IK-2/IK-4
Oligo3/4 IK-1/IK-3/IK-5

FIG. 9A

```
       ↓Ex3
mIk-1  Ala Ser Asn Val Lys Val Glu Thr Gln Ser Asp Glu Glu Asn Gly Arg Ala Cys Glu Met Asn Gly Glu Glu Cys Ala Glu
hIk-1  Ala Ser Asn Val Lys Val Glu Thr Gln Ser Asp Glu Glu Asn Gly Arg Ala Cys Glu Met Asn Gly Glu Glu Cys Ala Glu

Asp Leu Arg Met Leu Asp Ala Ser Gly Glu Lys Met Asn Gly Ser His Arg Asp Gln Gly Ser Ser Ala Leu Ser Gly Val Gly Gly
       Asp Leu Arg Met Leu Asp Ala Ser Gly Glu Lys Met Asn Gly Ser His Arg Asp Gln Gly Ser Ser Ala Leu Ser Gly Val Gly Gly

Ile Arg Leu Pro Asn Gly Lys Leu Lys Cys Asp Ile Cys Gly Ile Val Cys Ile Gly Pro Asn Val Leu Met Val His Lys Arg Ser
       Ile Arg Leu Pro Asn Gly Lys Leu Lys Cys Asp Ile Cys Gly Ile Ile Cys Ile Gly Pro Asn Val Leu Met Val His Lys Arg Ser
       ↓Ex4
       His Thr Gly Glu Arg Pro Phe Gln Cys Asn Gln Cys Gly Ala Ser Phe Thr Gln Lys Gly Asn Leu Leu Arg His Ile Lys Leu His
       His Thr Gly Glu Arg Pro Phe Gln Cys Asn Gln Cys Gly Ala Ser Phe Thr Gln Lys Gly Asn Leu Leu Arg His Ile Lys Leu His

Ser Gly Glu Lys Pro Phe Lys Cys His Leu Cys Asn Tyr Ala Cys Arg Arg Arg Asp Ala Leu Thr Gly His Leu Arg Thr His Ser
       Ser Gly Glu Lys Pro Phe Lys Cys His Leu Cys Asn Tyr Ala Cys Arg Arg Arg Asp Ala Leu Thr Gly His Leu Arg Thr His Ser
       ↓Ex5
       Val Gly Lys Pro His Lys Cys Gly Tyr Cys Gly Arg Ser Tyr Lys Gln Arg Ser Ser Leu Glu Glu His Lys Glu Arg Cys His Asn
       Val Gly Lys Pro His Lys Cys Gly Tyr Cys Gly Arg Ser Tyr Lys Gln Arg Thr Ser Leu Arg Thr Gln Lys Glu Arg Cys His Asn
                                              ↓Ex6
       Tyr Leu Glu Ser Met Gly Leu Pro Gly + Val Cys Pro Val Ile Lys Glu Glu Thr Asn His Ser Glu Met Ala Glu Asp Leu Cys
       Tyr Leu Glu Ser Met Gly Leu Pro Gly Thr Leu Tyr Pro Val Ile Lys Glu Glu Thr Lys His Ser Glu Met Ala Glu Asp Leu Cys

Lys Ile Gly Ala Glu Arg Ser Leu Val Leu Asp Arg Leu Ala Ser Asn Val Ala Lys Arg Lys Ser Ser Met Pro Gln Lys Phe Leu
       Lys Ile Gly Ser Glu Arg Ser Leu Val Leu Asp Arg Leu Ala Ser Asn Val Ala Lys Arg Lys Ser Ser Met Pro Gln Lys Phe Leu
```

↓Ex7
Gly Asp Lys Cys Leu Ser Asp Met Pro Tyr Asp Ser Ala Asn Tyr Glu Lys Glu * Asp Met Met Thr Ser His Val Met Asp Gln
Gly Asp Lys Gly Leu Ser Asp Thr Pro Tyr Asp Ser Ala Thr Tyr Glu Lys Glu Asn Glu Met Met Lys Ser His Val Met Asp Gln

Ala Ile Asn Asn Ala Ile Asn Tyr Leu Gly Ala Glu Ser Leu Arg Pro Leu Val Gln Thr Pro Pro Gly Ser Ser Glu Val Val Pro
Ala Ile Asn Asn Ala Ile Asn Tyr Leu Gly Ala Glu Ser Leu Arg Pro Leu Val Gln Thr Pro Pro Gly Ser Gly Ser Glu Val Val Pro

Val Ile Ser Ser Met Tyr Gln Leu His Lys Pro Pro Ser Asp Gly Pro Pro Arg Ser Asn His Ser Ala Gln Asp * Ala Val Asp
Val Ile Ser Pro Met Tyr Gln Leu His Arg * Arg Ser Glu Gly Thr Pro Arg Ser Asn His Ser Ala Gln Asp Ser Ala Val Glu

Asn Leu Leu Leu Leu Ser Lys Ala Lys Ser Val Ser Ser Glu Arg Glu Ala Ser Pro Ser Asn Ser Cys Gln Asp Ser Thr Asp Thr
Tyr Leu Leu Leu Leu Ser Lys Ala Lys Leu Val Pro Ser Glu Arg Glu Ala Ala Ser Pro Ser Asn Ser Cys Gln Asp Ser Thr Asp Thr

Glu Ser Asn Ala Glu Gln Gln Arg Ser Gly Leu Ile Tyr Leu Thr Asn His Ile Asn Pro His Ala Arg Asn Gly Leu Ala Leu Lys
Glu Ser Asn Asn Glu Gln Gln Arg Ser Gly Leu Ile Tyr Leu Thr Asn His Ile Ala Arg Ala Gln Arg * Val Ser Leu Lys

Glu Gln Arg Ala Tyr Glu Val Leu Arg Ala Ala Ala Ser Gln Asp Ala Phe Arg Val Val Ser Thr Ser Gly Glu Gln
Glu Glu His Arg Ala Tyr Asp Leu Arg Leu Leu Arg Ala Ser Gln Asp Ala Leu Arg Val Val Ser Thr Ser Gly Glu Gln

Leu Lys Val Tyr Lys Cys Glu His Cys Arg Val Leu Phe Leu Asp His Val Met Tyr Thr Ile His Met Gly Cys His Gly Glu His
Met Lys Val Tyr Lys Cys Glu His Cys Arg Val Leu Phe Leu Asp His Val Met Tyr Thr Ile His Met * * Gly Cys His

Gly Phe Arg Asp Pro Phe Glu Cys Asn Met Cys Gly Tyr His Ser Gln Asp Arg Tyr Glu Phe Ser Ser His Ile Thr Arg Gly Glu
Gly Phe Arg Asp Pro Phe Glu Cys Asn Met Cys Gly Tyr His Ser Gln Asp Arg Tyr Glu Phe Ser Ser His Ile Thr Arg Gly Glu

His Arg Tyr His Leu Ser  (SEQ.ID.NO: 5)
His Arg Phe His Met Ser  (SEQ.ID.NO: 3)

FIG. 9B hlk-UE1
```
ACTGATTTAGAGTCCAGTGTCTGGTATAGGTGTGTATTCTCCCTTTCGGTCTATGTCTCATTGTATTGTGTGGGG
AGAAGTGACTTTTTTATAAAAAGAAAAAGGTATATGCATCCCAGCAGAGAACACTGGTTCCACCAGTACCTGCCCT
CATGCCACCCTCTCAAGCCCTTGACCTTGACCATGACCGCCCCAGACTCACACTTCT
``` hlk-UE2
```
GAATTCCGGGCCATTGATGTACACAACCAAATCAAAGCACACCCCAAACTCCGAGTTCCTCTCTGAGCTCACGGCTCTTT
TTAGGCACATATGTCTGCCTATCATTTCTCTATGAGTTCATGAGGTTCAAGGCCTAGTGAGTTCAAGCCGATGATCTTTGGTTG
CCCTACACTTTCCCCAAACCACCGGGCCGGGGGTCCTGTTCTCAGCCGTTTGCATGACTCACCCAGTGAATCCTCACC
AAATCAATTAAGTAGGT
``` hlk-UE3
```
GAATTCCGGCCCTTTGGGGCTGACCCGGGACCCGGGAGCCCGGGGGATTCCAAAGTTTTTCGTGCGCCCCCTCTGGCCCGGAGTTCGGG
CTGAGACCGGCGCCGGCGGAGGGGACTCGGCGACGCAGGACGACCCCTCCTCCGGTCCGCTCTCGCC
CTTCTCGCGGCGCCCGGCGCCGCTCGTACCGGACGCAGCGGATCCGGGGCGGGGCCGAGA
```

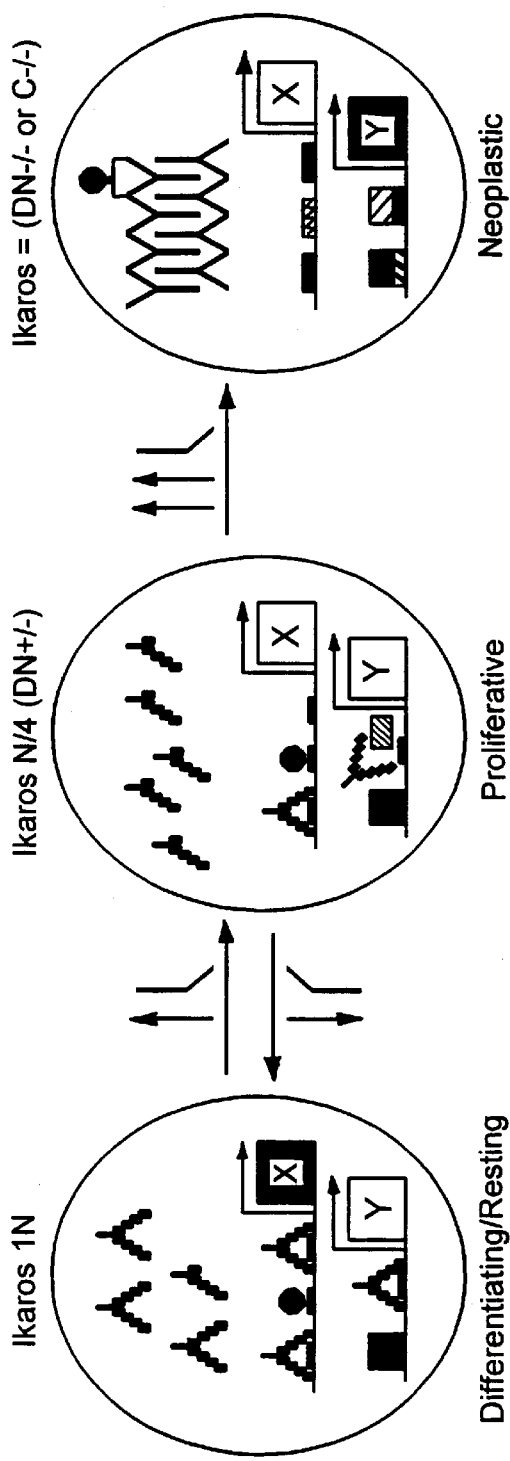

FIG. 14

An inverse correlation between Ikaros activity and thymocyte proliferation

 = Transcriptionally active Ikaros homo-and heterodimers (between Ik-1, Ik-2 and Ik-3)

 = Ikaros isoforms without a DNA binding domain (Ik-5, Ik-6, Ik-7 and Ik-8)

 = Transcriptionally inert Ikaros homo-and heterodimers (between Ik-1, Ik-2, Ik-3 and Ik-5, Ik-6, Ik-7 and Ik-8)

 = Transcription factors with similar DNA binding properties as Ikaros

 = Transcription factors with a distinct DNA binding specifically

X and Y = Ikaros gene targets involved in the regulation of lymphocyte proliferation/differentiation

//

US 6,630,141 B1

ISOLATED ANTIBODY THAT BINDS TO AN IKAROS POLYPEPTIDE

This application is a continuation of U.S. Ser. No. 08/711,417, filed Sep. 5, 1996, now U.S. Pat. No. 6,228,611 which is a continuation-in-part of U.S. Ser. No. 08/238,212, filed May 2, 1994 abandoned which is a continuation-in-part of U.S. Ser. No. 08/121,438, abandoned filed Sep. 14, 1993 which is a continuation-in-part of U.S. Ser. No. 07/946,233, filed Sep. 14, 1992, abandoned all of which are incorporated by reference herein.

BACKGROUND OF THE INVENTION

The invention relates to the Ikaros gene and to the differentiation and generation of T cells.

The generation of the T cell repertoire from a progenitor stem cell proceeds through a differentiation pathway in which the later intrathymic steps are well documented while the early extrathymic events are only poorly characterized. One of the earliest definitive T cell differentiation markers is the CD3δ gene of the CD3/TCR complex.

SUMMARY OF THE INVENTION

The Ikaros gene, a gene active in the early differentiation of lymphocytes, e.g. T cells and B cells, has been discovered. The gene encodes a family of unique zinc finger proteins, the Ikaros proteins. The proteins of the Ikaros family are isoforms which arise from differential splicing of Ikaros gene transcripts. The isoforms of the Ikaros family generally include a common 3' exon (Ikaros exon E7, which includes amino acid residues 283–518 of the mouse Ikaros protein represented by SEQ ID No. 5, and amino acid residues 229–461 of the human Ikaros protein represented by SEQ ID No. 3) but differ in the 5' region. The Ikaros family includes all naturally occurring splicing variants which arise from transcription and processing of the Ikaros gene. Eight such isoforms are described herein. The Ikaros family may also includes other isoforms, including those generated by mutagenesis and/or by in vitro exon shuffling. The naturally occurring Ikaros proteins can bind and activate (to differing extents) the enhancer of the CD3δ gene, and are expressed primarily if not solely in T cells in the adult. The expression pattern of this transcription factor during embryonic development suggests that Ikaros proteins play a role as a genetic switch regulating entry into the T cell lineage. The Ikaros gene is also expressed in the proximal corpus striatum during early embryogenesis in mice.

In general, the invention features, nucleic acid, e.g., DNA, preferably a purified DNA, including (or consisting essentially of) a sequence which encodes a peptide including (or consisting essentially of) one or more Ikaros exons. In preferred embodiments: the Ikaros exon is any of E1/2, E3, E4, E5, E6, or E7; the purified DNA does not encode exon E7.

In other preferred embodiments: the encoded peptide further includes a second Ikaros exon; the second exon is any of E1/2, E3, E4, E5, E6, or E7; the first exon is E7 and the second exon is any of E1/2, E3, E4, E5, E6.

In other preferred embodiments: the encoded peptide further includes a third Ikaros exon; the third exon is any of E1/2, E3, E4, E5, E6, or E7; the first exon is E7, said second exon is E3, and the third exon is E1/2; the peptide is Ikaros isoform 5.

In other preferred embodiments: the encoded peptide further includes a fourth Ikaros exon; the fourth exon is any of E1/2, E3, E4, E5, E6, or E7; the first exon is E7, the second exon is E6, the third exon is E4, and the fourth exon is E1/2; the first exon is E7 , the second exon is E4, the third exon is E3, and the fourth exon is E1/2; the peptide is Ikaros isoform 3 or 4.

In other preferred embodiments: the encoded peptide further includes a fifth Ikaros exon; the fifth exon is any of E 1/2, E3, E4, E5, E6, or E7; the first exon is E7, the second exon is E6, the third exon is E5, the fourth exon is E4, and the fifth exon is E1/2; the peptide is Ikaros isoform 2.

In preferred embodiments: the encoded peptide further includes a sixth Ikaros exon; the sixth exon is any of E1/2, E3, E4, E5, E6, or E7; the first exon is E7, the second exon is E6, the third exon is E5, the fourth exon is E4, the fifth exon is E3, and the sixth exon is E1/2; the peptide is Ikaros isoform 1.

In preferred embodiments: the sequence of the encoded Ikaros exon is essentially the same as that of a naturally occurring Ikaros exon, or a fragment thereof having Ikaros activity; the DNA sequence which encodes the Ikaros exon is at least 85%, more preferably at least 90%, yet more preferably at least 95%, and most preferably at least 98 or 99% homologous with DNA encoding a naturally occurring Ikaros exon, or a fragment thereof having Ikaros activity, e.g., Ikaros exon encoded by DNA from any of SEQ ID NOS: 2–8 or SEQ ID NO:165; the sequence which encodes an Ikaros exon hybridizes under high or low stringency to a nucleic acid which encodes a naturally occurring Ikaros exon, or a fragment thereof having Ikaros activity, e.g., an Ikaros exon with the same, or essentially the same, amino acid sequence as an Ikaros exon of any of SEQ ID NOS:2–8 or SEQ ID NO: 153 or SEQ ID NO:165; the amino acid sequence of the encoded Ikaros exon is at least 30, more preferably at least 40, more preferably at least 50, and most preferably at least 60, 80, 100, or 200 amino acid residues in length; the encoded Ikaros amino acid sequence is at least 50% more preferably 60%, more preferably 70%, more preferably 80%, more preferably 90%, and most preferably 95% as long as a naturally occurring Ikaros exon, or a fragment thereof having Ikaros activity; the encoded Ikaros exon is essentially equal in length to a naturally occurring Ikaros exon, or a fragment thereof having Ikaros activity; the amino acid sequence of the encoded Ikaros exon is at least 80%, more preferably at least 85%, yet more preferably at least 90%, yet more preferably at least 95%, and a most preferably at least 98 or 99% homologous with a naturally occurring Ikaros exon sequence, or a fragment thereof having Ikaros activity, e.g., an Ikaros exon sequence of SEQ ID NO:2, SEQ ID NO:3, SEQ ID NO:4, SEQ ID NO:5, SEQ ID NO:6, SEQ ID NO:7, SEQ ID NO: 8 or SEQ ID NO:165; the encoded Ikaros exon amino acid sequence is the same, or essentially the same, as that of a naturally occurring Ikaros exon, or a fragment of the sequence thereof, e.g., an Ikaros exon described in any of SEQ ID NOS:2–8 or SEQ ID NO:165, and the peptide has Ikaros peptide activity.

In preferred embodiments the Ikaros encoding DNA includes at least two exons and: the DNA can be represented by the general formula A-B-C-D-E, wherein A represents Exon 3 or is absent, B represents Exon 4 or is absent, C represents Exon 5 or is absent, D represents Exon 6 or is absent, and E represents Exon 7 or is absent; the polypeptide includes at least two of said exons; the encoded polypeptide includes at least one exon containing a zinc finger domain; the encoded polypeptide includes at least one exon selected from E3, E4 or E5.

In other embodiments, the Ikaros encoding DNA includes a sequence represented by the general formula $\{Ex_1-Ex_2 \ldots$ . $Ex_n$} wherein each of $Ex_1$ through $Ex_n$ represents any of the Ikaros Exons 1/2, 3, 4, 5, 6 or 7, and n is an integer from zero to 10, more preferably an integer from zero to 5, In preferred embodiments: the polypeptide is a combination of 2 or more Ikaros exons, the combination of which may or may not naturally occur; the polypeptide includes at least two of said exons and is represented by the formula $Ex_1$-$Ex_2$; the polypeptide includes at least three of said exons and is represented by the formula $Ex_1$-$Ex_2$-$Ex_3$; the polypeptide includes at least four of said exons and is represented by the formula $Ex_1$-$Ex_2$-$Ex_3$-$Ex_4$; the polypeptide includes at least five of said exons and is represented by the formula $Ex_1$-$Ex_2$-$Ex_3$-$Ex_4$-$Ex_5$; the polypeptide includes at least six of said exons and is represented by the formula $Ex_1$-$Ex_2$-$Ex_3$-$Ex_4$-$Ex_5$-$Ex_6$; the polypeptide includes at least one exon containing a zinc finger domain; the polypeptide includes at least one exon selected from E3, E4 or E5.

In preferred embodiments: the exons in the encoded peptide are arranged in the same relative linear order as found in a naturally occurring isoform, e.g., Ikaros isoform 1, e.g., in a peptide having the exons E3 and E7, E3 is located N-terminal to E7; the linear order of the encoded exons is different from that found in a naturally occurring isoform, e.g., in Ikaros isoform 1, e.g., in a peptide having exons E3, E5, and E7, the direction N-terminal to C-terminal end, is E5, E3, E7; the exons in the encoded peptide differ in one or more of composition (i.e., which exons are present), linear order, or number (i.e., how many exons are present or how many times a given exon is present) from a naturally occurring Ikaros isoform, e.g., from Ikaros isoform 1, 2, 3, 4, 5, 6, 7 or 8; e.g. the Ikaros isoform is generated by in vitro exon shuffling.

In preferred embodiments: the Ikaros polypeptide includes less than 4, 3, 2, or 1 functional N terminal Zinc finger domains (the N terminal Zinc finger domains include domains F1–4, the C terminal Zinc finger domains include domains F1–4); the Ikaros polypeptide includes one or two functional C terminal Zinc finger domains; the Ikaros polypeptide includes less than 4, 3, 2, or 1 functional N terminal Zinc finger domains and includes one or two functional C terminal Zinc finger domains.

In another preferred embodiment: the Ikaros polypeptide includes a point mutation in or a deletion for all or part of the DNA binding region, e.g., a point mutation in, or a deletion for all or part of one or more of F1, F2, F3, or F4; the Ikaros polypeptide includes a mutation in the DNA binding region, e.g., a point mutation in, or a deletion for all or part of one or more of F1, F2, F3, or F4.

Also included in the invention is a composition which includes an Ikaros polypeptide (or a nucleic acid which encodes it) and one or more additional components, e.g., a carrier, diluent, or solvent. The additional component can be one which renders the composition useful for in vitro, in vivo, pharmaceutical, or veterinary use.

In another aspect, the invention features, a peptide, preferably a substantially pure peptide, including (or consisting essentially of) one or more Ikaros exons. In preferred embodiments: the Ikaros exon is E1/2, E3, E4, E5, E6, or E7; the peptide does not include exon E7.

In other preferred embodiments: the peptide further includes a second Ikaros exon; the second exon is any of E1/2, E3, E4, E5, E6, or E7; the first exon is E7 and the second exon is any of E1/2, E3, E4, E5, E6.

In other preferred embodiments: the peptide further includes a third Ikaros exon; the third exon is any of E1/2, E3, E4, E5, E6, or E7; the first exon is E7, the second exon is E3, and the third exon is E1/2; the peptide is Ikaros isoform 5.

In other preferred embodiments: the peptide further includes a fourth Ikaros exon; the fourth exon is any of E1/2, E3, E4, E5, E6, or E7; the first exon is E7, the second exon is E4, the third exon is E3, and the fourth exon is E1/2; the first exon is E7, the second exon is E4, the third exon is E3, and the fourth exon is E1/2; the peptide is Ikaros isoform 3 or 4.

In other preferred embodiments: the peptide further includes a fifth Ikaros exon; the fifth exon is any of E1/2, E3, E4, E5, E6, or E7; the first exon is E7, the second exon is E6, the third exon is E5, the fourth exon is E4, and the fifth exon is E1/2; the peptide is Ikaros Isoform 2.

In other preferred embodiments: the peptide further includes a sixth Ikaros exon; the sixth exon is any of E1/2, E3, E4, E5, E6, or E7; the first exon is E7, the second exon is E6, the third exon is E5, the fourth exon is E4, the fifth exon is E3, and the sixth exon is E1/2; the peptide is Ikaros isoform 1.

In preferred embodiments: the sequence of the Ikaros exon is essentially the same as that of a naturally occurring Ikaros exon, or a fragment thereof having Ikaros activity; the amino acid sequence of the Ikaros exon is such that a nucleic acid sequence which encodes it is at least 85%, more preferably at least 90%, yet more preferably at least 95%, and most preferably at least 98 or 99% homologous with a naturally occurring Ikaros exon, or a fragment thereof having Ikaros activity, e.g., Ikaros having an amino acid sequence represented in any of SEQ ID NOS:2–8 or SEQ ID NO:153 or SEQ ID NO:165; the amino acid sequence of the Ikaros exon is such that a nucleic acid sequence which encodes it hybridizes under high or low stringency to a nucleic acid which encodes a naturally occurring Ikaros exon, or a fragment thereof having Ikaros activity, e.g., an Ikaros exon with the same, or essentially the same, amino acid sequence as an Ikaros exon represented in any of SEQ ID NOS:2–8 or SEQ ID NO:165; the amino acid sequence of the Ikaros exon is at least 30, more preferably at least 40, more preferably at least 50, and most preferably at least 60, 80, 100, or 200 amino acid residues in length; the encoded Ikaros amino acid sequence is at least 50% more preferably 60%, more preferably 70%, more preferably 80%, more preferably 90%, and most preferably 95% as long as a naturally occurring Ikaros exon, or a fragment thereof having Ikaros activity; the Ikaros exon is essentially equal in length to a naturally occurring Ikaros exon; the amino acid sequence of the Ikaros exon is at least 80%, more preferably at least 85%, yet more preferably at least 90%, yet more preferably at least 95%, and a most preferably at least 98 or 99% homologous with a naturally occurring Ikaros exon sequence, or a fragment thereof having Ikaros activity, e.g., an Ikaros exon sequence of SEQ ID NO:2, SEQ ID NO:3, SEQ ID NO:4, SEQ ID NO:5, SEQ ID NO: 6, SEQ ID NO:7, SEQ ID NO:8 or SEQ ID NO:165; the Ikaros exon amino acid sequence is the same, or essentially the same, as that of a naturally occurring Ikaros exon, or a fragment of the sequence thereof, e.g., an Ikaros exon described in any of SEQ ID NOS:2–8 or SEQ ID NO:165; and the peptide has Ikaros peptide activity; the peptide has Ikaros antagonist activity.

In preferred embodiments: the Ikaros protein comprises a polypeptide represented by the general formula A-B-C-D-E, wherein A represents Exon 3 or is absent, B represents Exon 4 or is absent, C represents Exon 5 or is absent, D represents Exon 6 or is absent, and E represents Exon 7 or is absent; the polypeptide includes at least two of said exons; the polypeptide includes at least one exon containing a zinc finger domain; the polypeptide includes at least one exon selected from E3, E4 or E5.

In preferred embodiments: the exons in the peptide are arranged in the same relative linear order as found in a naturally occurring isoform, e.g., in Ikaros isoform 1, e.g., in a peptide having the exons E3 and E7, E3 is located N-terminal to E7; the linear order of the exons is different from that found in a naturally occurring isoform, e.g., in Ikaros isoform 1, e.g., in a peptide having exons E3, E5, and E7, the direction N-terminal to C-terminal end, is E5, E3, E7; the exons in the peptide differ in one or more of composition (i.e., which exons are present), linear order, or number (i.e., how many exons are present or how many times a given exon is present) from a naturally occurring Ikaros isoform, e.g., from Ikaros isoform 1, 2, 3, 4, or 5; e.g. the Ikaros protein is an isoform generated by in vitro exon shuffling.

Another aspect the invention features a DNA, preferably a purified DNA, which includes (or consists essentially of) a DNA sequence encoding an Ikaros peptide, e.g., an Ikaros peptide having Ikaros activity, e.g., Ikaros isoform 1, 2, 3, 4, or 5, or an Ikaros peptide which is an antagonist of an Ikaros activity. In preferred embodiments: the sequence of the encoded Ikaros peptide is essentially the same as the sequence of a naturally occurring Ikaros peptide, or a fragment thereof having Ikaros activity; the DNA sequence is at least 85%, more preferably at least 90%, yet more preferably at least 95%, and most preferably at least 98 or 99% homologous with DNA encoding a naturally occurring Ikaros peptide, or a fragment thereof having Ikaros activity; e.g., with DNA from any of SEQ ID NOS:2–8 or SEQ ID NO:165; the amino acid sequence of the encoded peptide is such that it can be encoded by a nucleic acid which hybridizes under high or low stringency conditions to a nucleic acid which encodes a peptide with the same, or essentially the same, amino acid sequence as the peptide of any of SEQ ID NOS:2–8 or SEQ ID NO:153 or SEQ ID NO:165; the encoded peptide is at least 30, more preferably at least 40, more preferably at least 50, and most preferably at least 60, 80, 100, or 200 amino acid residues in length; the encoded peptide is at least 50% more preferably at least 60%, more preferably 70%, more preferably 80%, more preferably 90%, and most preferably 95% as long as a naturally occurring Ikaros peptide, or a fragment thereof having Ikaros activity; the encoded peptide is essentially the same length as a naturally occurring Ikaros peptide, or a fragment thereof having Ikaros activity; the encoded peptide is at least 80%, more preferably at least 85%, yet more preferably at least 90%, yet more preferably at least 95%, and a most preferably at least 98 or 99% homologous with an amino acid sequence which is the same, or essentially the same, as a naturally occurring Ikaros peptide, or a fragment thereof having Ikaros activity, e.g., the peptide sequence of any of SEQ ID NOS:2–8 or SEQ ID NO:153 or SEQ ID NO:165; and, the amino acid sequence of the peptide is essentially the same as the sequence of a naturally occurring Ikaros peptide, or a fragment thereof having Ikaros activity, e.g., the sequence, described in any of SEQ ID NOS:2–8 or SEQ ID NO: 153 or SEQ ID NO:165.

Another aspect, the invention features a DNA, preferably a purified DNA, which includes (or consists essentially of) a sequence encoding a peptide of 20 or more amino acids in length, the peptide having at least 90% homology with an amino acid sequence which is the same as the amino acid sequence of any of SEQ ID NOS:2–8, or SEQ ID NO:153 or SEQ ID NO:165. In preferred embodiments: the purified DNA encodes a peptide which is at least 30, more preferably at least 40, more preferably at least 50, and most preferably at least 60, 80, 100, or 200, amino acid residues in length; the encoded peptide is at least 50% more preferably at least 60%, more preferably 70%, more preferably 80%, more preferably 90%, and most preferably 95% as long as a naturally occurring Ikaros peptide, or fragment thereof having Ikaros activity; the encoded peptide is essentially the same length as a naturally occurring Ikaros peptide; a peptide which is at least 80, more preferably at least 85, yet more preferably at least 90, yet more preferably at least 95, and most preferably at least 98 or 99% homologous with an amino acid sequence which is the same, or essentially the same, as a naturally occurring Ikaros peptide, or a fragment thereof having Ikaros activity, e.g., as the amino acid sequence of any of SEQ ID NOS:2–8, SEQ ID NO:153 or SEQ ID NO:165; and, a peptide having one of either an Ikaros activity or an Ikaros antagonist activity.

In another aspect, the invention features, a DNA, preferably a purified DNA, which includes (or consists essentially of) a DNA sequence which hybridizes under high or low stringency to a nucleic acid which encodes a peptide with the same, or essentially the same, amino acid sequence as a naturally occurring Ikaros peptide, e.g., the peptide of any of SEQ ID NOS:2–8, or SEQ ID NO:153 or SEQ ID NO:165. In preferred embodiments: the DNA sequence is at least 85%, more preferably at least 90%, yet more preferably at least 95%, and most preferably at least 98 or 99% homologous with DNA encoding a naturally occurring Ikaros peptide, or a fragment thereof having Ikaros activity, e.g., with DNA from of any of SEQ ID NOS:2–8 or SEQ ID NO:165; the purified DNA encodes a peptide at least 30, more preferably at least 40, more preferably at least 50, and most preferably at least 60, 80, 100, or 200 amino acid residues in length; the encoded peptide is at least 50% more preferably at least 60%, more preferably 70%, more preferably 80%, more preferably 90%, and most preferably 95% as long as a naturally occurring Ikaros peptide, or fragment thereof having Ikaros activity; the encoded peptide is essentially the same length as a naturally occurring Ikaros peptide; the purified DNA encodes a peptide at least 80, more preferably at least 85, yet more preferably at least 90, yet more preferably at least 95, and most preferably at least 98 or 99% homologous with an amino acid sequence which is the same, or essentially the same, as a naturally occurring Ikaros peptide, e.g., the amino acid sequence of any of SEQ ID NOS:2–8 or SEQ ID NO:153 or SEQ ID NO:165; and, the purified DNA encodes a peptide having essentially the same amino acid sequence, or a fragment of the amino acid sequence, described in SEQ ID NOS:2–8 or SEQ ID NO:153 or SEQ ID NO:165.

In preferred embodiments: the encoded Ikaros polypeptide includes less than 4, 3, 2, or 1 functional N terminal Zinc finger domains (the N terminal Zinc finger domains include domains F1–4, the C terminal Zinc finger domains include domains F1–4); the encoded Ikaros polypeptide includes one or two functional C terminal Zinc finger domains; the encoded Ikaros polypeptide includes less than 4, 3, 2, or 1 functional N terminal Zinc finger domains and includes one or two functional C terminal Zinc finger domains.

In another preferred embodiment: the encoded Ikaros polypeptide includes a point mutation in or a deletion for all or part of the DNA binding region, e.g., a point mutation in, or a deletion for all or part of one or more of F1, F2, F3, or F4; the encoded Ikaros polypeptide includes a mutation in the DNA binding region, e.g., a point mutation in, or a deletion for all or part of one or more of F1, F2, F3, or F4.

In another aspect, the invention includes a vector which includes DNA of the invention, preferably a purified-DNA of the invention, which encodes a peptide of the invention.

The invention also includes: a cell, e.g., a cultured cell or a stem cell, containing purified Ikaros-protein-encoding-DNA; a cell capable of expressing an Ikaros protein; a cell capable of giving rise to a transgenic animal or to a homogeneous population of hemopoietic cells, e.g., lymphoid cells, e.g., T cells; an essentially homogeneous population of cells, each of which includes purified Ikaros-protein-encoding-DNA; and a method for manufacture of a peptide of the invention including culturing a cell which includes a DNA, preferably a purified DNA, of the invention in a medium to express the peptide.

In another aspect, the invention features a peptide of the invention, preferably a substantially pure peptide of the invention, e.g.: a peptide having Ikaros activity, e.g., Ikaros isoform 1, 2, 3, 4, 5, 6, 7 or 8; a peptide having Ikaros antagonistic activity, e.g. able to inhibit at least one biological activity of a naturally occurring Ikaros, e.g. any of isoforms or 1,2,3,4, 5, 6, 7 or 8. In preferred embodiments: the sequence of the encoded Ikaros peptide is essentially the same as the sequence of a naturally occurring Ikaros peptide, or a fragment thereof having Ikaros activity; the sequence of the peptide is such that it is encoded by a DNA sequence at least 85%, more preferably at least 90%, yet more preferably at least 95%, and most preferably at least 98 or 99% homologous with DNA encoding a naturally occurring Ikaros peptide, or a fragment thereof having Ikaros activity; e.g., with DNA from any of SEQ ID NOS:2–8 or SEQ ID NO:165; the amino acid sequence of the peptide having Ikaros activity or Ikaros antagonistic activity is such that it can be encoded by a nucleic acid which hybridizes under high or low stringency conditions to a nucleic acid which encodes a peptide with the same, or essentially the same, amino acid sequence as the peptide of any of SEQ ID NOS:2–8, or SEQ ID NO:153 or SEQ ID NO:165; the peptide is at least 30, more preferably at least 40, more preferably at least 50, and most preferably at least 60, 80, 100, or 200 amino acid residues in length; the peptide is at least 50% more preferably at least 60%, more preferably 70%. more preferably 80%, more preferably 90%, and most preferably 95% as long as a naturally occurring Ikaros peptide, or fragment thereof having Ikaros activity; the peptide is essentially the same length as a naturally occurring Ikaros peptide, or a fragment thereof having Ikaros activity; the peptide is at least 80%, more preferably at least 85%, yet more preferably at least 90%, yet more preferably at least 95%, and a most preferably at least 98 or 99% homologous with an amino acid sequence which is the same. or essentially the same, as a naturally occurring Ikaros peptide, or a fragment thereof having Ikaros activity, e.g., the peptide sequence of any of SEQ ID NOS:2–8, or SEQ ID NO:153 or SEQ ID NO:165; and, the amino acid sequence of the peptide is essentially the same as the sequence of a naturally occurring Ikaros peptide, or a fragment thereof having Ikaros activity, e.g., the sequence, described in SEQ ID NOS:2–8 or SEQ ID NO:165.

In preferred embodiments a peptide of the invention, preferably a purified peptide of the invention, is produced by expression of a DNA of the invention, preferably a purified DNA of the invention.

In another aspect, the present invention features recombinant Ikaros proteins which are encoded by genes derived from vertebrate organisms (e.g. a mammal, e.g. a human, a mouse or a pig) and which is capable of functioning in one of either role of an agonist or an antagonist of at least one biological activity of a naturally occurring Ikaros protein. The term "recombinant protein" refers to a Ikaros protein of the present invention which is produced by recombinant DNA techniques, wherein generally DNA encoding the Ikaros protein is inserted into a suitable expression vector which is in turn used to transform a host cell to produce the heterologous protein. Moreover, the phrase "derived from", with respect to a recombinant gene encoding the recombinant Ikaros, is meant to include within the meaning of "recombinant protein" those proteins having an amino acid sequence of a naturally occurring Ikaros isoform, or an amino acid sequence similar thereto which is generated by, for example, mutations including substitutions and deletions of a naturally occurring Ikaros isoform. Recombinant proteins preferred by the present invention, in addition to native vertebrate Ikaros proteins, are at least 85%, more preferably at least 90%, yet more preferably at least 95%, and most preferably at least 98 or 99% homologous with an amino acid sequence selected from the group consisting of any of SEQ ID NOS: 2–8 or SEQ ID NO:165, e.g. a protein represented by the general formula of SEQ ID NO:153.

In particular, recombinant Ikaros protein, as used herein, includes a protein of the same or similar sequence as a naturally occurring Ikaros protein (e.g. a protein having an amino acid sequence found in any of SEQ ID NOS: 2–8 or SEQ ID NO:165) but lacking amino acid sequences at either or both of its N-terminal and C-terminal ends. Examples of such proteins include, but are not limited to, Ikaros isoforms which lack either exon 1, or exon 7, or both. In other exemplary embodiments, the recombinant proteins are truncation mutants. In preferred embodiments, the truncation mutants comprise at least 50–60 amino acid residues, more preferably 90–100 amino acid residues, and most preferably at least 150 amino acid residues of an Ikaros protein, or variant thereof, while retaining the activity of either an Ikaros agonist or an Ikaros antagonist.

The present invention further pertains to recombinant Ikaros proteins which are encoded by genes derived from a vertebrate organism and which have amino acid sequences evolutionarily related to naturally occurring Ikaros protein. Such recombinant Ikaros proteins preferably are capable of functioning in one of either role of an agonist of antagonist of at least one biological activity of a vertebrate Ikaros. The term "evolutionarily related to", with respect to amino acid sequences of the present recombinant Ikaros proteins, refers to vertebrate Ikaros proteins having amino acid sequences which have arisen naturally. The term "evolutionarily related to" also refers to mutational variants of naturally occurring Ikaros proteins which are derived, for example, by combinatorial mutagenesis or in vitro exon shuffling. In an illustrative embodiment the recombinant Ikaros protein is an isoform encoded by a recombinant Ikaros gene generated through permutation of an exon order relative to a naturally occurring Ikaros protein, e.g. of SEQ ID NOS:2–8 or SEQ ID NO:165, e.g. of any exons 1/2, 3, 4, 5, 6, 7, e.g. wherein two different exons are permuted in sequential order relative to a naturally occurring Ikaros isoforms, e.g. when an Ikaros exon is present two or more times in the recombinant Ikaros gene.

The invention also includes substantially pure preparation of an antibody, preferably a monoclonal antibody directed against an Ikaros protein; a therapeutic composition including an Ikaros protein and a pharmaceutically acceptable carrier; a therapeutic composition which includes a purified DNA of the invention and a pharmaceutically acceptable carrier.

In another aspect, the invention features a method for treating an animal, e.g., a human, a mouse, a transgenic animal, or an animal model for an immune system disorder, e.g., a T or B cell related disorder, e.g., a nude mouse or a SCID mouse, including administering a therapeutically-effective amount of an Ikaros peptide to the animal.

In another aspect, the invention features a method for treating an animal, e.g., a human, a mouse, a transgenic animal, or an animal model for an immune system disorder, e.g., a T or B cell related disorder, e.g., a nude mouse or a SCID mouse including administering to the animal cells selected, e.g., selected in vitro, for the expression of a product of the Ikaros gene, e.g., hematopoietic stem cells, e.g., cells transformed with Ikaros-peptide-encoding DNA, e.g., hematopoietic stem cells transformed with Ikaros-peptide-encoding DNA.

In preferred embodiments: the cells are taken from the animal to which they are administered; the cells are taken from an animal which is MHC matched with the animal to which they are administered; the cells are taken from an animal which is syngeneic with the animal to which they are administered; the cells are taken from an animal which is of the same species as is the animal to which they are administered.

In another aspect, the invention features a method for treating an animal, e.g., a human, a mouse, a transgenic animal, or an animal model for an immune system disorder, e.g., a T or B cell related disorder, e.g., a nude mouse or a SCID mouse, including administering to the animal a nucleic acid encoding an Ikaros peptide and expressing the nucleic acid.

In another aspect, the invention features a method of evaluating the effect of a treatment, e.g., a treatment designed to promote or inhibit hematopoiesis, including carrying out the treatment and evaluating the effect of the treatment on the expression of the Ikaros gene.

In preferred embodiments the treatment is administered: to an animal, e.g., a human, a mouse, a transgenic animal, or an animal model for an immune system disorder, e.g., a T or B cell related disorder, e.g., a nude mouse or a SCID mouse, or a cell, e.g., a cultured stem cell.

In another aspect, the invention features a method for determining if a subject, e.g., a human, is at risk for a disorder related to mis-expression of the Ikaros gene, e.g., a leukemic disorder or other disorder of the immune system, e.g., an immunodeficiency, or a T or B cell related disorder, e.g., a disorder characterized by a shortage of T or B cells, including examining the subject for the expression of the Ikaros gene, non-wild type expression or mis-expression being indicative of risk.

In another aspect, the invention features a method for determining if a subject, e.g., a human, is at risk for a disorder related to mis-expression of the Ikaros gene, e.g., a leukemic disorder or other disorder of the immune system, e.g., an immunodeficiency, or a T or B cell related disorder, e.g., a disorder characterized by a shortage of T or B cells, including providing a nucleic acid sample from the subject and determining if the structure of an Ikaros gene allele of the subject differs from wild type.

In preferred embodiments: the determination includes determining if an Ikaros gene allele of the subject has a gross chromosomal rearrangement; the determination includes sequencing the subject's Ikaros gene.

In another aspect, the invention features, a method of evaluating an animal or cell model for an immune disorder, e.g., a T cell related disorder, e.g., a disorder characterized by a shortage of T or B cells, including determining if the Ikaros gene in the animal or cell model is expressed at a predetermined level or if the Ikaros gene is mis-expressed. In preferred embodiments: the predetermined level is lower than the level in a wild type or normal animal; the predetermined level is higher than the level in a wild type or normal animal; or the pattern of isoform expression is altered from wild type.

In another aspect, the invention features a transgenic rodent, e.g., a mouse, having a transgene which includes an Ikaros gene or Ikaros protein encoding DNA. In preferred embodiments: the Ikaros gene or DNA includes a deletion, e.g. a deletion of all or part of one or more Ikaros exons, e.g., a deletion of all or part of exon E7 or a deletion of all or part of exons E3 or E4, or is otherwise mis-expressed; the Ikaros gene encodes an Ikaros protein which is a competitive antagonist of a naturally occurring Ikaros protein.

In another aspect, the invention features a method of expressing a heterologous gene, e.g., in a cell e.g., a stem cell, including placing the gene under the control of an Ikaros-responsive control element, and contacting the Ikaros-responsive control element with an Ikaros protein.

In preferred embodiments: the Ikaros-responsive control element includes an enhancer, e.g., an δA element, an NFKB element, or one of the Ikaros binding sequences, e.g., one of the consensus sequences, disclosed herein; the Ikaros-responsive control element includes the regulatory region of the CD3δ gene; the heterologous gene and the Ikaros-responsive control element are carried on a vector; the method further includes the step of transforming a cell with a vector which includes a heterologous gene under the control of an Ikaros-responsive control agent; the heterologous gene is expressed in a cell which normally includes or expresses an Ikaros protein.

In another aspect, the invention features a method of expressing a gene under the control of an Ikaros-responsive control element in a cell including administering an Ikaros protein to the cell.

In preferred embodiments: the method further includes transforming the cell with DNA which encodes an Ikaros protein to supply an Ikaros protein, the gene is a heterologous gene.

In another aspect, the invention features a method for treating, an animal, e.g., a human, a mouse, a transgenic animal, or an animal model for a disorder of the nervous system, e.g., a disorder of the corpus striatum, e.g., Alzheimer's disease, immune system disorder, including administering a therapeutically effective amount of an Ikaros protein to the animal.

In another aspect, the invention features a method for treating an animal, e.g., a human, a mouse, a transgenic animal, or an animal model for a disorder of the nervous system, e.g., a disorder of the corpus striatum, e.g., Alzheimer's disease, including administering to the animal cells selected, e.g., selected in vitro, for the expression of a product of the Ikaros gene, e.g., hematopoietic stem cells, e.g., cells transformed with Ikaros-protein-encoding DNA, e.g., hematopoietic stem cells transformed with Ikaros-protein-encoding DNA.

In preferred embodiments: the cells are taken from the animal to which they are administered; the cells are taken from an animal which is MHC matched with the animal to which they are administered; the cells are taken from an animal which is syngeneic with the animal to which they are administered: the cells are taken from an animal which is of the same species as is the animal to which they are administered.

In another aspect, the invention features a method for treating an animal, e.g., a human, a mouse, a transgenic animal, or an animal model for a disorder of the nervous system. e.g., a disorder of the corpus striatum, e.g., Alzheimer's disease, including administering to the animal a nucleic acid encoding an Ikaros peptide and expressing, the nucleic acid.

In another aspect, the invention features a method of evaluating the effect of a treatment for a disorder of the nervous system, e.g., a disorder of the corpus striatum, e.g., Alzheimer's disease, including administering the treatment and evaluating the effect of the treatment on the expression of the Ikaros gene.

In preferred embodiments the treatment is administered: to an animal, e.g., a human, a mouse, a transgenic animal, or an animal model for a disorder of the nervous system, e.g., a disorder of the corpus striatum, e.g., Alzheimer's disease, or a cell, e.g., a cultured stem cell.

In another aspect, the invention features a method for determining if a subject, e.g., a human, is at risk for a disorder related to mis-expression of the Ikaros gene, e.g., a disorder of the nervous system, e.g., a disorder of the corpus striatum, e.g., Alzheimer's disease, including examining the subject for the expression of the Ikaros gene, non-wild type expression or mis-expression being indicative of risk.

In another aspect, the invention features a method for determining if a subject, e.g., a human, is at risk for a disorder related to mis-expression of the Ikaros gene, e.g., a disorder of the nervous system, e.g., a disorder of the corpus striatum, e.g., Alzheimer's disease, including providing a nucleic acid sample from the subject and determining if the structure of an Ikaros gene allele of the subject differs from wild type.

In preferred embodiments: the determination includes determining if an Ikaros gene allele of the subject has a gross chromosomal rearrangement; the determination includes sequencing the subject's Ikaros gene.

In another aspect, the invention features, a method of evaluating an animal or cell model for a disorder of the nervous system, e.g., a disorder of the corpus striatum, e.g., Alzheimer's disease, including determining if the Ikaros gene in the animal or cell model is expressed at a predetermined level or if the Ikaros gene is mis-expressed.

In preferred embodiments: the predetermined level is lower than the level in a wild type or normal animal; the predetermined level is higher than the level in a wild type or normal animal.

In another aspect, the invention features, a method of inhibiting an interaction, e.g., binding, between a protein, e.g., a first Ikaros isoform, and a DNA sequence, e.g., a DNA sequence under the control of a δA sequence, an NKFB sequence, a sequence which corresponds to an Ikaros binding oligonucleotide described herein, or a site present in the control region of a lymphocyte restricted gene, e.g., TCR-α, -β, or -δ, CD3-δ, -ε, -γ genes, the SL3 gene, or the HIV LTR gene. The methods includes contacting the DNA sequence with an effective amount of a second Ikaros isoform, or with a DNA binding fragment encoding an Ikaros isoform, e.g., of the second Ikaros isoform, e.g. of an Ikaros antagonist isoform.

In preferred embodiments: the fragment is deleted for all or part of an Ikaros exon, e.g., for all or part of E1/2, E3, E4, E5, E6, or E7; the antagonist contains one or more point mutations relative to a naturally occurring Ikaros isoform; the antagonist comprises at least two different exons which are sequentially oriented, in the antagonist, in a permuted (e.g. non wild-type) fashion relative to naturally occurring Ikaros isoforms (e.g. any of SEQ. NOS: 2–8); the antagonist comprises at least two of the same Ikaros exon.

In another aspect, the invention features, a method of inhibiting an interaction, e.g., binding, between a protein, e.g., a first Ikaros isoform, and a DNA sequence, e.g., a δA sequence, an NKFB sequence, a sequence which corresponds to an Ikaros binding oligonucleotide described herein, or a site present in the control region of a lymphocyte restricted gene, e.g., TCR-α, -β, or -δ, CD3-δ, -ε, -γ genes, the SL3 gene, or the HIV LTR gene. The methods includes contacting the protein with an effective amount of an Ikaros binding oligonucleotide. In preferred embodiments the oligonucleotide includes a sequence chosen from, IK-BS1, IK-BS2, IK-BS3, IK-BS4, IK-BS5, IK-BS6, IK-BS7, IK-BS8, or IK-BS9.

In preferred embodiments: the oligonucleotide preferentially binds to a first Ikaros isoform; the oligonucleotide preferentially binds to a second Ikaros isoform.

In another aspect the invention includes an Ikaros binding oligonucleotide, e.g., IK-BS 1, IK-BS2, IK-BS3, IK-BS4, IK-BS5, IK-BS6, IK-BS7, IK-BS8, or IK-BS9. In preferred embodiments the oligonucleotide contains at least two, three, four, or five copies of one of the Ikaros binding oligonucleotide sequences disclosed herein.

In another aspect, the invention features a method of attenuating the binding of a first Ikaros isoform to target DNA. The method includes contacting the target DNA with an effective amount of a second Ikaros isoform, or with a DNA binding fragment of said second isoform. The second Ikaros isoform can be, for example, an antagonists isoform of Ikaros, e.g. an Ikaros isoform generated point mutation, e.g. an Ikaros isoform generated by in vitro exon shuffling.

In another aspect, the invention features a method of modulating the rate of division or amplification of a cell, or entry of the cell into the cell cycle. The method includes administering to the cell, an effective amount of an Ikaros polypeptide, or a nucleic acid encoding an Ikaros polypeptide. The method can be practiced ex vivo, in vivo, or in vitro.

In preferred embodiments, the cell is a hematopoietic cell, e.g., a stem cell, e.g., a totipotent or a pluripotent stem cell, or a descendent of a stem cell, e.g., a lymphocyte. In preferred embodiments the cell is a human, a pig, a rabbit, or a rodent, e.g., a mouse or rat, cell.

In preferred embodiments the division or amplification, or entry into the cell cycle, is promoted. Generally, Ikaros mutations which inhibit or antagonize normal non-proliferative Ikaros function (e.g., the function of the Ik-1 isoform) increase cell division. Such mutants include: mutations which inhibit DNA binding, e.g., point mutations in, or deletions for all or part of, one or more of F1, F2, F3, or F4; mutations. e.g., point mutations in, or deletions for all or part of, one or more of exons 1/2, 3, 4, 5, or 6; mutations which results in the preferential expression of proliferation-promoting Ikaros dimer subunits as opposed to non-proliferation-promoting Ikaros dimer subunits; or mutants having defective DNA binding but functional dimerization domains. Less preferred are mutations which inactivate one or both of transcriptional activation or dimerization, which decrease the half life of the protein, or which inactivate one or both of the C terminal Zinc finger domains, e.g., F5 or F6; or a mutation is a C terminal deletion. Fragments or other mutants of Ikaros (or Aiolos) which inhibit dimerization of Ikaros proteins, e.g., fragments which include the C terminal dimerization region, e.g., fragments which include Zinc fingers F5 and F6, can also be used to promote cell division. Subunits of proliferation-promoting Ikaros dimers can also increase division, amplification, or entry into the cell cycle.

Methods for increasing cell division can be combined with procedures where it is desirable to increase cell division, e.g., the treatment, e.g., by chemotherapy or radiotherapy, of tumors or other cell-proliferative disorders.

In preferred embodiments the division, amplification, or entry into the cell cycle is decreased. Subunits of non-proliferation-promoting Ikaros dimers, e.g., Ik-1, can decrease division, amplification, or entry into the cell cycle.

The cell can be implanted into a mammal, e.g., into the mammal from which it was derived, or into a mammal of the same or a different species. The cell can be cultured prior to introduction into the mammal. E.g., the cell can be altered to modulate the rate of division or amplification of the cell, or entry of the cell into the cell cycle, and then implanted into the mammal. The mammal can be, e.g., a human, a non-human primate, a pig, a rat, a rabbit, or a rodent, e.g., a rat or mouse.

The invention also includes a cell, a purified preparation of cells, or an ex vivo preparation of cells, in which the rate of division or amplification of the cell, or entry of the cell into the cell cycle, has been modulated, e.g., changes as compared to a wild type or non-modulated cell of equivalent type.

In another aspect, the invention features a method of modulating the state of differentiation of a cell. The method includes administering to the cell, an Ikaros polypeptide, or a nucleic acid encoding an Ikaros polypeptide, in an amount sufficient to modulate, e.g., to promote the maintenance of the state of differentiation of the cell, or to promote differentiation. The method can be practiced ex vivo, in vivo, or in vitro.

In preferred embodiments, the cell is a hematopoietic cell, e.g., a stem cell, e.g., a totipotent or a pluripotent stem cell, or a descendent of a stem cell, e.g., a lymphocyte. In preferred embodiments the cell is a human, a pig, a rabbit, or a rodent, e.g., a mouse or rat, In preferred embodiments, the state of differentiation of the cell is maintained, e.g., differentiation is inhibited and a more primitive and more multipotent state is promoted. This can be achieved by providing Ikaros polypeptides having wild type non-proliferative function, e.g., Ikaros polypeptides having the function of the IK-1 isoform. Subunits of non-proliferation-promoting Ikaros dimers can promote maintenance of the differentiated state of the cell. In a particularly preferred embodiment wild type Ikaros function is provided to human hematopoietic cells, preferably stem cells, to maintain their differentiated state or to otherwise enhance culturing of the cells.

In preferred embodiments, differentiation of the cell, which is usually accompanied by entry into the cell cycle, is promoted. Generally, Ikaros mutations which inhibit or antagonize normal non-proliferative Ikaros function (e.g., the function of the Ik-1 isoform) promote differentiation. Such mutants include: mutations which inhibit DNA binding, e.g., point mutations in, or deletions for all or part of, one or more of F1, F2, F3, or F4; mutations e.g., point mutations in, or deletions for all or part of, one or more of exons 1/2, 3, 4, 5, or 6; mutations which results in the preferential expression of proliferation-promoting Ikaros dimer subunits as opposed to non-proliferation-promoting Ikaros dimer subunits; or mutants having defective DNA binding but functional dimerization domains. Less preferred for promoting differentiation are mutations which inactivate one or both of transcriptional activation or dimerization, which decrease the half life of the protein, or which inactivate one or both of the C terminal Zinc finger domains, e.g., F5 or F6; or a mutation is a C terminal deletion. Fragments or other mutants of Ikaros (or Aiolos) which inhibit dimerization of non-proliferative Ikaros proteins, e.g., fragments which include the C terminal dimerization region, e.g., fragments which include Zinc fingers F5 and F6, can also be used to promote differentiation. Subunits of proliferation-promoting Ikaros dimers can be used to promote differentiation.

The cell can be implanted into a mammal, e.g., into the mammal from which it was derived, or into a mammal of the same or a different species. The cell can be cultured prior to introduction into the mammal. E.g., the cell can be altered to modulate the state of differentiation of the cell, and then implanted into the mammal. The mammal can be, e.g., a human, a non-human primate, a pig, a rat, a rabbit, or a rodent, e.g., a rat or mouse.

The invention also includes a cell, a purified preparation of cells, or an ex vivo preparation of cells, in which the state of differentiation of the cell, has been modulated, e.g., changes as compared to a wild type or non-modulated cell of equivalent type.

In another aspect, the invention features a cell e.g., a hematopoietic cell, e.g., a stem cell, e.g., a totipotent or a pluripotent stem cell, or a descendent of a stem cell, e.g., a lymphocyte, which overexpresses an Ikaros dimer or isoform, preferably an NPID or an NPID isoform, e.g., the Ik-1 isoform. Also included in this aspect of the invention are purified or ex vivo preparations of the cells.

In preferred embodiments the cell is a human, a pig, a rabbit, or a rodent, e.g., a mouse or rat, cell.

In preferred embodiments, the NPID is e.g., a Ik-1/Ik-1, Ik-1/Ik-2, Ik-1/Ik-3, Ik-2/Ik-2, Ik-2/Ik-3 or Ik-3/Ik-3 dimer.

The cell can be implanted into a mammal, e.g., into the mammal from which it was derived, or into a mammal of the same or a different species. The cell can be cultured prior to introduction into the mammal. E.g., the cell can be altered to overexpress an Ikaros dimer or isoform and then implanted into the mammal. The mammal can be, e.g., a human, a non-human primate, a pig, a rat, a rabbit, or a rodent, e.g., a rat or mouse.

In another aspect, the invention features a cell, e.g., a hematopoietic cell, e.g., a stem cell, e.g., a totipotent or a pluripotent stem cell, or a descendent of a stem cell, e.g., a lymphocyte, in which the ratio of an NPID or NPID isoform to a PPID or PPID isoform (or generally of NPID's to PPID's) has been altered, e.g., increased or decreased, with respect to a wild-type or unaltered cell. Also included in this aspect of the invention are purified or ex vivo preparations of the cells.

In preferred embodiments the cell is a human, a pig, a rabbit, or a rodent, e.g., a mouse or rat, cell.

In preferred embodiments, the NPID is e.g., a Ik-1/Ik-1, Ik-1/Ik-2, Ik-1/Ik-3, Ik-2/Ik-2, Ik-3 or Ik-3/Ik-3 dimer.

In preferred embodiments, the PPID includes at least one Ikaros isoform which lacks one or more functional F1, F2, F3, or F4 zinc finger regions, e.g., Ik-4, Ik-5, Ik-6, Ik-7 or Ik-8.

In preferred embodiments, the ratio of an NPID or NPID isoform to a PPID or PPID isoform is increased, e.g., by increasing the amount of NPID or NPID isoform (relative to a PPID or PPID isoform) or by decreasing the amount of a PPID or PPID isoform (relative to an NPID or NPID isoform).

The cell can be implanted into a mammal, e.g., into the mammal from which it was derived, or into a mammal of the same or a different species. The cell can be cultured prior to introduction into the mammal. E.g., the cell can be altered with respect to the NPID/PPID ratio and then implanted into the mammal. The mammal can be, e.g., a human, a non-human primate, a pig, a rat, a rabbit, or a rodent, e.g., a rat or mouse.

A purified preparation of cells, is a preparation of cells which includes at least 10, 30, 50, 75, 90, 95, or 99%, by number or weight, the subject cells. An ex vivo preparation is a preparation of cells from a mammal or from cell culture which is suitable fro re-introduction into the same or a different mammal.

Heterologous gene, as used herein, is a gene which is not normally under the control of an Ikaros responsive control element.

An Ikaros-responsive control element, as used herein is a region of DNA which, when present upstream or downstream from a gene, results in regulation, e.g., increased transcription of the gene in the presence of an Ikaros protein.

Purified DNA is DNA that is not immediately contiguous with both of the coding sequences with which it is immediately contiguous (i.e., one at the 5' end and one at the 3' end) in the naturally occurring genome of the organism from which the DNA of the invention is derived. The term therefore includes, for example, a recombinant DNA which is incorporated into a vector: into an autonomously replicating plasmid or virus: or into the genomic DNA of a prokaryote or eukaryote, or which exists as a separate molecule (e.g., a cDNA or a genomic DNA fragment produced by PCR or restriction endonuclease treatment) independent of other DNA sequences. It also includes a recombinant DNA which is part of a hybrid gene encoding additional polypeptide sequence.

Homologous refers to the sequence similarity between two polypeptide molecules or between two nucleic acid molecules. When a position in both of the two compared sequences is occupied by the same base or amino acid monomeric subunit, e.g., if a position in each of two DNA molecules is occupied by adenine, then the molecules are homologous at that position. The homology between two sequences is a function of the number of matching or homologous positions shared by the two sequences. For example, 6 of 10, of the positions in two sequences are matched or homologous then the two sequences are 60% homologous. By way of example, the DNA sequences ATTGCC and TATGGC share 50% homology.

A transgene is defined as a piece of DNA which is inserted by artifice into a cell and becomes a part of the genome of the animal which develops in whole or part from that cell. Such a transgene may be partly or entirely heterologous to the transgenic animal.

A transgenic animal, e.g., a transgenic mouse, is an animal having cells that contain a transgene, which transgene was introduced into the animal, or an ancestor of the animal, at a prenatal, e.g., an embryonic stage.

An enhancer region is defined as a cis-acting DNA sequence capable of increasing transcription from a promoter that is located either upstream or downstream of the enhancer region. Such DNA sequences are well known to those skilled in the art of eukaryotic gene expression.

A substantially pure preparation of a peptide is a preparation which is substantially free of one or more of the peptides with which it naturally occurs in a cell. A substantially pure preparation of a non-naturally occurring peptide is one which is at least 10% by weight of the peptide of interest. In a preferred embodiment, a substantially pure preparation further lacks any nucleic acids, such as oligonucleotides, which bind to the subject Ikaros protein.

Mis-expression, as used herein, refers to a non-wild type pattern of gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of the tissue specificity of expression, e.g., increased or decreased expression (as compared with wild type) in a predetermined cell type or tissue type; a pattern of expression that differs from wild type in terms of the size, amino acid sequence, post-translational modification, or a biological activity of an Ikaros gene product; a pattern of expression that differs from wild type in terms of the effect of an environmental stimulus or extracellullar stimulus on expression of the gene, e.g., a pattern of increased or decreased expression (as compared with wild type) in the presence of an increase or decrease in the strength of the stimulus; or a pattern of isoform expression which differs from wild type.

The terms peptide, protein, and polypeptide are used interchangeably herein.

A peptide has Ikaros activity if it has one or more of the following properties: the ability to stimulate transcription of a DNA sequence under the control any of a δA element, an NFKB element, or one of the Ikaros binding oligonucleotide consensus sequences disclosed herein; the ability to bind to any of a δA element, an NFKB element, or one of the Ikaros binding oligonucleotide consensus sequences disclosed herein; or the ability to competitively inhibit the binding of a naturally occurring Ikaros isoform to any of a δA element, an NFKB element, or one of the Ikaros binding oligonucleotide consensus sequences disclosed herein. An Ikaros peptide is a peptide with Ikaros activity.

As used herein, the term "exon", refers to those gene (e.g. DNA) sequence which are transcribed and processed to form mature messenger RNA (mRNA) encoding an Ikaros protein, or portion thereof, e.g. Ikaros coding sequences, and which, at the chromosomal level, are interrupted by intron sequences. Exemplary exons of the subject Ikaros proteins and genes include: with reference to SEQ ID NO:5 (mIk-1), the nucleotide sequence encoding exon 1/2 (E1/2) corresponding to Met-1 through Met-53 (encoded by nucleotides 223 to 381 of SEQ ID NO:5); the nucleotide sequence encoding exon 3 (E3) corresponding to Ala-54 through Thr 140 (encoded by nucleotides 382 to 642 of SEQ ID NO:5); the nucleotide sequence encoding exon 4 (E4) corresponding to Gly-141 through Ser-196 (encoded by nucleotides 643 to 810 of SEQ ID NO:5); the nucleotide sequence encoding exon 5 (E5) corresponding to Val-197 through Pro-237 (encoded by nucleotides 811 to 933 of SEQ ID NO:5); the nucleotide sequence encoding exon 6 (6) corresponding to Val-238 through Leu-282 (encoded by nucleotides 934 to 1068 of SEQ ID NO:5); the nucleotide sequence encoding exon 7 (E7) corresponding to Gly-283 through Ser-518 (encoded by nucleotides 1069 to 1776 of SEQ ID NO:5), with reference to SEQ ID NO:3 (1-Ik-1), the nucleotide sequence encoding exon 3 (E3) corresponding to Asn-1 through Thr-85 (encoded by nucleotides 1 to 255 of SEQ ID NO:3); the nucleotide sequence encoding exon 4 (E4) corresponding to Gly-86 through Ser-141 (encoded by nucleotides 256 to 423 of SEQ ID NO:3); the nucleotide sequence encoding exon 5 (E5) corresponding to Val-142 through Pro-183 (encoded by nucleotides 424 to 549 of SEQ ID NO:3); the nucleotide sequence encoding exon 6 (6) corresponding to Val-184 through Leu-228 (encoded by nucleotides 550 to 684 of SEQ ID NO:3); the nucleotide sequence encoding exon 7 (E7) corresponding to Gly-229 through Ser-461 (encoded by nucleotides 685 to 1383 of SEQ ID NO:3). The term "intron" refers to a DNA sequence present in a given Ikaros gene which is not translated into protein and is generally found between exons. The term "gene" refers to a region of chromosomal DNA which contains DNA sequences encoding an Ikaros protein, including both exon and intron sequences. A "recombinant gene" refers to nucleic acid encoding an Ikaros protein and comprising Ikaros exon sequence, though it may optionally include intron sequences which are either derived from a chromosomal Ikaros gene or from an unrelated chromosomal gene. An exemplary recombinant gene is a nucleic acids having a sequence represented by any of SEQ ID NOS:2–8 or 153 or SEQ ID NO:165.

The term "Ikaros responsive element" or "IK-RE", refers to nucleic acid sequences which, when placed in proximity of a gene, act as transcriptional regulatory elements which control the level of transcription of the gene in an Ikaros protein-dependent manner. Exemplary IK-RE, as described below, include IK-BS1, IK-BS2, IK-BS4, IK-BS5, IK-BS6, IK-BS7, IK-BS8, or IK-BS9.

A "non-proliferative Ikaros dimer" (NPID), e.g., Ik-1/Ik-1, Ik-1/Ik-2, Ik-1/Ik-3, Ik-2/Ik-2, Ik-2/Ik-3 or Ik-3/Ik-3, inhibits proliferation of the cell. A "proliferative Ikaros dimer" (PPID), promotes proliferation and includes at least one Ikaros isoform which lacks one or more functional F1, F2, F3, or F4 zinc finger regions, e.g., Ik-4, Ik-5, Ik-6, Ik-7 or 8. Proliferation can mean proliferation as compared to an otherwise similar cell or as compared to a wild-type cell. The concentration or activity of an NPID or PPID can be manipulated by any means known to the art. For example, the concentration or activity of an NPID can be reduced by reducing the availability of one or more monomeric species which can form an NPID, e.g., by reducing the availability of one or more of Ik-1, Ik-2, or Ik-3. Such reduction can be effected by mutations which decrease production of Ik-1, Ik-2, or Ik-3, by the expression of antisense molecules which inhibit Ik-1, Ik-2, or Ik-3 expression or by compounds which inhibit dimerization of the subunits of NPID's. The concentration or activity of NPID's can be reduced by providing Ikaros species which lack one or more functional F1, F2, F3, or F4 zinc finger regions, e.g., by producing Ik-4, Ik-5, Ik-6, or Ik-7 isoforms. Such species can form proliferation-promoting Ikaros dimers (PPID). Thus, manipulations which reduce the concentration or activity of NPID, e.g., by sequestering available Ik-1, Ik-2, or Ik-3 in PPID's, can be used to provide an Ikaros-deregulated lymphocyte. The concentration of an NPID can be increased by providing isoforms which form NPID's. The ratio of NPID's/PPID's can be increased by decreasing the concentration of PPID's.

The invention is useful for identifying T cells; identifying cells which can develop into T cells; and generally, in the investigation of hemopoiesis, e.g., in the differentiation of progenitor stem cells into T cells. The role of the Ikaros gene and its products can be studied, e.g., in cells, e.g., cultured cells, transformed with the Ikaros gene or fragments thereof, or in transgenic animals. The invention is also useful for: promoting the expression of markers of cell lineage, e.g., CD3δ genes; enhancing the ability of a cell, e.g., a stem cell, to develop into a T cell; screening individuals at risk for genetic T cell disorders, e.g., leukemia; and treating immune disorders (e.g., immunodeficiencies, e.g., AIDS, or chemical, drug, or radiation induced immunodeficiencies, or cancers, e.g., leukemia) characterized by a shortage of T cells; for investigating the structure and expression of the Ikaros gene or iso forms of the gene product; for investigating species or tissue differences in the expression of the Ikaros gene or its isoforms; for investigating the structure and function of DNA binding proteins; for studying the structure and function of zinc finger containing proteins; for the construction of transgenic animals; for inhibiting the binding of Ikaros to a target molecule; for studying the relative affinities of Ikaros isoforms for target DNA; and for searching for or manipulating the expression of genes under the control of Ikaros isoforms.

Other features and advantages of the invention will be apparent from the following description and from the claims.

DETAILED DESCRIPTION

The drawings are first briefly described.

Drawings

FIG. 1A is a map of the δA element of the CD3enhancer (SEQ ID NO:1).

FIG. 1B is a graph of the contribution of the CRE and the G box to the activity of the element as analyzed by expression of tkCAT reporter gene under the control of various element sequences.

FIG. 1C is a graph of the effect of Ikaros expression on the activity of the δ element in non-T cells.

FIG. 2 is a map of the DNA sequence of a murine Ikaros cDNA and the desired amino acid sequence encoded thereby (SEQ ID NO:2).

FIG. 3 is a partial sequence of a human Ikaros cDNA (SEQ ID NO:3).

FIG. 4 is a depiction of the partial amino acid composition of the IK-1 cDNA, including Ex3, Ex4, Ex5, Ex6, and Ex7 (SEQ ID NO:5).

Figure 5:
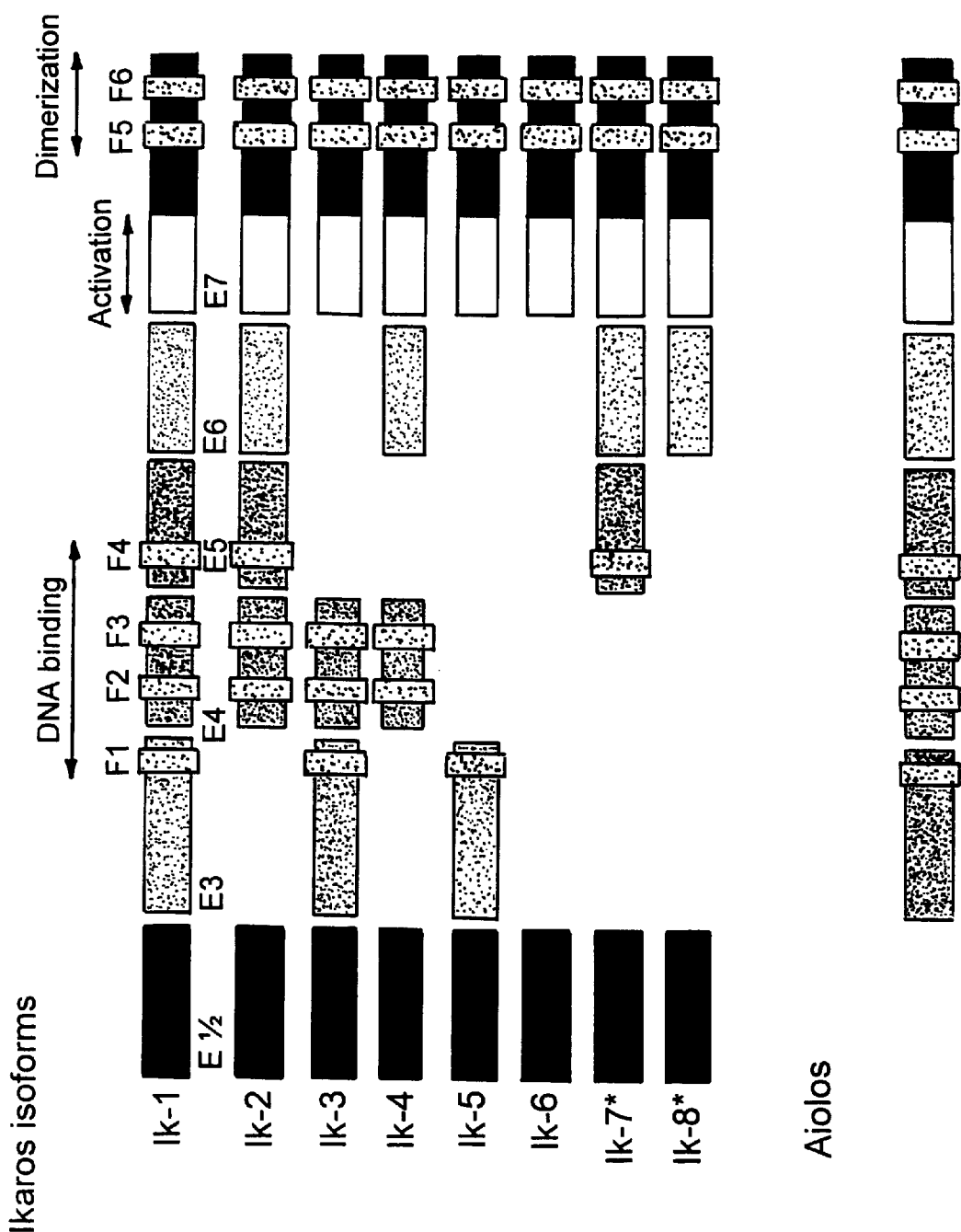

FIG. 5 is a schematic representation of Ikaros isoforms and their similarities to the Aiolos protein. Zinc finger domains involved in DNA binding and dimerization are indicated by arrows. The location of a conserved activation domain between Ikaros and Aiolos proteins is shown as a white box. Stars Ikaros isoforms indicates their exclusive production from the mutant dominant negative (Dn) locus.

Figure 6:
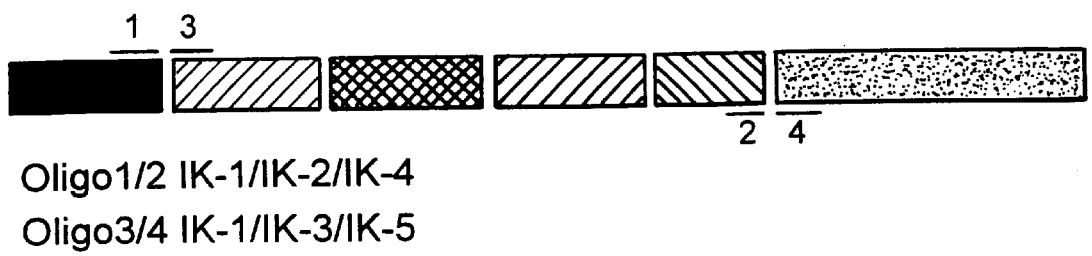

FIG. 6 is a depiction of the exon organization at the Ikaros locus indicating primer sets 1/2 and 3/4 used for amplification of the respective isoforms.

Figure 7:
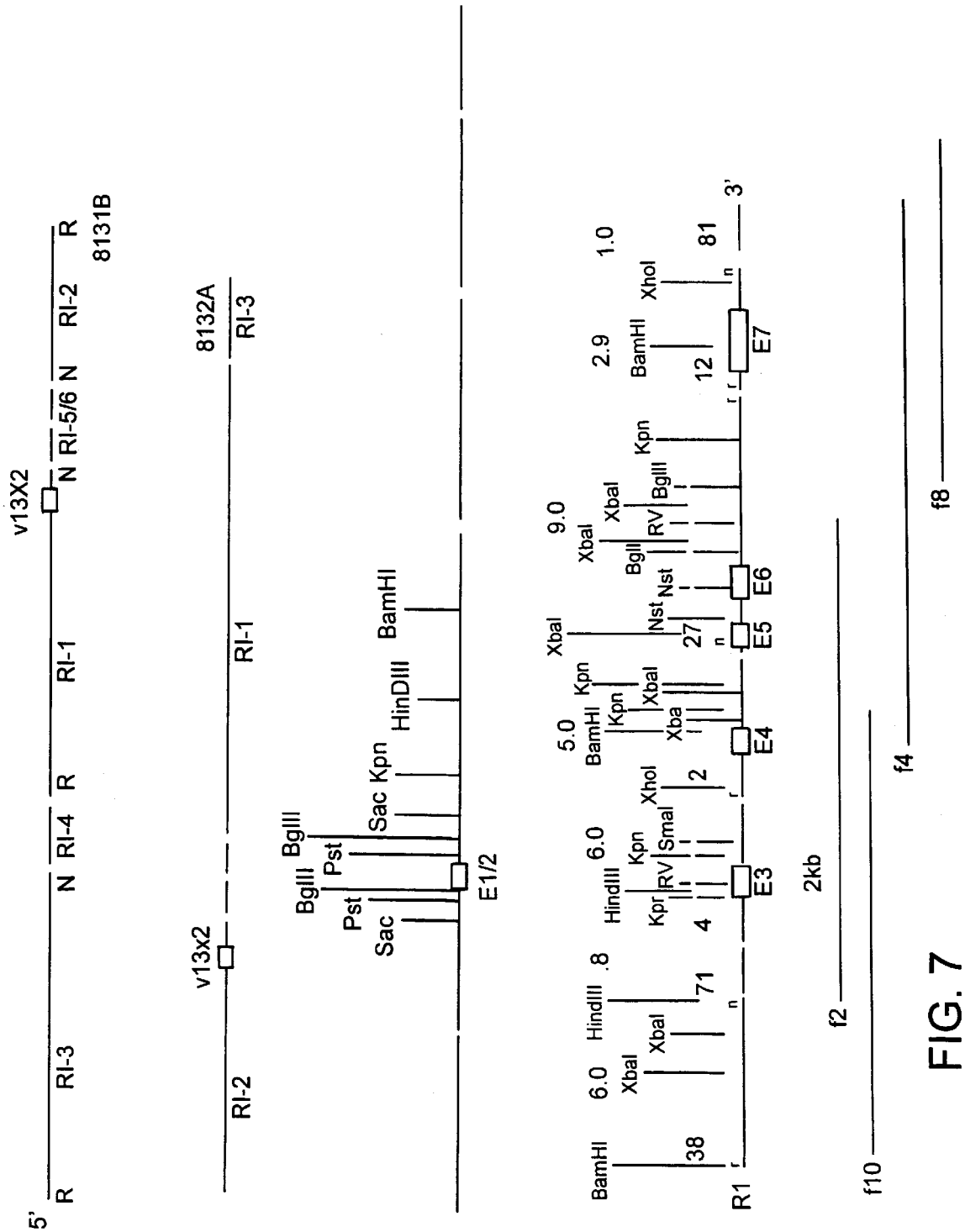

FIG. 7 is a map of the genomic organization of the mouse Ikaros gene. The entire gene is 80–90 kB in length. Intronic or uncharacterized DNA is indicated as a line between 5' and 3'. Exons are indicated as boxes. Lines numbered f2, f10, f4, and f8 indicate phage inserts corresponding to the sequence immediately above. Restriction sites are indicated by the usual abbreviations.

Figure 8:
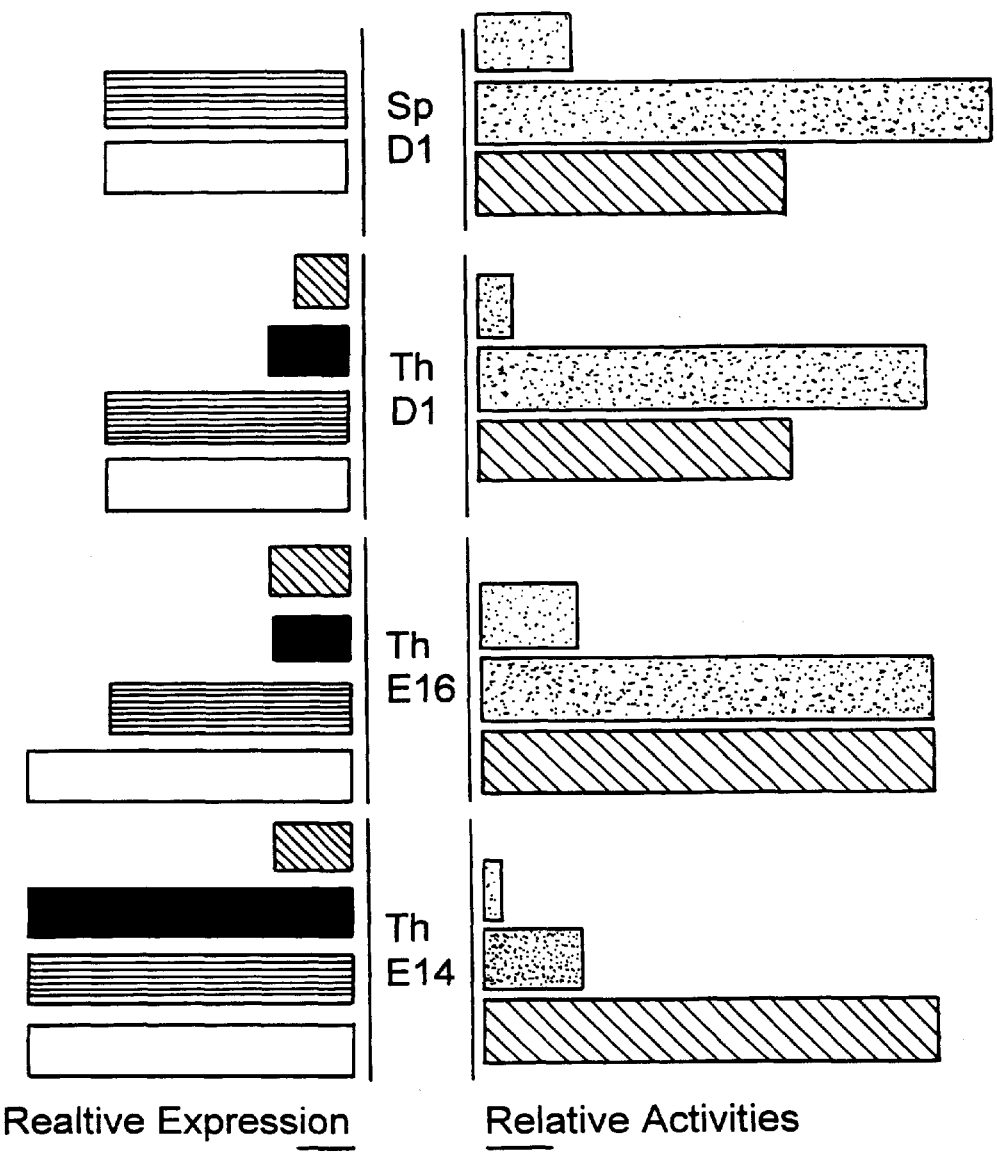

FIG. 8 is a model of Ikaros isoform control of differential gene expressions. Th=thymus; Sp=spleen; Ex=day of embryonic development; Dx=day of postnatal life. The left hand column represents the relative expression of an isoform at a given developmental stage. Open bar=mIk-1; Horizontal stripes=mIk-2; Diagonal stripes=mIk-3; and solid bar=mIk-4. The right hand side shows the resulting reactivity of Ikaros binding sites at a given developmental stage. Light bars=low affinity sites (sites at which isoforms 1, 2, 3 and 4 bind with similar affinities); Dark bars=high affinity inverted or direct repeat containing sites (e.g., NFKB sites, Ik1–4 bind with high affinity); Diagonal bars=single high affinity sites (sites where Ik1 and Ik2 bind but Ik3 and Ik4 don't bind (and therefore won't attenuate the binding of mIk-1 and mIk-2).

FIG. 9 is an amino acid sequence alignment of Exon 3-Exon 7 of the mouse Ik-1 isoform (SEQ ID NO: 5) and the human Ik-1 isoform (SEQ ID NO:3).

FIG. 10 is a diagrammatic representation of five human Ikaros cDNAs with unique 5' noncoding or internal sequences and their alignment to mouse Ikaros coding exons 1–7. Zinc finger modules are shown as perpendicular boxes on the encoding exons 3, 4, 5, and 7. The mouse probe A used for the cDNA library screening is indicated. Stop codons are indicated as asterisks. and translation initiation sites are shown as arrows (A). Sequence composition of 5' noncoding regions in human Ikaros cDNAs (UE-1, UE-2 and UE-3) (B).

Figure 11:
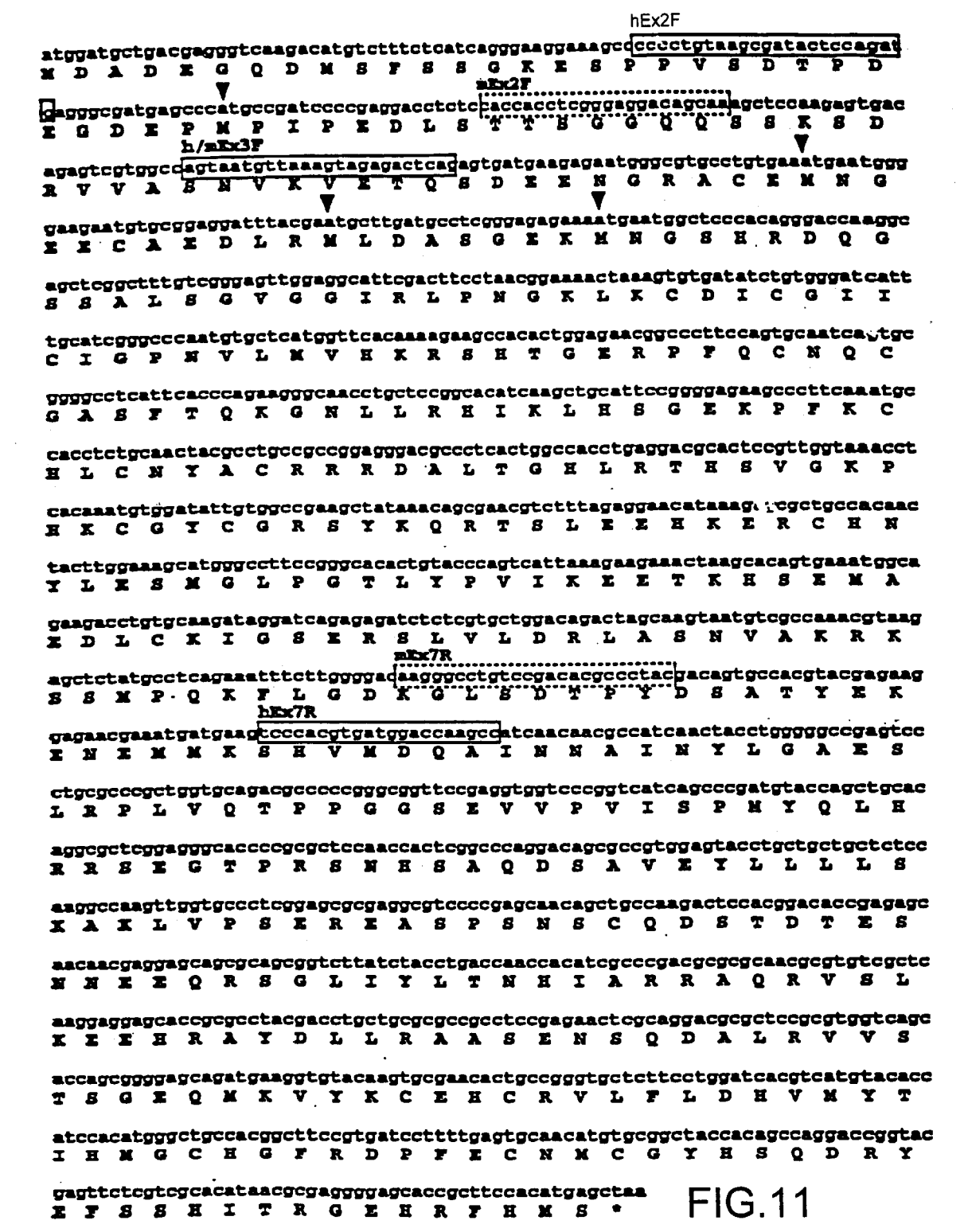

FIG. 11 is a nucleotide and deduced amino acid sequence of human Ik-1 cDNA (SEQ ID NO:165). Arrows indicate potential translation initiation sites. Sequences from which human and mouse Ikaros primers were derived are shown by solid and dashed boxes, respectively.

FIG. 12 is a representation of similarity between human and mouse Ikaros proteins. Alignment of amino acid sequences encoded by human cDNAs and mouse exons 1–7 (1k-1 isoform). The boundaries of mouse exons are indicated, vertical lines indicate identity;:, conservative substitution; ., non conservative substitution; *, stop codon (A). Alignment of potential translation initiation sites (TRI) in human cDNAs to the Kozak consensus (B).

Figure 13:
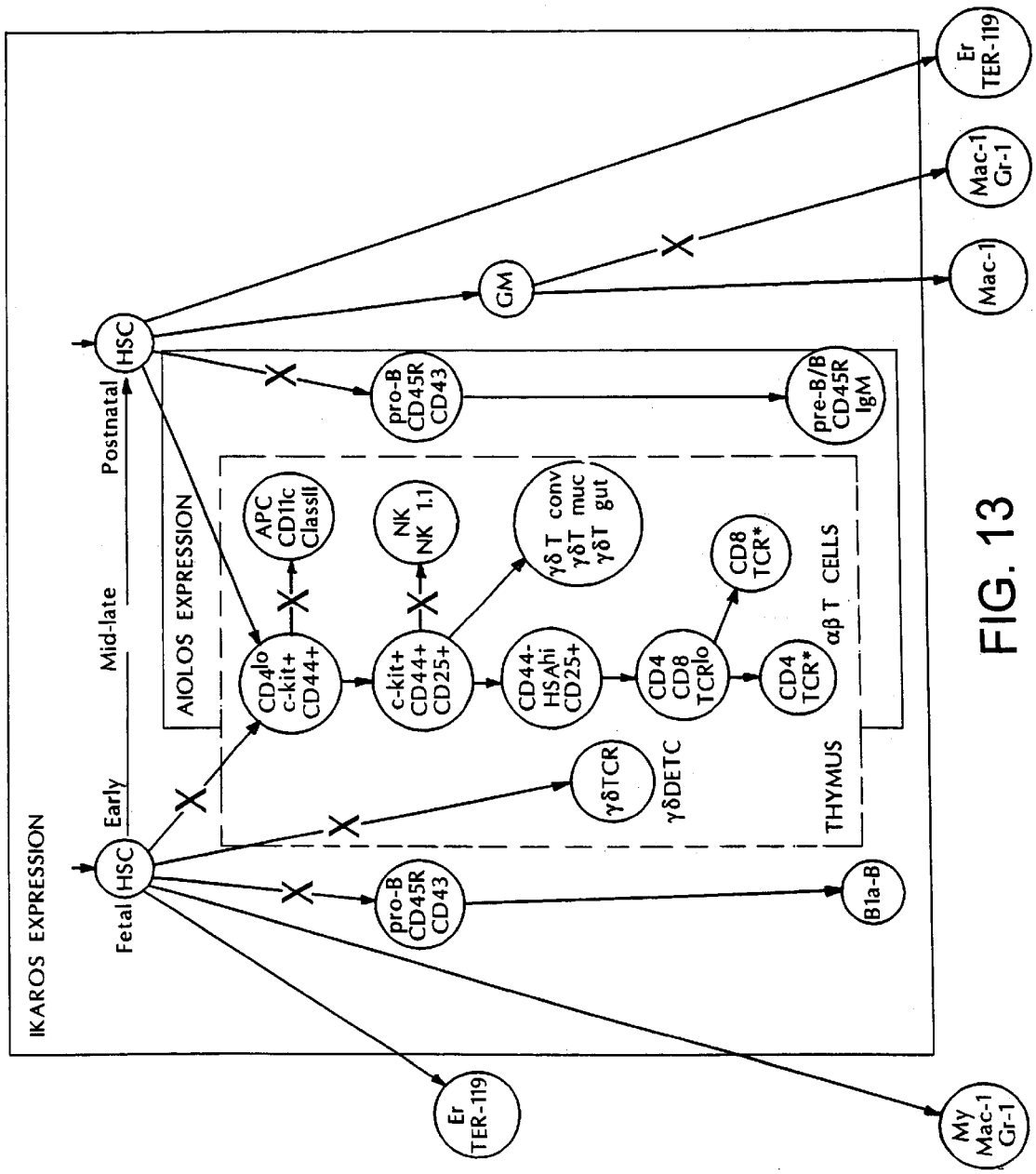

FIG. 13 is a schematic representation of hemopoiesis in the absence of Ikaros. HSC=hemopoietic stem cells, GM=granulocyte-monocyte progenitors, Er=erythroid, TCR=T cell receptor, NK=Natural Killer, APC=antigen presenting cell. The differentiation antigens used to study development along various hemo-lymphoid lineages in Ikaros mutant mice are shown. Arrows demarcate the proposed differentiation pathways. X on the arrows indicates a block in differentiation. Vertical arrows pointing to HSCs indicate the potentially distinct origin of fetal versus adult HSCs. The broken arrow between fetal and adult HSCs depicts a putative relationship. The thick arrow pointing towards CD4 T cells indicates their overproduction in the Ikaros null (C–/–) thymus. The dashed arrow in the T cell pathway marks the partial block in the differentiation of, γδ T cells. The asterisks on CD4 and CD8 T cells marks their hyperproliferative nature. The black transparent box depicts development in the thymus. Shaded areas indicate Ikaros and Aiolos expression (X) in the fetal and adult hemo-lymphoid systems. The grade of shade in the Aiolos box represents its different levels of expression in developing lymphocytes.

FIG. 14 is a schematic representation of an inverse correlation between Ikaros activity and thymocyte proliferation. The legend and its keys are described on the figure.

Figure 15:
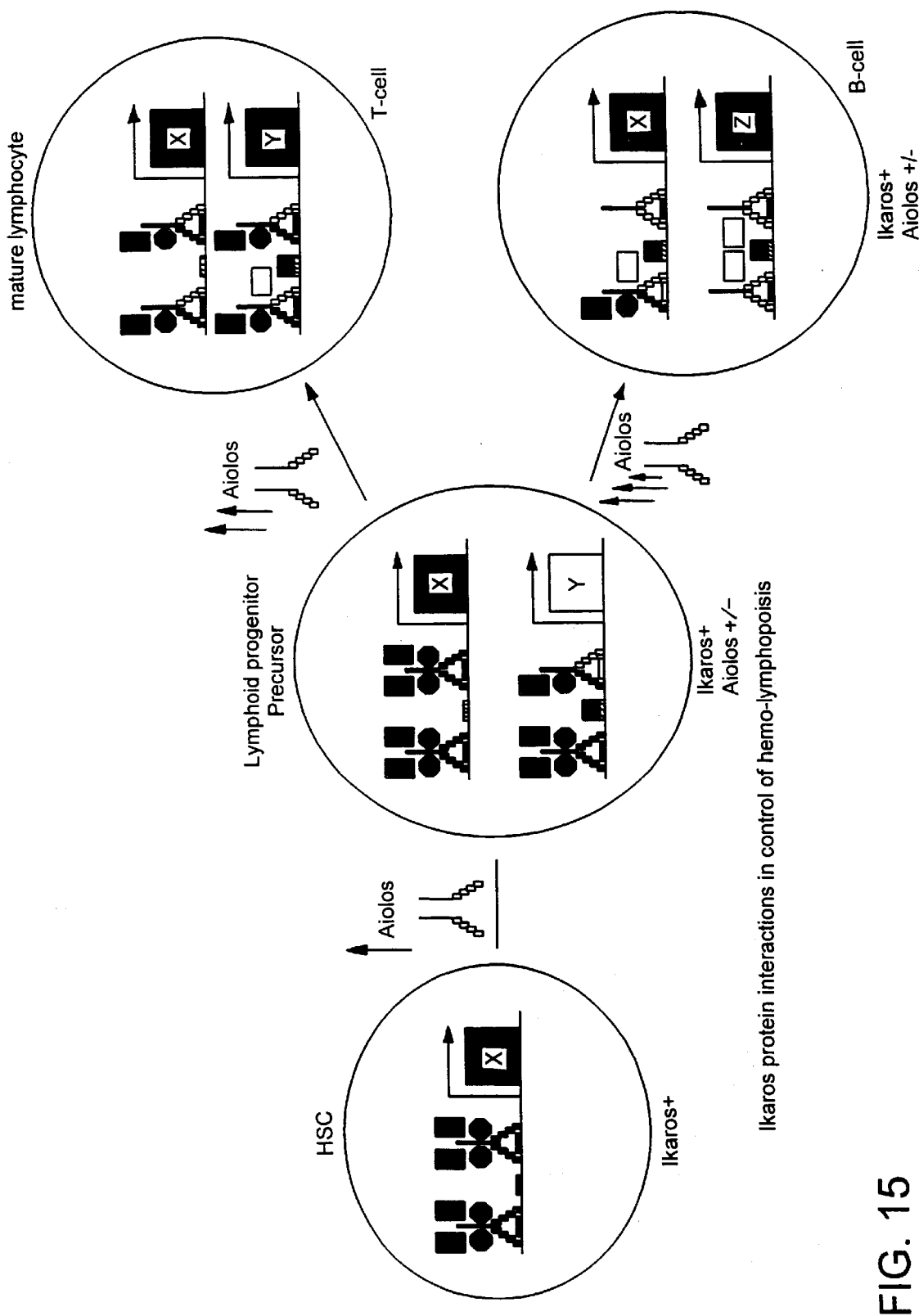

FIG. 15 is a schematic representation of Ikaros protein interactions in control of hemo-lymphopoiesis. Keys to the figure are as those described for FIG. 14.

IKAROS: A MASTER REGULATOR OF HEMOPOIETIC DIFFERENTIATION

A hemopoietic stem cell in the appropriate microenvironment will commit and differentiate into one of many cell lineages. Signal transduction molecules and transcription factors operating at distinct check points in this developmental pathway will specify the cell fate of these early progenitors. Such molecules are viewed as master regulators in development but also serve as markers for the ill defined stages of early hemopoiesis.

Studies on the transcriptional mechanisms that underlie gene expression in T and B cells have identified several transcriptional factors involved in lymphocyte differentiation. However, some of these genes appear to play a role in several developmental systems as determined by their non restricted pattern of expression in the adult and in the developing embryo. The HMG box DNA binding proteins TCF and LEF restricted to T cells and early lymphocytes in the adult are widely expressed in the developing embryo. The T cell specific GATA-3 transcription factor is also expressed outside the hemopoietic system in the early embryo. The ets family members Ets-1 and Elf-1 are widely distributed as well. In addition, the binding affinity and transcription potential of most of these proteins is controlled by other tissue restricted molecules. The ets proteins interact with additional factors for high affinity binding to their cognate sequences. TCFI, LEF and ets-1 must interact with other lymphoid restricted accessory proteins to activate transcription.

In search of a lymphoid restricted transcriptional enhancer, in control of gene expression in early T cells, the Ikaros gene family was isolated, which encode zinc finger DNA binding proteins. In the early embryo, the Ikaros gene is expressed in the hemopoietic liver but from mid to late gestation becomes restricted to the thymus. The only other embryonic site with Ikaros mRNA is a small area in the corpus striatum. In the adult, the Ikaros mRNA is detected only in the thymus and in the spleen (Georgopoulos et al. 1992). The Ikaros gene functions as a transcriptional enhancer when ectopically expressed in non lymphoid cells.

The Ikaros gene plays an important role in early lymphocyte and T cell differentiation. The Ikaros gene is abundantly expressed at early embryonic hemopoietic sites is later on restricted in the developing thymus. The thymus together with the spleen are the prime sites of expression in the adult. This highly enriched expression of the Ikaros gene was also found in early and mature primary T cells and cell lines. This restricted pattern of expression of the Ikaros gene at sites where embryonic and adult T cell progenitors originate together with the ability of the encoded protein to activate transcription from the regulatory domain of an early T cell differentiation antigen supported a determining role in T cell specification.

Differential splicing at the Ikaros genomic locus generates at least five transcripts (Ik-1, Ik-2, Ik-3, Ik-4 and Ik-5) that encode proteins with distinct DNA binding domains. A high level of conservation was found between the human and mouse homologs of the Ikaros gene. The human and mouse Ikaros proteins exhibit nearly 100% identity at their N-terminal zinc finger domain (F1) which was shown to determine the DNA binding specificity of these proteins. In the mouse, differential splicing allows for the distinct combinations of zinc finger modules present in the Ik-1, Ik-2 Ik-3 and Ik-4 isoforms. This differential usage of zinc finger modules in the mouse isoforms establishes the basis of their distinct DNA binding properties and abilities to activate transcription. Differential splicing of the exons encoding the zinc finger DNA binding modules is also manifested in the human Ikaros gene and generates at least two isoforms homologues of the mouse Ik-1 and Ik-4.

These Ikaros protein isoforms (IK-1, IK-2, IK-3, IK-4, IK-5, IK-6, IK-7, IK-8) have overlapping but also distinct DNA binding specificity dictated by the differential usage of zinc finger modules at their N-terminus. In the mouse isoforms (hereinafter designated "mIk), and presumably in the human isoforms (hereinafter designated "hIk"), the core binding site for four of the Ikaros proteins is the GGGA motif but outside this sequence their specificity differs dramatically. The mIK-3 protein shows strong preferences for bases at both the 5' and 3' flanking sequences which restricts the number of sites it can bind to. The mIk-1 protein also exhibits strong preference for some of these flanking bases and can bind to wider range of sequences. The mIk-2 protein, the most promiscuous of the three proteins, can bind to sites with just the GGGAa/t motif. Finally, the mIk-4 protein with similar sequences specificity to mIk-1 binds with high affinity only when a second site is in close proximity suggesting cooperative site occupancy by this protein. Given the identity between the human and mouse Ik-1 and Ik-4 DNA binding domains, the human isoforms are expected to bind similar sequences to, their mouse homologues and regulate transcription in a similar fashion. This extreme species conservation between these two functionally diverse Ikaros isoforms support an important role for these proteins in lymphocyte transcription. The C-terminal domain shared by all of the mouse and human Ikaros isoforms is also highly conserved. This portion of the Ikaros proteins contains conserved acidic motifs implicated as transcription activation domains.

A number of binding sites for the Ikaros proteins were identified by sequence homology, in the enhancers of the T cell receptor -δ, -β and -α and the CD3-δ, -ε and -γ genes, in the HIV-LTR, the IL2-Rα promoter and a variety of other lymphocyte restricted genes. Single and composite binding sites for the Ikaros proteins were found in the TCR-α, -β and -δ enhancers, and occupancy of these sites by the Ikaros proteins may underlie their temporal activation during T cell development. A number of well described NF-κB binding sites present in the promoter and enhancers of genes whose expression is modulated during lymphocyte differentiation and activation also represent composite high affinity binding sites for the Ik-1, Ik-2 and Ik-4 isoforms. In some cell types, such as in the terminally differentiated immunoglobulin secreting plasma cell, where Ikaros isoforms are expressed at minimal amounts, members of the NF-κB/rel family probably play a primary role in the activity of these NF-κB sites. However, in early B lymphocytes and in the activated T cell, functionally diverse Ikaros isoforms present in abundance may be involved in the transcriptional control of some of these NF-κB sites. Within the nucleus of a differentiating T or an early B cell, the Ikaros isoforms may compete for binding with the non-activating members of the NF-κB complex (e.g., $p50_2$, Bours et al. (1993) *Cell* 72:729–739; and Franzoso et al. (1993) *EMBO J* 12:3893–3901) as well as with the NF-κB complex in the activated T cell. Understanding the interaction between Ikaros proteins and other factors and their subcellular localization in the resting and activated T cell may help us determine their role in the activity of NF-κB sites. Thus, gene regulation of at least the IL2α Receptor during T cell differentiation and activation may be controlled by the intricate interplay of NFkB and Ikaros transcription factors interacting on common grounds.

The embryonic expression pattern and activation potential of the Ikaros isoforms are also markedly distinct. The stronger transcriptional activators, Ik-1 and Ik-2, are found in abundance in the early fetal liver, in the maturing thymus and in a small area in the developing brain, whereas the weak activators, e.g. Ik-3 and Ik-4, are present at significantly lower levels in these tissues during these times. Consequently, Ik-1 and Ik-2 are expected to play a primary role in transcription from sites that can bind all four of the Ikaros proteins. However, in the early embryonic thymus and in the late mid-gestation hemopoietic liver the weak activator Ik-4 is expressed at similar mRNA levels to the Ik-1 and Ik-2 isoforms. The Ik-4 weak activator can bind only to composite sites while Ik-1 and Ik-2 can bind to a range of single and composite sites. The Ik-1 and Ik-2 proteins recruited to composite sites (a fraction of the total protein), during early to mid gestation, will have to compete for binding with the Ik-4 isoform, solely recruited to these sites. Consequently the activity of these composite sites may be primarily controlled by the Ik-4 isoform, a weak transcription activator. Modulation of Ik-4 expression in the developing thymocyte, in combination with steady levels of the Ik-1 and Ik-2 expression may determine the temporal and stage specific expression of T cell differentiation antigens. Low affinity binding sites for these proteins may also become transcriptionally active in the late stages of T cell development when the most potent activators, Ik-1 and Ik-2, accumulate. In the fly embryo the NF-κB/rel homologue Dorsal, a maternal morphogen, engages in interactions with transcriptional factors binding to adjacent sites. These protein-protein interactions determine the activation level and threshold response from low and high affinity binding sites (Jiang et al. (1993) *Cell* 72:741–752). The transcriptional activity of the Ikaros proteins may be further regulated by such mechanisms in the developing lymphocyte. In addition, the activity of the Ikaros proteins may be under postranslational control operating during both lymphocyte differentiation and activation. FIG. 8 provides a model in which the relative concentrations of Ikaros isoforms at different developmental stages confer different reactivities on the various sites.

The transcriptional activity of the mIk-3 and mIk-4 proteins may be further regulated by T cell restricted signals mediating postranslational modifications or by protein-protein interactions. The mIk-4 protein binds NFkB motif in a cooperative fashion and may therefore interact in situ with other members of the Ikaros or of the NFkB family. These protein-protein-DNA complexes may dictate a differential transcriptional outcome.

The differential expression of the Ikaros isoforms during T cell ontogeny, their overlapping but also unique binding specificities and their diverse transcriptional potential may be responsible for the orderly activation of stage specific T cell differentiation markers. Multiple layers of gene expression in developing lymphocytes may be under the control of these Ikaros proteins. Synergistic interactions and/or competition between members of the Ikaros family and other transcription factors in these cells on qualitatively similar and distinct target sites could dictate the complex and ever changing gene expression in the differentiating and activated lymphocyte. This functional dissection of the Ikaros gene strongly suggest it functions as a master gene in lymphocytes, and an important genetic switch for early hemopoiesis and both B and T cell development.

Ikaros proteins with one or no N-terminal zinc fingers (e.g., Ik-5, Ik-6, Ik-7 and Ik-8) cannot engage in high affinity DNA binding. The C-terminal zinc finger domain shared by all the Ikaros isoforms is utilized to engage these proteins in stoichiometric homo and heterodimeric complexes. These protein interactions are pivotal for Ikaros activity. Formation of homo and heterodimers between isoforms with an N-terminal domain capable of binding DNA, i.e., Ik-1, Ik-2 and Ik-3, increases dramatically their affinity for DNA and activity in transcription. In contrast, heterodimers formed between Ikaros isoforms with and without an intact DNA binding domain (i.e., Ik-1, Ik-2 and Ik-3 with Ik-4, Ik-5, Ik-6, Ik-7 and Ik-8) cannot bind DNA and are transcriptionally inert. Thus, Ikaros proteins with fewer than three N-terminal zinc fingers can play a dominant negative role in transcription by interfering with the activity of isoforms that can bind DNA. Mutations that disrupt the structure of the C-terminal zinc fingers also prevent Ikaros proteins from binding DNA and activating transcription.

Therefore, the presence of functionally distinct combinations of zinc fingers in the Ikaros gene modulates the DNA binding potential of its protein product and, consequently, their effects in transcription. Interactions between the three DNA binding Ikaros isoforms, e.g., Ik-1, Ik-2 or Ik-3, generate six homo and heterodimeric complexes with distinct combinations of two DNA binding domains which can interact with a range of regulatory sequences. Evidence suggests that Ikaros dimers may form higher order complexes. These would contain multiple DNA binding domains which may serve to mediate interactions between distal sites in similar fashion to the GATA and Sp1 factors. Thus, an important aspect in the function of these Ikaros complexes may be to facilitate communication between distal regulatory elements.

The Ikaros gene maps to the proximal arm of human chromosome 7 between p11.2 and p13 next to Erbb In the mouse the Ikaros gene maps to the proximal arm of chromosome 11 tightly linked to Erbb. Other genes linked to the Ikaros locus in the mouse are the Leukemia inhibitory factor (Lif) and the oncogene Rel a member of the NFK-B family. All three of the genes linked to the Ikaros gene in the mouse appear to play an important role in the development of the hemopoietic system. The tight linkage between the Erbb and the Ikaros genes on syntenic loci in the mouse and human may be related to their genetic structure and regulation. Nevertheless, no known mutations were mapped to the Ikaros locus in the mouse However, this does not preclude the importance of the Ikaros gene for the lymphopoietic system Naturally occurring mutations that affect development of the immune system may not be readily obtained in mice since such mutant animals may only thrive under special care conditions.

That the Ikaros gene is a fundamentally important regulator of lymphocyte development is substantiated by analysis of its human homologue. The overall conservation of the Ikaros proteins between mice and men at the genetic level and protein level but also their restricted pattern of expression in the developing lymphocyte, e.g. in maturing T cells, e.g. in maturing B cell, strongly support their participation in the same regulatory pathway across species.

Mutational Analysis of the δ Element of the CD3δ Enhancer

One approach useful for characterizing early events in T cell differentiation is to study the regulation of transcription of T cell restricted antigens. The transcriptional control of one of the earliest and definitive T cell differentiation markers, the CD3δ gene of the CD3/TCR complex was chosen for study. In order to identify a transcription factor expressed at or earlier than T cell commitment which can function as a genetic switch regulating entry into the T cell lineage, a T cell specific enhancer mediating expression of this gene was characterized. This enhancer is comprised of two functionally distinct elements δA and δB with activity restricted in T cells. Mutational analysis of the δA element has further identified two transcriptionally active binding sites, a CRE (Cyclic AMP response)-like element and a G rich sequence motif both of which are required for full activity of the δA element and the CD3 enhancer, see FIG. 1.

FIG. 1 depicts the functional dissection of the δA element of the CD36δ enhancer. FIG. 1A shows the binding sites in the δ element (SEQ ID NO:1). The boxed sequences represent the CRE-like and the G rich motif both important for activity of the δA element. Mutations introduced in the δA element are shown below the sequence.

FIG. 1B shows the contribution of the CRE and the G box to the activity of the δA element and the CD3δ enhancer as analyzed by transient expression assays in the T cell line EL4. The activity of the tkCAT reporter gene under the control of wild type δA, δAmu1 and δAmu2 as reiterated elements or in the context of the CD36δ enhancer was determined as described in Georgopoulos et al. (1992) *Mol Cell Biol* 12:747. Reporter gene activation (R.A.) was expressed as the ratio of Chloramphenicol Acetyl Transferase (CAT) to Growth Hormone (GH) activity estimated for each transfection assay. FIG. 1C shows that the expression of the Ikaros gene (mIk-2)in non T cells upregulates the activity of the δA element. The CDM8 and CDM8:Ikaros recombinant I expression vectors were cotransfected with the tkcat 3δA, tkcat 3δAmu1, tkcat 3δAmu2 and tkcat δenhancer reporter genes in CV1 (kidney epithelial) cells as described in Georgopoulos et al. (1992). The ratio of reporter activation (R.A.=CAT/GH) in the presence and absence of Ikaros expression was estimated. Three isoforms of the ubiquitously expressed CRE-Binding Protein were cloned from T cells for their ability to interact with the CRE-like binding site of the δA element, see Georgopoulos et al. (1992). Although dominant negative mutants of this protein down regulate the activity of this enhancer element in T cells, expression of this transcription factor in all hemopoietic and non hemopoietic cells argues against it being the switch that activates the CD3δ enhancer in the early prothymocyte progenitor. A variant of the δA element (δAmu1-CRE) was used to screen a T cell expression library as described in Georgopoulos et al. (1992). As described below, a T cell restricted cDNA was cloned encoding for a novel zinc finger protein (Ikaros) that binds to the G box of the A element.

Cloning the Mouse Ikaros Gene

A T cell expression cDNA library from the mature T cell line E14 was constructed into the A ZAP phage vector.

A multimerized oligonucleotide encoding sequence (SEQ ID NO:154) from one of the protein binding sites of the CD38δ enhancer was used as a radiolabelled probe to screen this expression library for the T cell specific proteins that bind and mediate enhancer function by the southwestern protocol of Singh and McKnight. Four gene encoding DNA binding proteins were isolated. One, the Ikaros gene, encoded a T cell specific protein.

The Sequence of Mouse Ikaros

The sequence of the Ikaros gene was determined using the Sanger dideoxyl sequencing protocol. The derived amino acid sequence was determined using the MAP program of GCG (available from the University of Wisconsin) and Strider sequence analysis programs. FIG. 2 provides the sequence of a mouse Ikaros cDNA (mIk-2) and the derived amino acid sequence encoded thereby (SEQ ID NO:2). Sequence information for other isoforms of mouse Ikaros proteins (and cDNAs) are provided in SEQ ID NO:4 (mIk-3), SEQ ID NO:5 (mIk-1), SEQ ID NO:6 (mIk-4), and SEQ ID NO:7 (mIk-5).

A Mouse Ikaros Protein

The Ikaros protein shown in FIG. 2 (mIk-2) is comprised of 431 amino acids with five $CX_2CX_{12}HX_3H$ zinc finger motifs organized in two separate clusters. (See also FIG. 5.)

The first cluster of three fingers is located 59 amino acids from the initiating methionine, while the second cluster is found at the C terminus of the protein 245 amino acids downstream from the first. Two of the finger modules of this protein deviate from the consensus amino acid composition of the Cys-His family of zinc fingers; finger 3 in the first cluster and finger 5 at the C terminus have four amino acids between the histidine residues. This arrangement of zinc fingers in two widely separated regions is reminiscent of that of the Drosophila segmentation gap gene Hunchback. Similarity searches in the protein data base revealed a 43% identity between the second finger cluster of Ikaros and Hunchback at the C terminus of these molecules. This similarity at the C terminus of these proteins and the similar arrangement of their finger domains raises the possibility that these proteins are evolutionary related and belong to a subfamily of zinc finger proteins conserved across species.

Ikaros Isoforms

In addition to the cDNA corresponding to mIk-2, four other cDNAs produced by differential splicing at the Ikaros genomic locus were cloned. These isoform encoding cDNAs were identified using a 300 bp fragment from the 3' of the previously characterized Ikaros cDNA (mIk-2, FIG. 1). As shown in FIGS. 4 and 5, each isoform is derived from three or more of six exons, referred to as E1/2, E3, E4, E5, E6 and E7. All five cDNAs share exons E1/2 and E7 encoding respectively for the N-53 and C-terminal 236 amino acid domains. These five cDNAs consist of different combinations of exons E3–6 encoding the N-terminal zinc finger domain. The mIk-1 cDNA (SEQ ID NO: 5) encodes a 57.5 kD protein with four zinc fingers at its N-terminus and two at its C-terminus and has the strongest similarity to the Drosophila segmentation protein Hunchback (Zinc fingers are indicated as F1, F2+F3, F4, and F5+F6 in FIG. 5). The mIk-2 (SEQ ID NO:2) and mIk-3 (SEQ ID NO: 4) cDNAs encode 48 kd proteins with overlapping but different combinations of zinc fingers. The mIk-3 isoform contains fingers 1, 2, 3 while mIk-2 contains fingers 2, 3 and 4. The 43.5 kD mIk-4 protein (SEQ ID NO: 6) has two fingers at its N-terminus also present in mIk-1 and mIk-2. The mIk-5 cDNA (SEQ ID NO: 7) encodes a 42 kd protein with only one N-terminal finger shared by mIk-1 and mIk-3 (FIG. 1). This differential usage of the zinc finger modules by the Ikaros proteins support an overlapping but differential DNA binding specificity.

cDNA cloning of isoforms was performed as follows. A cDNA library made from the T cell line EL4 in λZAP was screened at high stringency with a 300 bp fragment from the 3' of the previously described Ikaros cDNA (isoform2). Positive clones were characterized by sequencing using an antisense primer from the 5' of exon 7.

Mouse Ikaros Expression

Tissue Specific Expression of the Ikaros Gene

The Ikaros gene is expressed in T cells and their progeny. In the adult mouse, Ikaros mRNA is restricted to the thymus and the spleen with expression in the thymus being about 3 fold higher than the spleen. Spleen cells preparations depleted of T cells expressed very low levels of this message. Examination of Ikaros expression in cell lines confirm the view that the Ikaros gene is expressed in T cells and their progeny. Ikaros mRNA was detected in a number of T lymphoma cell lines. The T cell line EL4 expressed the highest levels while DO11.10, BW5147 and SL12.1 lymphomas showed moderate to low expression. No expression or very low levels were detected in cell lines representing other hemopoietic lineages including the bone marrow derived progenitor cells FDCP1 that exhibit myeloid morphology and differentiation potential, the mast cell line RBL, the macrophage line J774 (detected expression is 25 fold lower than that in thymocytes) and MEL cells which were induced to differentiate into erythroid cells. Nevertheless, moderate levels of Ikaros mRNA were detected in the B cell lymphoma A20 and in the proerythroleukemia cell line MEL. Immortalization of these cell lines and their leukemic phenotype may account for aberrant expression of this nuclear factor which does not appear to be expressed at significant levels in normal B cells (spleen T cell depleted population, or in erythroid progenitors in vivo (from in situ data). Alternatively expression of this thymocyte restricted factor in these cell lines may reflect the existence of an early progenitor with the ability to differentiate into the lymphoid or the erythroid lineage.

Tissue distribution of the Ikaros gene was determined by Northern hybridization of total RNAs prepared from: the T lymphoma cell lines EL4, BW5147, DO11.10, SL12.1; the B cell lymphoma A20; the tissues of thymus, spleen, kidney, brain and heart isolated from an adult mouse; spleen thymocytes (total and polyA-RNA); bone marrow derived stem cell progenitors FDCP1; macrophage cell line J774; mast cell line RBL; undifferentiated MEL and 58 hr DMSO induced MEL cells; and finally T depleted spleen cells (TDSC). A 320 bp fragment (bp 1230–1550) from the 3' end of the Ikaros mIk-2 cDNA was used as a probe.

Temporal Regulation of the Expression of the Ikaros Gene

To determine when in hemopoiesis the Ikaros gene becomes activated its expression was studied in situ in the developing mouse embryo. Hemopoiesis begins at day seven in the yolk sac of the mouse embryo with the generation of a large population of primitive erythroblasts. The Ikaros mRNA is not detected in the yolk sac at day 8 in contrast to the erythroid specific transcription factor GATA-1 which is expressed at this time in development. In the embryo proper, expression of Ikaros is first detected in the early liver rudiment at the onset of its hemopoietic function (day—9½–10½). At this time, pluripotent stem cells as well as more restricted progenitors are found in the liver which can successfully reconstitute irradiated animals with the whole spectrum of hemopoietic lineages. Expression of the Ikaros gene remains strong in the liver up to day fourteen and begins to decline thereafter although the liver is the major site of hemopoiesis through mid gestation and remains active through birth. The declining expression of the Ikaros gene in the fetal liver at mid gestation is consistent with changes in the hemopoietic, profiles from pluripotent stem cells to more committed erythroid progenitors.

The second site of Ikaros expression is in the thymic rudiment around day 12 when lymphopoietic stem cells are first colonizing this organ. A group of expressing cells is detected at the center of the thymic rudiment surrounded by non expressing cells in the periphery. Expression in the developing thymus becomes quite prominent by day 16 and persists throughout embryogenesis to the adult organism. At these developmental stages expression of Ikaros mRNA is detected throughout the thymus with levels in the medulla sections being slightly more elevated than these in the cortex.

Ikaros expression is first detected in the spleen during late gestation at low levels compared to those of the thymus (day 19). Although the spleen is active in erythropoiesis and myelopoiesis from mid-gestation, its population with mature T cells from the thymus takes place late in embryogenesis and correlates with the late expression of the Ikaros gene. No expression of Ikaros message is detected in the bone marrow of the long bones or the spinal column at day 19 in contrast to the myeloid specific factor Spyl and to the erythroid factor GATA-1. The pattern of expression of the Ikaros gene detected in distinct hemopoietic sites throughout embryonic development is consistent with its restriction to T cells and their progenitors. The only other site in the mouse embryo that exhibited Ikaros expression was a restricted area in the brain which gives rise to the proximal corpus striatum (day 12 through 19).

Embryos were harvested from time pregnant CD1 mice (Charles River) and were fixed in 4% paraformaldehyde for 2 hours to 2 days depending on size. A series of dehydration steps was performed in alcohols followed by xylenes before paraplast embedding. Sections were prepared and treated according to published protocols. Sense and antisense P-UTP RNA probes 300 bp in size were made from the 3' untranslated region of the Ikaros cDNA and were used to hybridize to selected slides at 48° C. overnight. After high stringency washings slides were dehydrated and dipped in diluted photographic emulsion (NBT2) for 3 weeks. Dipped slides were developed, stained with Giemsa and analyzed by bright and dark field microscopy.

Expression of Ikaros Isoforms

The pattern of Ikaros isoforms expression in the developing embryo was studied. Two sets of primers were used to amplify the five cDNAs as distinct sized bands from embryonic and postnatal tissues (FIG. 6). A third set of primers complementary to the β-actin cDNA was used to normalize the amount of cDNA used n the reaction. Primers 1/2 amplified a 720, a 457 and a 335 bp fragment from the mIk-1, mIk-2 and mIk-4 cDNAs. Primers 3/4 amplified a 715, a 458 and a 293 bp fragment from the mIk-1, mIk-3 and mIk-5 cDNAs. A 650 bp band detected is an artifact of mIk-1 and mIk-2 coamplification representing mIk-1/mIk-2 and mIk-1/mIk-3 hybrid molecules. It is present at significant levels at the later amplification cycles when the primers to mIk-1, mIk-2 and mIk-3 ratio is decreased. This band is also detected when we coamplify mIk-1, mIk-2 and mIk-3 DNA templates. The identity of the above described bands were also confirmed by cloning and sequencing. It is noteworthy that the 650 bp species was never cloned as a novel of cDNA.

During embryonic development all five Ikaros mRNAs were expressed in hemopoietic centers and in the brain at relatively different levels. The mIk-1 and mIk-2 mRNA were abundantly expressed in the early fetal liver, the maturing thymus, and the postnatal spleen-. The mIk-4 isoform was expressed at low levels compared to mIK-1 and mIk-2 in the early fetal liver and in the maturing thymus (liver E14, thymus E16 and D1).

However it was expressed at comparable amounts to mIk-1 and mIk-2 in the early thymus and mid-gestation liver (Table 1, thymus E14, liver El 6). This equalization was due to a decrease in the expression of the latter two mRNAs rather than an increase in the expression of the mIk-4 transcript. In the embryonic day 14 thymus, the mIk-4 isoform was expressed at similar if not higher levels than the mIk-1 and mIk-2 mRNAs, but its expression declined during mid-gestation. The pattern of expression of mIk-1, mIk-2, and mIk-4 mRNAs detected in the day 16 embryonic thymus persisted past birth in this organ, in contrast to liver expression which was switched off in the neonate, mIk-1 and mIk-2, but not mIk-4, mRNAs were readily detectable in the spleen of the neonate. The mIk-3 and mIk-5 isoforms were expressed but at significantly lower levels than mIk-1 and mIk-2 throughout development (Table 1). Finally, the mIk-5 transcript present at very low amounts in the developing lymphocyte was readily seen after a higher number of amplification cycles.

All five isoforms were expressed in the embryonic brain. The mIk-1 was the most abundant mRNA, mIk-2 and mIk-4 were present at similar but lower levels, while mIk-3 and mIk-5 were the least expressed. The expression of Ikaros isoforms in the brain was decreased from mid gestation to day 1, and likely reflects it restriction to a discrete cellular compartment in this organ.

The expression pattern of the Ikaros isoforms detected in the late embryonic thymus persisted past birth while the declining liver expression was switched off. The neonatal spleen expressed only mIk-1 and mIk-2 mRNAs at significant amounts. Low concentration of mIk-1 were still detected in the neonatal brain. These data agree and further supplement our previous in situ hybridization studies performed using an RNA probe made from the 3' of the Ikaros gene shared by all identified Ikaros splicing products.

TABLE 1

A summary of the embryonic expression patterns for the mIk-1-5 transcripts.

|  |  | mIk-1 | mIk-2 | mIk-3 | mIk-4 | mIk-5 |
| --- | --- | --- | --- | --- | --- | --- |
| Liver | E14 | +++++ | ++++ | ++ | ++/− | − |
|  | E16 | +++ | ++ | +/− | ++/− | − |
|  | D1 | + | − | − | − | − |
| Thymus | E14 | +++ | +++ | +/− | +++ | − |
|  | E16 | ++++ | +++ | +/− | + | +/− |
|  | D1 | +++ | +++ | − | + | + |
| Brain | E14 | ++ | + | +/− | + | + |
|  | E16 | ++ | + | +/− | + | + |
|  | D1 | + | − | − | − | − |
| Spleen | D1 | +++ | +++ | − | − | − |

Embryonic tissues were obtained from embryos harvested from of time pregnant mothers (E14, E16, D1, obtained from TACONIC) and total RNA was prepared, 2–5μgs of total RNA prepared from the thymus, liver, brain and spleen at different stages of embryonic development were used for cDNA synthesis with random hexamers and Superscript RNaseH. 1/10th of cDNA made was used in PCR amplification with the 1/20, 3/4 and actin A/B set of primers. PCR reactions were denatured at 95° C. for 5 minutes, polymerase was added at 80° C., and then were amplified for 25 cycles at 94° C. for 45", 63° C. for 1' and 72° C. for 1'. PCR amplification for the actin cDNAs were performed for 30 cycles. Products were separated on 2% Seakam FMC agarose, bands were excised, cloned (TA cloning kit, Clonteck) and sequenced to verify their identity.

Ikaros Stimulates the Transcription from the δA Element

Initial Transcriptional Studies

The ability of an Ikaros protein that can bind to the δA element to also activate transcription from this binding site was examined. The tkCAT reporter gene under the control of either a reiterated δA binding site (+/−CRE/−G) or under the control of the CD3δ enhancer was cotransfected with a recombinant vector expressing the Ikaros gene in the kidney epithelial cell line CV1. Expression of the Ikaros gene in non T cells strongly stimulated transcription from the G box of a reiterated δA element and in the context of the CD3δ enhancer (see FIG. 1C). Activity of the δA and δAmu1 (−CRE) elements was stimulated by eight and seven fold respectively while expression of the CD3δ enhancer was stimulated by five fold. Since the CD3δ enhancer is comprised of at least two regulatory elements, expression of all the transcription factors that bind to these sites is necessary for its full activation potential. Expression of the Ikaros gene did not significantly stimulate the activity of the thymidine kinase promoter or of the δAmu2(−Gbox) element (see FIG. 1C). These data confirms our hypothesis that the Ikaros gene can control activity of the T cell specific δA element of the CD3δ enhancer and suggests that it can mediate expression of at least the CD3δ gene in T cells.

The expression pattern of the Ikaros protein, and its ability to modulate the activity of the CD3δ enhancer, is consistent with a role in mediating gene expression in T cells in the embryo and in the adult. Its early expression in fetal liver hemopoietic stem cells suggests that it may be expressed in early prothymocyte progenitors and raiser the possibility that it is responsible for commitment of a pluripotent stem cell to the T cell lineage.

Binding Site Selections for the Ikaros 1–3 Isoforms

To investigate the possibility that differential usage of zinc finger modules by the five Ikaros isoforms contributes to their DNA binding a specificity, we cloned high affinity binding sites for three of these proteins. The mIk-1, mIk-2 and mIk-3 proteins were selected since they contain either all four (mIk-1) or two distinct combination of three (mIk-2 and mIk-3) from the pool of the N-terminal four fingers (FIG. 5). We expected these proteins to overlap in specificity with mIk-4 and mIk-5 proteins which contain only two or one of these putative DNA binding modules. In addition, GST fusion proteins derived from the mIk-1, mIk-2 and mIk-3 isoforms lacking the C-terminal portion encoded by exon-7 (e.g. lacking the zinc fingers F5 and F6) were constructed, as well as truncated mIk-I (containing F1, F2, F3 and F4), mIk-2 (containing F2, F3 and F4) and mIk-3 (containing F1, F2 and F3).

After five rounds of binding site selections from a pool of random oligonucleotides the mIk-1-, mIk-2- and mIk-3 selected oligomers were cloned, sequenced and aligned to a shared motif (Tables 2, 3 and 4 in the tables, bold face type indicates conserved sequence).

TABLE 2

| | | |
|---|---|---|
| Ik1-1  | aggcgaTTTTGGGAATTTCacacc | (SEQ ID NO:9) |
| Ik1-2  | aggcCATGGGAATGAAGGAacacc | (SEQ ID NO:10) |
| Ik1-3  | ggtgtAAATTGGGAATGCTGtgcct | (SEQ ID NO:11) |
| lk1-4  | aggcATGGGAATGTC<u>TGGA</u>acacc | (SEQ ID NO:12) |
| Ik1-5  | aggcATTAAAATGGGAATAacacc | (SEQ ID NO:13) |
| Ik1-6  | ggtgtAGGAATGCGGTAATTgcct | (SEQ ID NO:14) |
| lk1-7  | ggtgtGGGAATAAC<u>TGGGAT</u>gcct | (SEQ ID NO:15) |
| Ik1-8  | ggtgtGGGAATGTCACTTCAgcct | (SEQ ID NO:16) |
| Ik1-9  | ggtgtGGGAATACTGAGTATGCCT-gcct | (SEQ ID NO:17) |
| Ik1-10 | aggcAAATTGGGAATACTacacc | (SEQ ID NO:18) |
| Ik1-11 | ggtgtGTGGGAACATGGGGgcct | (SEQ ID NO:19) |
| Ik1-12 | aggcCTAT<u>TTCCC</u>TTGGGAacacc | (SEQ ID NO:20) |
| Ik1-13 | ggtgt<u>GGAA</u>CATCGTGGGAAGCCgcct | (SEQ ID NO:21) |
| Ik1-14 | aggcGCTTGGGAAA<u>TTCCA</u>acacc | (SEQ ID NO:22) |
| Ik1-15 | aggcA<u>TTCCT</u>AAACCGGGAacacc | (SEQ ID NO:23) |
| Ik1-16 | aggcACAA<u>TTCCTT</u>CGGGAacacc | (SEQ ID NO:24) |
| Ik1-17 | ggtgtCGGGCTTCGGGAATAgcct | (SEQ ID NO:25) |
| Ik1-18 | gt<u>gtTCC</u>AAACTCGGGAATgcct | (SEQ ID NO:26) |
| Ik1-19 | ggtgt<u>GGAA</u>TCGGGAATTTAgcct | (SEQ ID NO:27) |
| Ik1-20 | aggcTTATCGGGAAAACTTacacc | (SEQ ID NO:28) |
| Ik1-21 | gt<u>gtTCC</u>AAACGGGGGAATgcct | (SEQ ID NO:29) |
| Ik1-22 | ggtgtGCAA<u>TTCCA</u>AGGAATgcct | (SEQ ID NO:30) |
| Ik1-23 | aggcGCCA<u>TTCC</u>AAGGATAacacc | (SEQ ID NO:31) |
| Ik1-24 | aggcTAATCTTGGAA<u>TTCC</u>acacc | (SEQ ID NO:32) |

TABLE 2-continued

| | A -3 | N -1 | T -2 | T 1 | G 2 | G 3 | G 4 | A 5 | A 6 | T 7 | A G 8 | C T 9 | C T 10 |
|---|---|---|---|---|---|---|---|---|---|---|---|---|---|
| G | 7 | 0 | 7 | 1 | 22 | 24 | 24 | 0 | 0 | 2 | 8 | 2 | |
| A | 7 | 6 | 3 | 2 | 2 | 0 | 0 | 24 | 22 | 3 | 11 | 3 | 3 |
| T | 5 | 9 | 11 | 15 | 0 | 0 | 0 | 0 | 2 | 15 | 3 | 6 | 4 |
| C | 5 | 9 | 3 | 6 | 0 | 0 | 0 | 0 | 0 | 4 | 2 | 13 | 14 |

TABLE 3

| | | |
|---|---|---|
| IK2-1 | ggtgtACGGTTGGGAATGCGgcct | (SEQ ID NO:36) |
| IK2-2 | ggtgtAGGAATGGGAATACAgcct | (SEQ ID NO:37) |
| IK2-3 | ggtgtTGGGATTGGGAATGTgcct | (SEQ ID NO:38) |
| IK2-4 | ggtgtCGGGAATTATTTTAGgcct | (SEQ ID NO:39) |
| IK2-5 | ggtgtAAAAATGGGAACAAAgcct | (SEQ ID NO:40) |
| IK2-6 | ggtgtGGGAAAGATATAGCCgcct | (SEQ ID NO:41) |
| IK2-7 | ggtgtTTAACCAATTGGGAAgcct | (SEQ ID NO:42) |
| IK2-8 | ggtg<u>tTCCG</u>GTATTTGGGAAgcct | (SEQ ID NO:43) |
| IK2-9 | ggtgtGGGATAACTTGGGAAgcct | (SEQ ID NO:44) |
| IK2-10 | aggcGGGAAACCCATAGGacacc | (SEQ ID NO:45) |
| IK2-11 | ggtAATCCGTCGGGAACAgcctA | (SEQ ID NO:46) |
| IK2-12 | ggcTTTAGATCAGGGAACacacc | (SEQ ID NO:47) |
| IK2-13 | gt<u>ATCCT</u>GGTAGGAATCgcct | (SEQ ID NO:48) |
| IK2-14 | aggcTATCCCAGGAATTTGacacc | (SEQ ID NO:49) |
| IK2-15 | aggcAAATTGTTCAGGAACACacacc | (SEQ ID NO:50) |
| IK2-16 | ggtgtCCATAAGGAACAATAgcct | (SEQ ID NO:51) |
| IK2-17 | aggcAGACCCAAGGAAGCCacaccc | (SEQ ID NO:52) |
| IK2-18 | aggcTATCCCAGGAATTTGacacc | (SEQ ID NO:53) |
| IK2-19 | agg<u>AGAATCCTAT</u>GGGATacacc | (SEQ ID NO:54) |
| IK2-20 | ggtgtTCATTGGGATAGCATgcct | (SEQ ID NO:55) |
| IK2-21 | ggtgtTGGGATTTCTGGAT-Agcct | (SEQ ID NO:56) |
| IK2-22 | aggcGTTTGGGATGTATTTacacc | (SEQ ID NO:57) |
| IK2-23 | ggtgtGGGATCGCCATATTC | (SEQ ID NO:58) |
| IK2-24 | ggtgtGGGATTGCTTTATTT | (SEQ ID NO:59) |
| IK2-25 | ggtgtGGGATTGGGACTAAAgccta | (SEQ ID NO:60) |
| IK2-26 | ggtgtGGGATTGGGACTAAAgcct | (SEQ ID NO:61) |
| IK2-27 | ggtgtAGGACAATGGGATAgcct | (SEQ ID NO:62) |
| IK2-28 | ggtgtCAGGATTTGGGACAcgcct | (SEQ ID NO:63) |
| IK2-29 | ggtgtGGGACTCAAAGAGGC | (SEQ ID NO:64) |
| IK2-30 | ggtgtCCTCCAGCGGGATAgcct | (SEQ ID NO:65) |
| IK2-31 | aggcATCCGGGATAATAAAacacc | (SEQ ID NO:66) |
| IK2-32 | ggtgtTCTTCGGGATGGCTTgcct | (SEQ ID NO:67) |
| IK2-33 | aggcTTCACCGGGAGCACgacacc | (SEQ ID NO:68) |
| IK2-34 | ggtgtAGATCCCAGGGATTTgcct | (SEQ ID NO:69) |
| IK2-35 | ggtgtAGGTAGGGACATCCCgcct | (SEQ ID NO:70) |
| IK2-36 | ggtgtGAGAAATAGGGATAgcct | (SEQ ID NO:71) |

| | N -3 | N -2 | T -1 | T 1 | G 2 | G 3 | G 4 | A 5 | A T 6 | N 7 | N 8 | C 9 |
|---|---|---|---|---|---|---|---|---|---|---|---|---|
| G | 12 | 7 | 7 | 0 | 30 | 36 | 36 | 0 | 1 | 6 | 9 | 5 |
| A | 9 | 11 | 5 | 6 | 6 | 0 | 0 | 36 | 18 | 10 | 12 | 9 |
| T | 5 | 13 | 17 | 20 | 0 | 0 | 0 | 0 | 12 | 13 | 7 | 4 |
| C | 10 | 5 | 7 | 10 | 0 | 0 | 0 | 0 | 5 | 7 | 8 | 18 |

TABLE 4

| | | |
|---|---|---|
| IK3-1 | aggcTTTTTGGGAATACCAGacacc | (SEQ ID NO:75) |
| IK3-2 | aggc<u>TTGGGAT</u>TGGGAATAacacc | (SEQ ID NO:76) |
| IK3-3 | ggtg<u>TTCCT</u>GGGAATGTTCGgccta | (SEQ ID NO:77) |
| IK3-4 | aggcGTGGGAATATC<u>AGG</u>acacc | (SEQ ID NO:78) |
| IK3-5 | aggcTGGGAATGCTGGGAAacacc | (SEQ ID NO:79) |
| IK3-6 | ggtgTTGGGAATGC<u>TGGAAT</u>gccta | (SEQ ID NO:80) |
| IK3-7 | ggtgTAATTGGGAATTTTTAgccta | (SEQ ID NO:81) |
| IK3-8 | ggtgTGGGAAAAGTGGGAATgccta | (SEQ ID NO:82) |
| IK3-9 | ggtgTTCCTGGGAATGCCAAgccta | (SEQ ID NO:83) |

TABLE 4-continued

| | | |
|---|---|---|
| IK3-10 | aggcTACAGAATACTGGGAacacc | (SEQ ID NO:84) |
| IK3-11 | aggcTAAAAA<u>TTCC</u>TGGGAacacc | (SEQ ID NO:85) |
| IK3-12 | aggcATTCCCGTTTTGGGAacacc | (SEQ ID NO:86) |
| IK3-13 | aggcATTCCCGTTTTGGGAacacc | (SEQ ID NO:87) |
| IK3-14 | ggtgTA<u>TCC</u>CGGGAATACCGgccta | (SEQ ID NO:88) |
| IK3-15 | aggcTAAGGAATACCGGGAacacc | (SEQ ID NO:89) |
| IK3-16 | aggcTC<u>TGGAAT</u>ATCGGGAacacc | (SEQ ID NO:90) |
| IK3-17 | ggtgTAAATCGGGAAT<u>TCC</u>Ggccta | (SEQ ID NO:91) |
| IK3-18 | aggcCGGGAATACC<u>GGAAA</u>acacc | (SEQ ID NO:92) |
| IK3-19 | aggcAAAACATTACAGGGAcacc | (SEQ ID NO:93) |
| IK3-20 | aggcAGGGAATAGGGATacacc | (SEQ ID NO:94) |
| IK3-21 | ggtgTAGGAATTCTAGGAATgccta | (SEQ ID NO:95) |
| IK3-22 | aggcA<u>TTCCA</u>AGGAATTTacacc | (SEQ ID NO:96) |
| IK3-23 | ggtgTAAGGAATAC<u>TGGAAT</u>gccta | (SEQ ID NO:97) |
| IK3-24 | ggcAGAA<u>TTCCA</u>AGGAATacacc | (SEQ ID NO:98) |
| IK3-25 | aggcCAAGGAATATCAGGAacacc | (SEQ ID NO:99) |

| | T | N | A C or T | T | G | G | G | A | A | T | A G | C | TC T |
|---|---|---|---|---|---|---|---|---|---|---|---|---|---|
| | -3 | -2 | -1 | 1 | 2 | 3 | 4 | 5 | 6 | 7 | 8 | 9 | 10 |
| G | 7 | 5 | 3 | 0 | 20 | 25 | 25 | 0 | 0 | 0 | 5 | 0 | 0 |
| A | 3 | 8 | 0 | 6 | 5 | 0 | 0 | 25 | 25 | 0 | 16 | 1 | 1 |
| T | 15 | 4 | 9 | 14 | 0 | 0 | 0 | 0 | 0 | 18 | 4 | 6 | 7 |
| C | 0 | 8 | 13 | 5 | 0 | 0 | 0 | 0 | 0 | 7 | 0 | 18 | 17 |

TABLE 5

| | | | |
|---|---|---|---|
| TCEα enhancer | | | |
| | m | TGGAGGGAAGTGGGBAAACTTTT | (SEQ ID NO: 103) |
| | | TGGAAGTGGGAGGC | (SEQ ID NO: 104) |
| | | GAGGAGAAAGGTCTCCTAC | (SEQ ID NO: 105) |
| TCRβ enhancer | | | |
| | h | AACAGGGAAACA | (SEQ ID NO: 106) |
| | m | GTCAGGGAAACAGG | (SEQ ID NO: 107) |
| | h | AAGGTGGGAAGTAA | (SEQ ID NO: 108) |
| | h | GGTAGGAATBGG | (SEQ ID NO: 109) |
| | m | GGAGGGGGAAGAA | (SEQ ID NO: 110) |
| | m | AGTGGGGAAAABTCT | (SEQ ID NO: 111) |
| | m | GGTCAGGGAAACAA | (SEQ ID NO: 112) |
| | m | TGGGGGAAGGGGTGGAAG | (SEQ ID NO: 113) |
| | m | TTTTGGGAACC | (SEQ ID NO: 114) |
| | m | AAAGGGGAACCC | (SEQ ID NO: 115) |
| | h/m | TGGAGGGAG | (SEQ ID NO: 116) |
| promoter | | | |
| | m | AGGGGAAA | (SEQ ID NO: 117) |

TABLE 5-continued

| | | | |
|---|---|---|---|
| | | TTTGGGAATT | (SEQ ID NO: 118) |
| | | TGAGAGGAAGAGGAGA | (SEQ ID NO: 119) |
| | | CAGGAATT | (SEQ ID NO: 120) |
| TCR-δ enhancer | | | |
| | δE5/m | AAGGAAACCAAAACAGGGGAAG | (SEQ ID NO: 121) |
| | δE3/m | TTGGAAACCT | (SEQ ID NO: 122) |
| CD3-δ enhancer | | | |
| | δA/h | GTTTCCATGACATCATGAATGGGACT | (SEQ ID NO: 123) |
| | /m | GTTTCCATGATGTCATGAATGGGGGT | (SEQ ID NO: 124) |
| | | TTCTTGGGGATTG | (SEQ ID NO: 125) |
| CD3-γδ promoter | | | |
| | m | GGAGGAACT | (SEQ ID NO: 126) |
| | m | TTTGGGATG | (SEQ ID NO: 127) |
| | m | TTCTAGGAAGTAAGGGAATTT | (SEQ ID NO: 128) |
| | m | GTGGGAAGA | (SEQ ID NO: 129) |
| | m | TAGGAATTCT | (SEQ ID NO: 130) |
| | m | TAAGGAAAGG | (SEQ ID NO: 131) |
| | m | TTTCCAAGTGGGAATC | (SEQ ID NO: 132) |
| CD3-ε enhancer | | | |
| | m | TGGGACAAGATTTCCA | (SEQ ID NO: 33) |
| | m | TGGGGAAGTGAAGGAGGGAGG | (SEQ ID NO: 34) |
| | m | GAGGGGGATC | (SEQ ID NO: 35) |
| CD4 promoter | | | |
| | m | TGGGGAAGTT | (SEQ ID NO: 133) |
| CD2 promoter | | | |
| | m | TTGGGAAGGAT | (SEQ ID NO: 134) |
| | m | AAGGAACA | (SEQ ID NO: 135) |
| IL2-R α promoter/ NFkB | | | |
| | h | CAGGGGAATCTCCCTCTCCAT | (SEQ ID NO: 136) |
| IL2 enhancer | | | |
| | PuBp | AAGAGGAAAA | (SEQ ID NO: 137) |
| | PuBd (NFAT-I) | AGGAGGAAAA | (SEQ ID NO: 148) |
| β-IFN (PRDII)/ NFkB | | | |
| | | GGGAAATTCC | (SEQ ID NO: 138) |
| MHC classII/ NFkB | | | |
| | m | GGGGAATCC | (SEQ ID NO: 139) |
| TDT- promoter/ LYF | | | |
| | | TGGGAG | (SEQ ID NO: 140) |
| mb-I promoter/ EBF | | | |
| | | CAAGGGAAT | (SEQ ID NO: 72) |
| HIV LTR | | | |
| | | CAGGGAAGTA | (SEQ ID |

TABLE 5-continued

| | |
|---|---|
| CAAGGGACTTTCCGCTGGGGACTTT CCAGGGAGGGCG | NO: 141) (SEQ ID NO: 142) |

A consensus recognition sequence for each of these proteins was derived. The mIk-1, mIk-2 and mIk-3 core motifs were, respectively;

N-N-[T/a/c]-T-G-G-G-A-A-T-[A/g/t]-[C/t]-[C/t]  (SEQ ID NO:155)

N-N-[T/c]-[T/c]-G-G-G-A-[A/T]-N-N-C  (SEQ ID NO:156)

and

T-N-[C/t]-T-G-G-G-A-A-T-[A/t/g]-[C/t]-[C/t]  (SEQ ID NO:157).

The mIk-1 and mIk-3 sequences shared the seven base pair core T-G-G-G-A-A-T (SEQ ID NO:149). The mIk-3 protein showed strong reference for particular nucleotides both at the 5' and 3' flanking positions of this motif while the mIk-1 protein did not select for any particular bases at these positions. The mIk-2 consensus shared five bases with the mIk-1 and mIk-3 heptanucleotide and exhibited great degeneracy outside this sequence. This may permit for the mIk-2 protein to bind with high affinity to a wider range of recognition sequences. Another feature of the oligonucleotides selected by the mIk-3 protein is that 85% of them contained a second consensus (as underlined in Table 2). In contrast, only 50% and 38% of the oligonucleotides selected by mIk-1 and mIk-2 respectively had the potential for a second binding site (as underlined in Table 1 and 3). Such double recognition sequences were also selected by the truncated Ikaros proteins (which lack the C-terminal finger domain) suggesting the interaction between their N-terminal finger domain and these sequences. This may suggest differences in the affinity of mIk-1, mIk-2 and mIk-3 for the selected core motif. Double recognition sequences may allow for an increase in the apparent binding affinity of these proteins for these sites.

The N-terminal truncated forms of mIk-1, mIk-2 and mIk-3, after 4,6 and 7 rounds of selections respectively, bound to a significant amount of the selected pool of oligonucleotides. Analysis of a limited number of cloned oligonucleotides revealed a core consensus similar to the one selected by their full length counterparts. In contrast, the truncated proteins comprising the C-terminal two zinc fingers (F5 and F6) did not appear to bind to any significant proportion of the oligonucleotide pool and to select for any specific sequence.

Binding site selections were performed as follows. A pool of random oligomers was designed with 25 base pairs of defined sequence at the 5' an 3' (including BamHI and EcoRI restriction sites) and 15 bases of random sequence in the middle. In the first round of selections Ikaros-GST fusions attached to gluathione agarose beads (20 µls bead volume) were used in binding assays together with 500,000 cpm of end labeled random primers. After a 20 minute binding reaction on ice the beads were spun down gently and washed twice to three times with ten fold excess of ice cold 1x binding buffer. Bound primers were eluted in 0.1%SDS 10 mMTris pH 7.5 recovered radioactivity was determined and then were phenol extracted and precipitated in the presence of 10 µgs of glycogen, ⅕th of recovered DNA was reamplified with primers complementary to the defined 5' and 3' sequences with $\alpha$-$P^{32}$ dCTP included in the reaction to generate a homogeneously labeled pool of selected oligomers. All probes were gel purified. In higher rounds decreasing amounts of selected oligomers were used in the binding reactions in order to enrich for higher affinity sites (2000, 000/100,000 cpm). Five rounds of selections were performed. At the end of the last round of the eluted DNAs were amplified, digested with EcoRI and BamHI restriction enzymes, cloned in pGEM3Z and sequenced with normal and reverse primers. Sequences of selected primers were aligned to a shared motif present in al DNAs.

Fusion protein and DNA binding studies were performed as follows. The coding region of the Ikaros isoforms were PCR amplified with Vent polymerase from their respective cDNAs using primers and cloned into the BamHI/EcoRI sites of pGEXIII. Recombinant plasmids were analyzed by sequencing. Overnight cultures of the appropriate recombinant pGEX vectors were diluted by ten fold and grown at 37° C. for 90 minutes before a 3 hours induction with 2 mM IPTG at 26° C. Crude bacterial lysates were produced as previously described (Georgopoulos 1992). Ikaros-GST fusions were partially purified on glutathione agarose beads, eluted in buffer D containing 20 mM free glutathione and 0.5 M NaCl at 4° C. for 1 hour. Eluted proteins were checked by SDS-Page there concentrations was estimated by the Lowry method and appropriate dilutions were used for DNA binding studies. DNA binding assays were performed. Binding reactions contained 50,000 cpm of labeled oligonucleotides (0.5–1 ng), 100 ngs of the fusion proteins, 0.1 µgs of dI/dC and the binding buffer was supplemented with 20 µM of $ZnCl_2$. Binding reactions for methylation interference assays were scaled up ten times and were performed as previously described (Georgopoulos 1990).

Binding Specificity of Ikaros Isoform mIk-1–5

The binding specificity of the five Ikaros proteins for a single recognition site derived from the selected consensus was tested in a gel retardation assay. A 24 bp oligonucleotide (IK-BS1, T-C-A-G-C-T-T-T-T-G-G-G-A-A-T-A-C-C-C-T-G-T-C-A) (SEQ ID NO:101) designed to accommodate high affinity binding of the three selecting proteins was tested in a gel retardation assay against equal amounts of the five Ikaros isoforms produced in bacteria as GST fusions. The Ikaros proteins interacted with the IK-BS1 site differentially. The mIk-1 isoform bound this sequence with the highest affinity followed by mIk-2 and mIk-3, in fact, scanning densitometry determined that the relative amounts of mIk-2 and mIk-3 complexes on the IK-BS1 DNA were 3.4 and 1.7 fold lower than that of the mIk-1 complex. Neither the mIk-4 or mIk-5 proteins bound this sequence. Apparently, the presence of only two or one zinc fingers at the N-terminus of mIk-5 and mIk-4 were not sufficient for their stable interaction with this site.

Given the number of potential double recognition sites selected by the Ikaros proteins, an oligonucleotide containing an inverted repeat of their core consensus was tested (IK-BS4) TCAGCTTTTGGGAATGTATTCCCTGTCA (SEQ ID NO: 73). Four of the five Ikaros proteins, including mIk-4, bound to this sequence with high affinity. In contrast to widely distinct binding affinities for a single recognition sequence, those isoforms appeared to interact similarly with this double recognition site. Significantly, the relative abundance of the mIk-2 protein complex on the palidromic IK-BS4 sequence was 6.3 fold higher than on the IK-BS1 single recognition site and its mobility was slower and indicative of a potential higher order complex. In addition, the mIk-4 protein which did not bind to IK-BS1, bound to the palindromic sequence with high affinity. This strongly suggests cooperative binding of mIk-4 and possibly mIk-2 proteins respectively, on proximal binding sites. The relative affinities of mIk-1 and mIk-3 were also enhanced, but to a lesser extent (2.3 and 3.5 fold respectively). Interestingly, the mobility of the mIk-1 complex was similar on both single and double recognition sequences. This may reflect stable dimer formation of this protein in solution or, alternatively, the conformation of the mIk-1 protein may prevent double occupancy of sites in proximity.

To determine whether the high affinity binding of the mIk-2 and mIk-4 proteins on IK-BS4 was due to an increase in the local concentration of binding sites or whether this was mediated by protein-protein interactions, the spacing between the two half sites was decreased to allow only for single site occupancy. The mIk-1, mIk-2 and mIk-3 proteins bound with similar affinities to the single site in the IK-BS6 oligomer which contains two inverted and partially overlapping core motifs, as they did to the IK-BS1 oligonucleotide. (IK-BS6) TCAGCTTTTGGGAATTCCCTGTCA (SEQ ID NO: 74). The mIk-4 protein did not bind to IK-BS6, strongly implicating its cooperative binding on proximal and appropriately spaced binding sites.

The Ikaros heptanucleotide core motif displays strong sequence similarities with a subset of NF-κB sites, e.g., NF-κ sites in IL-2α, H2-K$^b$β-interferon promoters. The NF-κB recognition sequence is an imperfect palindrome with a certain degree of base pair variation in the middle of the motif. These sequences bind with high affinity homo- and heterodimeric complexes formed between members of the NF-κB/rel family. The IK-BS2 oligonucleotide (TCAGCTTTTGGGAATCTCCTGTCA, SEQ ID NO: 100) which contains an Ikaros consensus sequence in the context of the IL2-Rα promoter NF-κB site was tested for binding the Ikaros proteins. The mIk-1 and mIk-2 proteins bound to the IK-BS2 with affinities similar to those shown for the selected IK-BS1 oligonucleotide. However, binding of the mIk-3 isoform to this site was greatly reduced, probably due to a non-conservative base pair substitution at position 8 of its consensus motif. Interestingly, the mIk-4 protein, which bound only to the palindromic sequence in the IK-BS4 oligonucleotide, also bound to the IK-BS2 oligonucleotide. This is probably due to the presence of a related motif on the bottom strand of this oligonucleotide which creates an imperfect palindrome. A higher order binding complex was again observed between the mIk-2 protein and the IK-BS2 oligonucleotide.

The IK-BS7 oligonucleotide (TCAGCTTT-TGAGAATACCCTGTCA) (SEQ ID NO:158), with abase pair substitution within the core consensus was tested for its ability to interact with the Ikaros proteins. A single base pair change at position 3 of the consensus, which substituted an adenine for the conserved guanine abrogated binding of the Ikaros proteins, underscoring the importance of this conserved residue. Substitution of a thymidine for an adenine at position 6 (e.g., to generate IK-BS3, TCAGCTTTTGGGATTACCCTGTCA, SEQ ID NO: 159) in the selected consensus prevented binding of the mIk-3 and mIk-4 proteins and decreased the relative affinity of the mIk-1 isoform by 2–3 fold. However there was no effect on the binding of the mIk-2 protein that selected for either bases at this position with a similar frequency. Non-conservative substitutions at the 3' of the mIk-1/–3 decanucleotide consensus (IK-BS9, TCAGCTTTTGGGAAAAACCTGTCA, SEQ ID NO: 160) abolished mIk-3 and mIk-4 binding, reduced the affinity of the mIk-1 protein but did not significantly affect the mIk-2-DNA interactions. Nevertheless, substitutions of four guanines for the thymidines at the 5' of the core consensus had a negative effect on the binding of all of Ikaros proteins (IK-BS5, TCAGCGGGG-GGGAATACCCTGTCA, SEQ ID NO:152).

Of the Ikaros isoforms, only mIk-5 with a single N-terminal zinc finger did not bind to any of the tested oligomers including the ones that contained a double recognition site. However, the C-terminal finger domain was shown to be able to bind to the δA element of the CD3δ enhancer in a sequence specific manner. Consequently, we tested binding of the Ikaros isoforms to the δA motif (GTTTCCATGACATCATGATGGGGT, SEQ ID NO:161). Two sequence specific binding complexes were formed with the mIk-1, mIk-2 and mIk-3 proteins that differed substantially in their relative abundance. Only the faster migrating complex was detected with the mIk-4 and mIk-5 proteins. Formation of this complex on the δA element may involve the C-terminal finger domain present in all of the Ikaros proteins. The mIk-5 isoform in particular with only one finger at its N-terminal domain may primarily utilize these C-terminal fingers for sequence specific DNA binding. However, these C-terminal zinc fingers were not able to select for any sequence motif in the binding site selections described previously. This may be due to low affinity protein-DNA interactions which do not stand up to the stringency of the selection assays and may also reflect a complexity in the DNA binding site not accommodated by the size of the random sequence in selecting oligonucleotides.

Since the Ikaros proteins belong to the $Cys_2$-$His_2$ zinc finger family of DNA binding proteins, the role of these N-terminal zinc fingers in determining sequence specificity can be predicted. The $Cys_2$-$His_2$ zinc finger proteins make base pair contacts by aligning their finger modules along the major grove of their recognition site in an anti-parallel fashion (Pavletich and Pabo (1991) Science 252:809–818), and in a protein with multiple zinc fingers, each module is capable from zero to a maximum of five base contacts (Pavletich et al. (1993) Science 261:1701–1707). The mIk-1 and mIk-3 proteins, with four (F1+F2+F3+F4) and three (F1+F2+F3) N-terminal fingers respectively, each selected the ten base pair consensus T-G-G-G-A-A-T-A-C-C (SEQ ID No. 162), mIk-3, with one finger less (–F4) than mIk-1, made more DNA contacts and displayed a stricter DNA specificity (T-N-C/t-T-G-G-G-A-A-T-A-C-C for Ik-3 (SEQ ID No. 157) versus N-N-T-T-G-G-G-A-A-T-A/g-C-C for Ik-1, (SEQ ID No. 155)). However, mIk-1bound to this recognition site with higher affinity. This suggests that finger –4, expected to make the most 5' base pair contacts, is not directly involved in DNA binding. Nevertheless, this finger module may dictate the specificity and affinity of the N-terminal DNA binding domain by affecting its protein conformation. The mIk-2 protein, with three N-terminal fingers (F2+F3+F4), selected the six base pair motif T-G-G-G-A-A/t (SEQ ID No. 156) contained within the selected consensus for mIk-1 and mIk-3. However the mIk-4 isoform, with the same two N-terminal fingers (F2+F3) as mIk-2 but lacking finger –4, did not bind to single recognition sites, and interacted only with appropriately spaced double recognition sequences in a cooperative fashion. The N-terminal zinc finger domain of the Ikaros proteins and its role in dictating their DNA binding specificities and affinities is reminiscent of a similar domain in the Evi-1 gene. The Evi-1 protein is comprised of seven N-terminal and three C-terminal zinc fingers and is involved in regulating differentiation in the myeloid lineage. The first three zinc finger motifs in this protein do not bind DNA but they determine the overall DNA binding specificity of the N-terminal domain (Delwel et al. (1993) *Mol Cell Biol* 7:4291–4300). The differential usage of zinc fingers by the Ikaros proteins is also reminiscent of the Drosophila chorion transcription factor CF2 which, by alternate splicing, encodes proteins with distinct combinations of $Cys_2$-$His_2$ zinc finger motifs. These zinc finger containing proteins, in a similar fashion to the Ikaros isoforms, display overlapping yet overall distinct DNA binding specificities (Gogos et al. (1992) *Science* 257:1951–1955; and Hsu et al. (1992) *Science* 257:1946–1950). In conclusion, the DNA binding specifically and affinity of an Ikaros protein with two or more fingers at its N-terminal part, is primarily dictated by these N-terminal fingers.

Chemical Footprinting of Ikaros Isoforms mIk-1–4 on their Cognate Sites

The protein/DNA interactions of mIk-1–4 were further established by chemical footprinting. The IK-BS2 oligonucleotide (TCAGCTTTTGGGAATCTCCTGTCA) (SEQ ID NO:102) that binds with high affinity to the four isoforms was used in a methylation interference assay. On the positive strand all four proteins gave similar footprints, indicating similar contacts. Methylation of the three guanines at positions 2, 3 and 4 of the consensus interfered 100% with the binding of all four proteins. The mIk-2 protein made additional major grove contacts with the guanine at position –5 and with the adenine at position 5. Methylation of adenines at position 5 and 6 enhanced binding of mIk-3 and mIk-2 respectively. However, on the negative strand, the four proteins made dramatically different contacts. The most extended footprint was that of mIk-4 which covered the purines from positions 8 through 12, while mIk-3 made contacts with bases at positions 7 through 10. The mIk-1 and mIk-2 proteins made only one full contact with the guanine at position 10, while mIk-1 also made partial contact with the purines at positions 7 through 9.

Of the three proteins used in the selections, mIk-3, with the strictest consensus, made the most base pair contacts on the negative strand. The overall foot print made by this protein suggests extensive interactions between fingers –1, –2, and –3 with eight of the tem bases of its recognition site. On the same recognition site, the mIk-2 protein, the most promiscuous of the three, made only six base pair contacts suggesting limited interaction between finger –4 and DNA. Surprisingly, the mIk-1 protein, containing fingers –1, –2, –3 and –4, made less full base pair contacts than the mIk-3 protein with fingers –1,–2 and –3. This suggests that the additional finger –4 present in mIk-1 may influence the ability of the other fingers and especially of finger –1 to interact with DNA, perhaps by dictating a different overall protein conformation. Finally the extensive and qualitatively distinct footprint made by mIk-4 further support the cooperative occupancy of close proximity recognition sites by this isoform of Ikaros. These methylation interference data demonstrate that the four Ikaros proteins make qualitative distinct DNA contacts and underling their ability to bind DNA differentially.

Transcriptional Activation by the IK Proteins.

The ability of the Ikaros proteins to activate transcription from a promoter juxtaposed to tandem copies of low and high affinity binding sites was tested in transient expression assays in NTH-3T3 fibroblasts. In one set of experiments, reporter genes (e.g. tkCAT expression constructs) under the control of four copies of the IK-BS1, IK-BS2 or IK-BS9 sites were cotransfected together with plasmids expressing each of the four Ikaros cDNAs mIk-1, mIk-2, mIk-3 and mIk-4 in NIH-3T3 fibroblast cells. Expression of mIk-1 increased the activity of the tkCAT gene under the control of the high affinity binding sites, IK-BS1 and IK-BS2. by 11 and 19 fold respectively, but stimulated the activity of this reporter gene under the control of the low affinity binding site IK-BS9 by only 3.3 fold. Expression of the mIk-2 protein increased the activity of the IK-BS2 reporter gene by 11 fold, but only stimulated the activity of the IK-BS1 and IK-BS9 reporter genes by 2–3 fold. However, the affinity of mIk-2 for the binding sites in the three reporter plasmids is similar. It is noteworthy that a higher order mIk-2 binding complex was only detected on the IK-BS2 oligonucleotide.

Binding site composition also appeared to play a role in the ability of the mIk-1 isoform to activate transcription. Although the mIk-1 protein can bind the IK-BS1 and 1K-BS2 sites with similar affinities, and to the IK-BS9 site with only a two fold difference, its ability to stimulate transcription from these sites was markedly different. Expression of the mIk-1 isoform stimulated the activity of the IK-BS2 reporter to a 6 fold higher level than of the IK-BS9 reporter.

Transcriptional stimulation of these reporter constructs by the mIk-3 and mIk-4 proteins was markedly lower. Expression of either mIk-3 or mIk-4 stimulated transcription only by –2 to –3 fold even from constructs containing high affinity binding sites for these isoforms. This effect was not due to differences in protein stability or expression in these assays, since a similar number of transfected cells with comparable levels of immunoreactive material were detected upon immunohistochemical analysis of transfected fibroblasts.

Difference in the transcriptional activity of mIk-1, mIk-2, mIk-3 and mIk-4 proteins combined with overlapping sequence specficities may be the key in regulating the activity of a number of control elements involved in lymphocyte specific gene expression. For example, mIk-4, a very weak transcriptional activator, could effectively compete with the mIk-1 and mIk-2 proteins on composite binding sites (e.g. on the IL2-Rα/NFκB site) during early T cell development when it and these isoforms are expressed at similar levels. Thus, either naturally occurring isoforms, or those produced by mutagenesis, may function to attenuate transcription from binding sites that also accommodate such isoforms as mIk-1 and mIk-2.

The mIk-1 and mIk-2 proteins were not able to activate transcription from a mutant binding site which did not bind any of these factors demonstrating that their activation potential is sequence specific.

Since the sequence composition for an Ikaros high affinity binding site is identical to the NFκB motifs present in the IL2-Receptor α and the β-interferon promoters its transcriptional activity in a mature T cell line in the absence and in the presence of mitogenic stimulation was examined. The human Jurkat T cell line was chosen for the following reasons. First the activity of NFκB recognition sequences that closely match the selected Ikaros binding sites have been extensively studied in this cell line and secondly because it is determined, as described herein, that the human Ikaros gene is highly conserved to the mouse gene in both amino acid composition and splicing variants. In contrast to previous reports, high levels of transcriptional activity from this multimerized site were detected which were not further stimulated upon mitogenic treatment. This activity was decreased by five fold when Ikaros antisense expression vectors were cotransfected together with this reporter gene. No such effect was detected when reporter genes driven by the RSV or SL3 LTRs were used in a parallel experiment suggesting that transcriptional inhibition by the Ikaros antisense RNA is specific to this site.

Transcriptional activation from a reiterated NFκB variant in NIH3T3 fibroblasts upon expression of Ikaros 1–4 isoforms was determined as follows. The stimulation of CAT activity in the presence of the Ikaros proteins was evaluated as the ratio of activity when cotransfected with a recombinant CDM8/CDM8 vector alone. This data represent an average of three/four experiments with each combination of transfected plasmids per experiment repeated twice. All transfections were normalized to GH levels as described in materials and methods.

Activity and repression of the reiterated NFκB like element in human T cells was determined as follows. The reporter gene under the control of IK-BS2 (FNKB like variant) or of RSV and SL3 LTRs was transfected in Jurat cells in the presence of CDM8 expressing Ikaros antisense plasmids. Fold induction relative to enhancerless plasmid and suppression in presence of antisense RNAs was determined.

Mammalian expression vector and transfection experiments were performed as follows. The five Ikaros isoforms were subcloned into the HindIII-Not I site of the CDM8 expression vector. The tkCAT reporter gene constructs, under the control of four sense copies of IKBS1 IKBS2, IKBS9, were cotransfected with the appropriate CDM8 expression vectors (e.g., for expressing a particular Ikaros isoform), in the NIH 3T3 fibroblasts and the mature T cell line Jurkat. Cells were harvested 36–48 hours later and analyzed for CAT activity and Growth hormone levels. Results determined as the average of 3/4 independent experiments where each combination of reporter to expression plasmids was performed twice.

Target Sites for the Ikaros Proteins in Lymphoid Restricted Regulatory Domains

Potential high affinity binding sites for the Ikaros proteins, e.g. containing the core motif G-G-G-A-A, were found in the enhancer and promoter regions of the regulatory domains of the members of the TCR antigen complex, i.e. the TCR-α, -β, and -δ, the CD3δ, -ε, and -γ genes, the SL3 and HIV LTR and in the regulatory domains of other T cell restricted antigens (Table 5). These sequences represent high affinity binding sites as determined by gel retardation assays. The multiplicity and often the proximity of potential high affinity binding sites in the regulatory domains of these genes was striking. Some of these sites can bind all four proteins while others interact only with mIk-2 and mIk-1 isoforms. High affinity binding sites for the Ikaros proteins were also found in the promoters of costimulatory T cell differentiation antigens CD4 and CD2, in the early pre-B cell differentiation antigen mb-1, and also in the NF-κB motifs present in the promoter of the IL2-Rα, in the PRDII element of the β-interferon gene, in the enhancer of the H-2K$^b$ gene and in the E-A$^d$ promoter. Four of the Ikaros proteins can bind with high affinity to these NF-κB sites.

Related sequences to the Ikaros motif were also found in the above described regulatory domains as well as to the Ikaros motif were also found in the above described regulatory domains as well as in the purine boxes of the IL2 gene, in the TDT gene, as well as in the NFκB variant sites of the HIV-LTR and in the early pre-B cell differentiation antigen mb-1 (Table 5). Single sites containing these related sequences bind substantially better to such sites present in proximity. This is clearly the case with the CD3 δA element which is comprised of two low affinity binding sites and possibly with other regulatory elements. The presence and proximity of low affinity binding sites may also influence the occupancy of the high affinity binding sites in these various regulatory domains and may dictate the sequential activation of the respective target genes during lymphocyte development.

As described above, to investigate the affinity of the Ikaros proteins for these sites, their ability to compete with the selected recognition sequences was studied. Base pair substitutions within and outside the seven base pair motif were introduced to match the sequence composition of some of these sites present in the lymphoid and T cell specific regulatory domains. Oligonucleotides with the appropriate base pair changes were used in competition experiments against the consensus motif (IKB-S1).

The IK-BS2 oligonucleotide, identical to the IL2-Rα NFkB motif, bound to the four proteins with a two fold higher affinity than a single copy of the consensus motif. We believe that this is due to the second low affinity binding site in the opposite strand.

The existence of low affinity binding sites in close proximity in a regulatory domain increases the relative affinity of the Ikaros proteins for these sites. This is clearly the case with δA and possibly with other elements. The occupancy of high affinity binding sites could also be affected by low affinity sites in the immediate region. The apparent binding constant of these proteins for these sites may raise to an even higher value and could dictate the order of target genes activated by the Ikaros enhancers in the developing lymphocyte.

Nuclear Complexes Forming Over Ikaros Recognition Sites

The composition of T cell nuclear complexes formed over the recognition sites selected by the Ikaros proteins was examined. The IK-BS4 oligonucleotide, a high affinity binding site for four of the Ikaros binding forms, was tested with nuclear extracts made from the T cell line EL4. Two sequence specific nuclear complexes were formed as determined by competition with 100 fold molar excess of the IK-BS4 and IK-BS7 oligonucleotides. Both complexes were supershifted by two different antisera raised against the C- and N-terminal domains of the Ikaros protein respectively. The majority of the IK-BS4 binding complexes were supershifted by these antibodies, but some binding activity remained. Distinct nuclear factors with similar mobility properties to the Ikaros proteins may be responsible for this residual binding. The supershifted complexes were not formed in the absence of the EL4 nuclear proteins supporting a specific interaction between antibodies and protein-DNA complexes. These Ikaros antibodies did not interact with other proteins that can also bind with high affinity to this site (e.g. the p50 homodimer member of the NF-κB complex). In addition, antibodies raised against the other member of the NF-κB complex, the p65 protein, or against an unrelated protein, had no effect on these nuclear complexes. It is therefore suggested that the majority of the T cell nuclear complexes forming over high affinity Ikaros binding sites are comprised of proteins that belong to the Ikaros family.

Cloning of the Human Ikaros Gene

Human Ikaros cDNAs were cloned by high stringency hybridization with a mouse Ikaros cDNA probe. The human Ikaros cDNAs isolated display strong sequence similarities to their mouse homologues over the entire coding region.

Figures 12A, 12B:
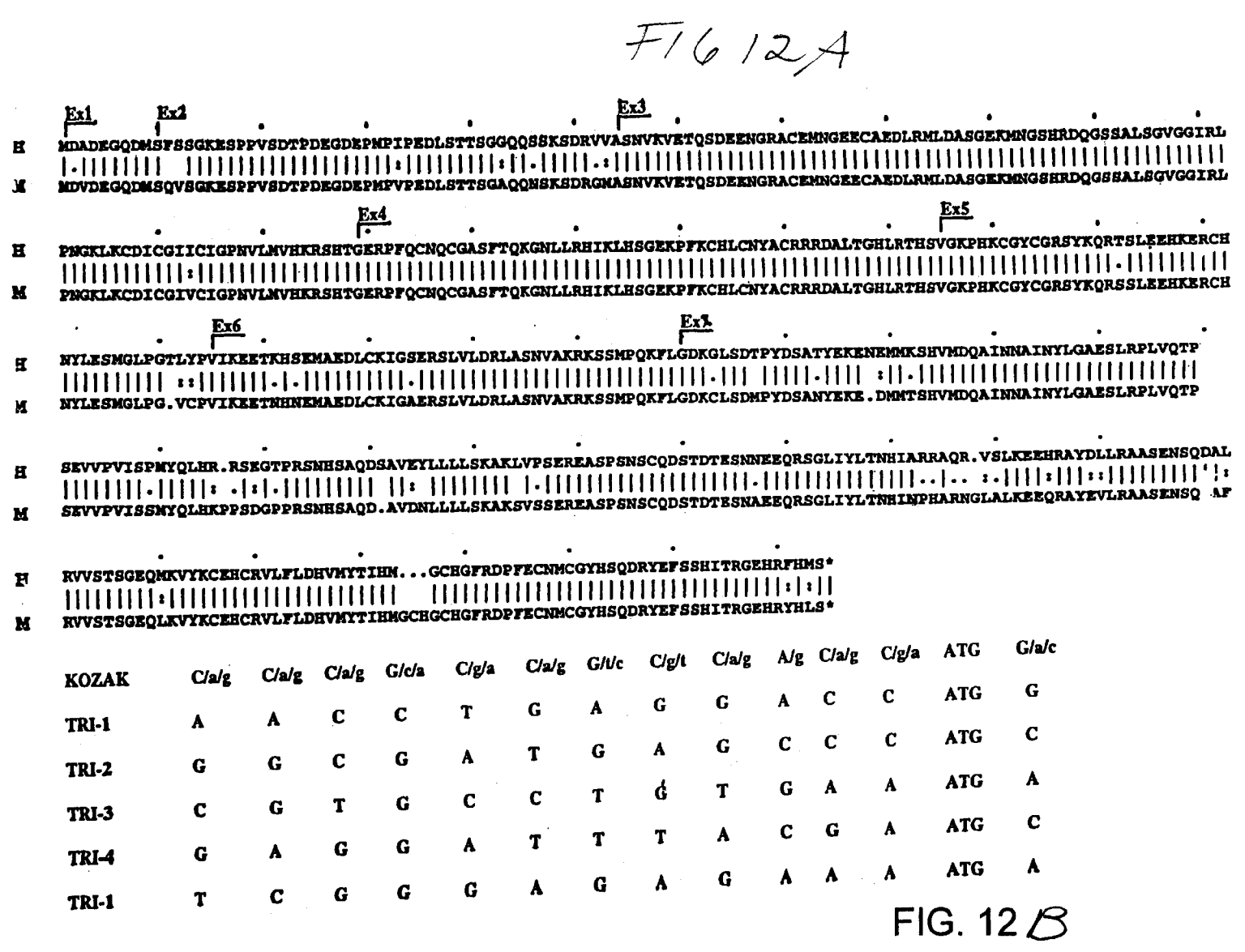

A single stranded DNA probe derived from exon 7 of the mouse Ikaros gene was used to screen for human Ikaros cDNAs. The Ikaros cDNAs isolated were partial and contained most of the coding region encountered in the mouse Ikaros isoforms (FIG. 10). RT-PCR analysis of human cDNAs revealed the existence of human Ikaros cDNAs consisting of sequences encoded by the seven coding exons in the mouse. Sequence identities over the coding region of human and mouse Ikaros cDNAs were 89% and 95% at the DNA and protein levels, respectively (FIG. 12). The three-amino acid repeat (GCH) present in exon 7 of the Ikaros gene in mice of the BALB/c but not those of the C57/BL genetic background was not found in the human Ikaros cDNAs isolated from Jurkat cells (alignment shown in FIG. 12A is between human and mouse BALB/c Ikaros cDNAs.

Figure 10A:
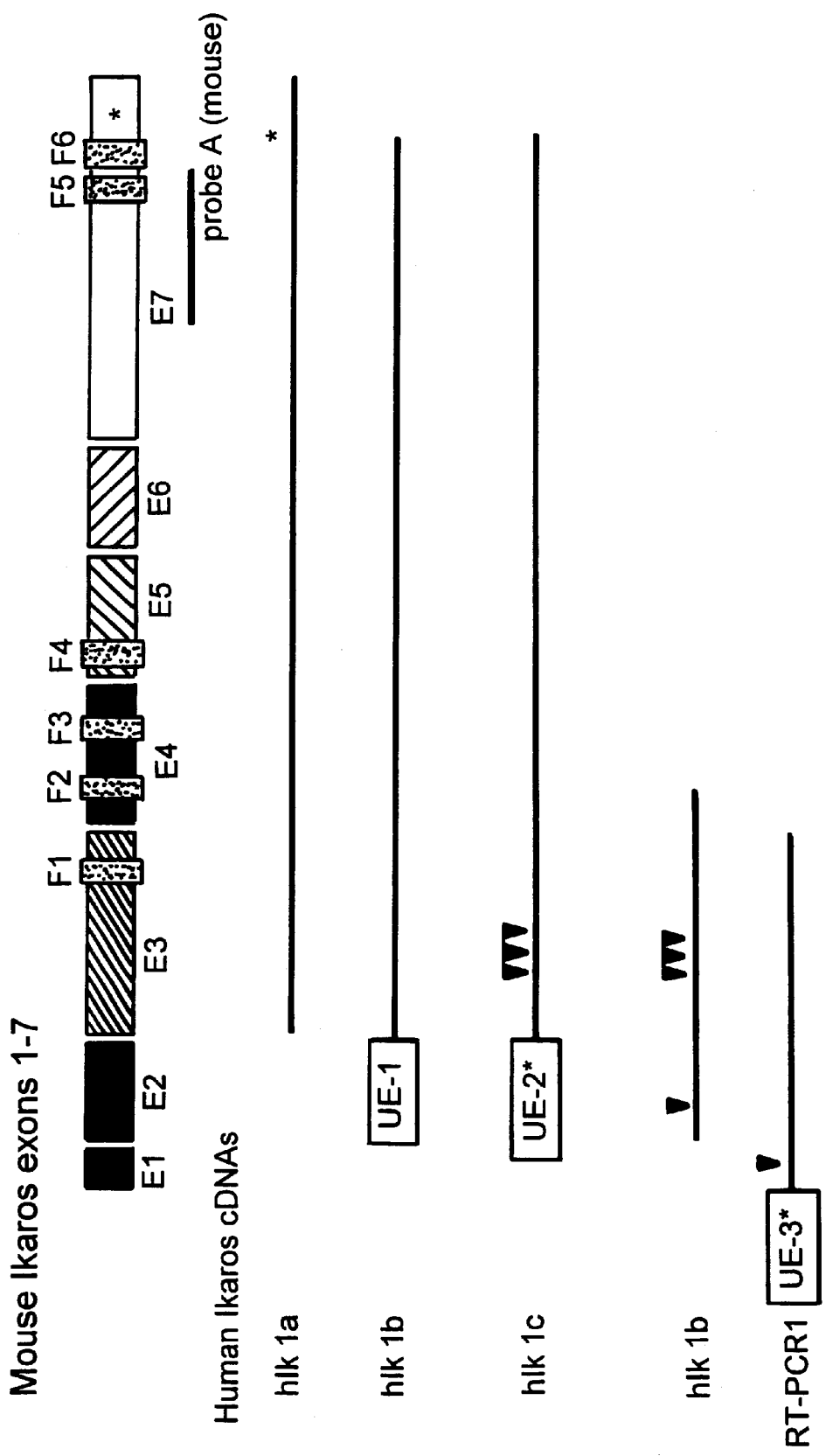

Three unique 5' sequences, not found in mouse Ikaros cDNAs, were identified in the human Ikaros clones (FIG. 10A). The existence of these sequences on Ikaros mRNAs was confirmed by RT-PCR and sequencing. Two of these unique 5' ends had stop codons in-frame to the Ikaros coding frame. Sequences encoded by mouse exons 1 and 2 were differentially used by human Ikaros transcripts (as determined by cDNA cloning and RT-PCR analysis). Therefore, initiation of translation in human Ikaros cDNAs, which contain distinct 5' ends, is expected to occur at different sequences that match the Kozak consensus (FIG. 12B). The distinct untranslated sequences present in human Ikaros cDNAs, are reminiscent of the 5/noncoding ends of mouse Ikaros cDNAs. In both human and mouse, these Ikaros cDNAs may be produced by distinct promoters. A diagrammatic representation of four human Ikaros cDNAs and one RT-PCR product with unique 5' noncoding and coding sequences and their alignment to the mouse Ikaros coding exons 1–7 is shown in FIG. 10A.

Human Ikaros isoforms were cloned as follows: A human cDNA library made from the Jurkat T cell line (Strategene, La Jolla, Calif.) was screened using a single stranded probe (150 hp in size) generated from mouse exon 7 (FIG. 10A, probe A). Filters with recombinant phage DNA were incubated in hybridization buffer (7% SDA, 1% BSA, 0.25 M sodium phosphate (pH 6.5), and 0.5 mM EDTA) with $1 \times 10^6$ cpm/ml of probe at 65° C. From the $8 \times 10^5$ recombinant phages screened, nine positive clones were obtained. The most full-length of these cDNAs, hIk-1a. was similar in sequence composition to mIk-1, with a stop codon at the 3' end of its coding frame. The 5' end of hIk-1a cDNA stopped short of sequences encoded by exons 1 and 3 in the mouse Ikaros gene. To obtain more upstream sequences, a probe generated from the 5' end of the human Ikaros cDNAs was used to screen a cDNA library made from human thymus (Clontech, Palo Alto, Calif.). From $1 \times 10^6$ recombinant phages screened, three Ikaros cDNAs were obtained with more upstream sequences (FIG. 10A, Ik-1b, Ik-1c, and Ik-1p). One of these three cDNAs consisted of sequences similar to those in mouse exon 2 and had an in-frame upstream stop codon (FIGS. 10A and 10B). Primers designed according to 5' untranslated and coding sequences were used in RT-PCR reactions to further investigate the existence of differentially spliced human Ikaros cDNA variants.

An overall 95% identity was detected over the entire coding region of human and mouse Ikaros proteins. In addition, the human and mouse Ikaros proteins were completely identical in their DNA binding, activation, and dimerization domains.

Expression of Ikaros Proteins is Conserved
Between Mouse and Human Lymphocytes

The Ikaros gene was abundantly expressed in the thymus, spleen, and peripheral blood leukocytes but not in other non hemolymphopoietic tissues. Thymocytes, in particular, expressed higher levels of Ikaros mRNAs than peripheral blood leukocytes and spleen cells. Two Ikaros transcripts, 7.5 and 4.5 kb in size, were detected in human leukocytes, in contrast to the single 4.5-kb Ikaros transcript detected in mouse lymphocytes. The 7.5-kb transcript was more abundant than the 4.5-kb transcript in thymocytes and splenocytes, but it was expressed at similar levels to the 4.5-kb transcript in peripheral blood leukocytes.

The expression of Ikaros proteins was compared between mouse and human lymphocytes. Ikaros proteins that matched in size the products of the more abundant Ik-1 and Ik-2 isoforms were readily detected in the mouse thymus and in the human T cell line Jurkat. A human Ikaros protein corresponding in size to the product of the less abundantly expressed Ik-4 isoform was also detected, albeit in lower amounts. Expression of the Ik-3 isoform could not be determined because of the similarity in size with the more abundantly expressed Ik-2 isoform. The Ikaros proteins in both mouse and human migrate at a higher position than that predicted by their m.w. This size difference may be accounted for by post-translational modifications, preserved across species. As expected, Ikaros proteins were not expressed in the mouse and human fibroblast cells lines, N1H-3T3 cells and W138. This apparent similarity in size between mouse and human Ik-1, Ik-2, and Ik-4 proteins suggest that there are no additional coding regions at the 5' end of the human Ikaros mRNAs.

Expression of the Ikaros gene in human tissues was determined by Northern hybridization. Nylon membranes with the following RNAs were tested: 1) 2 μg of poly(A)$^+$ RNA from human heart, brain, placenta, lung, liver, skeletal muscle, kidney, and pancreas (Clontech human blot), and 2) 2 μg of poly(A)$^+$ RNA from spleen, thymus, prostate, testis, ovary, small intestine, colon, and peripheral blood leukocytes (Clontech human blot II). Membranes were hybridized with a probe derived from the 3' end of the hIk-1a cDNA.

Nuclear extracts were prepared from the mouse and human fibroblast cell lines N1H-3T3 and W138, the human T cell line Jurkat, and mouse thymocytes as previously described (Molnar et al., Mol. Cell Biol. 14:8292, 1994). Total cell lysates were prepared from the human embryonal kidney cell line 293T transfected with vectors expressing mouse Ik-1, Ik-2, Ik-3, and Ik-4 isoforms by lysis in RIPA buffer (150 mM NaCl, 1% Nonidet P-40, 0.5% deoxycholate, 0.1% SDS, 50 mM Tris (pH 8.0), 5 mM NaF, 2 mM DTT, 10 μg/ml leupeptin, 20 μg/ml aprotinin, and 0.2 mM PMSF). Ten to twenty micrograms of protein were run on a 12% polyacrylamide gel, transferred to polyvinylidene difluoride membrane (Bio-Rad, Richmond, Calif.), and analyzed with an affinity-purified Ab raised to the N-terminal domain of mouse Ik-2 (1/500 dilution) (Molnar et al., Mol. Cell Biol. 14:8292, 1994). Horseradish peroxidase goat anti-rabbit secondary Ab (1/5000; Jackson ImmunoResearch, West Grove, Pa.), was used and Ab complexes were detected using the ECL kit from Amersham (Arlington Heights, Ill.).

Differential Splicing in Mouse and Human
Lymphocytes Generates Ikaros Isoforms with the
Same Composition and Relative Expression In the mouse Ikaros gene, alternative splicing of exons 3, 4, 5, and 6 generated six mRNAs that were expressed differentially in developing lymphocytes (Molnar et al., *Mol. Cell Biol.* 14:8292, 1994). The composition and relative abundance of these Ikaros splicing variants in human lymphocytes were determined by RT-PCT analysis of mRNA prepared from human thymus and peripheral blood leukocytes and was compared with the mouse Ikaros isoforms. A set of primers, hEx2F/hEx7R, derived from human Ikaros cDNAs that displayed sequence similarity to sites on mouse Ikaros exons 2 and 7 amplified similarly sized products in both human and mouse. However, due to the incomplete identity between human and mouse sequences, mouse Ikaros cDNAs were amplified with lower efficiency. Products of the Ik-5 and Ik-6 isoforms were also amplified, but their expression was very low compared with that of Ik-1, Ik-2, Ik-3, and Ik-4. Given that Ik-2 and Ik-3 cDNAs amplified with hEx2F/hEx7R primers, generated similarly sized products, a different combination of primers was used to distinguish between these two isoforms. Primers hEx3F/hEx7R derived from human cDNAs and very similar in composition to sequences in mouse exons 3 and 7, amplified mouse and human Ik-1 and Ik-3 isoforms with similar efficiency. In the human, as in the mouse, expression of Ik-3 was low relative to those of Ik-1 and Ik-2 (Molnar et al., *Mol. Cell Biol.* 14:8292, 1994).

From this RT-PCT analysis it was evident that Ikaros isoforms were expressed at similar levels and ratios in human and mouse leukocytes. Ik-1 and Ik-2, the most abundant of the Ikaros isoforms in the mouse, were also encountered at similar concentrations in human. The ration of Ik-1 to Ik-2 was similarly higher in thymocytes and lower in peripheral leukocytes. Finally Ik-4, Ik-3, Ik-5, and Ik-6 isoforms were expressed in decreasing order relative to Ik-1 and Ik-2 in both human and mouse.

RT-PCR analysis of human cDNAs with primers derived from UE-1, UE-2, UE-3, and the coding region of human and mouse Ikaros cDNAs was performed to verify their structure and expression in thymocytes and peripheral leukocytes. The following primers were used: hUE-1, GGT ATA GGT GTG TAT TCT TCC (SEQ ID NO:166); hUE-2, GAG TTG CTC TTC TCT GAG CTC (SEQ ID NO:167); hUE-3, AAG TTT TCG TGC GCG CCC CTC (SEQ ID NO:168); hEx2F, CCC CTG TAA GCG ATA CTC CAG ATG (SEQ ID NO:169); m/hEx3F, AGT AAT GTT AAA GTA GAG ACT CAG (SEQ ID NO:170); and hEx7R, GAT GGC TTG GTC CAT CAC GTG GGA (SEQ ID NO: 171).

RT-PCR analysis of human cDNAs generated from poly (A)+ and total RNA prepared from human thymus, peripheral blood leukocytes, and mouse thymus was performed as previously described (Molnar et al., *Mol. Cell Biol.* 14:8292, 1994). The human Ikaros RT-PCR products were cloned, and their sequence compositions were determined. Splicing variants with sequences similar to those in mouse Ikaros exon 1 were identified. Amplification of GAPDH cDNA was performed in parallel to determine the relative amounts of cDNA used in the PCR reactions. GAPDH primers were: GAPDH-F, ATG GTG AAG GTC GGT GTG AAC GGA TTT GGC (SEQ ID NO:172); and GAPDH-R, GCA TCG AAG GTG GAA GAG TGG GAG TTG CTG (SEQ ID NO:173).

The Ikaros Protein Isoforms are Conserved Between Mouse and Man

The expression of the Ikaros protein isoforms was examined in human and mouse T cell nuclear extracts by Western blotting. Nuclear extracts from mouse and human fibroblast and epithelial cells were used to determine the specificity of the Ikaros antibody. A number of crossreacting proteins were detected in the nuclear extract from the mouse EL-4 T cell line. Since cDNAs that encode at least five size distinct Ikaros proteins were cloned from this cell line, the proteins detected with the Ikaros antibody are probably Ikaros isoforms expressed in this cell line. In the human T cell line Jurkat, the largest of these proteins was the most abundant form but other smaller proteins were detected at lower abundance. These human T cell nuclear proteins may represent the homologues of the mouse Ik-1, Ik-2, Ik-3 and Ik-4 isoforms in order of decreasing relative concentration. No crossreacting proteins were detected in the nuclear extracts from the CV1 and NIH-3T3 non expressing cell lines, thus confirming the specificity of the detecting antibody.

Western analysis of human and mouse nuclear extracts were carried out as follows: 20 µgs of protein, from nuclear extracts prepared from the Ikaros expressing mouse and human T cell lines EL4 and Jurkat, and from the Ikaros non-expressing mouse and monkey fibroblast and kidney epithelial lines NIH-3T3 and CV1, were run on 12% PAGE. Proteins were transferred to a nitrocellulose membrane and were analyzed with a 1:250 dilution of Ikaros antibody raised to the N-terminal portion of the mouse Ik-2 isoform containing exons 1, 3, 4, 5, and 6. The second step was performed using 1:3000 dilution of goat anti-rabbit antibody (BioRAD) conjugated to alkaline phosphatase. Antibody complexes were detected with BCIP and NBT substrates.

The Ikaros Mouse Genomic Locus

Based on sequence analysis of variant cDNAs, the (genomic locus is thought to include about 9–11 exons. Genomic DNAs encompassing most or all of the Ikaros exons present in the genome were isolated by screening a mouse genomic SV129 library made into the λDASH II phage vector using the various Ikaros cDNAs as probes. The Ikaros gene includes at least 80–90 kb of genomic sequence which was isolated as distinct but also overlapping genomic clones. Some of the Ikaros genomic clones are indicated in FIG. 7. The exons are depicted as boxes while the introns as lines. The DNA sequence for: the 5' boundary (SEQ ID NO:143) and the 3' boundary (SEQ ID NO:144) of exon E5; the 5' boundary (SEQ ID NO:145) of exon E3; and the 5' boundary (SEQ ID NO:146) and the 3' boundary (SEQ ID NO:147) of exon E7, were determined.

The Mouse Ikaros Gene is Located at the Proximal Arm of Chromosome 11

The mouse chromosomal location of Ikaros was determined by interspecific backcross analysis using progeny derived from matings of [(C57BL/6J×F1×C57BL/6J] mice. This interspecific backcross mapping panel has been typed for over 1300 loci that are well distributed among all the autosomes as well as the X chromosome. C57BL/6J and M spretus DNAs were digested with several enzymes and analyzed by Southern blot hybridization for informative restriction fragment length polymorphisms (RFLPs) using a mouse cDNA fragment as a probe. The 6.5 kb M. Spretus PstI restriction-fragment-length polymorphism (RFLP) was used to follow the segregation of the Ikaros locus in backcross mice. The mapping results indicated that Ikaros is located in the proximal region of mouse chromosome 11 linked to Lif, Erbb and Rel. Although 129 mice were analyzed for every marker, up to 157 mice were typed for some pairs of markers. Each locus was analyzed in pairwise combinations for recombination frequencies using the additional data. The ratios of the total number of mice exhibiting recombinant chromosomes to the total number of mice analyzed for each pair of loci and the most likely gene order are: centromere-Lif-6/167-Ikaros-3/146-Erbb-6/158-Rel. The recombination frequencies [expressed as genetic distances in centiMorgans (cM)+/− the standard error] are -Lif-3.6/+/−1.4-Ikaros-2.1+/−1.2-Erbb-3.8+/−1.5-Rel.

The interspecific map of chromosome 11 was composed with a composite mouse linkage map that reports the map location of many uncloned mouse mutations (compiled by M. T. Davisson, T. H. Roderick, A. L. Hillyard, and D. P. Doolittle and provided from GBASE, a computerized database maintained at The Jackson Laboratory, Bar Harbor, Me.). Ikaros mapped in a region of the composite map that lacks mouse mutations with a phenotype that might be expected for an alteration in this locus.

The proximal region of mouse chromosome 11 shares a region of homology with human chromosomes 22, 7 and 2. In particular Erbb has been placed on human 7p12. The tight linkage between Erbb and Ikaros in mouse suggests that Ikaros will reside on 7p as well.

Interspecific backcross progeny were generated by mating (C57BL/6J×M. spretus) F1 females and C57BL/6J males as described (Copeland and Jenkins, 1991). *Trends Genet* 7: 113–118. A total of 205 F2 mice were used to map the Ikaros locus DNA isolation, restriction enzyme digestion, agarose gel electrophoresis, Southern blot transfer and hybridization were performed essentially as described (Jenkins et al. (1982) *J Virol* 43:26–36; and Jenkins et al (1982) *J Virol* 42:379–388). All blots were prepared with Zetabind nylon membrane (AMF-Cuno). The probe, a 350 bp mouse cDNA fragment was labeled with [$\alpha$-$^{32}$P] dCTP using a random prime labeling kit (Amersham); washing was done to a final stringency of 1.0×SSCP, 0.1% SDS, 65° C. A fragment of 8.4 kh was detected in PstI digested C57BL/6J DNA and a fragment of 6.5 kb was detected in PstI digested M. spretus DNA. The presence or absence of the 6.5 kb M. spretus-specific PstI fragment was followed in backcross mice.

A description of the probes and RFLPs for the loci linked to Ikaros including leukemia inhibitory factor (Lif), avian erythroblastosis oncogene B (Erbb) and reticuloendotheliosis oncogene (Rel) has been reported previously (Karl et al. (1993) *Mol Cell Biol* 10:342–301; Karl et al. (1992) *Genetics* 131:103–173; and Karl et al. (1992) *Science* 256:100–102) Recombination distances were calculated using the computer program SPRETUS MADNESS. Gene order was determined by minimizing the number of recombination events required to explain the allele distribution patterns.

The Ikaros Gene Maps Between p11.2-p13 on Human Chromosome 7

The human chromosome assignment of the Ikaros gene was performed using DNAs prepared from a panel of somatic cell hybrids made between human and rodent. Primers designed after non-conserved sequences at the 3' end of the human cDNAs were used to distinguish between the human and rodent genes. A 375 bp fragment, as predicted from the human Ik-1 cDNA was amplified from human DNA used as a control and from DNA prepared from the cell hybrid 10791 which contains chromosome 7. The identity of the amplified band was confirmed using a probe derived from this region. To fine map the location of the Ikaros gene a panel of somatic cell hybrids which contained parts of chromosome 7 fused to the rodent genome were analyzed. A hybridizing 10 kb BglII genomic fragment was detected with human genomic DNA. A fragment of similar size was readily detected with DNA from the cell lines Ru Rag 4–13 and 1365 Rag 12–9. The former cell line contained the proximal arm of chromosome 7 while the latter contained the distal arm and part of the proximal up to segment p13. DNA from Rag GN6, a cell line that contains the whole distal arm of chromosome 7 and the proximal arm up to segment p11.2, did not hybridize. Another cell line which contained part of the proximal arm of chromosome 7 from p- to the telomere did not hybridize. This mapping restricts the location of the Ikaros gene between p11.2 and p13, placing it proximate to the Erbb gene locus, as predicted from the mouse.

PCR analysis of somatic cell hybrid DNA prepared from human mouse hamster and human-rodent somatic cell hybrids were used for the chromosome assignment of the human Ikaros gene DNAs from the following cell lines were used in PCR reactions h/h human-hamster hybrid h/m: human-mouse hybrid, 1 to 24 respectively 07299-h/h, 1082613-h/h, 10253-h/h, 10115-h/h 10114-h/h, 10629-h/h 10791-h/h, 10156-h/h,10611-h/h, 10926B-h/h, 10927A-h/h 10868-h/h, 10898-h/h 10479-h/m 11418-h/m 10567-h/m 10498-h/m 11010-h/h 10449-h/h 10478-h/m 10323-h/m 10888-h/h, 06318B-h/h 06317-h/h 25 human 26 mouse and 27: hamster DNAs were also used in control reactions 100 ngs of these DNAs were used in a PCR reaction together with 150 ngs of primers hIK-1 GGCTGCCACGGCTTC-CGTGATCCT (SEQ ID No. 163) and hIk-2: AGCG-GTCTGGGGAAACATCTAGGA (SEQ ID No. 164) designed after non-conserved sequences at the 3 min. of the human cDNA. Amplification parameters were: 95° C. for 5 min., 80° C. for 10 min. (with addition of 2.5 units of Taq polymerase), followed by 30 cycles at 93° C. for 1 min., 65° C. for 1 min. and 72° C. for 40", with an additional cycle at 93° C. for 5 min., 65° C. for 2 min. and 72° C. for 7 min. The amplified 375 bp product corresponds to the predicted size from the human cDNA. Fragment identity was confirmed by Southern hybridization with a probe derived from this region.

Fine mapping on human chromosome was further obtained by preparing 7 DNAs from a chromosome 7 hybrid panel which was used either in PCR amplification reactions with the primers described above, or in Southern analysis. The human chromosome 7 content of the hybrid cell lines used were 1365 Rag 12–9: 7 qter-p13; Rag GN6:7 qter-p11.2; Ru Rag 4–13: 7 cen-pter (Vortkamp et. al. (1991) *Genomics* 11:737–743). For Southern blot analysis, 5 $\mu$g of human DNA and 10 $\mu$gs of hybrid and mouse DNA digested with BglII were hybridized with a 375 bp fragment contained within the hIk-1 and hIk-2 primers.

Homologous Recombination Experiments in vitro and in vivo and Knockout Mice

To address the role of the lymphoid restricted transcription factor Ikaros in vivo we targeted mutations at the mouse Ikaros genomic locus in embryonic stem cells (E.S). Two targeting vectors carrying distinct deletions at the Ikaros genomic locus were transfected in the J1 E.S line derived from the SV129 mouse (En li, Cell 1992). Homologous recombination events in the E.S cells were scored by a double selection counter selection scheme; G418 and FIAU were used in the media to select for neomycin gene activity and for the absence of thymidine kinase gene activity. The neo gene is located in the middle of the construct while the tk gene is present at the 5' or 3' of the targeting vector and allows for selecting against non-homologous recombination events. E.S. cell lines carrying either mutation one or two were established by Southern analysis and were injected in the blastocysts of Balbe or C57 black mice. The chimeric blastocysts were reimplanted in pseudopregnant mice and gave rise to chimeric animals. Mice which were more than 70% chimeric for the SV129 strain as determined by coat color (agouti vs white or black background) were bred further. Germ line transmission was determined by coat color (agouti) and by Southern analysis of tail DNA. We are in the process of breeding these mice to obtain animals which are homozygous for these mutations.

Both of the targeted mutations are deletions. The first mutation deletes the last exon, E7, which is shared by al the Ikaros isoforms. This should generate proteins which can bind DNA but which cannot activate transcription. These proteins may function as dominant negative regulators of transcription since they can compete for DNA binding with wild type Ikaros proteins but cannot activate transcription. Mice heterozygous for this mutation may exhibit a decrease in the level of expression of genes that rely on the Ikaros proteins for their regulation. These mice may exhibit a less sever phenotype than the ones with total lack of expression of Ikaros proteins. Analysis of these animals may prove to be necessary if the phenotype on mice with total loss of function is severe.

The second mutation (a deletion of exon E3 and E4) should result in a total loss of function of the Ikaros gene. Mice homozygous for this mutation may have a severe impairment of the Ikaros gene. Mice homozygous for this mutation may have a severe impairment of their immune system as a result of altered expression of genes regulated by the Ikaros gene. Possible candidates for Ikaros regulation are TDT (recombination pathway) CD3 complex. TCR complex IL2 gene HIV LTR etc. Lymphoid cell lines derived from these mice can be used to delineate the regulatory pathway that leads to mature T and B cells but the mice themselves can be used to study the complex interaction between the different lineages in the hemopoietic pathway and design in vivo experiments to study and correct immunodeficiency syndromes. Finally, ES cell lines derived from these animals can be studied by in vivo differentiation into the hemopoietic/lymphopoietic lineage.

Use

The peptides of the invention may be administered to a mammal, particularly a human, in one of the traditional modes (e.g., orally, parenterally, transdermally, or transmucosally), in a sustained release formulation using a biodegradable biocompatible polymer, or by on-site delivery using micelles, gels and liposomes or by transgenic modes.

Other Embodiments

Nucleic acid encoding all or part of the Ikaros gene can be used to transform cells. For example, the Ikaros gene, e.g., a mis-expressing or mutant form of the Ikaros gene, e.g., a deletion, or DNA encoding an Ikaros protein can be used to transform a cell and to produce a cell in which the cell's genomic Ikaros gene has been replaced by the transformed gene, producing, e.g., a cell deleted for the Ikaros gene. As described above, this approach can be used with cells capable of being grown in culture, e.g., cultured stem cells, to investigate the function of the Ikaros gene.

Analogously, nucleic acid encoding all or part of the Ikaros gene, e.g., a mis-expressing or mutant form of the gene, e.g., a deletion, can be used to transform a cell which subsequently gives rise to a transgenic animal. This approach can be used to create, e.g., a transgenic animal in which the Ikaros gene is, e.g., inactivated, e.g., by a deletion.

Homozygous transgenic animals can be made by crosses between the offspring of a founder transgenic animal. Cell or tissue cultures can be derived from a transgenic animal. A subject at risk for a disorder characterized by an abnormality in T cell development or function, e.g., leukemia, can be detected by comparing the structure of the subject's Ikaros gene with the structure of a wild type Ikaros gene. Departure from the wild type structure by, e.g., frameshifts, critical point mutations, deletions, insertions, or translocations, are indicative of risk. The DNA sequence of the coding region of several exons as well as several intron exon boundaries are included herein. Other regions can be obtained or sequenced by methods known to those skilled in the art.

The invention includes any protein which is substantially homologous to an Ikaros protein, e.g., the Ikaros protein shown in SEQ ID NO:2, SEQ ID NO:3, or SEQ ID NO:5, or other isoforms. Also included are: allelic variations; natural mutants; induced mutants, e.g., in vitro deletions; proteins encoded by DNA that hybridizes under high or low (e.g., washing at 2×SSC at 40 C with a probe length of at least 40 nucleotides) stringency conditions to a nucleic acid naturally occurring (for other definitions of high and low stringency see Current Protocols in Molecular Biology, John Wiley & Sons, New York, 1989, 6.3.1–6.3.6, hereby incorporated by reference); and polypeptides or proteins specifically bound by antisera to an Ikaros protein, especially by antisera to the active site or binding domain of an Ikaros protein. The term also includes chimeric polypeptides that include an Ikaros protein.

DNA and peptide sequences of the invention can be, e.g., mouse, primate, e.g., human, or non-naturally occurring sequences.

The invention also includes any biologically active fragment or analog of an Ikaros protein. By "biologically active" is meant possessing any in vivo or in vitro activity which is characteristic of an Ikaros isoform, e.g., an isoform shown in (SEQ ID NO:2) or FIG. 3 (SEQ ID NO:3) or (SEQ ID NO:5), e.g., Ikaros activity as described above. Because the Ikaros proteins exhibit a range of physiological properties and because such properties may be attributable to different portions of the Ikaros protein molecule, a useful Ikaros protein fragment or Ikaros protein analog is one which exhibits a biological activity in any one (or more) of a variety of the Ikaros protein assays, for example, the ability to bind to or stimulate transcription from a δA element or an NKFB element, as described above. An Ikaros protein fragment or analog possesses, most preferably 90%, preferably 40%, or at least 10%, of the activity of a naturally occurring Ikaros isoform, e.g., of the Ikaros protein shown in (SEQ ID NO:2), (SEQ ID NO:3) or (SEQ ID NO:5), in any in vivo or in vitro Ikaros assay.

As described above, differential splicing of Ikaros transcripts generates at least five mRNAs that encode proteins with overlapping but distinct DNA binding specificity and affinity. The DNA binding specificity of the Ikaros proteins are apparently dictated primarily by the differential usage of exons encoding the N-terminal zinc fingers.

The present invention further pertains to recombinant Ikaros proteins which are encoded by genes derived from an animal and which have amino acid sequences evolutionarily related to an Ikaros protein represented by any of SEQ ID NOS: 2–8. Such recombinant Ikaros proteins preferably are capable of functioning in one of either role of an agonist of antagonist of at least one biological activity of a naturally-occurring Ikaros protein. The term "evolutionarily related to", with respect to either amino acid sequence or nucleic acid sequence, refers to Ikaros sequences which have arisen naturally, preferably in vertebrate organism, more preferably in mammals (e.g. humans, mice, pigs). The term also refers to nucleic acid sequences which, while derived from a naturally occurring Ikaros, have been altered by mutagenesis, as for example, combinatorial mutagenesis described below. Recombinant proteins evolutionarily related to the Ikaros proteins preferably at least 50% homologous, more preferably in the range of 60%–70% homologous and most preferably in the range of 80%–90% homologous with an amino acid sequence selected from the group consisting of SEQ ID NO: 2, SEQ ID NO: 3, SEQ ID NO: 4, SEQ ID NO: 5, SEQ ID NO: 6, SEQ ID NO: 7 and SEQ ID NO: 8. Polypeptides having a biological activity of a naturally-occurring Ikaros protein, or which can function antagonistically to naturally occurring Ikaros proteins, and having at least about 95%, more preferably at least about 98–99% homology with a sequence selected from the group consisting of SEQ ID NO: 2, SEQ ID NO: 3, SEQ ID NO: 4, SEQ ID NO: 5, SEQ ID NO: 6, SEQ ID NO: 7 and SEQ ID NO: 8 are also within the scope of the invention.

Isolated peptides having the activity of an Ikaros protein can be obtained by screening peptides recombinantly produced from the corresponding fragment of a nucleic acid selected from a group consisting of SEQ ID NO: 2, SEQ ID NO:3, SEQ ID NO: 4, SEQ ID NO: 5, SEQ ID NO: 6, SEQ ID NO: 7 and SEQ ID NO: 8. In addition, fragments can be chemically synthesized using techniques known in the art such as conventional Merrifield solid phase f-Moc or t-Boc chemistry. For example, the subject Ikaros proteins may be arbitrarily divided into fragments of desired length with no overlap of the fragments, or preferably divided into overlapping fragments of a desired length. The fragments, whether produced recombinantly or by chemical synthesis, can be tested to identify those peptides having an Ikaros protein activity, such as by first measuring the ability of the fragment to bind to a particular DNA sequence as described above.

Moreover, it is possible to modify the structure of an Ikaros protein for such purposes as altering the biological activity, increasing solubility, improving bioavailability, enhancing therapeutic or prophylactic efficacy, or stability (e.g., shelf life ex vivo and resistance to proteolytic degradation in vivo). Such modified peptides are considered functional equivalents of peptides having an activity of an Ikaros protein as defined herein. A modified peptide can be produced in which the amino acid sequence has been altered, such as by amino acid substitution, deletion, or addition. In one embodiment, mutagenesis can give rise to Ikaros homologs which have intracellular half-lives dramatically different than the corresponding wild-type protein. For example, the altered protein can be rendered either more stable or less stable to proteolytic degradation or other cellular process which result in destruction of, or otherwise inactivation of, an Ikaros protein. Such Ikaros homologs, and the genes which encode them, can be utilized to alter the envelope of Ikaros expression by modulating the half-life of the protein. For instance, a short half-life can give rise to more transient Ikaros biological effects and, when part of an inducible expression system, can allow tighter control of Ikaros levels within the cell. Such modifications can also be used to generate Ikaros antagonists. which can be used, for example, to inhibit the biological consequences of wild-type Ikaros expression. Such Ikaros homologs can be especially useful to generate transgenic, and the antagonistic homologs can be especially useful where "knock-out" phenotypes are sought.

Thus, it will be apparent that variations of the Ikaros peptides and DNA molecules are also contemplated as being equivalent to those peptides and DNA molecules that are set forth in more detail above. For example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule, though such homologs can be screened for antagonistic activity as well. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing= cysteine and methoinine, (see, for example, *Biochemistry*, 2nd ed, Ed. by L. Stryer, WH Freeman and Co.:1981). Whether a change in the amino acid sequence of a peptide results in a functional Ikaros homolog can be readily determined by assessing the ability of the variant peptide to produce a response in cells in a fashion similar to the wild-type Ikaros. Likewise, the ability of an Ikaros homolog to function as an antagonist can be readily assessed from its ability to competitively inhibit the biological activity of a wild-type form of an Ikaros protein. Peptides in which more than one replacement has taken place can readily be tested in the same manner.

This invention further contemplates Ikaros homologs generated by a method used to create and screen sets of combinatorial mutants of Ikaros, as well as truncation mutants, and is especially useful for identifying potential variant sequences (e.g. homologs) that are functional in binding to a receptor for Ikaros. The purpose of screening such combinatorial libraries is to generate, for example, novel Ikaros homologs which can act as either agonists or antagonist, or alternatively, possess novel activities all together. To illustrate, Ikaros homologs can be engineered by the present method to provide more efficient binding to an Ikaros binding oligonucleotide which may be a part of an Ikaros-responsive element (IK-RE), yet still retain at least a portion of an activity associated with Ikaros. Alternatively, Ikaros homologs can be generated according to the present invention which retain the DNA binding ability of a naturally occurring Ikaros protein, but which competitively inhibit the biological function of naturally occurring Ikaros proteins (e.g., is an antagonist).

In one aspect of this method, the amino acid sequences for a population of Ikaros homologs or other related proteins are aligned, preferably to promote the highest homology possible. Such a population of variants can include, for example, Ikaros homologs from one or more species, such as illustrated in FIG. 9 (alignment of human and mouse Ik-1 E3 through E7). Amino acids which appear at each position of the aligned sequences are selected to create a degenerate set of combinatorial sequences.

In a preferred embodiment, the combinatorial Ikaros library is produced by way of a degenerate library of genes encoding a library of polypeptides which each include at least a portion of potential Ikaros sequences. A mixture of synthetic oligonucleotides can be enzymatically ligated into gene sequences such that the degenerate set of potential Ikaros sequences are expressible as individual polypeptides, or alternatively, as a set of larger fusion proteins (e.g. for phage display) containing the set of Ikaros sequences therein.

As illustrated in FIG. 9, to analyze the sequences of a population of variants, the amino acid sequences of interest can be aligned relative to sequence homology. The presence or absence of amino acids from an aligned sequence of a particular variant is relative to a chosen consensus length of a reference sequence, which can be real or artificial. In order to maintain the highest homology in alignment of sequences, deletions in the sequence of a variant relative to the reference sequence can be represented by an amino acid space (•), while insertional mutations in the variant relative to the reference sequence can be disregarded and left out of the sequence of the variant when aligned. For instance, FIG. 9 includes the alignment of several cloned forms of Ikaros from different species. Analysis of the alignment of the Ikaros clones shown in FIG. 9 can give rise to the generation of a degenerate library of polypeptides comprising potential Ikaros sequences, such as, to illustrate:

```
                                                   (SEQ ID NO:153)
Xaa-Xaa-Ala-Ser-Asn-Val-Lys-Val-Glu-Thr-Gln-Ser-Asp-Glu-Glu-Asn-Gly-Arg-

Ala-Cys-Glu-Met-Asn-Gly-Glu-Glu-Cys-Ala-Glu-Asp-Leu-Arg-Met-Leu-Asp-Ala-

Ser-Gly-Glu-Lys-Met-Asn-Gly-Ser-His-Arg-Asp-Gln-Gly-Ser-Ser-Ala-Leu-Ser-

Gly-Val-Gly-Gly-Ile-Arg-Leu-Pro-Asn-Gly-Lys-Leu-Lys-Cys-Asp-Ile-Cys-Gly-

Ile-Xaa-Cys-Ile-Gly-Pro-Asn-Val-Leu-Met-Val-His-Lys-Arg-Ser-His-Thr-Gly-

Glu-Arg-Pro-Phe-Gln-Cys-Asn-Gln-Cys-Gly-Ala-Ser-Phe-Thr-Gln-Lys-Gly-Asn-

Leu-Leu-Arg-His-Ile-Lys-Leu-His-Ser-Gly-Glu-Lys-Pro-Phe-Lys-Cys-His-Leu-

Cys-Asn-Tyr-Ala-Cys-Arg-Arg-Arg-Asp-Ala-Leu-Thr-Gly-His-Leu-Arg-Thr-His-

Ser-Val-Gly-Lys-Pro-His-Lys-Cys-Gly-Tyr-Cys-Gly-Arg-Ser-Tyr-Lys-Gln-Arg-

Xaa-Ser-Leu-Glu-Glu-His-Lys-Glu-Arg-Cys-His-Asn-Tyr-Leu-Glu-Ser-Met-Gly-

Leu-Pro-Gly-Xaa-Xaa-Xaa-Pro-Val-Ile-Lys-Glu-Glu-Thr-Xaa-His-Xaa-Glu-Met-

Ala-Glu-Asp-Leu-Cys-Lys-Ile-Gly-Xaa-Glu-Arg-Ser-Leu-Val-Leu-Asp-Arg-Leu-

Ala-Ser-Asn-Val-Ala-Lys-Arg-Lys-Ser-Ser-Met-Pro-Gln-Lys-Phe-Leu-Gly-Asp-

Lys-Xaa-Leu-Ser-Asp-Xaa-Pro-Tyr-Asp-Ser-Ala-Xaa-Tyr-Glu-Lys-Glu-Xaa-Xaa-

Met-Met-Xaa-Ser-His-Val-Met-Asp-Xaa-Ala-Ile-Asn-Asn-Ala-Ile-Asn-Tyr-Leu-

Gly-Ala-Glu-Ser-Leu-Arg-Pro-Leu-Val-Gln-Thr-Pro-Pro-Gly-Xaa-Ser-Glu-Val-

Val-Pro-Val-Ile-Ser-Pro-Met-Tyr-Gln-Leu-His-Xaa-Xaa-Xaa-Ser-Xaa-Gly-Xaa-

Pro-Arg-Ser-Asn-His-Ser-Ala-Gln-Asp-Xaa-Ala-Val-Xaa-Xaa-Leu-Leu-Leu-Leu-

Ser-Lys-Ala-Lys-Xaa-Val-Xaa-Ser-Glu-Arg-Glu-Ala-Ser-Pro-Ser-Asn-Ser-Cys-

Gln-Asp-Ser-Thr-Asp-Thr-Glu-Ser-Asn-Xaa-Glu-Glu-Gln-Arg-Ser-Gly-Leu-Ile-

Tyr-Leu-Thr-Asn-His-Ile-Xaa-Xaa-Xaa-Ala-Xaa-Xaa-Xaa-Xaa-Xaa-Leu-Lys-Glu-

Glu-Xaa-Arg-Ala-Tyr-Xaa-Xaa-Leu-Arg-Ala-Ala-Ser-Glu-Asn-Ser-Gln-Asp-Ala-

Xaa-Arg-Val-Val-Ser-Thr-Ser-Gly-Glu-Gln-Xaa-Lys-Val-Tyr-Lys-Cys-Glu-His-

Cys-Arg-Val-Leu-Phe-Leu-Asp-His-Val-Met-Tyr-Thr-Ile-His-Met-Xaa-Xaa-Xaa-

Gly-Cys-His-Gly-Phe-Arg-Asp-Pro-Phe-Glu-Cys-Asn-Met-Cys-Gly-Tyr-His-Ser-

Gln-Asp-Arg-Tyr-Glu-Phe-Ser-Ser-His-Ile-Thr-Arg-Gly-Glu-His-Arg-Xaa-His-

Xaa-Ser-
```

Each of the degenerate positions Xaa can be generated to include just the amino acid residues which occur in either mIk-1 or hIk-1, or, alternatively, to include those amino acid plus others, e.g. all conservative mutations based on the actual sequences of mIk-1 and hIk-1, or completely random mutations, e.g. all 20 amino acids. For example, Xaa(3) (the third degenerate residue from the N-terminus) is either a valine or an isoleucine in the naturally occurring isoforms, but in a degenerate library derived by conserved mutations, Xaa(3) can represent Gly, Ala, Val, Ile, Leu, Ser or Thr. Likewise, in such a degenerate library, Xaa(5), which corresponds to a Thr in hIk-1 but which is not present in mIk-1, represents Gly, Ala, Val, Ile, Leu, Ser, Thr or an amino acid gap (e.g. not present). Furthermore, the degenerate library can be constructed such that the at least the codons for the last amino acid residue in each exon are degenerate to include a stop codon, such that the library also includes truncation mutations. For example, the codons for Thr-89, Ser-145, Pro-187, and Gly-232 (in SEQ ID NO:153) can be made degenerate to further provide stop codons (e.g. TAA) in some of the recombinant genes of the degenerate library.

In a preferred embodiment, the variegated library of Ikaros variants is generated by combinatorial mutagenesis at the nucleic acid level, and is encoded by a variegated gene library. These are many ways which the library of potential Ikaros homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential Ikaros sequences. The synthesis of degenerate oligonucleotides is known in the art (see for example, Narang, SA (1983) *Tetrahedron* 39:3; Itakura et al. (1981) *Recombinant DNA, Proc 3rd Cleveland Sympos. Macromolecules,* ed. AG Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et: al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

In light of the present disclosure, other forms of mutagenesis generally applicable will be apparent to those skilled in the art in addition to the aforementioned rationale mutagenesis based on conserved versus non-conserved residues. For example, Ikaros homologs (both agonist and antagonist forms) can be generated and screened using, for example, alanine scanning mutagenesis and the like (Ruf et al. (1994) *Biochemistry* 33:1565–1572; Wang et al. (1994) *J Biol Chem* 269:3095–3099; Balint et al. (1993) *Gene* 137:109–118; Grodberg et al. (1993) *Eur J Biochem* 218:597–601; Nagashima et al. (1993) *J Biol Chem* 268:2888–2892; Lowman et al. (1991) *Biochemistry* 30:10832–10838; and Cunningham et al. (1989) *Science* 244:1081–1085), by linker scanning mutagenesis (Gustin et al. (1993) *Virology* 193:653–660; Brown et al. (1992) *Mol Cell Biol* 12:2644–2652; McKnight et al. (1982) *Science* 232:316); or by saturation mutagenesis (Meyers et al. (1986) *Science* 232:613);

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of Ikaros homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate Ikaros sequences created by combinatorial mutagenesis techniques.

In one embodiment, the candidate Ikaros gene products are displayed on the surface of a cell or viral particle, and the ability of particular cells or viral particles to bind an Ikaros-binding oligonucleotide (such as an Ik-BS described above) via this gene product is detected using an affinity selection metrices. For instance, the gene library can be cloned into the gene for a surface membrane protein of a bacterial cell, and the resulting fusion protein detected through bio-panning (Ladner et al., WO 88/06630; Fuchs et al. (1991) *Bio/Technology* 9:11370–1371; and Goward et al. (1992) *TIBS* 18:1136–140). In a similar fashion, fluorescently labeled oligonucleotides which bind Ikaros can be used to search the library for useful Ikaros homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd, and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) *J. Biol. Chem.* 267:16007–16010; Griffths et al. (1993) *EMBO J* 12:725–734; Clackson et al. (1991) Nature 352:624–628; and Barbas et al. (1992) *PNAS* 89:4457–4461).

In an illustrative embodiment, the recombinant phage antibody system (RPAS, Pharamacia Catalog number 27-9400-01) can be easily modified for use in expressing and screening Ikaros combinatorial libraries. For instance, the pCANTAB 5 phagemid of the RPAS kit contains the gene which encodes the phage gIII coat protein. The Ikaros combinatorial gene library can be cloned into the phagemid adjacent to the gIII signal sequence such that it will be expressed as a gIII fusion protein. After ligation. the phagemid is used to transform competent *E. coil* TG1 cells. Transformed cells are subsequently infected with M13KO7 helper phage to rescue the phagemid and its candidate Ikaros gene insert. The resulting recombinant phage contain phagemid DNA encoding a specific candidate Ikaros, and display one or more copies of the corresponding fusion coat protein. The phage-displayed candidate Ikaros proteins which are capable of binding an Ik-RE are selected or enriched by bio-panning. For instance, as described by Rebar et al. (1994) *Science* 35 263:671–673, the phage library can be equilibrated with biotinylated target DNA and then applied to streptavidin-coated microtiter wells. After washing, the retained phage can be eluted, such as in high salt buffer, amplified in *E coli,* and purified. Successive rounds of reinfection of *E. coli,* and panning will greatly enrich for Ikaros homologs, which can then be screened for further biological activities in order to differentiate agonists and antagonists.

In yet a further illustrative embodiment, the combination Ikaros library can be recombinantly expressed in cultured cells, and the ability of members of the combinatorial library to act as one of either an agonist or antagonist of wild-type Ikaros proteins can be assessed through the use of selectable markers. Following such protocols as described in, for example, the Ladner et al. U.S. Pat. No. 5,198,346, the ability of members of the combinatorial library to either promote or inhibit expression of a selectable marker can facilitate forced evolution of Ikaros homologs. For example, there are many genes that, when expressed, confer detectable phenotypes on cells. By placing Ikaros responsive elements (such as described above in the tkCAT constructs) proximate the selectable gene, the expression of the selectable marker can be brought under the control of an Ikaros protein able to bind that Ik-RE. As will be apparent, the level of expression of the gene, or lack thereof, will be indicative of the activity of the Ikaros homolog, i.e. whether it is an antagonist or agonist, and the assay can therefore be constructed to appropriately search for one or the other.

The selectable marker gene can be, to illustrate, a gene whose product confers drug resistance. In another embodiment, the selectable marker gene can encode a protein which, when expressed by the cell, inhibits cell growth (i.e., is cytotoxic or cytostatic). In still a further embodiment, the selectable marker can be a gene product which does not affect cell growth, but which is detectable by, for instance, immunoassay or photometric techniques. An exemplary embodiment of an immunoassay-detectable marker comprises a gene product encoding a cell surface antigen whose expression permits sorting of cells (and hence, of the combinatorial library) by immuno-affinity or FACS techniques. Likewise, an illustrative example of a photometric reporter gene is luciferase.

To score for those members of the combinatorial library which are Ikaros agonists, the reporter gene constructs can be transfected into the same cells, either eukaryotic (and which preferably lack an endogenously expressed Ikaros) or prokaryotic, as the combinatorial Ikaros library. To score for Ikaros antagonists, cells harboring the reporter gene construct and expressing a wild-type Ikaros protein can be used to detect inhibition of the expression of the reporter gene by an antagonist expressed from the combinatorial library. Because proliferation of a cell will generally be a more desirable mode of detecting a particular Ikaros activity (e.g. agonist or antagonist), as between the drug resistance marker and the cytotoxic/cytostatic factor, the former is favored when attempting to detect agonists and the latter favored to detect antagonists. Moreover, it will be appreciated that, in light of the foregoing description, it may be possible to isolate Ikaros homologs which are active in only a limited subset of the tissue in which Ikaros naturally occurs. For instance, by exploiting light differences in DNA binding specificity between cell-types, an Ikaros antagonist can be derived which particularly inhibits the function of Ikaros in T cells, and can be used to electively disrupt development of just that cell-type.

In a still further embodiment, the present invention contemplates the generation of Ikaros homologs by in vitro exon shuffling (de Vries et al. (1988) *Biochemistry* 27:2505–2572; and Langer-Safer et al. (1991) *J. Biol Chem* 266:3715–3723). As demonstrated above, each of the zinc finger domains can exert differing effects on binding specificity and transcriptional activation ability of the subject Ikaros proteins. Moreover, the naturally occurring ikaros proteins have arisen by alternate splicing mechanisms, and that given the exon arrangement of the Ikaros gene locus apparently displays a modular organization, it may be possible to "mix and match" exons to obtain proteins with novel DNA binding specificities and/or activities relative to naturally occurring forms of Ikaros. Such exon shuffling can be carried our in a rational fashion, in a semi-random fashion, or in a completely random fashion, the latter two being useful to generate screenable variegated libraries of potential Ikaros homologs. For example, each exon can be engineered to contain the same registration endonuclease site at each exon boundary. Admixing a variegated population of such Ikaros exons (e.g. 1/2, 3, 4. 5, 6, and 7 which were previously cleared to leave complementary "sticky ends", then allowing the exons to reanneal, will produce randomly recombined gene constructs. Selecting a portion of those constructs based on size (e.g. all genes less than 4250 base pairs) will allow the library to be reduced to a particular number of exons (e.g. 1 to about 7 to 10 exons ligated). Adding, as necessary, non-coding sequences and start and stop radons, the random library can be cloned into an expression vector and screened on described above.

Especially when synthesized in vitro, such as where peptide fragments, e.g. of lengths ranging from 10–20 residues, 50–70 residues, 100–120 residues, the amino acid residues at particular positions may further include analogs, derivatives and congeners of any specific amino acid referred to herein. For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject peptide can include an amino acid analog as for example, β-cyanoalanine, canavanine, djenkolic acid, norleucine, 3-phosphoserine, homoserine, dihydroxyphenylalanine, 5-hydroxytryptophan, 1-methylhistidine, or 3-methylhistidine. Other naturally occurring amino acid metabolites or precursors having side chains which are suitable herein will be recognized by those skilled in the art and are included in the scope of the present invention. Such derivatives can be used for such purposes as altering the biological activity, increasing solubility, improving bioavailability, enhancing therapeutic or prophylactic efficacy, or stability (e.g., shelf life ex vivo and resistance to proteolytic degradation in vivo).

Other useful modifications include those which increase peptide stability; such analogs may contain, for example, one or more non-peptide bonds (which replace peptide bonds) or D-amino acids in the peptide sequence.

Analogs can differ from a naturally occurring Ikaros protein in amino acid sequence or can modified in ways that do not affect sequence, or both. Analogs of the invention will Generally exhibit at least 70% more preferably 80%, more preferably 90%, and most preferably 95% or even, 99%, homology with a segment of 20 amino acid residues. preferably more than 40 amino acid residues or more preferably the entire sequence of naturally occurring Ikaros protein sequence.

As set forth above, alterations in primary sequence include genetic variations, both natural and induced. Also included are analogs that include residues other than naturally occurring L-amino acids, e.g., D-amino acids or non-naturally occurring or synthetic amino acids, e.g., β or γ amino acids. Alternatively, increased stability or solubility may be conferred by cyclizing the peptide molecule.

Nonsequence modification include in vivo or in vitro chemical derivatization or polypeptides, e.g., acetylation, methylation, phosphorylation, carboxylation, or glycosylation; glycosylation can be modified, e.g., by modifying the glycosylation patterns of a polypeptide during its synthesis and processing or in further processing steps, e.g., by exposing the polypeptide to glycosylation-affecting enzymes derived from cells that normally provide such processing, e.g., mammalian glycosylation enzymes; phosphorylation can be modified by exposing the polypeptide to phosphorylation-altering enzymes, e.g., kinases or phosphatases.

In addition to substantially full-length polypeptides, the invention also includes biologically active fragments of the polypeptides. As used herein, the term "fragment", as applied to a polypeptide, will be of a length described for an Ikaros peptide above and will ordinarily be at least about 20 residues, more typically at least about 40 residues, preferably at least about 60 residues in length.

Fragments of Ikaros peptides or introns can be made by methods known to those skilled in the art, e.g., by expressing Ikaros DNA which has been manipulated in vitro to encode the desired fragment; e.g., by restriction digestion of an Ikaros DNA e.g., the sequence in SEQ ID NO:1 or SEQ ID NO:2. Analogs can be made by methods known to those skilled in the art,, e.g., by in vitro DNA sequence modifications of the sequence of an Ikaros DNA e.g., the sequence in SEQ ID NO:1 or SEQ ID NO:2. For example, in vitro mutagenesis can be used to convert the DNA sequence of SEQ ID NO:1 into a sequence which encodes an analog in which one or more amino acid residues has undergone a replacement, e.g., a conservative replacement as described in the table of conservative amino acid substitutions provided herein. Fragments or analogs can be tested by methods known to those skilled in the art for the presence of Ikaros activity.

Also included are Ikaros protein polypeptides containing residues that are not required for biological activity of the peptide, such as residues that are not required for the biological activity of the polypeptide, or that result from alternative mRNA splicing or alternative protein processing events.

The invention also includes nucleic acids encoding the potypeptides of the invention.

In order to obtain an Ikaros protein one can insert Ikaros-encoding DNA into an expression vector, introduce the vector into a cell suitable for expression of the desired protein, and recover and purify the desired protein by prior art methods. Antibodies to Ikaros proteins can be made by immunizing an animal, e.g., a rabbit or mouse, and recovering anti-Ikaros antibodies by prior art methods.

To obtain a specific splicing-product (i.e., a specific isoform) one can make a synthetic structural gene including only the exons which code for the desired splicing product and express the gene as described above.

All of the above-cited references and publications are hereby incorporated by reference.

SEQUENCE LISTING (1) GENERAL INFORMATION:

(iii) NUMBER OF SEQUENCES: 202

(2) INFORMATION FOR SEQ ID NO: 1:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

AGAAGTTTCC ATGACATCAT GAATGGGGGT GGCAGAGA                38

(2) INFORMATION FOR SEQ ID NO: 2:

(i) SEQUENCE CHARACTERISTICS:
      (A) LENGTH: 1788 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: Coding Sequence
      (B) LOCATION: 223...1515

(xi) SEQUENCE DESCRIPTION: SEQ ID NO: 2:

AATTCGTTCT ACCTTCTCTG AACCCCAGTG GTGTGTCAAG GCCGGACTGG GAGCTTGGGG    60

GAAGAGGAAG AGGAAGAGGA ATCTGCGGCT CATCCAGGGA TCAGGGTCCT TCCCAAGTGG   120

CCACTCAGAG GGGACTCAGA GCAAGTCTAG ATTTGTGTGG CAGAGAGAGA CAGCTCTCGT   180

-continued

```
TTGGCCTTGG GGAGGCACAA GTCTGTTGAT AACCTGAAGA CA ATG GAT GTC GAT           234
                                                Met Asp Val Asp
                                                  1

GAG GGT CAA GAC ATG TCC CAA GTT TCA GGA AAG GAG AGC CCC CCA GTC          282
Glu Gly Gln Asp Met Ser Gln Val Ser Gly Lys Glu Ser Pro Pro Val
  5              10                  15                      20

AGT GAC ACT CCA GAT GAA GGG GAT GAG CCC ATG CCT GTC CCT GAG GAC          330
Ser Asp Thr Pro Asp Glu Gly Asp Glu Pro Met Pro Val Pro Glu Asp
                 25                  30                      35

CTG TCC ACT ACC TCT GGA GCA CAG CAG AAC TCC AAG AGT GAT CGA GGC          378
Leu Ser Thr Thr Ser Gly Ala Gln Gln Asn Ser Lys Ser Asp Arg Gly
             40                  45                  50

ATG GGT GAA CGG CCT TTC CAG TGC AAC CAG TCT GGG GCC TCC TTT ACC          426
Met Gly Glu Arg Pro Phe Gln Cys Asn Gln Ser Gly Ala Ser Phe Thr
         55                  60                  65

CAG AAA GGC AAC CTC CTG CGG CAC ATC AAG CTG CAC TCG GGT GAG AAG          474
Gln Lys Gly Asn Leu Leu Arg His Ile Lys Leu His Ser Gly Glu Lys
 70                  75                  80

CCC TTC AAA TGC CAT CTT TGC AAC TAT GCC TGC CGC CGG AGG GAC GCC          522
Pro Phe Lys Cys His Leu Cys Asn Tyr Ala Cys Arg Arg Arg Asp Ala
 85                  90                  95                 100

CTC ACC GGC CAC CTG AGG ACG CAC TCC GTT GGT AAG CCT CAC AAA TGT          570
Leu Thr Gly His Leu Arg Thr His Ser Val Gly Lys Pro His Lys Cys
                105                 110                 115

GGA TAT TGT GGC CGG AGC TAT AAA CAG CGA AGC TCT TTA GAG GAG CAT          618
Gly Tyr Cys Gly Arg Ser Tyr Lys Gln Arg Ser Ser Leu Glu Glu His
            120                 125                 130

AAA GAG CGA TGC CAC AAC TAC TTG GAA AGC ATG GGC CTT CCG GGC GTG          666
Lys Glu Arg Cys His Asn Tyr Leu Glu Ser Met Gly Leu Pro Gly Val
        135                 140                 145

TGC CCA GTC ATT AAG GAA GAA ACT AAC CAC AAC GAG ATG GCA GAA GAC          714
Cys Pro Val Ile Lys Glu Glu Thr Asn His Asn Glu Met Ala Glu Asp
    150                 155                 160

CTG TGC AAG ATA GGA GCA GAG AGG TCC CTT GTC CTG GAC AGG CTG GCA          762
Leu Cys Lys Ile Gly Ala Glu Arg Ser Leu Val Leu Asp Arg Leu Ala
165                 170                 175                 180

AGC AAT GTC GCC AAA CGT AAG AGC TCT ATG CCT CAG AAA TTT CTT GGA          810
Ser Asn Val Ala Lys Arg Lys Ser Ser Met Pro Gln Lys Phe Leu Gly
                185                 190                 195

GAC AAG TGC CTG TCA GAC ATG CCC TAT GAC AGT GCC AAC TAT GAG AAG          858
Asp Lys Cys Leu Ser Asp Met Pro Tyr Asp Ser Ala Asn Tyr Glu Lys
            200                 205                 210

GAG GAT ATG ATG ACA TCC CAC GTG ATG GAC CAG GCC ATC AAC AAT GCC          906
Glu Asp Met Met Thr Ser His Val Met Asp Gln Ala Ile Asn Asn Ala
        215                 220                 225

ATC AAC TAC CTG GGG GCT GAG TCC CTG CGC CCA TTG GTG CAG ACA CCC          954
Ile Asn Tyr Leu Gly Ala Glu Ser Leu Arg Pro Leu Val Gln Thr Pro
    230                 235                 240

CCC GGT AGC TCC GAG GTG GTG CCA GTC ATC AGC TCC ATG TAC CAG CTG         1002
Pro Gly Ser Ser Glu Val Val Pro Val Ile Ser Ser Met Tyr Gln Leu
245                 250                 255                 260

CAC AAG CCC CCC TCA GAT GGC CCC CCA CGG TCC AAC CAT TCA GCA CAG         1050
His Lys Pro Pro Ser Asp Gly Pro Pro Arg Ser Asn His Ser Ala Gln
                265                 270                 275

GAC GCC GTG GAT AAC TTG CTG CTG CTG TCC AAG GCC AAG TCT GTG TCA         1098
Asp Ala Val Asp Asn Leu Leu Leu Leu Ser Lys Ala Lys Ser Val Ser
            280                 285                 290

TCG GAG CGA GAG GCC TCC CCG AGC AAC AGC TGC CAA GAC TCC ACA GAT         1146
Ser Glu Arg Glu Ala Ser Pro Ser Asn Ser Cys Gln Asp Ser Thr Asp
```

-continued

```
              295                 300                 305
ACA GAG AGC AAC GCG GAG GAA CAG CGC AGC GGC CTT ATC TAC CTA ACC       1194
Thr Glu Ser Asn Ala Glu Glu Gln Arg Ser Gly Leu Ile Tyr Leu Thr
    310                 315                 320

AAC CAC ATC AAC CCG CAT GCA CGC AAT GGG CTG GCT CTC AAG GAG GAG       1242
Asn His Ile Asn Pro His Ala Arg Asn Gly Leu Ala Leu Lys Glu Glu
325                 330                 335                 340

CAG CGC GCC TAC GAG GTG CTG AGG GCG GCC TCA GAG AAC TCG CAG GAT       1290
Gln Arg Ala Tyr Glu Val Leu Arg Ala Ala Ser Glu Asn Ser Gln Asp
                345                 350                 355

GCC TTC CGT GTG GTC AGC ACG AGT GGC GAG CAG CTG AAG GTG TAC AAG       1338
Ala Phe Arg Val Val Ser Thr Ser Gly Glu Gln Leu Lys Val Tyr Lys
            360                 365                 370

TGC GAA CAC TGC CGC GTG CTC TTC CTG GAT CAC GTC ATG TAT ACC ATT       1386
Cys Glu His Cys Arg Val Leu Phe Leu Asp His Val Met Tyr Thr Ile
        375                 380                 385

CAC ATG GGC TGC CAT GGC TGC CAT GGC TTT CGG GAT CCC TTT GAG TGT       1434
His Met Gly Cys His Gly Cys His Gly Phe Arg Asp Pro Phe Glu Cys
    390                 395                 400

AAC ATG TGT GGT TAT CAC AGC CAG GAC AGG TAC GAG TTC TCA TCC CAT       1482
Asn Met Cys Gly Tyr His Ser Gln Asp Arg Tyr Glu Phe Ser Ser His
405                 410                 415                 420

ATC ACG CGG GGG GAG CAT CGT TAC CAC CTG AGC TAAACCCAGC CAGGCCCCAC     1535
Ile Thr Arg Gly Glu His Arg Tyr His Leu Ser
                425                 430

TGAAGCACAA AGATAGCTGG TTATGCCTCC TTCCCGGCAG CTGGACCCAC AGCGGACAAT    1595

GTGGGAGTGG ATTTGCAGGC AGCATTTGTT CTTTTATGTT GGTTGTTTGG CGTTTCATTT    1655

GCGTTGGAAG ATAAGTTTTT AATGTTAGTG ACAGGATTGC ATTGCATCAG CAACATTCAC    1715

AACATCCATC CTTCTAGCCA GTTTTGTTCA CTGGTAGCTG AGGTTTCCCG GATATGTGGC    1775

TTCCTAACAC TCT                                                       1788

(2) INFORMATION FOR SEQ ID NO: 3:

(i) SEQUENCE CHARACTERISTICS:
        (A) LENGTH: 1386 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 1...1383

(xi) SEQUENCE DESCRIPTION: SEQ ID NO: 3:

AAT GTT AAA GTA GAG ACT CAG AGT GAT GAA GAG AAT GGG CGT GCC TGT        48
Asn Val Lys Val Glu Thr Gln Ser Asp Glu Glu Asn Gly Arg Ala Cys
1               5                   10                  15

GAA ATG AAT GGG GAA GAA TGT GCG GAG GAT TTA CGA ATG CTT GAT GCC        96
Glu Met Asn Gly Glu Glu Cys Ala Glu Asp Leu Arg Met Leu Asp Ala
            20                  25                  30

TCG GGA GAG AAA ATG AAT GGC TCC CAC AGG GAC CAA GGC AGC TCG GCT       144
Ser Gly Glu Lys Met Asn Gly Ser His Arg Asp Gln Gly Ser Ser Ala
        35                  40                  45

TTG TCG GGA GTT GGA GGC ATT CGA CTT CCT AAC GGA AAA CTA AAG TGT       192
Leu Ser Gly Val Gly Gly Ile Arg Leu Pro Asn Gly Lys Leu Lys Cys
    50                  55                  60

GAT ATC TGT GGG ATC ATT TGC ATC GGG CCC AAT GTG CTC ATG GTT CAC       240
Asp Ile Cys Gly Ile Ile Cys Ile Gly Pro Asn Val Leu Met Val His
```

-continued

```
       65                  70                  75                  80
AAA AGA AGC CAC ACT GGA GAA CGG CCC TTC CAG TGC AAT CAG TGC GGG         288
Lys Arg Ser His Thr Gly Glu Arg Pro Phe Gln Cys Asn Gln Cys Gly
                     85                  90                  95

GCC TCA TTC ACC CAG AAG GGC AAC CTG CTC CGG CAC ATC AAG CTG CAT         336
Ala Ser Phe Thr Gln Lys Gly Asn Leu Leu Arg His Ile Lys Leu His
                100                 105                 110

TCC GGG GAG AAG CCC TTC AAA TGC CAC CTC TGC AAC TAC GCC TGC CGC         384
Ser Gly Glu Lys Pro Phe Lys Cys His Leu Cys Asn Tyr Ala Cys Arg
            115                 120                 125

CGG AGG GAC GCC CTC ACT GGC CAC CTG AGG ACG CAC TCC GTT GGT AAA         432
Arg Arg Asp Ala Leu Thr Gly His Leu Arg Thr His Ser Val Gly Lys
        130                 135                 140

CCT CAC AAA TGT GGA TAT TGT GGC CGA AGC TAT AAA CAG CGA ACG TCT         480
Pro His Lys Cys Gly Tyr Cys Gly Arg Ser Tyr Lys Gln Arg Thr Ser
145                 150                 155                 160

TTA GAG GAA CAT AAA GAG CGC TGC CAC AAC TAC TTG GAA AGC ATG GGC         528
Leu Glu Glu His Lys Glu Arg Cys His Asn Tyr Leu Glu Ser Met Gly
                165                 170                 175

CTT CCG GGC ACA CTG TAC CCA GTC ATT AAA GAA GAA ACT AAG CAC AGT         576
Leu Pro Gly Thr Leu Tyr Pro Val Ile Lys Glu Glu Thr Lys His Ser
            180                 185                 190

GAA ATG GCA GAA GAC CTG TGC AAG ATA GGA TCA GAG AGA TCT CTC GTG         624
Glu Met Ala Glu Asp Leu Cys Lys Ile Gly Ser Glu Arg Ser Leu Val
        195                 200                 205

CTG GAC AGA CTA GCA AGT AAT GTC GCC AAA CGT AAG AGC TCT ATG CCT         672
Leu Asp Arg Leu Ala Ser Asn Val Ala Lys Arg Lys Ser Ser Met Pro
    210                 215                 220

CAG AAA TTT CTT GGG GAC AAG GGC CTG TCC GAC ACG CCC TAC GAC AGT         720
Gln Lys Phe Leu Gly Asp Lys Gly Leu Ser Asp Thr Pro Tyr Asp Ser
225                 230                 235                 240

GCC ACG TAC GAG AAG GAG AAC GAA ATG ATG AAG TCC CAC GTG ATG GAC         768
Ala Thr Tyr Glu Lys Glu Asn Glu Met Met Lys Ser His Val Met Asp
                245                 250                 255

CAA GCC ATC AAC AAC GCC ATC AAC TAC CTG GGG GCC GAG TCC CTG CGC         816
Gln Ala Ile Asn Asn Ala Ile Asn Tyr Leu Gly Ala Glu Ser Leu Arg
            260                 265                 270

CCG CTG GTG CAG ACG CCC CCG GGC GGT TCC GAG GTG GTC CCG GTC ATC         864
Pro Leu Val Gln Thr Pro Pro Gly Gly Ser Glu Val Val Pro Val Ile
        275                 280                 285

AGC CCG ATG TAC CAG CTG CAC AGG CGC TCG GAG GGC ACC CCG CGC TCC         912
Ser Pro Met Tyr Gln Leu His Arg Arg Ser Glu Gly Thr Pro Arg Ser
    290                 295                 300

AAC CAC TCG GCC CAG GAC AGC GCC GTG GAG TAC CTG CTG CTG CTC TCC         960
Asn His Ser Ala Gln Asp Ser Ala Val Glu Tyr Leu Leu Leu Leu Ser
305                 310                 315                 320

AAG GCC AAG TTG GTG CCC TCG GAG CGC GAG GCG TCC CCG AGC AAC AGC         1008
Lys Ala Lys Leu Val Pro Ser Glu Arg Glu Ala Ser Pro Ser Asn Ser
                325                 330                 335

TGC CAA GAC TCC ACG GAC ACC GAG AGC AAC AAC GAG GAG CAG CGC AGC         1056
Cys Gln Asp Ser Thr Asp Thr Glu Ser Asn Asn Glu Glu Gln Arg Ser
            340                 345                 350

GGT CTT ATC TAC CTG ACC AAC CAC ATC GCC CGA CGC GCG CAA CGC GTG         1104
Gly Leu Ile Tyr Leu Thr Asn His Ile Ala Arg Arg Ala Gln Arg Val
        355                 360                 365

TCG CTC AAG GAG GAG CAC CGC GCC TAC GAC CTG CTG CGC GCC GCC TCC         1152
Ser Leu Lys Glu Glu His Arg Ala Tyr Asp Leu Leu Arg Ala Ala Ser
    370                 375                 380

GAG AAC TCG CAG GAC GCG CTC CGC GTG GTC AGC ACC AGC GGG GAG CAG         1200
Glu Asn Ser Gln Asp Ala Leu Arg Val Val Ser Thr Ser Gly Glu Gln
```

```
Glu Asn Ser Gln Asp Ala Leu Arg Val Val Ser Thr Ser Gly Glu Gln
385                 390                 395                 400

ATG AAG GTG TAC AAG TGC GAA CAC TGC CGG GTG CTC TTC CTG GAT CAC      1248
Met Lys Val Tyr Lys Cys Glu His Cys Arg Val Leu Phe Leu Asp His
                405                 410                 415

GTC ATG TAC ACC ATC CAC ATG GGC TGC CAC GGC TTC CGT GAT CCT TTT      1296
Val Met Tyr Thr Ile His Met Gly Cys His Gly Phe Arg Asp Pro Phe
                420                 425                 430

GAG TGC AAC ATG TGC GGC TAC CAC AGC CAG GAC CGG TAC GAG TTC TCG      1344
Glu Cys Asn Met Cys Gly Tyr His Ser Gln Asp Arg Tyr Glu Phe Ser
                435                 440                 445

TCG CAC ATA ACG CGA GGG GAG CAC CGC TTC CAC ATG AGC TAA              1386
Ser His Ile Thr Arg Gly Glu His Arg Phe His Met Ser
            450                 455                 460

(2) INFORMATION FOR SEQ ID NO: 4:

(i) SEQUENCE CHARACTERISTICS:
        (A) LENGTH: 1296 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1296

(xi) SEQUENCE DESCRIPTION: SEQ ID NO: 4:

ATG GAT GTC GAT GAG GGT CAA GAC ATG TCC CAA GTT TCA GGA AAG GAG        48
Met Asp Val Asp Glu Gly Gln Asp Met Ser Gln Val Ser Gly Lys Glu
1               5                   10                  15

AGC CCC CCA GTC AGT GAC ACT CCA GAT GAA GGG GAT GAG CCC ATG CCT       96
Ser Pro Pro Val Ser Asp Thr Pro Asp Glu Gly Asp Glu Pro Met Pro
                20                  25                  30

GTC CCT GAG GAC CTG TCC ACT ACC TCT GGA GCA CAG CAG AAC TCC AAG      144
Val Pro Glu Asp Leu Ser Thr Thr Ser Gly Ala Gln Gln Asn Ser Lys
            35                  40                  45

AGT GAT CGA GGC ATG GCC AGT AAT GTT AAA GTA GAG ACT CAG AGT GAT      192
Ser Asp Arg Gly Met Ala Ser Asn Val Lys Val Glu Thr Gln Ser Asp
50                  55                  60

GAA GAG AAT GGG CGT GCC TGT GAA ATG AAT GGG GAA GAA TGT GCA GAG      240
Glu Glu Asn Gly Arg Ala Cys Glu Met Asn Gly Glu Glu Cys Ala Glu
65                  70                  75                  80

GAT TTA CGA ATG CTT GAT GCC TCG GGA GAG AAA ATG AAT GGC TCC CAC      288
Asp Leu Arg Met Leu Asp Ala Ser Gly Glu Lys Met Asn Gly Ser His
                85                  90                  95

AGG GAC CAA GGC AGC TCG GCT TTG TCA GGA GTT GGA GGC ATT CGA CTT      336
Arg Asp Gln Gly Ser Ser Ala Leu Ser Gly Val Gly Gly Ile Arg Leu
                100                 105                 110

CCT AAC GGA AAA CTA AAG TGT GAT ATC TGT GGG ATC GTT TGC ATC GGG      384
Pro Asn Gly Lys Leu Lys Cys Asp Ile Cys Gly Ile Val Cys Ile Gly
            115                 120                 125

CCC AAT GTG CTC ATG GTT CAC AAA AGA AGT CAT ACT GGT GAA CGG CCT      432
Pro Asn Val Leu Met Val His Lys Arg Ser His Thr Gly Glu Arg Pro
130                 135                 140

TTC CAG TGC AAC CAG TCT GGG GCC TCC TTT ACC CAG AAA GGC AAC CTC      480
Phe Gln Cys Asn Gln Ser Gly Ala Ser Phe Thr Gln Lys Gly Asn Leu
145                 150                 155                 160

CTG CGG CAC ATC AAG CTG CAC TCG GGT GAG AAG CCC TTC AAA TGC CAT      528
Leu Arg His Ile Lys Leu His Ser Gly Glu Lys Pro Phe Lys Cys His
                165                 170                 175
```

```
CTT TGC AAC TAT GCC TGC CGC CGG AGG GAC GCC CTC ACC GGC CAC CTG      576
Leu Cys Asn Tyr Ala Cys Arg Arg Arg Asp Ala Leu Thr Gly His Leu
            180                 185                 190

AGG ACG CAC TCC GGA GAC AAG TGC CTG TCA GAC ATG CCC TAT GAC AGT      624
Arg Thr His Ser Gly Asp Lys Cys Leu Ser Asp Met Pro Tyr Asp Ser
            195                 200                 205

GCC AAC TAT GAG AAG GAG GAT ATG ATG ACA TCC CAC GTG ATG GAC CAG      672
Ala Asn Tyr Glu Lys Glu Asp Met Met Thr Ser His Val Met Asp Gln
            210                 215                 220

GCC ATC AAC AAT GCC ATC AAC TAC CTG GGG GCT GAG TCC CTG CGC CCA      720
Ala Ile Asn Asn Ala Ile Asn Tyr Leu Gly Ala Glu Ser Leu Arg Pro
225                 230                 235                 240

TTG GTG CAG ACA CCC CCC GGT AGC TCC GAG GTG GTG CCA GTC ATC AGC      768
Leu Val Gln Thr Pro Pro Gly Ser Ser Glu Val Val Pro Val Ile Ser
                245                 250                 255

TCC ATG TAC CAG CTG CAC AAG CCC CCC TCA GAT GGC CCC CCA CGG TCC      816
Ser Met Tyr Gln Leu His Lys Pro Pro Ser Asp Gly Pro Pro Arg Ser
                260                 265                 270

AAC CAT TCA GCA CAG GAC GCC GTG GAT AAC TTG CTG CTG CTG TCC AAG      864
Asn His Ser Ala Gln Asp Ala Val Asp Asn Leu Leu Leu Leu Ser Lys
                275                 280                 285

GCC AAG TCT GTG TCA TCG GAG CGA GAG GCC TCC CCG AGC AAC AGC TGC      912
Ala Lys Ser Val Ser Ser Glu Arg Glu Ala Ser Pro Ser Asn Ser Cys
            290                 295                 300

CAA GAC TCC ACA GAT ACA GAG AGC AAC GCG GAG GAA CAG CGC AGC GGC      960
Gln Asp Ser Thr Asp Thr Glu Ser Asn Ala Glu Glu Gln Arg Ser Gly
305                 310                 315                 320

CTT ATC TAC CTA ACC AAC CAC ATC AAC CCG CAT GCA CGC AAT GGG CTG     1008
Leu Ile Tyr Leu Thr Asn His Ile Asn Pro His Ala Arg Asn Gly Leu
                325                 330                 335

GCT CTC AAG GAG GAG CAG CGC GCC TAC GAG GTG CTG AGG GCG GCC TCA     1056
Ala Leu Lys Glu Glu Gln Arg Ala Tyr Glu Val Leu Arg Ala Ala Ser
                340                 345                 350

GAG AAC TCG CAG GAT GCC TTC CGT GTG GTC AGC ACG AGT GGC GAG CAG     1104
Glu Asn Ser Gln Asp Ala Phe Arg Val Val Ser Thr Ser Gly Glu Gln
            355                 360                 365

CTG AAG GTG TAC AAG TGC GAA CAC TGC CGC GTG CTC TTC CTG GAT CAC     1152
Leu Lys Val Tyr Lys Cys Glu His Cys Arg Val Leu Phe Leu Asp His
370                 375                 380

GTC ATG TAT ACC ATT CAC ATG GGC TGC CAT GGC TGC CAT GGC TTT CGG     1200
Val Met Tyr Thr Ile His Met Gly Cys His Gly Cys His Gly Phe Arg
385                 390                 395                 400

GAT CCC TTT GAG TGT AAC ATG TGT GGT TAT CAC AGC CAG GAC AGG TAC     1248
Asp Pro Phe Glu Cys Asn Met Cys Gly Tyr His Ser Gln Asp Arg Tyr
                405                 410                 415

GAG TTC TCA TCC CAT ATC ACG CGG GGG GAG CAT CGT TAC CAC CTG AGC     1296
Glu Phe Ser Ser His Ile Thr Arg Gly Glu His Arg Tyr His Leu Ser
                420                 425                 430
```

(2) INFORMATION FOR SEQ ID NO: 5:

(i) SEQUENCE CHARACTERISTICS:
        (A) LENGTH: 2049 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 223...1776

(xi) SEQUENCE DESCRIPTION: SEQ ID NO: 5:

```
AATTCGTTCT ACCTTCTCTG AACCCCAGTG GTGTGTCAAG GCCGGACTGG GAGCTTGGGG      60

GAAGAGGAAG AGGAAGAGGA ATCTGCGGCT CATCCAGGGA TCAGGGTCCT TCCCAAGTGG     120

CCACTCAGAG GGGACTCAGA GCAAGTCTAG ATTTGTGTGG CAGAGAGAGA CAGCTCTCGT     180

TTGGCCTTGG GGAGGCACAA GTCTGTTGAT AACCTGAAGA CA ATG GAT GTC GAT       234
                                                  Met Asp Val Asp
                                                   1
```

| | | | | | | | | | | | | | | |
|---|---|---|---|---|---|---|---|---|---|---|---|---|---|---|
| GAG | GGT | CAA | GAC | ATG | TCC | CAA | GTT | TCA | GGA | AAG | GAG | AGC | CCC | CCA | GTC | 282 |
| Glu | Gly | Gln | Asp | Met | Ser | Gln | Val | Ser | Gly | Lys | Glu | Ser | Pro | Pro | Val |
| 5 | | | | 10 | | | | | 15 | | | | | 20 |

```
AGT GAC ACT CCA GAT GAA GGG GAT GAG CCC ATG CCT GTC CCT GAG GAC     330
Ser Asp Thr Pro Asp Glu Gly Asp Glu Pro Met Pro Val Pro Glu Asp
             25                  30                  35

CTG TCC ACT ACC TCT GGA GCA CAG CAG AAC TCC AAG AGT GAT CGA GGC     378
Leu Ser Thr Thr Ser Gly Ala Gln Gln Asn Ser Lys Ser Asp Arg Gly
             40                  45                  50

ATG GCC AGT AAT GTT AAA GTA GAG ACT CAG AGT GAT GAA GAG AAT GGG     426
Met Ala Ser Asn Val Lys Val Glu Thr Gln Ser Asp Glu Glu Asn Gly
             55                  60                  65

CGT GCC TGT GAA ATG AAT GGG GAA GAA TGT GCA GAG GAT TTA CGA ATG     474
Arg Ala Cys Glu Met Asn Gly Glu Glu Cys Ala Glu Asp Leu Arg Met
 70                  75                  80

CTT GAT GCC TCG GGA GAG AAA ATG AAT GGC TCC CAC AGG GAC CAA GGC     522
Leu Asp Ala Ser Gly Glu Lys Met Asn Gly Ser His Arg Asp Gln Gly
 85                  90                  95                 100

AGC TCG GCT TTG TCA GGA GTT GGA GGC ATT CGA CTT CCT AAC GGA AAA     570
Ser Ser Ala Leu Ser Gly Val Gly Gly Ile Arg Leu Pro Asn Gly Lys
             105                 110                 115

CTA AAG TGT GAT ATC TGT GGG ATC GTT TGC ATC GGG CCC AAT GTG CTC     618
Leu Lys Cys Asp Ile Cys Gly Ile Val Cys Ile Gly Pro Asn Val Leu
             120                 125                 130

ATG GTT CAC AAA AGA AGT CAT ACT GGT GAA CGG CCT TTC CAG TGC AAC     666
Met Val His Lys Arg Ser His Thr Gly Glu Arg Pro Phe Gln Cys Asn
             135                 140                 145

CAG TCT GGG GCC TCC TTT ACC CAG AAA GGC AAC CTC CTG CGG CAC ATC     714
Gln Ser Gly Ala Ser Phe Thr Gln Lys Gly Asn Leu Leu Arg His Ile
 150                 155                 160

AAG CTG CAC TCG GGT GAG AAG CCC TTC AAA TGC CAT CTT TGC AAC TAT     762
Lys Leu His Ser Gly Glu Lys Pro Phe Lys Cys His Leu Cys Asn Tyr
165                 170                 175                 180

GCC TGC CGC CGG AGG GAC GCC CTC ACC GGC CAC CTG AGG ACG CAC TCC     810
Ala Cys Arg Arg Arg Asp Ala Leu Thr Gly His Leu Arg Thr His Ser
             185                 190                 195

GTT GGT AAG CCT CAC AAA TGT GGA TAT TGT GGC CGG AGC TAT AAA CAG     858
Val Gly Lys Pro His Lys Cys Gly Tyr Cys Gly Arg Ser Tyr Lys Gln
             200                 205                 210

CGA AGC TCT TTA GAG GAG CAT AAA GAG CGA TGC CAC AAC TAC TTG GAA     906
Arg Ser Ser Leu Glu Glu His Lys Glu Arg Cys His Asn Tyr Leu Glu
             215                 220                 225

AGC ATG GGC CTT CCG GGC GTG TGC CCA GTC ATT AAG GAA GAA ACT AAC     954
Ser Met Gly Leu Pro Gly Val Cys Pro Val Ile Lys Glu Glu Thr Asn
 230                 235                 240

CAC AAC GAG ATG GCA GAA GAC CTG TGC AAG ATA GGA GCA GAG AGG TCC    1002
His Asn Glu Met Ala Glu Asp Leu Cys Lys Ile Gly Ala Glu Arg Ser
245                 250                 255                 260

CTT GTC CTG GAC AGG CTG GCA AGC AAT GTC GCC AAA CGT AAG AGC TCT    1050
Leu Val Leu Asp Arg Leu Ala Ser Asn Val Ala Lys Arg Lys Ser Ser
```

-continued

```
                     265                 270                 275
ATG CCT CAG AAA TTT CTT GGA GAC AAG TGC CTG TCA GAC ATG CCC TAT     1098
Met Pro Gln Lys Phe Leu Gly Asp Lys Cys Leu Ser Asp Met Pro Tyr
            280                 285                 290

GAC AGT GCC AAC TAT GAG AAG GAG GAT ATG ATG ACA TCC CAC GTG ATG     1146
Asp Ser Ala Asn Tyr Glu Lys Glu Asp Met Met Thr Ser His Val Met
        295                 300                 305

GAC CAG GCC ATC AAC AAT GCC ATC AAC TAC CTG GGG GCT GAG TCC CTG     1194
Asp Gln Ala Ile Asn Asn Ala Ile Asn Tyr Leu Gly Ala Glu Ser Leu
    310                 315                 320

CGC CCA TTG GTG CAG ACA CCC CCC GGT AGC TCC GAG GTG GTG CCA GTC     1242
Arg Pro Leu Val Gln Thr Pro Pro Gly Ser Ser Glu Val Val Pro Val
325                 330                 335                 340

ATC AGC TCC ATG TAC CAG CTG CAC AAG CCC CCC TCA GAT GGC CCC CCA     1290
Ile Ser Ser Met Tyr Gln Leu His Lys Pro Pro Ser Asp Gly Pro Pro
                345                 350                 355

CGG TCC AAC CAT TCA GCA CAG GAC GCC GTG GAT AAC TTG CTG CTG CTG     1338
Arg Ser Asn His Ser Ala Gln Asp Ala Val Asp Asn Leu Leu Leu Leu
            360                 365                 370

TCC AAG GCC AAG TCT GTG TCA TCG GAG CGA GAG GCC TCC CCG AGC AAC     1386
Ser Lys Ala Lys Ser Val Ser Ser Glu Arg Glu Ala Ser Pro Ser Asn
        375                 380                 385

AGC TGC CAA GAC TCC ACA GAT ACA GAG AGC AAC GCG GAG GAA CAG CGC     1434
Ser Cys Gln Asp Ser Thr Asp Thr Glu Ser Asn Ala Glu Glu Gln Arg
    390                 395                 400

AGC GGC CTT ATC TAC CTA ACC AAC CAC ATC AAC CCG CAT GCA CGC AAT     1482
Ser Gly Leu Ile Tyr Leu Thr Asn His Ile Asn Pro His Ala Arg Asn
405                 410                 415                 420

GGG CTG GCT CTC AAG GAG GAG CAG CGC GCC TAC GAG GTG CTG AGG GCG     1530
Gly Leu Ala Leu Lys Glu Glu Gln Arg Ala Tyr Glu Val Leu Arg Ala
                425                 430                 435

GCC TCA GAG AAC TCG CAG GAT GCC TTC CGT GTG GTC AGC ACG AGT GGC     1578
Ala Ser Glu Asn Ser Gln Asp Ala Phe Arg Val Val Ser Thr Ser Gly
            440                 445                 450

GAG CAG CTG AAG GTG TAC AAG TGC GAA CAC TGC CGC GTG CTC TTC CTG     1626
Glu Gln Leu Lys Val Tyr Lys Cys Glu His Cys Arg Val Leu Phe Leu
        455                 460                 465

GAT CAC GTC ATG TAT ACC ATT CAC ATG GGC TGC CAT GGC TGC CAT GGC     1674
Asp His Val Met Tyr Thr Ile His Met Gly Cys His Gly Cys His Gly
    470                 475                 480

TTT CGG GAT CCC TTT GAG TGT AAC ATG TGT GGT TAT CAC AGC CAG GAC     1722
Phe Arg Asp Pro Phe Glu Cys Asn Met Cys Gly Tyr His Ser Gln Asp
485                 490                 495                 500

AGG TAC GAG TTC TCA TCC CAT ATC ACG CGG GGG GAG CAT CGT TAC CAC     1770
Arg Tyr Glu Phe Ser Ser His Ile Thr Arg Gly Glu His Arg Tyr His
                505                 510                 515

CTG AGC TAAACCCAGC CAGGCCCCAC TGAAGCACAA AGATAGCTGG TTATGCCTCC      1826
Leu Ser

TTCCCGGCAG CTGGACCCAC AGCGGACAAT GTGGGAGTGG ATTTGCAGGC AGCATTTGTT   1886

CTTTTATGTT GGTTGTTTGG CGTTTCATTT GCGTTGGAAG ATAAGTTTTT AATGTTAGTG   1946

ACAGGATTGC ATTGCATCAG CAACATTCAC AACATCCATC CTTCTAGCCA GTTTTGTTCA   2006

CTGGTAGCTG AGGTTTCCCG GATATGTGGC TTCCTAACAC TCT                    2049

(2) INFORMATION FOR SEQ ID NO: 6:

(i) SEQUENCE CHARACTERISTICS:
        (A) LENGTH: 1170 base pairs
        (B) TYPE: nucleic acid
```

-continued

```
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1170

(xi) SEQUENCE DESCRIPTION: SEQ ID NO: 6:

ATG GAT GTC GAT GAG GGT CAA GAC ATG TCC CAA GTT TCA GGA AAG GAG        48
Met Asp Val Asp Glu Gly Gln Asp Met Ser Gln Val Ser Gly Lys Glu
 1               5                  10                  15

AGC CCC CCA GTC AGT GAC ACT CCA GAT GAA GGG GAT GAG CCC ATG CCT        96
Ser Pro Pro Val Ser Asp Thr Pro Asp Glu Gly Asp Glu Pro Met Pro
                20                  25                  30

GTC CCT GAG GAC CTG TCC ACT ACC TCT GGA GCA CAG CAG AAC TCC AAG       144
Val Pro Glu Asp Leu Ser Thr Thr Ser Gly Ala Gln Gln Asn Ser Lys
            35                  40                  45

AGT GAT CGA GGC ATG GGT GAA CGG CCT TTC CAG TGC AAC CAG TCT GGG       192
Ser Asp Arg Gly Met Gly Glu Arg Pro Phe Gln Cys Asn Gln Ser Gly
        50                  55                  60

GCC TCC TTT ACC CAG AAA GGC AAC CTC CTG CGG CAC ATC AAG CTG CAC       240
Ala Ser Phe Thr Gln Lys Gly Asn Leu Leu Arg His Ile Lys Leu His
 65                  70                  75                  80

TCG GGT GAG AAG CCC TTC AAA TGC CAT CTT TGC AAC TAT GCC TGC CGC       288
Ser Gly Glu Lys Pro Phe Lys Cys His Leu Cys Asn Tyr Ala Cys Arg
                85                  90                  95

CGG AGG GAC GCC CTC ACC GGC CAC CTG AGG ACG CAC TCC GTC ATT AAG       336
Arg Arg Asp Ala Leu Thr Gly His Leu Arg Thr His Ser Val Ile Lys
                100                 105                 110

GAA GAA ACT AAC CAC AAC GAG ATG GCA GAA GAC CTG TGC AAG ATA GGA       384
Glu Glu Thr Asn His Asn Glu Met Ala Glu Asp Leu Cys Lys Ile Gly
            115                 120                 125

GCA GAG AGG TCC CTT GTC CTG GAC AGG CTG GCA AGC AAT GTC GCC AAA       432
Ala Glu Arg Ser Leu Val Leu Asp Arg Leu Ala Ser Asn Val Ala Lys
        130                 135                 140

CGT AAG AGC TCT ATG CCT CAG AAA TTT CTT GGA GAC AAG TGC CTG TCA       480
Arg Lys Ser Ser Met Pro Gln Lys Phe Leu Gly Asp Lys Cys Leu Ser
145                 150                 155                 160

GAC ATG CCC TAT GAC AGT GCC AAC TAT GAG AAG GAG GAT ATG ATG ACA       528
Asp Met Pro Tyr Asp Ser Ala Asn Tyr Glu Lys Glu Asp Met Met Thr
                165                 170                 175

TCC CAC GTG ATG GAC CAG GCC ATC AAC AAT GCC ATC AAC TAC CTG GGG       576
Ser His Val Met Asp Gln Ala Ile Asn Asn Ala Ile Asn Tyr Leu Gly
                180                 185                 190

GCT GAG TCC CTG CGC CCA TTG GTG CAG ACA CCC CCC GGT AGC TCC GAG       624
Ala Glu Ser Leu Arg Pro Leu Val Gln Thr Pro Pro Gly Ser Ser Glu
            195                 200                 205

GTG GTG CCA GTC ATC AGC TCC ATG TAC CAG CTG CAC AAG CCC CCC TCA       672
Val Val Pro Val Ile Ser Ser Met Tyr Gln Leu His Lys Pro Pro Ser
        210                 215                 220

GAT GGC CCC CCA CGG TCC AAC CAT TCA GCA CAG GAC GCC GTG GAT AAC       720
Asp Gly Pro Pro Arg Ser Asn His Ser Ala Gln Asp Ala Val Asp Asn
225                 230                 235                 240

TTG CTG CTG CTG TCC AAG GCC AAG TCT GTG TCA TCG GAG CGA GAG GCC       768
Leu Leu Leu Leu Ser Lys Ala Lys Ser Val Ser Ser Glu Arg Glu Ala
                245                 250                 255

TCC CCG AGC AAC AGC TGC CAA GAC TCC ACA GAT ACA GAG AGC AAC GCG       816
Ser Pro Ser Asn Ser Cys Gln Asp Ser Thr Asp Thr Glu Ser Asn Ala
                260                 265                 270
```

```
GAG GAA CAG CGC AGC GGC CTT ATC TAC CTA ACC AAC CAC ATC AAC CCG       864
Glu Glu Gln Arg Ser Gly Leu Ile Tyr Leu Thr Asn His Ile Asn Pro
            275                 280                 285

CAT GCA CGC AAT GGG CTG GCT CTC AAG GAG GAG CAG CGC GCC TAC GAG       912
His Ala Arg Asn Gly Leu Ala Leu Lys Glu Glu Gln Arg Ala Tyr Glu
        290                 295                 300

GTG CTG AGG GCG GCC TCA GAG AAC TCG CAG GAT GCC TTC CGT GTG GTC       960
Val Leu Arg Ala Ala Ser Glu Asn Ser Gln Asp Ala Phe Arg Val Val
305                 310                 315                 320

AGC ACG AGT GGC GAG CAG CTG AAG GTG TAC AAG TGC GAA CAC TGC CGC      1008
Ser Thr Ser Gly Glu Gln Leu Lys Val Tyr Lys Cys Glu His Cys Arg
                325                 330                 335

GTG CTC TTC CTG GAT CAC GTC ATG TAT ACC ATT CAC ATG GGC TGC CAT      1056
Val Leu Phe Leu Asp His Val Met Tyr Thr Ile His Met Gly Cys His
            340                 345                 350

GGC TGC CAT GGC TTT CGG GAT CCC TTT GAG TGT AAC ATG TGT GGT TAT      1104
Gly Cys His Gly Phe Arg Asp Pro Phe Glu Cys Asn Met Cys Gly Tyr
        355                 360                 365

CAC AGC CAG GAC AGG TAC GAG TTC TCA TCC CAT ATC ACG CGG GGG GAG      1152
His Ser Gln Asp Arg Tyr Glu Phe Ser Ser His Ile Thr Arg Gly Glu
370                 375                 380

CAT CGT TAC CAC CTG AGC                                              1170
His Arg Tyr His Leu Ser
385                 390

(2) INFORMATION FOR SEQ ID NO: 7:

(i) SEQUENCE CHARACTERISTICS:
         (A) LENGTH: 1128 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: Coding Sequence
         (B) LOCATION: 1...1128

(xi) SEQUENCE DESCRIPTION: SEQ ID NO: 7:

ATG GAT GTC GAT GAG GGT CAA GAC ATG TCC CAA GTT TCA GGA AAG GAG        48
Met Asp Val Asp Glu Gly Gln Asp Met Ser Gln Val Ser Gly Lys Glu
1               5                   10                  15

AGC CCC CCA GTC AGT GAC ACT CCA GAT GAA GGG GAT GAG CCC ATG CCT        96
Ser Pro Pro Val Ser Asp Thr Pro Asp Glu Gly Asp Glu Pro Met Pro
            20                  25                  30

GTC CCT GAG GAC CTG TCC ACT ACC TCT GGA GCA CAG CAG AAC TCC AAG       144
Val Pro Glu Asp Leu Ser Thr Thr Ser Gly Ala Gln Gln Asn Ser Lys
        35                  40                  45

AGT GAT CGA GGC ATG GCC AGT AAT GTT AAA GTA GAG ACT CAG AGT GAT       192
Ser Asp Arg Gly Met Ala Ser Asn Val Lys Val Glu Thr Gln Ser Asp
    50                  55                  60

GAA GAG AAT GGG CGT GCC TGT GAA ATG AAT GGG GAA GAA TGT GCA GAG       240
Glu Glu Asn Gly Arg Ala Cys Glu Met Asn Gly Glu Glu Cys Ala Glu
65                  70                  75                  80

GAT TTA CGA ATG CTT GAT GCC TCG GGA GAG AAA ATG AAT GGC TCC CAC       288
Asp Leu Arg Met Leu Asp Ala Ser Gly Glu Lys Met Asn Gly Ser His
                85                  90                  95

AGG GAC CAA GGC AGC TCG GCT TTG TCA GGA GTT GGA GGC ATT CGA CTT       336
Arg Asp Gln Gly Ser Ser Ala Leu Ser Gly Val Gly Gly Ile Arg Leu
            100                 105                 110

CCT AAC GGA AAA CTA AAG TGT GAT ATC TGT GGG ATC GTT TGC ATC GGG       384
Pro Asn Gly Lys Leu Lys Cys Asp Ile Cys Gly Ile Val Cys Ile Gly
```

```
CCC AAT GTG CTC ATG GTT CAC AAA AGA AGT CAT ACT GGA GAC AAG TGC      432
Pro Asn Val Leu Met Val His Lys Arg Ser His Thr Gly Asp Lys Cys
    130                 135                 140

CTG TCA GAC ATG CCC TAT GAC AGT GCC AAC TAT GAG AAG GAG GAT ATG      480
Leu Ser Asp Met Pro Tyr Asp Ser Ala Asn Tyr Glu Lys Glu Asp Met
145                 150                 155                 160

ATG ACA TCC CAC GTG ATG GAC CAG GCC ATC AAC AAT GCC ATC AAC TAC      528
Met Thr Ser His Val Met Asp Gln Ala Ile Asn Asn Ala Ile Asn Tyr
                165                 170                 175

CTG GGG GCT GAG TCC CTG CGC CCA TTG GTG CAG ACA CCC CCC GGT AGC      576
Leu Gly Ala Glu Ser Leu Arg Pro Leu Val Gln Thr Pro Pro Gly Ser
            180                 185                 190

TCC GAG GTG GTG CCA GTC ATC AGC TCC ATG TAC CAG CTG CAC AAG CCC      624
Ser Glu Val Val Pro Val Ile Ser Ser Met Tyr Gln Leu His Lys Pro
        195                 200                 205

CCC TCA GAT GGC CCC CCA CGG TCC AAC CAT TCA GCA CAG GAC GCC GTG      672
Pro Ser Asp Gly Pro Pro Arg Ser Asn His Ser Ala Gln Asp Ala Val
    210                 215                 220

GAT AAC TTG CTG CTG CTG TCC AAG GCC AAG TCT GTG TCA TCG GAG CGA      720
Asp Asn Leu Leu Leu Leu Ser Lys Ala Lys Ser Val Ser Ser Glu Arg
225                 230                 235                 240

GAG GCC TCC CCG AGC AAC AGC TGC CAA GAC TCC ACA GAT ACA GAG AGC      768
Glu Ala Ser Pro Ser Asn Ser Cys Gln Asp Ser Thr Asp Thr Glu Ser
                245                 250                 255

AAC GCG GAG GAA CAG CGC AGC GGC CTT ATC TAC CTA ACC AAC CAC ATC      816
Asn Ala Glu Glu Gln Arg Ser Gly Leu Ile Tyr Leu Thr Asn His Ile
            260                 265                 270

AAC CCG CAT GCA CGC AAT GGG CTG GCT CTC AAG GAG GAG CAG CGC GCC      864
Asn Pro His Ala Arg Asn Gly Leu Ala Leu Lys Glu Glu Gln Arg Ala
        275                 280                 285

TAC GAG GTG CTG AGG GCG GCC TCA GAG AAC TCG CAG GAT GCC TTC CGT      912
Tyr Glu Val Leu Arg Ala Ala Ser Glu Asn Ser Gln Asp Ala Phe Arg
    290                 295                 300

GTG GTC AGC ACG AGT GGC GAG CAG CTG AAG GTG TAC AAG TGC GAA CAC      960
Val Val Ser Thr Ser Gly Glu Gln Leu Lys Val Tyr Lys Cys Glu His
305                 310                 315                 320

TGC CGC GTG CTC TTC CTG GAT CAC GTC ATG TAT ACC ATT CAC ATG GGC     1008
Cys Arg Val Leu Phe Leu Asp His Val Met Tyr Thr Ile His Met Gly
                325                 330                 335

TGC CAT GGC TGC CAT GGC TTT CGG GAT CCC TTT GAG TGT AAC ATG TGT     1056
Cys His Gly Cys His Gly Phe Arg Asp Pro Phe Glu Cys Asn Met Cys
            340                 345                 350

GGT TAT CAC AGC CAG GAC AGG TAC GAG TTC TCA TCC CAT ATC ACG CGG     1104
Gly Tyr His Ser Gln Asp Arg Tyr Glu Phe Ser Ser His Ile Thr Arg
        355                 360                 365

GGG GAG CAT CGT TAC CAC CTG AGC                                    1128
Gly Glu His Arg Tyr His Leu Ser
    370                 375

(2) INFORMATION FOR SEQ ID NO: 8:

(i) SEQUENCE CHARACTERISTICS:
        (A) LENGTH: 1004 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
```

(B) LOCATION: 1...1002

(xi) SEQUENCE DESCRIPTION: SEQ ID NO: 8:

```
GGA AAC CGG CCC TTC CAG TGC AAT CAG TGC GGG GCC TCA TTC ACC CAG        48
Gly Glu Arg Pro Phe Gln Cys Asn Gln Cys Gly Ala Ser Phe Thr Gln
 1               5                  10                  15

AAG GGC AAC CTG CTC CGG CAC ATC AAG CTG CAT TCC GGG GAG AAG CCC        96
Lys Gly Asn Leu Leu Arg His Ile Lys Leu His Ser Gly Glu Lys Pro
             20                  25                  30

TTC AAA TGC CAC CTC TGC AAC TAC GCC TGC CGC CGG AGG GAC GCC CTC       144
Phe Lys Cys His Leu Cys Asn Tyr Ala Cys Arg Arg Arg Asp Ala Leu
         35                  40                  45

ACT GGC CAC CTG AGG ACG CAC TCC GTC ATT AAA GAA GAA ACT AAG CAC       192
Thr Gly His Leu Arg Thr His Ser Val Ile Lys Glu Glu Thr Lys His
     50                  55                  60

AGT GAA ATG GCA GAA GAC CTG TGC AAG ATA GGA TCA GAG AGA TCT CTC       240
Ser Glu Met Ala Glu Asp Leu Cys Lys Ile Gly Ser Glu Arg Ser Leu
 65                  70                  75                  80

GTG CTG GAC AGA CTA GCA AGT AAT GTC GCC AAA CGT AAG AGC TCT ATG       288
Val Leu Asp Arg Leu Ala Ser Asn Val Ala Lys Arg Lys Ser Ser Met
                 85                  90                  95

CCT CAG AAA TTT CTT GGG GAC AAG GGC CTG TCC GAC ACG CCC TAC GAC       336
Pro Gln Lys Phe Leu Gly Asp Lys Gly Leu Ser Asp Thr Pro Tyr Asp
            100                 105                 110

AGT GCC ACG TAC GAG AAG GAG AAC GAA ATG ATG AAG TCC CAC GTG ATG       384
Ser Ala Thr Tyr Glu Lys Glu Asn Glu Met Met Lys Ser His Val Met
        115                 120                 125

GAC CAA GCC ATC AAC AAC GCC ATC AAC TAC CTG GGG GCC GAG TCC CTG       432
Asp Gln Ala Ile Asn Asn Ala Ile Asn Tyr Leu Gly Ala Glu Ser Leu
    130                 135                 140

CGC CCG CTG GTG CAG ACG CCC CCG GGC GGT TCC GAG GTG GTC CCG GTC       480
Arg Pro Leu Val Gln Thr Pro Pro Gly Gly Ser Glu Val Val Pro Val
145                 150                 155                 160

ATC AGC CCG ATG TAC CAG CTG CAC AGG CGC TCG GAG GGC ACC CCG CGC       528
Ile Ser Pro Met Tyr Gln Leu His Arg Arg Ser Glu Gly Thr Pro Arg
                165                 170                 175

TCC AAC CAC TCG GCC CAG GAC AGC GCC GTG GAG TAC CTG CTG CTG CTC       576
Ser Asn His Ser Ala Gln Asp Ser Ala Val Glu Tyr Leu Leu Leu Leu
            180                 185                 190

TCC AAG GCC AAG TTG GTG CCC TCG GAG CGC GAG GCG TCC CCG AGC AAC       624
Ser Lys Ala Lys Leu Val Pro Ser Glu Arg Glu Ala Ser Pro Ser Asn
        195                 200                 205

AGC TGC CAA GAC TCC ACG GAC ACC GAG AGC AAC AAC GAG GAG CAG CGC       672
Ser Cys Gln Asp Ser Thr Asp Thr Glu Ser Asn Asn Glu Glu Gln Arg
    210                 215                 220

AGC GGT CTT ATC TAC CTG ACC AAC CAC ATC GCC CGA CGC GCG CAA CGC       720
Ser Gly Leu Ile Tyr Leu Thr Asn His Ile Ala Arg Arg Ala Gln Arg
225                 230                 235                 240

GTG TCG CTC AAG GAG GAG CAC CGC GCC TAC GAC CTG CTG CGC GCC GCC       768
Val Ser Leu Lys Glu Glu His Arg Ala Tyr Asp Leu Leu Arg Ala Ala
                245                 250                 255

TCC GAG AAC TCG CAG GAC GCG CTC CGC GTG GTC AGC ACC AGC GGG GAG       816
Ser Glu Asn Ser Gln Asp Ala Leu Arg Val Val Ser Thr Ser Gly Glu
            260                 265                 270

CAG ATG AAG GTG TAC AAG TGC GAA CAC TGC CGG GTG CTC TTC CTG GAT       864
Gln Met Lys Val Tyr Lys Cys Glu His Cys Arg Val Leu Phe Leu Asp
        275                 280                 285

CAC GTC ATG TAC ACC ATC CAC ATG GGC TGC CAC GGC TTC CGT GAT CCT       912
His Val Met Tyr Thr Ile His Met Gly Cys His Gly Phe Arg Asp Pro
    290                 295                 300
```

```
TTT GAG TGC AAC ATG TGC GGC TAC CAC AGC CAG GAC CGG TAC GAG TTC      960
Phe Glu Cys Asn Met Cys Gly Tyr His Ser Gln Asp Arg Tyr Glu Phe
305                 310                 315                 320

TCG TCG CAC ATA ACG CGA GGG GAG CAC CGC TTC CAC ATG AGC            1002
Ser Ser His Ile Thr Arg Gly Glu His Arg Phe His Met Ser
                325                 330

TA                                                                  1004
```

(2) INFORMATION FOR SEQ ID NO: 9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

```
AGGCGATTTT GGGAATTTCA CACC                                            24
```

(2) INFORMATION FOR SEQ ID NO: 10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

```
AGGCCATGGG AATGAAGGAA CACC                                            24
```

(2) INFORMATION FOR SEQ ID NO: 11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

```
GGTGTAAATT GGGAATGCTG TGCCT                                           25
```

(2) INFORMATION FOR SEQ ID NO: 12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

```
AGGCATGGGA ATGTCTGGAA CACC                                            24
```

(2) INFORMATION FOR SEQ ID NO: 13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

AGGCATTAAA ATGGAATAA CACC                                            24

(2) INFORMATION FOR SEQ ID NO: 14:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 14:

GGTGTAGGAA TGCGGTAATT GCCT                                           24

(2) INFORMATION FOR SEQ ID NO: 15:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 15:

GGTGTGGGAA TAACTGGGAT GCCT                                           24

(2) INFORMATION FOR SEQ ID NO: 16:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 16:

GGTGTGGGAA TGTCACTTCA GCCT                                           24

(2) INFORMATION FOR SEQ ID NO: 17:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 17:

GGTGTGGGAA TACTGAGTAT GCCTGCCT                                       28

(2) INFORMATION FOR SEQ ID NO: 18:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 18:

AGGCAAATTT GGGAATACTA CACC                24

(2) INFORMATION FOR SEQ ID NO: 19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

GGTGTGTGGG AACATGGGAT GCCT                24

(2) INFORMATION FOR SEQ ID NO: 20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 20:

AGGCCTATTT CCCTTGGGAA CACC                24

(2) INFORMATION FOR SEQ ID NO: 21:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 21:

GGTGTGGAAC ATCGTGGGAA GCCGCCT             27

(2) INFORMATION FOR SEQ ID NO: 22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 22:

AGGCGCTTGG GAAATTCCAA CACC                24

(2) INFORMATION FOR SEQ ID NO: 23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 23:

AGGCATTCCT AAACCGGGAA CACC                24

(2) INFORMATION FOR SEQ ID NO: 24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 24:

AGGCACAATT CCTTCGGGAA CACC                      24

(2) INFORMATION FOR SEQ ID NO: 25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 25:

GGTGTCGGGC TTCGGGAATA GCCT                      24

(2) INFORMATION FOR SEQ ID NO: 26:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 26:

GGTGTTCCAA ACTCGGGAAT GCCT                      24

(2) INFORMATION FOR SEQ ID NO: 27:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 27:

GGTGTGGAAT CGGGAATTTA GCCT                      24

(2) INFORMATION FOR SEQ ID NO: 28:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 28:

AGGCTTATCG GGAAAACTTA CACC                      24

(2) INFORMATION FOR SEQ ID NO: 29:

(i) SEQUENCE CHARACTERISTICS:
        (A) LENGTH: 24 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 29:

GGTGTTCCAA ACGGGGGAAT GCCT                                              24

(2) INFORMATION FOR SEQ ID NO: 30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 30:

GGTGTGCAAT TCCAAGGAAT GCCT                                              24

(2) INFORMATION FOR SEQ ID NO: 31:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 31:

AGGCGCCATT CCAAGGATAA CACC                                              24

(2) INFORMATION FOR SEQ ID NO: 32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 32:

AGGCTAATCT TGGAATTCCA CACC                                              24

(2) INFORMATION FOR SEQ ID NO: 33:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 33:

TGGGACAAGA TTTCCA                                                       16

(2) INFORMATION FOR SEQ ID NO: 34:

(i) SEQUENCE CHARACTERISTICS:
        (A) LENGTH: 21 base pairs
        (B) TYPE: nucleic acid
        (C) STRANDEDNESS: single
        (D) TOPOLOGY: linear

```
    (ii) MOLECULE TYPE: cDNA (xi) SEQUENCE DESCRIPTION: SEQ ID NO: 34:

TGGGGAAGTG AAGGAGGGAG G                                              21

(2) INFORMATION FOR SEQ ID NO: 35:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 35:

GAGGGGGATC                                                           10

(2) INFORMATION FOR SEQ ID NO: 36:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 36:

GGTGTACGGT TGGGAATGCG GCCT                                           24

(2) INFORMATION FOR SEQ ID NO: 37:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 37:

GGTGTAGGAA TGGGAATACA GCCT                                           24

(2) INFORMATION FOR SEQ ID NO: 38:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 38:

GGTGTTGGGA TTGGGAATGT GCCT                                           24

(2) INFORMATION FOR SEQ ID NO: 39:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 39:
```

```
GGTGTCGGGA ATTATTTTAG GCCT                                              24

(2) INFORMATION FOR SEQ ID NO: 40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 40:

GGTGTAAAAA TGGGAACAAA GCCT                                              24

(2) INFORMATION FOR SEQ ID NO: 41:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 41:

GGTGTGGGAA AGATATAGCC GCCT                                              24

(2) INFORMATION FOR SEQ ID NO: 42:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 42:

GGTGTTTAAC CAATTGGGAA GCCT                                              24

(2) INFORMATION FOR SEQ ID NO: 43:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 43:

GGTGTTCCGG TATTTGGGAA GCCT                                              24

(2) INFORMATION FOR SEQ ID NO: 44:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 44:

GGTGTGGGAT AACTTGGGAA GCCT                                              24

(2) INFORMATION FOR SEQ ID NO: 45:
```

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 45:

AGGCGGGAAA ACCCATAGGA CACC                                         24

(2) INFORMATION FOR SEQ ID NO: 46:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 46:

GGTGTAATCC GTCGGGAACA GCCTA                                        25

(2) INFORMATION FOR SEQ ID NO: 47:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 47:

GGCTTTAGAT CAGGGAACAC ACC                                          23

(2) INFORMATION FOR SEQ ID NO: 48:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 48:

GGTGTATCCT GGTAGGAATC GCCT                                         24

(2) INFORMATION FOR SEQ ID NO: 49:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 49:

AGGCTATCCC AGGAATTTGA CACC                                         24

(2) INFORMATION FOR SEQ ID NO: 50:

(i) SEQUENCE CHARACTERISTICS:
       (A) LENGTH: 26 base pairs
       (B) TYPE: nucleic acid

```
        (C) STRANDEDNESS: single
        (D) TOPOLOGY: linear (ii) MOLECULE TYPE: cDNA (xi) SEQUENCE DESCRIPTION: SEQ ID NO: 50:

AGGCAAATTG TTCAGGAACA CACACC                                              26

(2) INFORMATION FOR SEQ ID NO: 51:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 51:

GGTGTCCATA AGGAACAATA GCCT                                                24

(2) INFORMATION FOR SEQ ID NO: 52:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 52:

AGGCAGACCC AAGGAAGCCA CACC                                                24

(2) INFORMATION FOR SEQ ID NO: 53:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 53:

AGGCTATCCC AGGAATTTGA CACC                                                24

(2) INFORMATION FOR SEQ ID NO: 54:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 54:

AGGAGAATCC TATGGGATAC ACC                                                 23

(2) INFORMATION FOR SEQ ID NO: 55:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO: 55:

GGTGTTCATT GGGATAGCAT GCCT                                          24

(2) INFORMATION FOR SEQ ID NO: 56:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 56:

GGTGTTGGGA TTTCTGGATA GCCT                                          24

(2) INFORMATION FOR SEQ ID NO: 57:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 57:

AGGCGTTTGG GATGTATTTA CACC                                          24

(2) INFORMATION FOR SEQ ID NO: 58:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 58:

GGTGTGGGAT CGCCATATTC                                               20

(2) INFORMATION FOR SEQ ID NO: 59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 59:

GGTGTGGGAT TGCTTTATTT                                               20

(2) INFORMATION FOR SEQ ID NO: 60:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 60:

GGTGTGGGAT TGGGACTAAA GCCTA                                         25

(2) INFORMATION FOR SEQ ID NO: 61:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 61:

GGTGTGGGAT TGGGACTAAA GCCT                                24

(2) INFORMATION FOR SEQ ID NO: 62:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 62:

GGTGTAAGGA CAATGGGATA GCCT                                24

(2) INFORMATION FOR SEQ ID NO: 63:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 63:

GGTGTCAGGA TTTGGGACAC GCCT                                24

(2) INFORMATION FOR SEQ ID NO: 64:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 64:

GGTGTGGGAC TCAAAGAGGC                                         20

(2) INFORMATION FOR SEQ ID NO: 65:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 65:

GGTGTCCTCC AGCGGGATAA GCCT                                24

(2) INFORMATION FOR SEQ ID NO: 66:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 66:

AGGCATCCGG GATAATAAAA CACC                                          24

(2) INFORMATION FOR SEQ ID NO: 67:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 67:

GGTGTTCTTC GGGATGGCTT GCCT                                          24

(2) INFORMATION FOR SEQ ID NO: 68:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 68:

AGGCTTCACC GGGAGCACGA CACC                                          24

(2) INFORMATION FOR SEQ ID NO: 69:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 69:

GGTGTAGATC CCAGGGATTT GCCT                                          24

(2) INFORMATION FOR SEQ ID NO: 70:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 70:

GGTGTAGGTA GGGACATCCC GCCT                                          24

(2) INFORMATION FOR SEQ ID NO: 71:

(i) SEQUENCE CHARACTERISTICS:
        (A) LENGTH: 24 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO: 71:

GGTGTGAGAA ATAAGGGATA GCCT                                              24

(2) INFORMATION FOR SEQ ID NO: 72:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 72:

CAAGGGAAT                                                               9

(2) INFORMATION FOR SEQ ID NO: 73:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 73:

TCAGCTTTTG GGAATGTATT CCCTGTCA                                          28

(2) INFORMATION FOR SEQ ID NO: 74:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 74:

TCAGCTTTTG GGAATTCCCT GTCA                                              24

(2) INFORMATION FOR SEQ ID NO: 75:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 75:

AGGCTTTTGG GAATACCAGA CACC                                              24

(2) INFORMATION FOR SEQ ID NO: 76:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 76:

AGGCTTGGGA TTGGGAATAA CACC                                          24

(2) INFORMATION FOR SEQ ID NO: 77:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 77:

GGTGTTCCTG GGAATGTTCG GCCTA                                         25

(2) INFORMATION FOR SEQ ID NO: 78:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 78:

AGGCGTGGGA ATATCAGGAC ACC                                           23

(2) INFORMATION FOR SEQ ID NO: 79:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 79:

AGGCTGGGAA TGCTGGGAAA CACC                                          24

(2) INFORMATION FOR SEQ ID NO: 80:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 80:

GGTGTTGGGA ATGCTGGAAT GCCTA                                         25

(2) INFORMATION FOR SEQ ID NO: 81:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 81:

GGTGTAATTG GGAATTTTTA GCCTA                                         25

(2) INFORMATION FOR SEQ ID NO: 82:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 82:

GGTGTGGGAA AAGTGGGAAT GCCTA                                             25

(2) INFORMATION FOR SEQ ID NO: 83:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 83:

GGTGTTCCTG GGAATGCCAA GCCTA                                             25

(2) INFORMATION FOR SEQ ID NO: 84:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 84:

AGGCTACAGA ATACTGGGAA CACC                                              24

(2) INFORMATION FOR SEQ ID NO: 85:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 85:

AGGCTAAAAA TTCCTGGGAA CACC                                              24

(2) INFORMATION FOR SEQ ID NO: 86:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 86:

AGGCATTCCC GTTTTGGGAA CACC                                              24

(2) INFORMATION FOR SEQ ID NO: 87:

(i) SEQUENCE CHARACTERISTICS:

(A) LENGTH: 24 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 87:

AGGCATTCCC GTTTTGGGAA CACC                                              24

(2) INFORMATION FOR SEQ ID NO: 88:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 88:

GGTGTATCCC GGGAATACCG GCCTA                                             25

(2) INFORMATION FOR SEQ ID NO: 89:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 89:

AGGCTAAGGA ATACCGGGAA CACC                                              24

(2) INFORMATION FOR SEQ ID NO: 90:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 90:

AGGCTCTGGA ATATCGGGAA CACC                                              24

(2) INFORMATION FOR SEQ ID NO: 91:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 91:

GGTGTAAATC GGGAATTCCG GCCTA                                             25

(2) INFORMATION FOR SEQ ID NO: 92:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 92:

AGGCCGGGAA TACCGGAAAA CACC                                    24

(2) INFORMATION FOR SEQ ID NO: 93:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 93:

AGGCAAAACA TTACAGGGAA CACC                                    24

(2) INFORMATION FOR SEQ ID NO: 94:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 94:

AGGCAGGGAA TATCGGGATA CACC                                    24

(2) INFORMATION FOR SEQ ID NO: 95:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 95:

GGTGTAGGAA TTCTAGGAAT GCCTA                                   25

(2) INFORMATION FOR SEQ ID NO: 96:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 96:

AGGCATTCCA AGGAATTTTA CACC                                    24

(2) INFORMATION FOR SEQ ID NO: 97:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 97:

```
GGTGTAAGGA ATACTGGAAT GCCTA                                          25
```

(2) INFORMATION FOR SEQ ID NO: 98:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 98:

```
GGCAGAATTC CAAGGAATAC ACC                                            23
```

(2) INFORMATION FOR SEQ ID NO: 99:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 99:

```
AGGCCAAGGA ATATCAGGAA CACC                                           24
```

(2) INFORMATION FOR SEQ ID NO: 100:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 100:

```
TCAGCTTTTG GGAATCTCCT GTCA                                           24
```

(2) INFORMATION FOR SEQ ID NO: 101:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 101:

```
TCAGCTTTTG GGAATACCCT GTCA                                           24
```

(2) INFORMATION FOR SEQ ID NO: 102:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 102:

```
TCAGCTTTTG GGAATCTCCT GTCA                                           24
```

(2) INFORMATION FOR SEQ ID NO: 103:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 103:

TGGAGGGAAG TGGGAAACTT TT                                           22

(2) INFORMATION FOR SEQ ID NO: 104:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 104:

TGGAAGTGGG AGGC                                                    14

(2) INFORMATION FOR SEQ ID NO: 105:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 105:

GAGGAGAAAG GTCTCCTAC                                               19

(2) INFORMATION FOR SEQ ID NO: 106:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 106:

AACAGGGAAA CA                                                      12

(2) INFORMATION FOR SEQ ID NO: 107:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 107:

GTCAGGGAAC AGG                                                     13

(2) INFORMATION FOR SEQ ID NO: 108:

(i) SEQUENCE CHARACTERISTICS:
        (A) LENGTH: 14 base pairs

```
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 108:

AAGGTGGGAA GTAA                                                           14

(2) INFORMATION FOR SEQ ID NO: 109:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 109:

GGTAGGAATG G                                                              11

(2) INFORMATION FOR SEQ ID NO: 110:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 110:

GGAGGGGGAA GAA                                                            13

(2) INFORMATION FOR SEQ ID NO: 111:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 111:

AGTGGGGAAA TCT                                                            13

(2) INFORMATION FOR SEQ ID NO: 112:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 112:

GGTCAGGGAA ACAA                                                           14

(2) INFORMATION FOR SEQ ID NO: 113:

(i) SEQUENCE CHARACTERISTICS:
            (A) LENGTH: 18 base pairs
            (B) TYPE: nucleic acid
            (C) STRANDEDNESS: single
            (D) TOPOLOGY: linear
```

```
        (ii) MOLECULE TYPE: cDNA (xi) SEQUENCE DESCRIPTION: SEQ ID NO: 113:

TGGGGGAAGG GGTGGAAG                                                 18

(2) INFORMATION FOR SEQ ID NO: 114:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 114:

TTTTGGGAAC C                                                        11

(2) INFORMATION FOR SEQ ID NO: 115:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 115:

AAAGGGGAAC CC                                                       12

(2) INFORMATION FOR SEQ ID NO: 116:

(i) SEQUENCE CHARACTERISTICS:
            (A) LENGTH: 9 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 116:

TGGAGGGAG                                                           9

(2) INFORMATION FOR SEQ ID NO: 117:

(i) SEQUENCE CHARACTERISTICS:
            (A) LENGTH: 8 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 117:

AGGGGAAA                                                            8

(2) INFORMATION FOR SEQ ID NO: 118:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 118:
```

```
TTTGGGAATT                                                              10
```

(2) INFORMATION FOR SEQ ID NO: 119:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 119:

```
TGAGAGGAAG AGGAGA                                                       16
```

(2) INFORMATION FOR SEQ ID NO: 120:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 120:

```
CAGGAATT                                                                 8
```

(2) INFORMATION FOR SEQ ID NO: 121:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 121:

```
AAGGAAACCA AAACAGGGGA AG                                                22
```

(2) INFORMATION FOR SEQ ID NO: 122:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 122:

```
TTGGAAACCT                                                              10
```

(2) INFORMATION FOR SEQ ID NO: 123:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 123:

```
GTTTCCATGA CATCATGAAT GGGAGT                                            26
```

(2) INFORMATION FOR SEQ ID NO: 124:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 124:

GTTTCCATGA TGTCATGAAT GGGGGT                                              26

(2) INFORMATION FOR SEQ ID NO: 125:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 125:

TTCTTGGGGA TTG                                                            13

(2) INFORMATION FOR SEQ ID NO: 126:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 126:

GGAGGAACT                                                                  9

(2) INFORMATION FOR SEQ ID NO: 127:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 127:

TTTGGGATG                                                                  9

(2) INFORMATION FOR SEQ ID NO: 128:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 128:

TTCTAGGAAG TAAGGGAATT T                                                   21

(2) INFORMATION FOR SEQ ID NO: 129:

(i) SEQUENCE CHARACTERISTICS:
        (A) LENGTH: 9 base pairs
        (B) TYPE: nucleic acid

```
        (C) STRANDEDNESS: single
        (D) TOPOLOGY: linear (ii) MOLECULE TYPE: cDNA (xi) SEQUENCE DESCRIPTION: SEQ ID NO: 129:

GTGGGAAGA                                                              9

(2) INFORMATION FOR SEQ ID NO: 130:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 130:

TAGGAATTCT                                                            10

(2) INFORMATION FOR SEQ ID NO: 131:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 131:

TAAGGAAAGG                                                            10

(2) INFORMATION FOR SEQ ID NO: 132:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 132:

TTTCCAAGTG GGAATC                                                     16

(2) INFORMATION FOR SEQ ID NO: 133:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 133:

TGGGGAGTT                                                              9

(2) INFORMATION FOR SEQ ID NO: 134:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO: 134:

TTGGGAAGGA T                                                                11

(2) INFORMATION FOR SEQ ID NO: 135:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 135:

AAGGAACA                                                                    8

(2) INFORMATION FOR SEQ ID NO: 136:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 136:

CAGGGGAATC TCCCTCTCCA T                                                     21

(2) INFORMATION FOR SEQ ID NO: 137:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 137:

AAGAGGAAAA                                                                  10

(2) INFORMATION FOR SEQ ID NO: 138:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 138:

GGGAAATTCC                                                                  10

(2) INFORMATION FOR SEQ ID NO: 139:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 139:

GGGGAATCCC                                                                  10

(2) INFORMATION FOR SEQ ID NO: 140:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 140:

```
TGGGAG                                                              6
```

(2) INFORMATION FOR SEQ ID NO: 141:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 141:

```
CAGGGAAGTA                                                         10
```

(2) INFORMATION FOR SEQ ID NO: 142:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 142:

```
CAAGGGACTT TCCGCTGGGG ACTTTCCAGG GAGGCG                             36
```

(2) INFORMATION FOR SEQ ID NO: 143:

(i) SEQUENCE CHARACTERISTICS:
        (A) LENGTH: 103 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 143:

```
TTTGGTTATA AATGTATTGA TTGCATCCCC ATTACCCAGA AGGCCAATAT TTAATTGGAG    60

TCTTAACTCA ATTGTGTTTT CGTCAGTTGG TAAGCCTCAC AAA                    103
```

(2) INFORMATION FOR SEQ ID NO: 144:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 144:

```
ATGGGCCTTC CGGGCATGTA CCCAGGTAAG CACTGAGGCC CTGCTGAGCT GCACCCCTCC    60

CCCTCCCAGC GCCTGGGCCA GGATGGGGCT CTGTGGCCTG TTTCAGCCAC AGGAGG       116
```

(2) INFORMATION FOR SEQ ID NO: 145:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 145:

```
CCTTGTTGCT GCTGTGTTGC TATCTTGTGA CTTATTTTTG CAGTGACACT GAGTGGCCTC      60

CTGTGTTGTC TCTTTCAGCC AGTAATGTTA AAGT                                 94
```

(2) INFORMATION FOR SEQ ID NO: 146:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 146:

```
GAGCCCTGGC AGATGTGTCC TGTCTGCTGT GACACTAGAA CACCATTCAA CCCCTGGGTG      60

TAGATTTCAC TTATGACCAT CTACTTCCCG CAGGAGACAA GTGCCTGTCA GACATGCCCT     120
```

(2) INFORMATION FOR SEQ ID NO: 147:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 147:

```
ACATGTGTGG TTATCACAGC CAGGACAGGT ACGAGTTCTC ATCCCATATC ACGCGGGGGG      60

AGCATCGTTA CCACCTGAGC TAAACCCAGC CAGGCCCCAC TGAAGCACAA AGATAGCTGG    120
```

(2) INFORMATION FOR SEQ ID NO: 148:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 148:

```
AGGAGGAAAA                                                            10
```

(2) INFORMATION FOR SEQ ID NO: 149:

(i) SEQUENCE CHARACTERISTICS:
        (A) LENGTH: 7 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 149:

```
TGGGAAT                                                                  7

(2) INFORMATION FOR SEQ ID NO: 150:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 150:

TCAGCTTTTG GGAATCTCCT GTCA                                              24

(2) INFORMATION FOR SEQ ID NO: 151:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 151:

TCAGCTTTTG GGATTCCTCT CA                                                22

(2) INFORMATION FOR SEQ ID NO: 152:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 152:

TCAGCGGGGG GGAATACCCT GTCA                                              24

(2) INFORMATION FOR SEQ ID NO: 153

(i) SEQUENCE CHARACTERISTICS:
        (A) LENGTH: 470 amino acids
        (B) TYPE: amino acid
        (D) TOPOLOGY: linear (ii) MOLECULE TYPE: peptide (v) FRAGMENT TYPE: C-terminal (ix) FEATURE:
        (A) NAME/KEY: Other
        (B) LOCATION: 1...470
        (D) OTHER INFORMATION: Xaa = any amino acid (xi) SEQUENCE DESCRIPTION: SEQ ID NO: 153:

Xaa Xaa Ala Ser Asn Val Lys Val Glu Thr Gln Ser Asp Glu Asp
 1               5                  10                  15

Gly Arg Ala Cys Glu Met Asn Gly Glu Cys Ala Glu Asp Leu Arg
                20                  25                  30

Met Leu Asp Ala Ser Gly Glu Lys Met Asn Gly Ser His Arg Asp Gln
         35                  40                  45

Gly Ser Ser Ala Leu Ser Gly Val Gly Gly Ile Arg Leu Pro Asn Gly
         50                  55                  60
```

-continued

```
Lys Leu Lys Cys Asp Ile Cys Gly Ile Xaa Cys Ile Gly Pro Asn Val
 65                  70                  75                  80

Leu Met Val His Lys Arg Ser His Thr Gly Glu Arg Pro Phe Gln Cys
             85                  90                  95

Asn Gln Cys Gly Ala Ser Phe Thr Gln Lys Gly Asn Leu Leu Arg His
            100                 105                 110

Ile Lys Leu His Ser Gly Glu Lys Pro Phe Lys Cys His Leu Cys Asn
            115                 120                 125

Tyr Ala Cys Arg Arg Arg Asp Ala Leu Thr Gly His Leu Arg Thr His
        130                 135                 140

Ser Val Gly Lys Pro His Lys Cys Gly Tyr Cys Gly Arg Ser Tyr Lys
145                 150                 155                 160

Gln Arg Xaa Ser Leu Glu Glu His Lys Glu Arg Cys His Asn Tyr Leu
                165                 170                 175

Glu Ser Met Gly Leu Pro Gly Xaa Xaa Xaa Pro Val Ile Lys Glu Glu
            180                 185                 190

Thr Xaa His Xaa Glu Met Ala Glu Asp Leu Cys Lys Ile Gly Xaa Glu
        195                 200                 205

Arg Ser Leu Val Leu Asp Arg Leu Ala Ser Asn Val Ala Lys Arg Lys
        210                 215                 220

Ser Ser Met Pro Gln Lys Phe Leu Gly Asp Lys Xaa Leu Ser Asp Xaa
225                 230                 235                 240

Pro Tyr Asp Ser Ala Xaa Tyr Glu Lys Glu Xaa Xaa Met Met Xaa Ser
                245                 250                 255

His Val Met Asp Xaa Ala Ile Asn Asn Ala Ile Asn Tyr Leu Gly Ala
            260                 265                 270

Glu Ser Leu Arg Pro Leu Val Gln Thr Pro Gly Xaa Ser Glu Val
        275                 280                 285

Val Pro Val Ile Ser Pro Met Tyr Gln Leu His Xaa Xaa Xaa Ser Xaa
        290                 295                 300

Gly Xaa Pro Arg Ser Asn His Ser Ala Gln Asp Xaa Ala Val Xaa Xaa
305                 310                 315                 320

Leu Leu Leu Leu Ser Lys Ala Lys Xaa Val Xaa Ser Glu Arg Glu Ala
                325                 330                 335

Ser Pro Ser Asn Ser Cys Gln Asp Ser Thr Asp Thr Glu Ser Asn Xaa
            340                 345                 350

Glu Glu Gln Arg Ser Gly Leu Ile Tyr Leu Thr Asn His Ile Xaa Xaa
            355                 360                 365

Xaa Ala Xaa Xaa Xaa Xaa Xaa Leu Lys Glu Glu Xaa Arg Ala Tyr Xaa
        370                 375                 380

Xaa Leu Arg Ala Ala Ser Glu Asn Ser Gln Asp Ala Xaa Arg Val Val
385                 390                 395                 400

Ser Thr Ser Gly Glu Gln Xaa Lys Val Tyr Lys Cys Glu His Cys Arg
                405                 410                 415

Val Leu Phe Leu Asp His Val Met Tyr Thr Ile His Met Xaa Xaa Xaa
            420                 425                 430

Gly Cys His Gly Phe Arg Asp Pro Phe Glu Cys Asn Met Cys Gly Tyr
        435                 440                 445

His Ser Gln Asp Arg Tyr Glu Phe Ser Ser His Ile Thr Arg Gly Glu
        450                 455                 460

His Arg Xaa His Xaa Ser
465                 470
```

(2) INFORMATION FOR SEQ ID NO: 154:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 154:

AGAAGTTTCC ATAAGATGAT GAATGGGGGT GGCAGAGA        38

(2) INFORMATION FOR SEQ ID NO: 155:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 155:

NNHTGGGAAT DYY        13

(2) INFORMATION FOR SEQ ID NO: 156:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 156:

NNYYGGGAAT HNC        13

(2) INFORMATION FOR SEQ ID NO: 157:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 157:

TMYGGGAATD YY        12

(2) INFORMATION FOR SEQ ID NO: 158:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 158:

TCAGCTTTTG AGAATACCCT GTCA        24

(2) INFORMATION FOR SEQ ID NO: 159:

(i) SEQUENCE CHARACTERISTICS:
        (A) LENGTH: 24 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 159:

TCAGCTTTTG GGATTACCCT GTCA                                              24

(2) INFORMATION FOR SEQ ID NO: 160:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 160:

TCAGCTTTTG GGAAAAACCT GTCA                                              24

(2) INFORMATION FOR SEQ ID NO: 161:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 161:

GTTTCCATGA CATCATGATG GGGGT                                             25

(2) INFORMATION FOR SEQ ID NO: 162:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 162:

TGGGAATACC                                                              10

(2) INFORMATION FOR SEQ ID NO: 163:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 163:

GGCTGCCACG GCTTCCGTGA TCCT                                              24

(2) INFORMATION FOR SEQ ID NO: 164:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 164:

AGCGGTCTGG GGAAACATCT AGGA                                                    24

(2) INFORMATION FOR SEQ ID NO: 165:

(i) SEQUENCE CHARACTERISTICS:
            (A) LENGTH: 1551 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: Coding Sequence
            (B) LOCATION: 1...1548

(xi) SEQUENCE DESCRIPTION: SEQ ID NO: 165:

```
ATG GAT GCT GAC GAG GGT CAA GAC ATG TCT TTC TCA TCA GGG AAG GAA        48
Met Asp Ala Asp Glu Gly Gln Asp Met Ser Phe Ser Ser Gly Lys Glu
  1               5                  10                  15

AGC CCC CCT GTA AGC GAT ACT CCA GAT GAG GGC GAT GAG CCC ATG CCG        96
Ser Pro Pro Val Ser Asp Thr Pro Asp Glu Gly Asp Glu Pro Met Pro
             20                  25                  30

ATC CCC GAG GAC CTC TCC ACC ACC TCG GGA GGA CAG CAA AGC TCC AAG       144
Ile Pro Glu Asp Leu Ser Thr Thr Ser Gly Gly Gln Gln Ser Ser Lys
         35                  40                  45

AGT GAC AGA GTC GTG GCC AGT AAT GTT AAA GTA GAG ACT CAG AGT GAT       192
Ser Asp Arg Val Val Ala Ser Asn Val Lys Val Glu Thr Gln Ser Asp
     50                  55                  60

GAA GAG AAT GGG CGT GCC TGT GAA ATG AAT GGG GAA GAA TGT GCG GAG       240
Glu Glu Asn Gly Arg Ala Cys Glu Met Asn Gly Glu Glu Cys Ala Glu
 65                  70                  75                  80

GAT TTA CGA ATG CTT GAT GCC TCG GGA GAG AAA ATG AAT GGC TCC CAC       288
Asp Leu Arg Met Leu Asp Ala Ser Gly Glu Lys Met Asn Gly Ser His
                 85                  90                  95

AGG GAC CAA GGC AGC TCG GCT TTG TCG GGA GTT GGA GGC ATT CGA CTT       336
Arg Asp Gln Gly Ser Ser Ala Leu Ser Gly Val Gly Gly Ile Arg Leu
            100                 105                 110

CCT AAC GGA AAA CTA AAG TGT GAT ATC TGT GGG ATC ATT TGC ATC GGG       384
Pro Asn Gly Lys Leu Lys Cys Asp Ile Cys Gly Ile Ile Cys Ile Gly
        115                 120                 125

CCC AAT GTG CTC ATG GTT CAC AAA AGA AGC CAC ACT GGA GAA CGG CCC       432
Pro Asn Val Leu Met Val His Lys Arg Ser His Thr Gly Glu Arg Pro
    130                 135                 140

TTC CAG TGC AAT CAG TGC GGG GCC TCA TTC ACC CAG AAG GGC AAC CTG       480
Phe Gln Cys Asn Gln Cys Gly Ala Ser Phe Thr Gln Lys Gly Asn Leu
145                 150                 155                 160

CTC CGG CAC ATC AAG CTG CAT TCC GGG GAG AAG CCC TTC AAA TGC CAC       528
Leu Arg His Ile Lys Leu His Ser Gly Glu Lys Pro Phe Lys Cys His
                165                 170                 175

CTC TGC AAC TAC GCC TGC CGC CGG AGG GAC GCC CTC ACT GGC CAC CTG       576
Leu Cys Asn Tyr Ala Cys Arg Arg Arg Asp Ala Leu Thr Gly His Leu
            180                 185                 190

AGG ACG CAC TCC GTT GGT AAA CCT CAC AAA TGT GGA TAT TGT GGC CGA       624
Arg Thr His Ser Val Gly Lys Pro His Lys Cys Gly Tyr Cys Gly Arg
        195                 200                 205

AGC TAT AAA CAG CGA ACG TCT TTA GAG GAA CAT AAA GAG CGC TGC CAC       672
Ser Tyr Lys Gln Arg Thr Ser Leu Glu Glu His Lys Glu Arg Cys His
    210                 215                 220
```

```
AAC TAC TTG GAA AGC ATG GGC CTT CCG GGC ACA CTG TAC CCA GTC ATT      720
Asn Tyr Leu Glu Ser Met Gly Leu Pro Gly Thr Leu Tyr Pro Val Ile
225                 230                 235                 240

AAA GAA GAA ACT AAG CAC AGT GAA ATG GCA GAA GAC CTG TGC AAG ATA      768
Lys Glu Glu Thr Lys His Ser Glu Met Ala Glu Asp Leu Cys Lys Ile
                245                 250                 255

GGA TCA GAG AGA TCT CTC GTG CTG GAC AGA CTA GCA AGT AAT GTC GCC      816
Gly Ser Glu Arg Ser Leu Val Leu Asp Arg Leu Ala Ser Asn Val Ala
            260                 265                 270

AAA CGT AAG AGC TCT ATG CCT CAG AAA TTT CTT GGG GAC AAG GGC CTG      864
Lys Arg Lys Ser Ser Met Pro Gln Lys Phe Leu Gly Asp Lys Gly Leu
                275                 280                 285

TCC GAC ACG CCC TAC GAC AGT GCC ACG TAC GAG AAG GAG AAC GAA ATG      912
Ser Asp Thr Pro Tyr Asp Ser Ala Thr Tyr Glu Lys Glu Asn Glu Met
290                 295                 300

ATG AAG TCC CAC GTG ATG GAC CAA GCC ATC AAC AAC GCC ATC AAC TAC      960
Met Lys Ser His Val Met Asp Gln Ala Ile Asn Asn Ala Ile Asn Tyr
305                 310                 315                 320

CTG GGG GCC GAG TCC CTG CGC CCG CTG GTG CAG ACG CCC CCG GGC GGT     1008
Leu Gly Ala Glu Ser Leu Arg Pro Leu Val Gln Thr Pro Pro Gly Gly
                325                 330                 335

TCC GAG GTG GTC CCG GTC ATC AGC CCG ATG TAC CAG CTG CAC AGG CGC     1056
Ser Glu Val Val Pro Val Ile Ser Pro Met Tyr Gln Leu His Arg Arg
            340                 345                 350

TCG GAG GGC ACC CCG CGC TCC AAC CAC TCG GCC CAG GAC AGC GCC GTG     1104
Ser Glu Gly Thr Pro Arg Ser Asn His Ser Ala Gln Asp Ser Ala Val
                355                 360                 365

GAG TAC CTG CTG CTG CTC TCC AAG GCC AAG TTG GTG CCC TCG GAG CGC     1152
Glu Tyr Leu Leu Leu Leu Ser Lys Ala Lys Leu Val Pro Ser Glu Arg
370                 375                 380

GAG GCG TCC CCG AGC AAC AGC TGC CAA GAC TCC ACG GAC ACC GAG AGC     1200
Glu Ala Ser Pro Ser Asn Ser Cys Gln Asp Ser Thr Asp Thr Glu Ser
385                 390                 395                 400

AAC AAC GAG GAG CAG CGC AGC GGT CTT ATC TAC CTG ACC AAC CAC ATC     1248
Asn Asn Glu Glu Gln Arg Ser Gly Leu Ile Tyr Leu Thr Asn His Ile
                405                 410                 415

GCC CGA CGC GCG CAA CGC GTG TCG CTC AAG GAG GAG CAC CGC GCC TAC     1296
Ala Arg Arg Ala Gln Arg Val Ser Leu Lys Glu Glu His Arg Ala Tyr
                420                 425                 430

GAC CTG CTG CGC GCC GCC TCC GAG AAC TCG CAG GAC GCG CTC CGC GTG     1344
Asp Leu Leu Arg Ala Ala Ser Glu Asn Ser Gln Asp Ala Leu Arg Val
            435                 440                 445

GTC AGC ACC AGC GGG GAG CAG ATG AAG GTG TAC AAG TGC GAA CAC TGC     1392
Val Ser Thr Ser Gly Glu Gln Met Lys Val Tyr Lys Cys Glu His Cys
450                 455                 460

CGG GTG CTC TTC CTG GAT CAC GTC ATG TAC ACC ATC CAC ATG GGC TGC     1440
Arg Val Leu Phe Leu Asp His Val Met Tyr Thr Ile His Met Gly Cys
465                 470                 475                 480

CAC GGC TTC CGT GAT CCT TTT GAG TGC AAC ATG TGC GGC TAC CAC AGC     1488
His Gly Phe Arg Asp Pro Phe Glu Cys Asn Met Cys Gly Tyr His Ser
                485                 490                 495

CAG GAC CGG TAC GAG TTC TCG TCG CAC ATA ACG CGA GGG GAG CAC CGC     1536
Gln Asp Arg Tyr Glu Phe Ser Ser His Ile Thr Arg Gly Glu His Arg
                500                 505                 510

TTC CAC ATG AGC TAA                                                  1551
Phe His Met Ser
            515

(2) INFORMATION FOR SEQ ID NO: 166:
```

-continued

```
    (i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 166:

GGTATAGGTG TGTATTCTTC C                                              21

(2) INFORMATION FOR SEQ ID NO: 167:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 167:

GAGTTGCTCT TCTCTGAGCT C                                              21

(2) INFORMATION FOR SEQ ID NO: 168:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 168:

AAGTTTTCGT GCGCGCCCCT C                                              21

(2) INFORMATION FOR SEQ ID NO: 169:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 169:

CCCCTGTAAG CGATACTCCA GATG                                           24

(2) INFORMATION FOR SEQ ID NO: 170:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 170:

AGTAATGTTA AAGTAGAGAC TCAG                                           24

(2) INFORMATION FOR SEQ ID NO: 171:

(i) SEQUENCE CHARACTERISTICS:
        (A) LENGTH: 24 base pairs
        (B) TYPE: nucleic acid
        (C) STRANDEDNESS: single
```

(D) TOPOLOGY: linear (ii) MOLECULE TYPE: cDNA (xi) SEQUENCE DESCRIPTION: SEQ ID NO: 171:

GATGGCTTGG TCCATCACGT GGGA                                                      24

(2) INFORMATION FOR SEQ ID NO: 172:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 172:

ATGGTGAAGG TCGGTGTGAA CGGATTTGGC                                                30

(2) INFORMATION FOR SEQ ID NO: 173:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 173:

GCATCGAAGG TGGAAGAGTG GGAGTTGCTG                                                30

(2) INFORMATION FOR SEQ ID NO: 174:

(i) SEQUENCE CHARACTERISTICS:
        (A) LENGTH: 236 amino acids
        (B) TYPE: amino acid
        (D) TOPOLOGY: linear (ii) MOLECULE TYPE: protein (xi) SEQUENCE DESCRIPTION: SEQ ID NO: 174:

Gly Asp Lys Cys Leu Ser Asp Met Pro Tyr Asp Ser Ala Asn Tyr Glu
 1               5                  10                  15

Lys Glu Asp Met Met Thr Ser His Val Met Asp Gln Ala Ile Asn Asn
                20                  25                  30

Ala Ile Asn Tyr Leu Gly Ala Glu Ser Leu Arg Pro Leu Val Gln Thr
             35                  40                  45

Pro Pro Gly Ser Ser Glu Val Val Pro Val Ile Ser Ser Met Tyr Gln
 50                  55                  60

Leu His Lys Pro Pro Ser Asp Gly Pro Pro Arg Ser Asn His Ser Ala
 65                  70                  75                  80

Gln Asp Ala Val Asp Asn Leu Leu Leu Ser Lys Ala Lys Ser Val
                 85                  90                  95

Ser Ser Glu Arg Glu Ala Ser Pro Ser Asn Ser Cys Gln Asp Ser Thr
                100                 105                 110

Asp Thr Glu Ser Asn Ala Glu Glu Gln Arg Ser Gly Leu Ile Tyr Leu
            115                 120                 125

Thr Asn His Ile Asn Pro His Ala Arg Asn Gly Leu Ala Leu Lys Glu
        130                 135                 140

Glu Gln Arg Ala Tyr Glu Val Leu Arg Ala Ala Ser Glu Asn Ser Gln
145                 150                 155                 160

```
Asp Ala Phe Arg Val Val Ser Thr Ser Gly Glu Gln Leu Lys Val Tyr
                165                 170                 175

Lys Cys Glu His Cys Arg Val Leu Phe Leu Asp His Val Met Tyr Thr
            180                 185                 190

Ile His Met Gly Cys His Gly Cys His Gly Phe Arg Asp Pro Phe Glu
            195                 200                 205

Cys Asn Met Cys Gly Tyr His Ser Gln Asp Arg Tyr Glu Phe Ser Ser
            210                 215                 220

His Ile Thr Arg Gly Glu His Arg Tyr His Leu Ser
225                 230                 235
```

(2) INFORMATION FOR SEQ ID NO: 175:

(i) SEQUENCE CHARACTERISTICS:
        (A) LENGTH: 236 amino acids
        (B) TYPE: amino acid
        (D) TOPOLOGY: linear (ii) MOLECULE TYPE: protein (xi) SEQUENCE DESCRIPTION: SEQ ID NO: 175:

```
Gly Asp Lys Gly Leu Ser Asp Thr Pro Tyr Asp Ser Ala Thr Tyr Glu
1               5                   10                  15

Lys Glu Asn Glu Met Met Lys Ser His Val Met Asp Gln Ala Ile Asn
            20                  25                  30

Asn Ala Ile Asn Tyr Leu Gly Ala Glu Ser Leu Arg Pro Leu Val Gln
            35                  40                  45

Thr Pro Pro Gly Gly Ser Glu Val Pro Val Ile Ser Pro Met Tyr
    50                  55                  60

Gln Leu His Arg Arg Ser Glu Gly Thr Pro Arg Ser Asn His Ser Ala
65                  70                  75                  80

Gln Asn Ser Ala Val Glu Tyr Leu Leu Leu Ser Lys Ala Lys Leu
                85                  90                  95

Glu Lys Lys Lys Val Pro Ser Gly Arg Glu Ala Ser Pro Ser Asn Ser
                100                 105                 110

Cys Gln Asp Ser Thr Asp Thr Glu Ser Asn Asn Glu Glu Gln Arg Ser
            115                 120                 125

Gly Leu Ile Tyr Leu Thr Asn His Ile Ala Arg Arg Ala Gln Arg Val
130                 135                 140

Ser Leu Lys Glu Glu His Arg Ala Tyr Asp Leu Leu Arg Ala Ala Ser
145                 150                 155                 160

Glu Asn Ser Gln Asp Ala Leu Arg Val Val Ser Thr Ser Gly Glu Gln
                165                 170                 175

Met Lys Val Tyr Lys Cys Glu His Cys Arg Val Leu Phe Leu Asp His
                180                 185                 190

Val Met Tyr Thr Ile His Met Gly Cys His Gly Phe Arg Asp Pro Phe
                195                 200                 205

Glu Cys Asn Met Cys Gly Tyr His Ser Gln Asp Arg Tyr Glu Phe Ser
            210                 215                 220

Ser His Ile Thr Arg Gly Glu His Arg Phe His Met
225                 230                 235
```

(2) INFORMATION FOR SEQ ID NO: 176:

(i) SEQUENCE CHARACTERISTICS:
        (A) LENGTH: 238 amino acids
        (B) TYPE: amino acid (D) TOPOLOGY: linear (ii) MOLECULE TYPE: peptide (ix) FEATURE:
          (A) NAME/KEY: Other
          (B) LOCATION: 1...238
          (D) OTHER INFORMATION: Xaa = any amino acid (xi) SEQUENCE DESCRIPTION: SEQ ID NO: 176:

Gly Asp Lys Xaa Leu Ser Asp Xaa Pro Tyr Asp Ser Ala Xaa Tyr Glu
 1               5                  10                  15

Lys Glu Xaa Xaa Met Met Xaa Ser His Val Met Asp Xaa Ala Ile Asn
            20                  25                  30

Asn Ala Ile Asn Tyr Leu Gly Ala Glu Ser Leu Arg Pro Leu Val Gln
         35                  40                  45

Thr Pro Pro Gly Xaa Ser Glu Val Val Pro Val Ile Ser Pro Met Tyr
     50                  55                  60

Gln Leu His Xaa Xaa Xaa Ser Xaa Gly Xaa Pro Arg Ser Asn His Ser
 65                  70                  75                  80

Ala Gln Asp Xaa Ala Val Xaa Xaa Leu Leu Leu Leu Ser Lys Ala Lys
                 85                  90                  95

Xaa Val Xaa Ser Glu Arg Glu Ala Ser Pro Ser Asn Ser Cys Gln Asp
            100                 105                 110

Ser Thr Asp Thr Glu Ser Asn Xaa Glu Glu Gln Arg Ser Gly Leu Ile
        115                 120                 125

Tyr Leu Thr Asn His Ile Xaa Xaa Xaa Ala Xaa Xaa Xaa Xaa Xaa Leu
    130                 135                 140

Lys Glu Glu Xaa Arg Ala Tyr Xaa Xaa Leu Arg Ala Ala Ser Glu Asn
145                 150                 155                 160

Ser Gln Asp Ala Xaa Arg Val Val Ser Thr Ser Gly Glu Gln Xaa Lys
                165                 170                 175

Val Tyr Lys Cys Glu His Cys Arg Val Leu Phe Leu Asp His Val Met
            180                 185                 190

Tyr Thr Ile His Met Xaa Xaa Xaa Gly Cys His Gly Phe Arg Asp Pro
        195                 200                 205

Phe Glu Cys Asn Met Cys Gly Tyr His Ser Gln Asp Arg Tyr Glu Phe
    210                 215                 220

Ser Ser His Ile Thr Arg Gly Glu His Arg Xaa His Xaa Ser
225                 230                 235

(2) INFORMATION FOR SEQ ID NO: 177:

(i) SEQUENCE CHARACTERISTICS:
          (A) LENGTH: 238 amino acids
          (B) TYPE: amino acid
          (D) TOPOLOGY: linear (ii) MOLECULE TYPE: protein (ix) FEATURE:
          (A) NAME/KEY: Other
          (B) LOCATION: 1...238
          (D) OTHER INFORMATION: Xaa = any amino acid (xi) SEQUENCE DESCRIPTION: SEQ ID NO: 177:

Gly Asp Lys Gly Leu Ser Asp Thr Pro Tyr Asp Ser Ala Thr Tyr Glu
 1               5                  10                  15

Lys Glu Asn Glu Met Met Lys Ser His Val Met Asp Gln Ala Ile Asn
            20                  25                  30

```
Asn Ala Ile Asn Tyr Leu Gly Ala Glu Ser Leu Arg Pro Leu Val Gln
            35                  40                  45

Thr Pro Pro Gly Gly Ser Glu Val Val Pro Val Ile Ser Pro Met Tyr
     50                  55                  60

Gln Leu His Arg Xaa Arg Ser Glu Gly Thr Pro Arg Ser Asn His Ser
 65                  70                  75                  80

Ala Gln Asp Ser Ala Val Glu Tyr Leu Leu Leu Ser Lys Ala Lys
                 85                  90                  95

Leu Val Pro Ser Glu Arg Glu Ala Ser Pro Ser Asn Ser Cys Gln Asp
                100                 105                 110

Ser Thr Asp Thr Glu Ser Asn Asn Glu Glu Gln Arg Ser Gly Leu Ile
            115                 120                 125

Tyr Leu Thr Asn His Ile Ala Arg Arg Ala Gln Arg Xaa Val Ser Leu
        130                 135                 140

Lys Glu Glu His Arg Ala Tyr Asp Leu Leu Arg Ala Ala Ser Glu Asn
145                 150                 155                 160

Ser Gln Asp Ala Leu Arg Val Val Ser Thr Ser Gly Glu Gln Met Lys
                165                 170                 175

Val Tyr Lys Cys Glu His Cys Arg Val Leu Phe Leu Asp His Val Met
            180                 185                 190

Tyr Thr Ile His Met Xaa Xaa Xaa Gly Cys His Gly Phe Arg Asp Pro
        195                 200                 205

Phe Glu Cys Asn Met Cys Gly Tyr His Ser Gln Asp Arg Tyr Glu Phe
    210                 215                 220

Ser Ser His Ile Thr Arg Gly Glu His Arg Phe His Met Ser
225                 230                 235

(2) INFORMATION FOR SEQ ID NO: 178:

(i) SEQUENCE CHARACTERISTICS:
        (A) LENGTH: 45 amino acids
        (B) TYPE: amino acid
        (D) TOPOLOGY: linear (ii) MOLECULE TYPE: protein (xi) SEQUENCE DESCRIPTION: SEQ ID NO: 178:

Val Ile Lys Glu Glu Thr Asn His Asn Glu Met Ala Glu Asp Leu Cys
 1               5                  10                  15

Lys Ile Gly Ala Glu Arg Ser Leu Val Leu Asp Arg Leu Ala Ser Asn
                20                  25                  30

Val Ala Lys Arg Lys Ser Ser Met Pro Asp Lys Phe Leu
            35                  40                  45

(2) INFORMATION FOR SEQ ID NO: 179:

(i) SEQUENCE CHARACTERISTICS:
        (A) LENGTH: 45 amino acids
        (B) TYPE: amino acid
        (D) TOPOLOGY: linear (ii) MOLECULE TYPE: protein (xi) SEQUENCE DESCRIPTION: SEQ ID NO: 179:

Val Ile Lys Glu Glu Thr Lys His Ser Glu Met Ala Glu Asp Leu Cys
 1               5                  10                  15

Lys Ile Gly Ser Glu Arg Ser Leu Val Leu Asp Arg Leu Ala Ser Asn
                20                  25                  30

Val Ala Lys Arg Lys Ser Ser Met Pro Gln Lys Phe Leu
```

```
                35                  40                  45
```

(2) INFORMATION FOR SEQ ID NO: 180:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (ix) FEATURE:
        (A) NAME/KEY: Other
        (B) LOCATION: 1...45
        (D) OTHER INFORMATION: Xaa = any amino acid (xi) SEQUENCE DESCRIPTION: SEQ ID NO: 180:

```
Val Ile Lys Glu Glu Thr Xaa His Xaa Glu Met Ala Glu Asp Leu Cys
 1               5                  10                  15

Lys Ile Gly Xaa Glu Arg Ser Leu Val Leu Asp Arg Leu Ala Ser Asn
                20                  25                  30

Val Ala Lys Arg Lys Ser Ser Met Pro Gln Lys Phe Leu
                35                  40                  45
```

(2) INFORMATION FOR SEQ ID NO: 181:

(i) SEQUENCE CHARACTERISTICS:
        (A) LENGTH: 45 amino acids
        (B) TYPE: amino acid
        (D) TOPOLOGY: linear (ii) MOLECULE TYPE: protein (xi) SEQUENCE DESCRIPTION: SEQ ID NO: 181:

```
Val Ile Lys Glu Glu Thr Lys His Ser Glu Met Ala Glu Asp Leu Cys
 1               5                  10                  15

Lys Ile Gly Ser Glu Arg Ser Leu Val Leu Asp Arg Leu Ala Ser Asn
                20                  25                  30

Val Ala Lys Arg Lys Ser Ser Met Pro Gln Lys Phe Leu
                35                  40                  45
```

(2) INFORMATION FOR SEQ ID NO: 182:

(i) SEQUENCE CHARACTERISTICS:
        (A) LENGTH: 41 amino acids
        (B) TYPE: amino acid
        (D) TOPOLOGY: linear (ii) MOLECULE TYPE: protein (xi) SEQUENCE DESCRIPTION: SEQ ID NO: 182:

```
Val Gly Lys Pro His Lys Cys Gly Tyr Cys Gly Arg Ser Tyr Lys Gln
 1               5                  10                  15

Arg Ser Ser Leu Glu Glu His Lys Glu Arg Cys His Asn Tyr Leu Glu
                20                  25                  30

Ser Met Gly Leu Pro Gly Val Cys Pro
                35                  40
```

(2) INFORMATION FOR SEQ ID NO: 183:

(i) SEQUENCE CHARACTERISTICS:
        (A) LENGTH: 42 amino acids
        (B) TYPE: amino acid
        (D) TOPOLOGY: linear (ii) MOLECULE TYPE: peptide (xi) SEQUENCE DESCRIPTION: SEQ ID NO: 183:

Val Gly Lys Pro His Lys Cys Gly Tyr Cys Gly Arg Ser Tyr Lys Gln
1               5                   10                  15

Arg Thr Ser Leu Glu Glu His Lys Glu Arg Cys His Asn Tyr Leu Glu
                20                  25                  30

Ser Met Gly Leu Pro Gly Thr Leu Tyr Pro
            35                  40

(2) INFORMATION FOR SEQ ID NO: 184:

(i) SEQUENCE CHARACTERISTICS:
        (A) LENGTH: 42 amino acids
        (B) TYPE: amino acid
        (D) TOPOLOGY: linear (ii) MOLECULE TYPE: protein (ix) FEATURE:
        (A) NAME/KEY: Other
        (B) LOCATION: 1...42
        (D) OTHER INFORMATION: Xaa = any amino acid (xi) SEQUENCE DESCRIPTION: SEQ ID NO: 184:

Val Gly Lys Pro His Lys Cys Gly Tyr Cys Gly Arg Ser Tyr Lys Gln
1               5                   10                  15

Arg Xaa Ser Leu Glu Glu His Lys Glu Arg Cys His Asn Tyr Leu Glu
                20                  25                  30

Ser Met Gly Leu Pro Gly Xaa Xaa Xaa Pro
            35                  40

(2) INFORMATION FOR SEQ ID NO: 185:

(i) SEQUENCE CHARACTERISTICS:
        (A) LENGTH: 42 amino acids
        (B) TYPE: amino acid
        (D) TOPOLOGY: linear (ii) MOLECULE TYPE: protein (xi) SEQUENCE DESCRIPTION: SEQ ID NO: 185:

Val Gly Lys Pro His Lys Cys Gly Tyr Cys Gly Arg Ser Tyr Lys Gln
1               5                   10                  15

Arg Thr Ser Leu Glu Glu His Lys Glu Arg Cys His Asn Tyr Leu Glu
                20                  25                  30

Ser Met Gly Leu Pro Gly Thr Leu Tyr Pro
            35                  40

(2) INFORMATION FOR SEQ ID NO: 186:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO: 186:

Gly Glu Arg Pro Phe Gln Cys Asn Gln Ser Gly Ala Ser Phe Thr Gln
1               5                   10                  15

Lys Gly Asn Leu Leu Arg His Ile Lys Leu His Ser Gly Glu Lys Pro
                20                  25                  30

Phe Lys Cys His Leu Cys Asn Tyr Ala Cys Arg Arg Arg Asp Ala Leu
            35                  40                  45

Thr Gly His Leu Arg Thr His Ser
    50                  55

(2) INFORMATION FOR SEQ ID NO: 187:

(i) SEQUENCE CHARACTERISTICS:
        (A) LENGTH: 56 amino acids
        (B) TYPE: amino acid
        (D) TOPOLOGY: linear (ii) MOLECULE TYPE: peptide (xi) SEQUENCE DESCRIPTION: SEQ ID NO: 187:

Gly Glu Arg Pro Phe Gln Cys Asn Gln Cys Gly Ala Ser Phe Thr Gln
1               5                   10                  15

Lys Gly Asn Leu Leu Arg His Ile Lys Leu His Ser Gly Glu Lys Pro
            20                  25                  30

Phe Lys Cys His Leu Cys Asn Tyr Ala Cys Arg Arg Arg Asp Ala Leu
        35                  40                  45

Thr Gly His Leu Arg Thr His Ser
    50                  55

(2) INFORMATION FOR SEQ ID NO: 188:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO: 188:

Gly Glu Arg Pro Phe Gln Cys Asn Gln Cys Gly Ala Ser Phe Thr Gln
1               5                   10                  15

Lys Gly Asn Leu Leu Arg His Ile Lys Leu His Ser Gly Glu Lys Pro
            20                  25                  30

Phe Lys Cys His Leu Cys Asn Tyr Ala Cys Arg Arg Arg Asp Ala Leu
        35                  40                  45

Thr Gly His Leu Arg Thr His Ser
    50                  55

(2) INFORMATION FOR SEQ ID NO: 189:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO: 189:

Gly Glu Arg Pro Phe Gln Cys Asn Gln Cys Gly Ala Ser Phe Thr Gln
1               5                   10                  15

Lys Gly Asn Leu Leu Arg His Ile Lys Leu His Ser Gly Glu Lys Pro
            20                  25                  30

Phe Lys Cys His Leu Cys Asn Tyr Ala Cys Arg Arg Arg Asp Ala Leu
        35                  40                  45

Thr Gly His Leu Arg Thr His Ser
    50                  55

(2) INFORMATION FOR SEQ ID NO: 190:

(i) SEQUENCE CHARACTERISTICS:
    (A) LENGTH: 85 amino acids
    (B) TYPE: amino acid
    (D) TOPOLOGY: linear (ii) MOLECULE TYPE: protein (xi) SEQUENCE DESCRIPTION: SEQ ID NO: 190:

Asn Val Lys Val Glu Thr Gln Ser Asp Glu Glu Asn Gly Arg Ala Cys
1               5                   10                  15

Glu Met Asn Gly Glu Glu Cys Ala Glu Asp Leu Arg Met Leu Asp Ala
            20                  25                  30

Ser Gly Glu Lys Met Asn Gly Ser His Arg Asp Gln Gly Ser Ser Ala
        35                  40                  45

Leu Ser Gly Val Gly Gly Ile Arg Leu Pro Asn Gly Lys Leu Lys Cys
    50                  55                  60

Asp Ile Cys Gly Ile Ile Cys Ile Gly Pro Asn Val Leu Met Val His
65                  70                  75                  80

Lys Arg Ser His Thr
            85

(2) INFORMATION FOR SEQ ID NO: 191:

(i) SEQUENCE CHARACTERISTICS:
        (A) LENGTH: 90 amino acids
        (B) TYPE: amino acid
        (D) TOPOLOGY: linear (ii) MOLECULE TYPE: peptide (xi) SEQUENCE DESCRIPTION: SEQ ID NO: 191:

Ala Ser Asn Val Lys Val Glu Thr Gln Ser Asp Glu Glu Asn Gly Arg
1               5                   10                  15

Ala Cys Glu Met Asn Gly Glu Glu Cys Ala Glu Asp Leu Arg Met Leu
            20                  25                  30

Asp Ala Ser Gly Glu Lys Met Asn Gly Ser His Arg Asp Gln Gly Ser
        35                  40                  45

Ser Ala Leu Ser Gly Val Gly Gly Ile Arg Leu Pro Asn Gly Lys Leu
    50                  55                  60

Lys Cys Asp Ile Cys Gly Ile Cys Gly Ile Val Cys Ile Gly Pro Asn
65                  70                  75                  80

Val Leu Met Val His Lys Arg Ser His Thr
            85                  90

(2) INFORMATION FOR SEQ ID NO: 192:

(i) SEQUENCE CHARACTERISTICS:
        (A) LENGTH: 87 amino acids
        (B) TYPE: amino acid
        (D) TOPOLOGY: linear (ii) MOLECULE TYPE: protein (ix) FEATURE:
        (A) NAME/KEY: Other
        (B) LOCATION: 1...87
        (D) OTHER INFORMATION: Xaa = any amino acid (xi) SEQUENCE DESCRIPTION: SEQ ID NO: 192:

Ala Ser Asn Val Lys Val Glu Thr Gln Ser Asp Glu Glu Asp Gly Arg
1               5                   10                  15

Ala Cys Glu Met Asn Gly Glu Glu Cys Ala Glu Asp Leu Arg Met Leu
            20                  25                  30

```
Asp Ala Ser Gly Glu Lys Met Asn Gly Ser His Arg Asp Gln Gly Ser
        35                  40                  45
Ser Ala Leu Ser Gly Val Gly Gly Ile Arg Leu Pro Asn Gly Lys Leu
    50                  55                  60
Lys Cys Asp Ile Cys Gly Ile Xaa Cys Ile Gly Pro Asn Val Leu Met
65                  70                  75                  80
Val His Lys Arg Ser His Thr
                85
```

(2) INFORMATION FOR SEQ ID NO: 193:

(i) SEQUENCE CHARACTERISTICS:
        (A) LENGTH: 87 amino acids
        (B) TYPE: amino acid
        (D) TOPOLOGY: linear (ii) MOLECULE TYPE: protein (xi) SEQUENCE DESCRIPTION: SEQ ID NO: 193:

```
Ala Ser Asn Val Lys Val Glu Thr Gln Ser Asp Glu Glu Asn Gly Arg
1               5                   10                  15
Ala Cys Glu Met Asn Gly Glu Glu Cys Ala Glu Asp Leu Arg Met Leu
            20                  25                  30
Asp Ala Ser Gly Glu Lys Met Asn Gly Ser His Arg Asp Gln Gly Ser
        35                  40                  45
Ser Ala Leu Ser Gly Val Gly Gly Ile Arg Leu Pro Asn Gly Lys Leu
    50                  55                  60
Lys Cys Asp Ile Cys Gly Ile Ile Cys Ile Gly Pro Asn Val Leu Met
65                  70                  75                  80
Val His Lys Arg Ser His Thr
                85
```

(2) INFORMATION FOR SEQ ID NO: 194:

(i) SEQUENCE CHARACTERISTICS:
        (A) LENGTH: 53 amino acids
        (B) TYPE: amino acid
        (D) TOPOLOGY: linear (ii) MOLECULE TYPE: protein (xi) SEQUENCE DESCRIPTION: SEQ ID NO: 194:

```
Met Asp Val Asp Glu Gly Gln Asp Met Ser Gln Val Ser Gly Lys Glu
1               5                   10                  15
Ser Pro Pro Val Ser Asp Thr Pro Asp Glu Gly Asp Glu Pro Met Pro
            20                  25                  30
Val Pro Glu Asp Leu Ser Thr Thr Ser Gly Ala Gln Gln Asn Ser Lys
        35                  40                  45
Ser Asp Arg Gly Met
    50
```

(2) INFORMATION FOR SEQ ID NO: 195:

(i) SEQUENCE CHARACTERISTICS:
        (A) LENGTH: 431 amino acids
        (B) TYPE: amino acid
        (D) TOPOLOGY: linear (ii) MOLECULE TYPE: protein (v) FRAGMENT TYPE: internal -continued (xi) SEQUENCE DESCRIPTION: SEQ ID NO: 195:

Met Asp Val Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Val Pro Glu Asp Leu Ser Thr Thr Ser Gly Ala Gln Gln Asn Ser Lys
        35                  40                  45

Ser Asp Arg Gly Met Gly Glu Arg Pro Phe Gln Cys Asn Gln Ser Gly
    50                  55                  60

Ala Ser Phe Thr Gln Lys Gly Asn Leu Leu Arg His Ile Lys Leu His
65                  70                  75                  80

Ser Gly Glu Lys Pro Phe Lys Cys His Leu Cys Asn Tyr Ala Cys Arg
                85                  90                  95

Arg Arg Asp Ala Leu Thr Gly His Leu Arg Thr His Ser Val Gly Lys
            100                 105                 110

Pro His Lys Cys Gly Tyr Cys Gly Arg Ser Tyr Lys Gln Arg Ser Ser
        115                 120                 125

Leu Glu Glu His Lys Glu Arg Cys His Asn Tyr Leu Glu Ser Met Gly
130                 135                 140

Leu Pro Gly Val Cys Pro Val Ile Lys Glu Glu Thr Asn His Asn Glu
145                 150                 155                 160

Met Ala Glu Asp Leu Cys Lys Ile Gly Ala Glu Arg Ser Leu Val Leu
                165                 170                 175

Asp Arg Leu Ala Ser Asn Val Ala Lys Arg Lys Ser Ser Met Pro Gln
            180                 185                 190

Lys Phe Leu Gly Asp Lys Cys Leu Ser Asp Met Pro Tyr Asp Ser Ala
        195                 200                 205

Asn Tyr Glu Lys Glu Asp Met Met Thr Ser His Val Met Asp Gln Ala
    210                 215                 220

Ile Asn Asn Ala Ile Asn Tyr Leu Gly Ala Glu Ser Leu Arg Pro Leu
225                 230                 235                 240

Val Gln Thr Pro Pro Gly Ser Ser Glu Val Val Pro Val Ile Ser Ser
                245                 250                 255

Met Tyr Gln Leu His Lys Pro Pro Ser Asp Gly Pro Pro Arg Ser Asn
            260                 265                 270

His Ser Ala Gln Asp Ala Val Asp Asn Leu Leu Leu Leu Ser Lys Ala
        275                 280                 285

Lys Ser Val Ser Ser Glu Arg Glu Ala Ser Pro Ser Asn Ser Cys Gln
    290                 295                 300

Asp Ser Thr Asp Thr Glu Ser Asn Ala Glu Glu Gln Arg Ser Gly Leu
305                 310                 315                 320

Ile Tyr Leu Thr Asn His Ile Asn Pro His Ala Arg Asn Gly Leu Ala
                325                 330                 335

Leu Lys Glu Glu Gln Arg Ala Tyr Glu Val Leu Arg Ala Ala Ser Glu
            340                 345                 350

Asn Ser Gln Asp Ala Phe Arg Val Ser Thr Ser Gly Glu Gln Leu
        355                 360                 365

Lys Val Tyr Lys Cys Glu His Cys Arg Val Leu Phe Leu Asp His Val
    370                 375                 380

Met Tyr Thr Ile His Met Gly Cys His Gly Cys His Gly Phe Arg Asp
385                 390                 395                 400

Pro Phe Glu Cys Asn Met Cys Gly Tyr His Ser Gln Asp Arg Tyr Glu
                405                 410                 415

```
Phe Ser Ser His Ile Thr Arg Gly Glu His Arg Tyr His Leu Ser
            420                 425                 430
```

(2) INFORMATION FOR SEQ ID NO: 196:

(i) SEQUENCE CHARACTERISTICS:
        (A) LENGTH: 461 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 196:

```
Asn Val Lys Val Glu Thr Gln Ser Asp Glu Asn Gly Arg Ala Cys
 1               5                  10                  15

Glu Met Asn Gly Glu Glu Cys Ala Glu Asp Leu Arg Met Leu Asp Ala
            20                  25                  30

Ser Gly Glu Lys Met Asn Gly Ser His Arg Asp Gln Gly Ser Ser Ala
            35                  40                  45

Leu Ser Gly Val Gly Gly Ile Arg Leu Pro Asn Gly Lys Leu Lys Cys
        50                  55                  60

Asp Ile Cys Gly Ile Ile Cys Ile Gly Pro Asn Val Leu Met Val His
 65                  70                  75                  80

Lys Arg Ser His Thr Gly Glu Arg Pro Phe Gln Cys Asn Gln Cys Gly
                85                  90                  95

Ala Ser Phe Thr Gln Lys Gly Asn Leu Leu Arg His Ile Lys Leu His
            100                 105                 110

Ser Gly Glu Lys Pro Phe Lys Cys His Leu Cys Asn Tyr Ala Cys Arg
            115                 120                 125

Arg Arg Asp Ala Leu Thr Gly His Leu Arg Thr His Ser Val Gly Lys
130                 135                 140

Pro His Lys Cys Gly Tyr Cys Gly Arg Ser Tyr Lys Gln Arg Thr Ser
145                 150                 155                 160

Leu Glu Glu His Lys Glu Arg Cys His Asn Tyr Leu Glu Ser Met Gly
                165                 170                 175

Leu Pro Gly Thr Leu Tyr Pro Val Ile Lys Glu Glu Thr Lys His Ser
            180                 185                 190

Glu Met Ala Glu Asp Leu Cys Lys Ile Gly Ser Glu Arg Ser Leu Val
            195                 200                 205

Leu Asp Arg Leu Ala Ser Asn Val Ala Lys Arg Lys Ser Ser Met Pro
        210                 215                 220

Gln Lys Phe Leu Gly Asp Lys Gly Leu Ser Asp Thr Pro Tyr Asp Ser
225                 230                 235                 240

Ala Thr Tyr Glu Lys Glu Asn Glu Met Met Lys Ser His Val Met Asp
                245                 250                 255

Gln Ala Ile Asn Asn Ala Ile Asn Tyr Leu Gly Ala Glu Ser Leu Arg
            260                 265                 270

Pro Leu Val Gln Thr Pro Pro Gly Gly Ser Glu Val Val Pro Val Ile
            275                 280                 285

Ser Pro Met Tyr Gln Leu His Arg Arg Ser Glu Gly Thr Pro Arg Ser
            290                 295                 300

Asn His Ser Ala Gln Asp Ser Ala Val Glu Tyr Leu Leu Leu Ser
305                 310                 315                 320

Lys Ala Lys Leu Val Pro Ser Glu Arg Glu Ala Ser Pro Ser Asn Ser
```

```
              325                 330                 335
Cys Gln Asp Ser Thr Asp Thr Glu Ser Asn Asn Glu Gln Arg Ser
            340                 345                 350

Gly Leu Ile Tyr Leu Thr Asn His Ile Ala Arg Arg Ala Gln Arg Val
            355                 360                 365

Ser Leu Lys Glu Glu His Arg Ala Tyr Asp Leu Leu Arg Ala Ala Ser
370                 375                 380

Glu Asn Ser Gln Asp Ala Leu Arg Val Val Ser Thr Ser Gly Glu Gln
385                 390                 395                 400

Met Lys Val Tyr Lys Cys Glu His Cys Arg Val Leu Phe Leu Asp His
                405                 410                 415

Val Met Tyr Thr Ile His Met Gly Cys His Gly Phe Arg Asp Pro Phe
                420                 425                 430

Glu Cys Asn Met Cys Gly Tyr His Ser Gln Asp Arg Tyr Glu Phe Ser
            435                 440                 445

Ser His Ile Thr Arg Gly Glu His Arg Phe His Met Ser
450                 455                 460

(2) INFORMATION FOR SEQ ID NO: 197:

(i) SEQUENCE CHARACTERISTICS:
        (A) LENGTH: 432 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 197:

Met Asp Val Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
                20                  25                  30

Val Pro Glu Asp Leu Ser Thr Thr Ser Gly Ala Gln Gln Asn Ser Lys
            35                  40                  45

Ser Asp Arg Gly Met Ala Ser Asn Val Lys Val Glu Thr Gln Ser Asp
        50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
                85                  90                  95

Arg Asp Gln Gly Ser Ser Ala Leu Ser Gly Val Gly Gly Ile Arg Leu
            100                 105                 110

Pro Asn Gly Lys Leu Lys Cys Asp Ile Cys Gly Ile Val Cys Ile Gly
            115                 120                 125

Pro Asn Val Leu Met Val His Lys Arg Ser His Thr Gly Glu Arg Pro
130                 135                 140

Phe Gln Cys Asn Gln Ser Gly Ala Ser Phe Thr Gln Lys Gly Asn Leu
145                 150                 155                 160

Leu Arg His Ile Lys Leu His Ser Gly Glu Lys Pro Phe Lys Cys His
                165                 170                 175

Leu Cys Asn Tyr Ala Cys Arg Arg Arg Asp Ala Leu Thr Gly His Leu
            180                 185                 190

Arg Thr His Ser Gly Asp Lys Cys Leu Ser Asp Met Pro Tyr Asp Ser
            195                 200                 205
```

-continued

```
Ala Asn Tyr Glu Lys Glu Asp Met Met Thr Ser His Val Met Asp Gln
    210                 215                 220

Ala Ile Asn Asn Ala Ile Asn Tyr Leu Gly Ala Glu Ser Leu Arg Pro
225                 230                 235                 240

Leu Val Gln Thr Pro Pro Gly Ser Ser Glu Val Val Pro Val Ile Ser
            245                 250                 255

Ser Met Tyr Gln Leu His Lys Pro Pro Ser Asp Gly Pro Pro Arg Ser
            260                 265                 270

Asn His Ser Ala Gln Asp Ala Val Asp Asn Leu Leu Leu Leu Ser Lys
            275                 280                 285

Ala Lys Ser Val Ser Ser Glu Arg Glu Ala Ser Pro Ser Asn Ser Cys
    290                 295                 300

Gln Asp Ser Thr Asp Thr Glu Ser Asn Ala Glu Gln Arg Ser Gly
305                 310                 315                 320

Leu Ile Tyr Leu Thr Asn His Ile Asn Pro His Ala Arg Asn Gly Leu
            325                 330                 335

Ala Leu Lys Glu Glu Gln Arg Ala Tyr Glu Val Leu Arg Ala Ala Ser
            340                 345                 350

Glu Asn Ser Gln Asp Ala Phe Arg Val Val Ser Thr Ser Gly Glu Gln
    355                 360                 365

Leu Lys Val Tyr Lys Cys Glu His Cys Arg Val Leu Phe Leu Asp His
    370                 375                 380

Val Met Tyr Thr Ile His Met Gly Cys His Gly Cys His Gly Phe Arg
385                 390                 395                 400

Asp Pro Phe Glu Cys Asn Met Cys Gly Tyr His Ser Gln Asp Arg Tyr
            405                 410                 415

Glu Phe Ser Ser His Ile Thr Arg Gly Glu His Arg Tyr His Leu Ser
            420                 425                 430

(2) INFORMATION FOR SEQ ID NO: 198:

(i) SEQUENCE CHARACTERISTICS:
        (A) LENGTH: 518 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 198:

Met Asp Val Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Val Pro Glu Asp Leu Ser Thr Thr Ser Gly Ala Gln Gln Asn Ser Lys
        35                  40                  45

Ser Asp Arg Gly Met Ala Ser Asn Val Lys Val Glu Thr Gln Ser Asp
    50                  55                  60

Glu Glu Asn Gly Arg Ala Cys Glu Met Asn Gly Glu Cys Ala Glu
65                  70                  75                  80

Asp Leu Arg Met Leu Asp Ala Ser Gly Glu Lys Met Asn Gly Ser His
            85                  90                  95

Arg Asp Gln Gly Ser Ser Ala Leu Ser Gly Val Gly Gly Ile Arg Leu
            100                 105                 110

Pro Asn Gly Lys Leu Lys Cys Asp Ile Cys Gly Ile Val Cys Ile Gly
            115                 120                 125
```

```
            Pro Asn Val Leu Met Val His Lys Arg Ser His Thr Gly Glu Arg Pro
                130                 135                 140

Phe Gln Cys Asn Gln Ser Gly Ala Ser Phe Thr Gln Lys Gly Asn Leu
            145                 150                 155                 160

Leu Arg His Ile Lys Leu His Ser Gly Glu Lys Pro Phe Lys Cys His
                            165                 170                 175

Leu Cys Asn Tyr Ala Cys Arg Arg Asp Ala Leu Thr Gly His His Leu
                        180                 185                 190

Arg Thr His Ser Val Gly Lys Pro His Lys Cys Gly Tyr Cys Gly Arg
                    195                 200                 205

Ser Tyr Lys Gln Arg Ser Ser Leu Glu Glu His Lys Glu Arg Cys His
                210                 215                 220

Asn Tyr Leu Glu Ser Met Gly Leu Pro Gly Val Cys Pro Val Ile Lys
            225                 230                 235                 240

Glu Glu Thr Asn His Asn Glu Met Ala Glu Asp Leu Cys Lys Ile Gly
                            245                 250                 255

Ala Glu Arg Ser Leu Val Leu Asp Arg Leu Ala Ser Asn Val Ala Lys
                        260                 265                 270

Arg Lys Ser Ser Met Pro Gln Lys Phe Leu Gly Asp Lys Cys Leu Ser
                    275                 280                 285

Asp Met Pro Tyr Asp Ser Ala Asn Tyr Glu Lys Glu Asp Met Met Thr
                290                 295                 300

Ser His Val Met Asp Gln Ala Ile Asn Asn Ala Ile Asn Tyr Leu Gly
            305                 310                 315                 320

Ala Glu Ser Leu Arg Pro Leu Val Gln Thr Pro Pro Gly Ser Ser Glu
                            325                 330                 335

Val Val Pro Val Ile Ser Ser Met Tyr Gln Leu His Lys Pro Pro Ser
                        340                 345                 350

Asp Gly Pro Pro Arg Ser Asn His Ser Ala Gln Asp Ala Val Asp Asn
                    355                 360                 365

Leu Leu Leu Leu Ser Lys Ala Lys Ser Val Ser Ser Glu Arg Glu Ala
                370                 375                 380

Ser Pro Ser Asn Ser Cys Gln Asp Ser Thr Asp Thr Glu Ser Asn Ala
            385                 390                 395                 400

Glu Glu Gln Arg Ser Gly Leu Ile Tyr Leu Thr Asn His Ile Asn Pro
                            405                 410                 415

His Ala Arg Asn Gly Leu Ala Leu Lys Glu Glu Gln Arg Ala Tyr Glu
                        420                 425                 430

Val Leu Arg Ala Ala Ser Glu Asn Ser Gln Asp Ala Phe Arg Val Val
                    435                 440                 445

Ser Thr Ser Gly Glu Gln Leu Lys Val Tyr Lys Cys Glu His Cys Arg
                450                 455                 460

Val Leu Phe Leu Asp His Val Met Tyr Thr Ile His Met Gly Cys His
            465                 470                 475                 480

Gly Cys His Gly Phe Arg Asp Pro Phe Glu Cys Asn Met Cys Gly Tyr
                            485                 490                 495

His Ser Gln Asp Arg Tyr Glu Phe Ser Ser His Ile Thr Arg Gly Glu
                        500                 505                 510

His Arg Tyr His Leu Ser
                    515

(2) INFORMATION FOR SEQ ID NO: 199:
```

-continued

```
    (i) SEQUENCE CHARACTERISTICS:
        (A) LENGTH: 390 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 199:

Met Asp Val Asp Glu Gly Gln Asp Met Ser Gln Val Ser Gly Lys Glu
 1               5                  10                  15

Ser Pro Pro Val Ser Asp Thr Pro Asp Glu Gly Asp Glu Pro Met Pro
                20                  25                  30

Val Pro Glu Asp Leu Ser Thr Thr Ser Gly Ala Gln Gln Asn Ser Lys
            35                  40                  45

Ser Asp Arg Gly Met Gly Glu Arg Pro Phe Gln Cys Asn Gln Ser Gly
        50                  55                  60

Ala Ser Phe Thr Gln Lys Gly Asn Leu Leu Arg His Ile Lys Leu His
65                  70                  75                  80

Ser Gly Glu Lys Pro Phe Lys Cys His Leu Cys Asn Tyr Ala Cys Arg
                85                  90                  95

Arg Arg Asp Ala Leu Thr Gly His Leu Arg Thr His Ser Val Ile Lys
            100                 105                 110

Glu Glu Thr Asn His Asn Glu Met Ala Glu Asp Leu Cys Lys Ile Gly
        115                 120                 125

Ala Glu Arg Ser Leu Val Leu Asp Arg Leu Ala Ser Asn Val Ala Lys
        130                 135                 140

Arg Lys Ser Ser Met Pro Gln Lys Phe Leu Gly Asp Lys Cys Leu Ser
145                 150                 155                 160

Asp Met Pro Tyr Asp Ser Ala Asn Tyr Glu Lys Glu Asp Met Met Thr
                165                 170                 175

Ser His Val Met Asp Gln Ala Ile Asn Asn Ala Ile Asn Tyr Leu Gly
            180                 185                 190

Ala Glu Ser Leu Arg Pro Leu Val Gln Thr Pro Pro Gly Ser Ser Glu
        195                 200                 205

Val Val Pro Val Ile Ser Ser Met Tyr Gln Leu His Lys Pro Pro Ser
        210                 215                 220

Asp Gly Pro Pro Arg Ser Asn His Ser Ala Gln Asp Ala Val Asp Asn
225                 230                 235                 240

Leu Leu Leu Leu Ser Lys Ala Lys Ser Val Ser Ser Glu Arg Glu Ala
                245                 250                 255

Ser Pro Ser Asn Ser Cys Gln Asp Ser Thr Asp Thr Glu Ser Asn Ala
            260                 265                 270

Glu Glu Gln Arg Ser Gly Leu Ile Tyr Leu Thr Asn His Ile Asn Pro
        275                 280                 285

His Ala Arg Asn Gly Leu Ala Leu Lys Glu Glu Gln Arg Ala Tyr Glu
        290                 295                 300

Val Leu Arg Ala Ala Ser Glu Asn Ser Gln Asp Ala Phe Arg Val Val
305                 310                 315                 320

Ser Thr Ser Gly Glu Gln Leu Lys Val Tyr Lys Cys Glu His Cys Arg
                325                 330                 335

Val Leu Phe Leu Asp His Val Met Tyr Thr Ile His Met Gly Cys His
            340                 345                 350

Gly Cys His Gly Phe Arg Asp Pro Phe Glu Cys Asn Met Cys Gly Tyr
        355                 360                 365
```

```
His Ser Gln Asp Arg Tyr Glu Phe Ser Ser His Ile Thr Arg Gly Glu
    370                 375                 380

His Arg Tyr His Leu Ser
385                 390

(2) INFORMATION FOR SEQ ID NO: 200:

(i) SEQUENCE CHARACTERISTICS:
        (A) LENGTH: 376 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 200:

Met Asp Val Asp Glu Gly Gln Asp Met Ser Gln Val Ser Gly Lys Glu
  1                 5                  10                  15

Ser Pro Pro Val Ser Asp Thr Pro Asp Glu Gly Asp Glu Pro Met Pro
                 20                  25                  30

Val Pro Glu Asp Leu Ser Thr Thr Ser Gly Ala Gln Gln Asn Ser Lys
             35                  40                  45

Ser Asp Arg Gly Met Ala Ser Asn Val Lys Val Glu Thr Gln Ser Asp
         50                  55                  60

Glu Glu Asn Gly Arg Ala Cys Glu Met Asn Gly Glu Glu Cys Ala Glu
 65                  70                  75                  80

Asp Leu Arg Met Leu Asp Ala Ser Gly Glu Lys Met Asn Gly Ser His
                 85                  90                  95

Arg Asp Gln Gly Ser Ser Ala Leu Ser Gly Val Gly Gly Ile Arg Leu
                100                 105                 110

Pro Asn Gly Lys Leu Lys Cys Asp Ile Cys Gly Ile Val Cys Ile Gly
            115                 120                 125

Pro Asn Val Leu Met Val His Lys Arg Ser His Thr Gly Asp Lys Cys
        130                 135                 140

Leu Ser Asp Met Pro Tyr Asp Ser Ala Asn Tyr Glu Lys Glu Asp Met
145                 150                 155                 160

Met Thr Ser His Val Met Asp Gln Ala Ile Asn Asn Ala Ile Asn Tyr
                165                 170                 175

Leu Gly Ala Glu Ser Leu Arg Pro Leu Val Gln Thr Pro Pro Gly Ser
            180                 185                 190

Ser Glu Val Val Pro Val Ile Ser Ser Met Tyr Gln Leu His Lys Pro
        195                 200                 205

Pro Ser Asp Gly Pro Pro Arg Ser Asn His Ser Ala Gln Asp Ala Val
    210                 215                 220

Asp Asn Leu Leu Leu Leu Ser Lys Ala Lys Ser Val Ser Ser Glu Arg
225                 230                 235                 240

Glu Ala Ser Pro Ser Asn Ser Cys Gln Asp Ser Thr Asp Thr Glu Ser
                245                 250                 255

Asn Ala Glu Glu Gln Arg Ser Gly Leu Ile Tyr Leu Thr Asn His Ile
            260                 265                 270

Asn Pro His Ala Arg Asn Gly Leu Ala Leu Lys Glu Glu Gln Arg Ala
        275                 280                 285

Tyr Glu Val Leu Arg Ala Ala Ser Glu Asn Ser Gln Asp Ala Phe Arg
    290                 295                 300

Val Val Ser Thr Ser Gly Glu Gln Leu Lys Val Tyr Lys Cys Glu His
```

```
305                 310                 315                 320
Cys Arg Val Leu Phe Leu Asp His Val Met Tyr Thr Ile His Met Gly
                325                 330                 335

Cys His Gly Cys His Gly Phe Arg Asp Pro Phe Glu Cys Asn Met Cys
                340                 345                 350

Gly Tyr His Ser Gln Asp Arg Tyr Glu Phe Ser Ser His Ile Thr Arg
            355                 360                 365

Gly Glu His Arg Tyr His Leu Ser
370                 375
```

(2) INFORMATION FOR SEQ ID NO: 201:

(i) SEQUENCE CHARACTERISTICS:
        (A) LENGTH: 334 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 201:

```
Gly Glu Arg Pro Phe Gln Cys Asn Gln Cys Gly Ala Ser Phe Thr Gln
1               5                   10                  15

Lys Gly Asn Leu Leu Arg His Ile Lys Leu His Ser Gly Glu Lys Pro
                20                  25                  30

Phe Lys Cys His Leu Cys Asn Tyr Ala Cys Arg Arg Arg Asp Ala Leu
            35                  40                  45

Thr Gly His Leu Arg Thr His Ser Val Ile Lys Glu Glu Thr Lys His
        50                  55                  60

Ser Glu Met Ala Glu Asp Leu Cys Lys Ile Gly Ser Glu Arg Ser Leu
65                  70                  75                  80

Val Leu Asp Arg Leu Ala Ser Asn Val Ala Lys Arg Lys Ser Ser Met
                85                  90                  95

Pro Gln Lys Phe Leu Gly Asp Lys Gly Leu Ser Asp Thr Pro Tyr Asp
            100                 105                 110

Ser Ala Thr Tyr Glu Lys Glu Asn Glu Met Met Lys Ser His Val Met
        115                 120                 125

Asp Gln Ala Ile Asn Asn Ala Ile Asn Tyr Leu Gly Ala Glu Ser Leu
    130                 135                 140

Arg Pro Leu Val Gln Thr Pro Gly Gly Ser Glu Val Val Pro Val
145                 150                 155                 160

Ile Ser Pro Met Tyr Gln Leu His Arg Arg Ser Glu Gly Thr Pro Arg
                165                 170                 175

Ser Asn His Ser Ala Gln Asp Ser Ala Val Glu Tyr Leu Leu Leu Leu
            180                 185                 190

Ser Lys Ala Lys Leu Val Pro Ser Glu Arg Glu Ala Ser Pro Ser Asn
        195                 200                 205

Ser Cys Gln Asp Ser Thr Asp Thr Glu Ser Asn Asn Glu Glu Gln Arg
210                 215                 220

Ser Gly Leu Ile Tyr Leu Thr Asn His Ile Ala Arg Arg Ala Gln Arg
225                 230                 235                 240

Val Ser Leu Lys Glu Glu His Arg Ala Tyr Asp Leu Leu Arg Ala Ala
                245                 250                 255

Ser Glu Asn Ser Gln Asp Ala Leu Arg Val Val Ser Thr Ser Gly Glu
            260                 265                 270
```

```
Gln Met Lys Val Tyr Lys Cys Glu His Cys Arg Val Leu Phe Leu Asp
        275                 280                 285

His Val Met Tyr Thr Ile His Met Gly Cys His Gly Phe Arg Asp Pro
        290                 295                 300

Phe Glu Cys Asn Met Cys Gly Tyr His Ser Gln Asp Arg Tyr Glu Phe
305                 310                 315                 320

Ser Ser His Ile Thr Arg Gly Leu His Arg Phe His Met Ser
                325                 330
```

(2) INFORMATION FOR SEQ ID NO: 202:

(i) SEQUENCE CHARACTERISTICS:
        (A) LENGTH: 516 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 202:

```
Met Asp Ala Asp Glu Gly Gln Asp Met Ser Phe Ser Ser Gly Lys Glu
 1                   5                  10                  15

Ser Pro Pro Val Ser Asp Thr Pro Asp Glu Gly Asp Glu Pro Met Pro
                20                  25                  30

Ile Pro Glu Asp Leu Ser Thr Thr Ser Gly Gly Gln Gln Ser Ser Lys
            35                  40                  45

Ser Asp Arg Val Val Ala Ser Asn Val Lys Val Glu Thr Gln Ser Asp
        50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
                85                  90                  95

Arg Asp Gln Gly Ser Ser Ala Leu Ser Gly Val Gly Gly Ile Arg Leu
            100                 105                 110

Pro Asn Gly Lys Leu Lys Cys Asp Ile Cys Gly Ile Ile Cys Ile Gly
        115                 120                 125

Pro Asn Val Leu Met Val His Lys Arg Ser His Thr Gly Glu Arg Pro
130                 135                 140

Phe Gln Cys Asn Gln Cys Gly Ala Ser Phe Thr Gln Lys Gly Asn Leu
145                 150                 155                 160

Leu Arg His Ile Lys Leu His Ser Gly Glu Lys Pro Phe Lys Cys His
                165                 170                 175

Leu Cys Asn Tyr Ala Cys Arg Arg Arg Asp Ala Leu Thr Gly His Leu
            180                 185                 190

Arg Thr His Ser Val Gly Lys Pro His Lys Cys Gly Tyr Cys Gly Arg
        195                 200                 205

Ser Tyr Lys Gln Arg Thr Ser Leu Glu Glu His Lys Glu Arg Cys His
        210                 215                 220

Asn Tyr Leu Glu Ser Met Gly Leu Pro Gly Thr Leu Tyr Pro Val Ile
225                 230                 235                 240

Lys Glu Glu Thr Lys His Ser Glu Met Ala Glu Asp Leu Cys Lys Ile
                245                 250                 255

Gly Ser Glu Arg Ser Leu Val Leu Asp Arg Leu Ala Ser Asn Val Ala
            260                 265                 270

Lys Arg Lys Ser Ser Met Pro Gln Lys Phe Leu Gly Asp Lys Gly Leu
        275                 280                 285
```

-continued

```
Ser Asp Thr Pro Tyr Asp Ser Ala Thr Tyr Glu Lys Glu Asn Glu Met
    290                 295                 300
Met Lys Ser His Val Met Asp Gln Ala Ile Asn Asn Ala Ile Asn Tyr
305                 310                 315                 320
Leu Gly Ala Glu Ser Leu Arg Pro Leu Val Gln Thr Pro Pro Gly Gly
                325                 330                 335
Ser Glu Val Val Pro Val Ile Ser Pro Met Tyr Gln Leu His Arg Arg
            340                 345                 350
Ser Glu Gly Thr Pro Arg Ser Asn His Ser Ala Gln Asp Ser Ala Val
            355                 360                 365
Glu Tyr Leu Leu Leu Ser Lys Ala Lys Leu Val Pro Ser Glu Arg
    370                 375                 380
Glu Ala Ser Pro Ser Asn Ser Cys Gln Asp Ser Thr Asp Thr Glu Ser
385                 390                 395                 400
Asn Asn Glu Glu Gln Arg Ser Gly Leu Ile Tyr Leu Thr Asn His Ile
                405                 410                 415
Ala Arg Arg Ala Gln Arg Val Ser Leu Lys Glu Glu His Arg Ala Tyr
            420                 425                 430
Asp Leu Leu Arg Ala Ala Ser Glu Asn Ser Gln Asp Ala Leu Arg Val
        435                 440                 445
Val Ser Thr Ser Gly Glu Gln Met Lys Val Tyr Lys Cys Glu His Cys
    450                 455                 460
Arg Val Leu Phe Leu Asp His Val Met Tyr Thr Ile His Met Gly Cys
465                 470                 475                 480
His Gly Phe Arg Asp Pro Phe Glu Cys Asn Met Cys Gly Tyr His Ser
            485                 490                 495
Gln Asp Arg Tyr Glu Phe Ser Ser His Ile Thr Arg Gly Glu His Arg
            500                 505                 510
Phe His Met Ser
        515
```

Other embodiments are within the following claims.

What is claimed is:

1. An isolated antibody that binds to an Ikaros polypeptide consisting of an amino acid sequence encoded by one or more of:
   (a) Ikaros exon 1/2 (nucleotides 223 to 381 of SEQ ID NO:5);
   (b) Ikaros exon 3 (nucleotides 382 to 642 of SEQ ID NO:5);
   (c) Ikaros exon 4 (nucleotides 643 to 810 of SEQ ID NO:5);
   (d) Ikaros exon 5 (nucleotides 811 to 933 of SEQ ID NO:5);
   (e) Ikaros exon 6 (nucleotides 934 to 1068 of SEQ ID NO:5); and
   (f) Ikaros exon 7 (nucleotides 1069 to 1776 of SEQ ID NO:5).

2. The antibody of claim 1, wherein the antibody is a monoclonal antibody.

3. An isolated antibody that binds to an Ik-1 polypeptide encoded by SEQ ID NO:5.

4. An isolated antibody that binds to an Ik-2 polypeptide encoded by SEQ ID NO:2.

5. An isolated antibody that binds to an Ik-3 polypeptide encoded by SEQ ID NO:4.

6. An isolated antibody that binds to an Ik-4 polypeptide encoded by SEQ ID NO:6.

7. An isolated antibody that binds to an Ik-5 polypeptide encoded by SEQ ID NO:7.

8. An isolated antibody that binds to an Ikaros polypeptide consisting of an amino acid sequence encoded by one or more of:
   (a) Ikaros exon 1/2 (nucleotides 1–55 of SEQ ID NO:165)
   (b) Ikaros exon 3 (nucleotides 1 to 255 of SEQ ID NO:3);
   (c) Ikaros exon 4 (nucleotides 256 to 423 of SEQ ID NO:3);
   (d) Ikaros exon 5 (nucleotides 424 to 549 of SEQ ID NO:3);
   (e) Ikaros exon 6 (nucleotides 550 to 684 of SEQ ID NO:3); and
   (f) Ikaros exon 7 (nucleotides 685 to 1383 of SEQ ID NO:3).

9. An isolated antibody that binds an Ik-1 polypeptide encoded by SEQ ID NO:165.

10. The antibody of claim 8, wherein the antibody is a monoclonal antibody.

11. A composition comprising the antibody of claim 1 and a pharmaceutically acceptable carrier.

12. A composition comprising the antibody of claim 8 and a pharmaceutically acceptable carrier.

* * * * *